(12) United States Patent
Martin et al.

(10) Patent No.: US 11,046,670 B2
(45) Date of Patent: Jun. 29, 2021

(54) PIPERAZINYL NORBENZOMORPHAN COMPOUNDS AND METHODS FOR USING THE SAME

(71) Applicant: BOARD OF REGENTS, THE UNIVERSITY OF TEXAS SYSTEM, Austin, TX (US)

(72) Inventors: Stephen F. Martin, Austin, TX (US); James J. Sahn, Austin, TX (US); Timothy R. Hodges, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/769,297

(22) PCT Filed: Oct. 19, 2016

(86) PCT No.: PCT/US2016/057739
§ 371 (c)(1),
(2) Date: Apr. 18, 2018

(87) PCT Pub. No.: WO2017/070229
PCT Pub. Date: Apr. 27, 2017

(65) Prior Publication Data
US 2019/0077789 A1  Mar. 14, 2019

Related U.S. Application Data

(60) Provisional application No. 62/243,568, filed on Oct. 19, 2015.

(51) Int. Cl.
| | |
|---|---|
| *A61K 31/5377* | (2006.01) |
| *C07D 221/24* | (2006.01) |
| *C07D 223/16* | (2006.01) |
| *C07D 401/06* | (2006.01) |
| *C07D 403/04* | (2006.01) |
| *C07D 221/22* | (2006.01) |
| *A61P 25/28* | (2006.01) |
| *A61P 25/22* | (2006.01) |
| *A61P 25/24* | (2006.01) |
| *A61P 25/16* | (2006.01) |
| *A61P 25/06* | (2006.01) |
| *A61P 35/00* | (2006.01) |
| *C07D 401/14* | (2006.01) |

(52) U.S. Cl.
CPC ............ *C07D 403/04* (2013.01); *A61P 25/06* (2018.01); *A61P 25/16* (2018.01); *A61P 25/22* (2018.01); *A61P 25/24* (2018.01); *A61P 25/28* (2018.01); *A61P 35/00* (2018.01); *C07D 221/22* (2013.01); *C07D 401/14* (2013.01)

(58) Field of Classification Search
CPC .. C07D 221/24; C07D 223/16; C07D 401/06; A61K 31/5377
See application file for complete search history.

(56) References Cited

U.S. PATENT DOCUMENTS

| | | | |
|---|---|---|---|
| 3,887,686 A | 6/1975 | Merz et al. |
| 4,963,563 A | 10/1990 | Debernardis et al. |
| 5,354,758 A | 10/1994 | Lawson et al. |
| 7,786,165 B2 | 8/2010 | Yasuma et al. |
| 2005/0107432 A1 | 5/2005 | Iimura et al. |
| 2010/0256137 A1 | 10/2010 | Buchstaller et al. |
| 2011/0082154 A1 | 4/2011 | Oksenberg et al. |
| 2011/0269791 A1 | 11/2011 | Peters et al. |
| 2014/0206686 A1 | 7/2014 | Glunz |
| 2014/0323487 A1 | 10/2014 | Cowan et al. |
| 2015/0158831 A1 | 6/2015 | Alcalde-Pais et al. |
| 2015/0376166 A1 | 12/2015 | Lopez-Tapia |
| 2016/0280657 A1 | 9/2016 | Martin et al. |
| 2019/0177301 A1 | 6/2019 | Martin et al. |

FOREIGN PATENT DOCUMENTS

| | | |
|---|---|---|
| DE | 10 2007 028521 | 12/2008 |
| EP | 0 415 634 | 3/1991 |
| WO | WO 91/14674 | 10/1991 |
| WO | WO 96/38471 | 12/1996 |
| WO | WO 99/24022 | 5/1999 |
| WO | WO 2004/037788 | 5/2004 |
| WO | WO 2005/009941 | 2/2005 |
| WO | WO 2006/021463 | 3/2006 |
| WO | WO 2006/082001 | 8/2006 |
| WO | WO 2006/109085 | 10/2006 |
| WO | WO 2007/146122 | 12/2007 |
| WO | WO 2008/044027 | 4/2008 |
| WO | WO 2008/044029 | 4/2008 |
| WO | WO 2009/003719 | 1/2009 |
| WO | WO 2009/016218 | 2/2009 |
| WO | WO 2009/063061 | 5/2009 |
| WO | WO 2013/15844 | 10/2013 |
| WO | WO 2014/113620 | 7/2014 |

(Continued)

OTHER PUBLICATIONS

Sahn et al. (ACS Combinatorial Science (2012), 14(9), 496-502).*
Burkhard, Johannes A., et al. "Synthesis and structural analysis of a new class of azaspiro [3,3] heptanes as building blocks for medicinal chemistry," *Organic letters* 12.9 (2010): 1944-1947.
Coe, Jotham W., et al. "Syntheses of the opioid substructures 1, 2, 3, 4, 5, 6-hexahydro-2, 6-methano-3-benzazocine and 2, 3, 4, 5-tetrahydro-1, 5-methano-1H-2-benzazepine." *Tetrahedron Letters* 52.9 (2011): 953-954.
Extended European Search Report and Written Opinion, issued in European Application No. 16858145.2, dated May 8, 2019.

(Continued)

Primary Examiner — Bruck Kifle
(74) *Attorney, Agent, or Firm* — Parker Highlander PLLC

(57) ABSTRACT

Disclosed herein, inter alia, are piperazinyl norbenzomorphan compounds and uses thereof, including, for example, methods for treating a CNS disease, treating traumatic brain injury, improving cognition, or diagnosing and treating cancer.

14 Claims, 20 Drawing Sheets
Specification includes a Sequence Listing.

(56) References Cited

FOREIGN PATENT DOCUMENTS

| WO | WO 2015/009742 | 1/2015 |
|---|---|---|
| WO | WO 2015/116923 | 8/2015 |
| WO | WO 2015/145322 | 10/2015 |
| WO | WO 2017/007756 | 1/2017 |
| WO | WO 2017/190107 | 11/2017 |
| WO | WO 2017/190109 | 11/2017 |

OTHER PUBLICATIONS

Guo, L.; Zhen, X. "Sigma-2 receptor ligands: neurobiological effects." *Curr. Med. Chem.* 2015, 22, 989-1003.

Huang, Y.S.; Lu, H.L.; Zhang, L.J.; Wu, Z. "Sigma-2 receptor ligands and their perspectives in cancer diagnosis and therapy." *Med. Res. Rev.* 2014, 34, 532-566.

International Search Report and Written Opinion, issued in International Application No. PCT/US16/57739, dated Mar. 31, 2017.

Invitation to Pay Additional Fees, issued in International Application No. PCT/US16/57739, dated Jan. 18, 2017.

Mach, R. H.; Zheng, C.; Hawkins, W. G. "The σ2 Receptor: A Novel Protein for the Imaging and Treatment of Cancer." *J. Med. Chem.* 2013, 56, 7137-7160.

Mazzocchi, Paul H., and Barbara C. Stahly. "Synthesis and pharmacological properties of 1, 2, 3, 4, 5, 6-hexahydro-1, 6-methano-2-benzazocines." *Journal of medicinal chemistry* 24.4 (1981): 457-462.

Mokotoff, Michael, and Arthur E. Jacobson. "Azribicyclo chemistry II. Synthesis of 1, 5-methano-2, 3, 4, 5-tetrahydro-1H-2-benzazepines. B-norbenzomorphans." *Journal of Heterocyclic Chemistry* 7.4 (1970): 773-778.

PubChem CID 44825925, 2010.

PubChem CID 70613730, 2012.

Sahn, James J., and Stephen F. Martin. "Expedient synthesis of norbenzomorphan library via multicomponent assembly process coupled with ring-closing reactions." *ACS combinatorial science* 14.9 (2012): 496-502.

Sahn, James J., Justin Y. Su, and Stephen F. Martin. "Facile and unified approach to skeletally diverse, privileged scaffolds." *Organic letters* 13.10 (2011): 2590-2593.

Sunderhaus, James D., Chris Dockendorff, and Stephen F. Martin. "Sythnthesis of diverse heterocyclic scaffolds via tandem additions to imine derivatives and ring-forming reactions." *Tetrahedron* 65.33 (2009): 6454-6469.

Abate, Carmen, et al. "Analogues of E receptor ligand 1-Cyclohexyl-4-[3-(5-methoxy-1, 2, 3, 4-tetrahydronaphthalen-1-yl) propyl] piperazine (PB28) with added polar functionality and reduced lipophilicty for potential use as positron emission tomography radiotracers." *Journal of medicinal chemistry* 54.4 (2011): 1022-1032.

European Partial Search Report and Invitation to Pay Additional fees, issued in European Application No. 17790616.1, dated Sep. 17, 2019.

Pati, Maria Laura, et al. "Deconstruction of 6, 7-dimethoxy-1, 2, 3, 4-tetrahydroisoquinoline moiety to separate P-glycoprotein (P-gp) activity from σ2 receptor affinity in mixed P-gp/E2 receptor agents." *European journal of medicinal chemistry* 89 (2015): 691-700.

Rajagopalan, P., et al. "DuP 747: a new, potent, kappa opioid analgesic. Synthesis and pharmacology1." *Bioorganic & medicinal chemistry letters* 2.7 (1992): 715-720.

Zhang, Ji-Cheng, et al. "Direct Oxidative Arylation of Aryl C—H Bonds with Aryl Boronic Acids via Pd Catalysis Directed by the N, N-Dimethylaminomethyl Group." *Chemistry—An Asian Journal* 10.4 (2015): 840-843.

CAS Abstract and indexed compounds G. Chessari et al., WO 2006/109085. Accession No. 2006:1095040. Dated Apr. 13, 2006.

CAS Abstract. RN=1823304-19-3. Dated Dec. 6, 2015.

Extended European Search Report issued in corresponding European Application No. 17790618.7, dated Jun. 26, 2020.

Partial Supplementary European Search Report issued in corresponding European Application No. 17790618.7, dated Feb. 27, 2020.

Pinard, Emmanuel, et al. "Discovery of benzoylisoindolines as a novel class of potent, selective and orally active GlyT1 inhibitors." *Bioorganic & Medicinal Chemistry Letters* 20.23 (2010): 6960-6965.

\* cited by examiner non-selective: $R^1 = R^2 = H$
Sig2R selective: $R^1 = Ar, NR_2; R^2 = H$
Sig1R selective: $R^1 = H; R^2 = Ar, NR_2$

JJS-1-166

SAS -101

SAS-0132

SAS-0132 significantly reduces IL1β levels

SAS-0132 slightly reduces TNFα levels

SAS-0132 slightly reduces CD14 levels

SAS-0132 *inhibits* long-term depression (LTD)

SFM1534 HCl

SFM1535 HCl

FIG. 14A - cont'd.
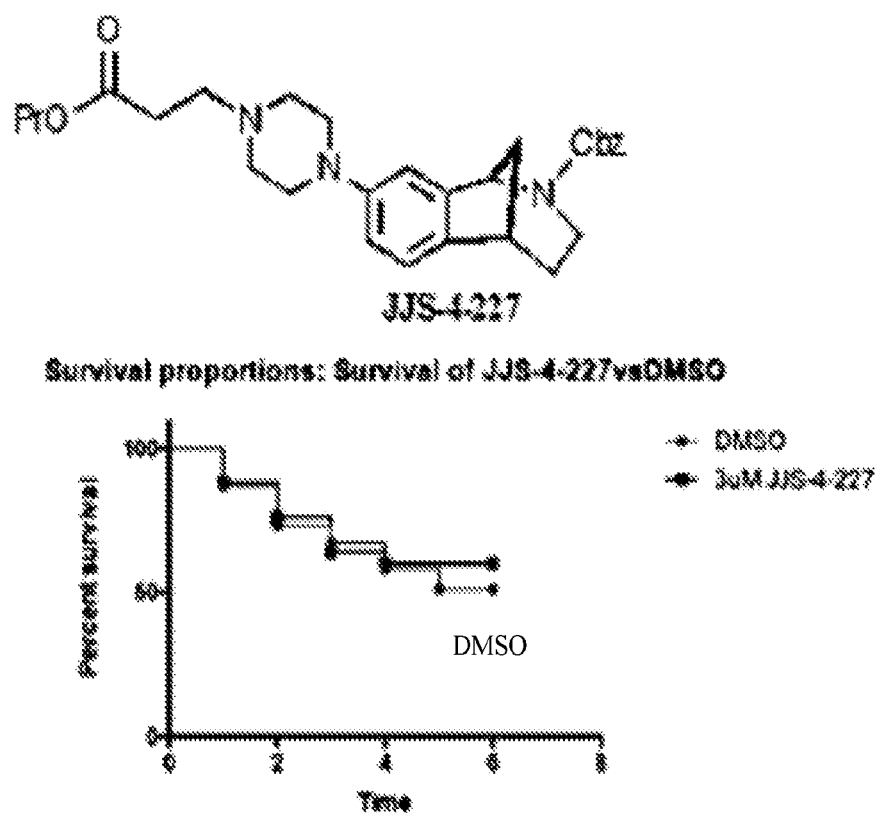

FIG. 14A - cont'd.
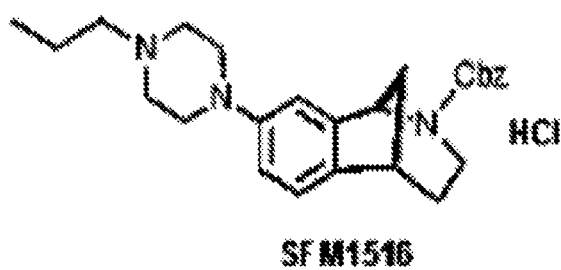
SFM1516
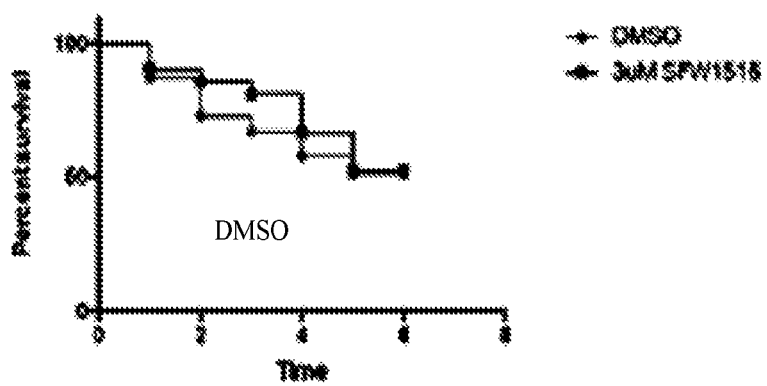
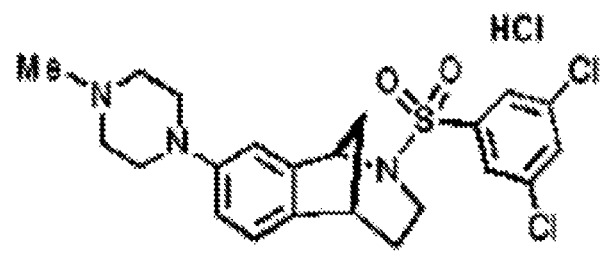
SFM1501
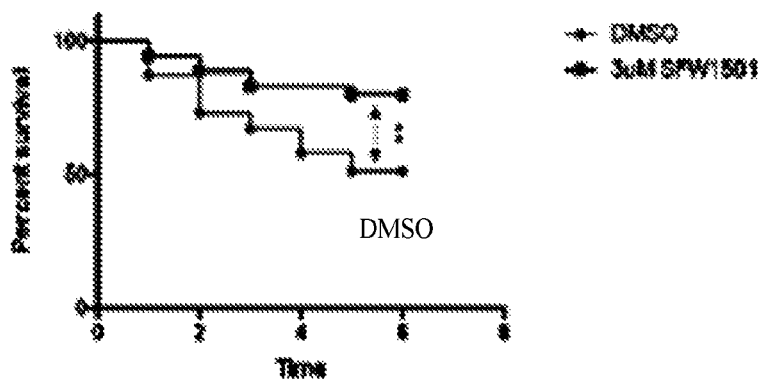

TH-4-20

Survival proportions: Survival of TH-4-20

JJS-5-003 HCl

Survival proportions: Survival of JJS-5-003vsDMSO

FIG. 14B - cont'd.
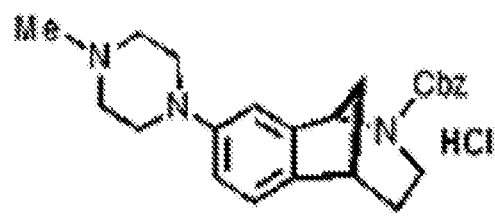
SAS-0132 HCl
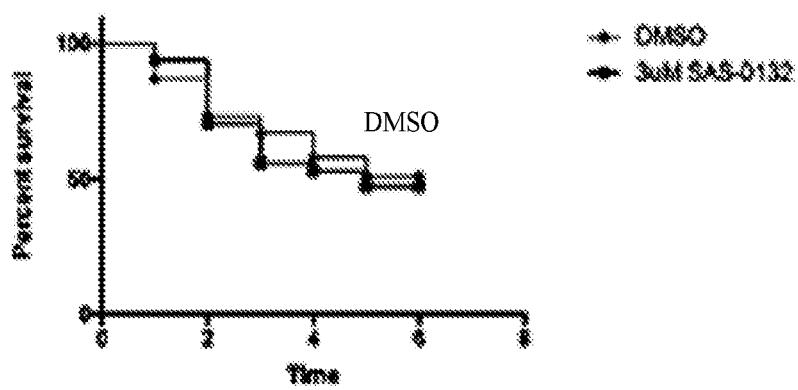
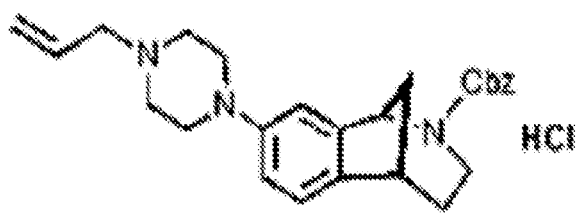
SFM1500
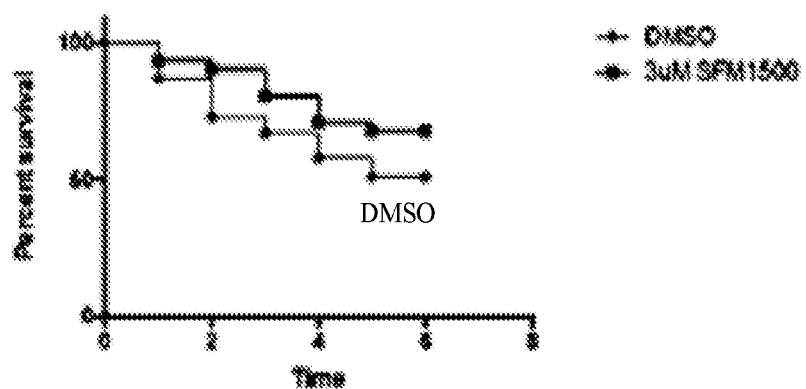

SAS-0132

SAS-0132

SEQUENCE LISTING

```
<160> NUMBER OF SEQ ID NOS: 2

<210> SEQ ID NO 1
<211> LENGTH: 223
<212> TYPE: PRT
<213> ORGANISM: Homo sapiens

<400> SEQUENCE: 1

Met Gln Trp Ala Val Gly Arg Arg Trp Ala Ala Leu Leu Leu
1               5                   10                  15

Ala Val Ala Ala Val Leu Thr Gln Val Val Trp Leu Trp Leu Gly Thr
                20                  25                  30

Gln Ser Phe Val Phe Gln Arg Glu Glu Ile Ala Gln Leu Ala Arg Gln
            35                  40                  45

Tyr Ala Gly Leu Asp His Glu Leu Ala Phe Ser Arg Leu Ile Val Glu
        50                  55                  60

Leu Arg Arg Leu His Pro Gly His Val Leu Pro Asp Glu Glu Leu Gln
65                  70                  75                  80

Trp Val Phe Val Asn Ala Gly Gly Trp Met Gly Ala Met Cys Leu Leu
                85                  90                  95

His Ala Ser Leu Ser Glu Tyr Val Leu Leu Phe Gly Thr Ala Leu Gly
                100                 105                 110
```

```
Ser Arg Gly His Ser Gly Arg Tyr Trp Ala Glu Ile Ser Asp Thr Ile
            115                 120                 125

Ile Ser Gly Thr Phe His Gln Trp Arg Glu Gly Thr Thr Lys Ser Glu
        130                 135                 140

Val Phe Tyr Pro Gly Glu Thr Val Val His Gly Pro Gly Glu Ala Thr
145                 150                 155                 160

Ala Val Glu Trp Gly Pro Asn Thr Trp Met Val Glu Tyr Gly Arg Gly
                165                 170                 175

Val Ile Pro Ser Thr Leu Ala Phe Ala Leu Ala Asp Thr Val Phe Ser
            180                 185                 190

Thr Gln Asp Phe Leu Thr Leu Phe Tyr Thr Leu Arg Ser Tyr Ala Arg
        195                 200                 205

Gly Leu Arg Leu Glu Leu Thr Thr Tyr Leu Phe Gly Gln Asp Pro
    210                 215                 220

<210> SEQ ID NO 2
<211> LENGTH: 195
<212> TYPE: PRT
<213> ORGANISM: Homo sapiens

<400> SEQUENCE: 2

Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
        35                  40                  45

Asp Gln Pro Ala Ala Ser Gly Asp Ser Asp Asp Glu Pro Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
            100                 105                 110

Tyr Gly Val Phe Ala Gly Arg Asp Ala Ser Arg Gly Leu Ala Thr Phe
        115                 120                 125

Cys Leu Asp Lys Glu Ala Leu Lys Asp Glu Tyr Asp Asp Leu Ser Asp
    130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Pro Lys Asp Glu Ser Ala Arg
            180                 185                 190

Lys Asn Asp
    195
```

PIPERAZINYL NORBENZOMORPHAN COMPOUNDS AND METHODS FOR USING THE SAME

CROSS-REFERENCES TO RELATED APPLICATIONS

This application is a national phase application under 35 U.S.C. § 371 of International Application No. PCT/US2016/057,739 filed Oct. 19, 2016, which claims the benefit of U.S. Provisional Application No. 62/243,568 filed Oct. 19, 2015, each of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48932-530001WO_ST25.TXT, created Oct. 19, 2016, 4,084 bytes, machine format IBM-PC, MS Windows operating system, is hereby incorporated by reference.

BACKGROUND

Sigma 2 receptors are lipid raft proteins that are involved in cell proliferation and regulation of cytosolic calcium concentration and expressed in many tissues, including those of the central nervous system. Sigma 2 receptors have been implicated, for example, in neurological function, cognition, cardiovascular function, substance abuse, and cancer. Many known sigma 2 receptor ligands lack either sigma subtype selectivity or general selectivity. It has been suggested that sigma 2 receptors reside within the progesterone receptor membrane component 1. The progesterone receptor membrane component 1 is also widely distributed in the CNS and is involved in neuroprotection and axonal migration. There is evidence for its role in neurological disorders and cancer.

It is desirable to have new therapeutics effective for treating, for example, diseases or conditions related to sigma 2 receptor biological activities or pathways. Provided herein are solutions to these and other problems in the art.

SUMMARY

In an aspect is provided a compound having the formula:

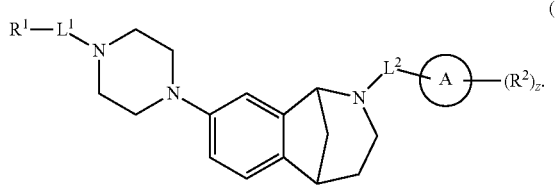

(I)

Ring A is cycloalkyl, heterocycloalkyl, aryl, or heteroaryl. $L^1$ is a bond or unsubstituted alkylene. $L^2$ is a bond, —$SO_2$—, —C(O)NH—, —NHC(O)—, —C(O)O—, —OC(O)—, —$SO_2CH_2$—, —C(O)$NHCH_2$—, —NHC(O)$CH_2$— C(O)$OCH_2$—, —OC(O)$CH_2$—, or unsubstituted alkylene. $R^1$ is a hydrogen, halogen, —$CX_3^1$, —$CHX_2^1$, —$CH_2X^1$, —CN, —$NR^7R^8$, —C(O)$R^9$, —C(O)$OR^9$, —C(O)$NR^7R^8$, —$OR^{10}$, —OC(O)$OR^9$, —OC(O)$NR^7R^8$, —OC(O)$R^9$, —C(S)$R^9$, —C(S)$OR^9$, —C(S)$NR^7R^8$, —$SR^{10}$, —OC(S)$OR^9$, —OC(S) $NR^7R^8$, —OC(S)$R^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently a halogen, —$CX_3^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX_3^2$, —$OCHX_2^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents bonded to adjacent atoms may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl. z is an integer from 0 to 5. X, $X^1$, and $X^2$ are independently —Cl, —Br, —I, or —F.

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In an aspect is provided a method of treating a disease including administering an effective amount of a compound as described herein.

In an aspect is provided a method of treating cancer in a subject in need thereof, the method including administering an effective amount of a compound described herein.

In an aspect is provided a method to treating a neurodegenerative disease in a subject in need thereof, the method including administering an effective amount of a compound described herein.

In an aspect is provided a method of treating drug abuse in a subject in need thereof, the method including administering an effective amount of a compound described herein.

In an aspect is provided a method of treating drug addiction in a subject in need thereof, the method including administering an effective amount of a compound described herein.

In an aspect is provided a method of treating a psychiatric disease in a subject in need thereof, the method including administering an effective amount of a compound described herein.

In an aspect is provided a method of treating anxiety, depression, schizophrenia, or epilepsy in a subject in need thereof, the method including administering an effective amount of a compound described herein.

In an aspect is provided a method of treating pain in a subject in need thereof, the method including administering an effective amount of a compound described herein.

In an aspect is provided a method of treating migraine or neuropathic pain in a subject in need thereof, the method including administering an effective amount of a compound described herein.

In an aspect is provided a method to treating an inflammatory disease in a subject in need thereof, the method including administering an effective amount of a compound described herein.

In an aspect is provided a method to treating a cardiovascular disease in a subject in need thereof, the method including administering an effective amount of a compound described herein.

In an aspect is provided a method of treating amnesia, traumatic brain injury, inflammatory pain, stroke, a cardiovascular disease, multiple sclerosis, or retinal neural degeneration in a subject in need thereof, the method including administering an effective amount of a compound described herein.

In an aspect is provided a method of modulating a sigma 2 receptor, the method including contacting a sigma 2 receptor with a compound described herein, thereby modulating the sigma 2 receptor.

In an aspect is provided a method of modulating progesterone receptor membrane component 1 (PGRMC1), the method including contacting a progesterone receptor membrane component 1 with a compound described herein, thereby modulating the progesterone receptor membrane component 1.

In an aspect is provided a method of improving cognition in a subject, the method including administering an effective amount of a compound described herein.

In an aspect is provided a method of detecting a sigma 2 receptor including: (a) administering to a sample a detectable compound described herein; (b) allowing the detectable compound described herein to bind to a sigma 2 receptor within the sample, thereby forming a detectable compound-sigma 2 receptor complex; and (c) detecting the detectable compound-sigma 2 receptor complex in the sample.

In an aspect is provided a method of detecting a sigma 2 receptor in an individual including: (a) administering to the individual an effective amount of a detectable compound described herein; (b) allowing the detectable compound described herein to bind to a sigma 2 receptor within the individual thereby forming a detectable compound-sigma 2 receptor complex;

and (c) detecting the detectable compound-sigma 2 receptor complex in the individual.

BRIEF DESCRIPTION OF THE DRAWINGS

FIG. 14A: enantiopure SFM1534, enantiopure SFM1535, JJS-4-227, SFM1516, SFM1501; FIG. 14B: TH-4-20, JJS-5-003, SAS-0132, SFM1500.

DETAILED DESCRIPTION

A. Definitions

Figure 1:
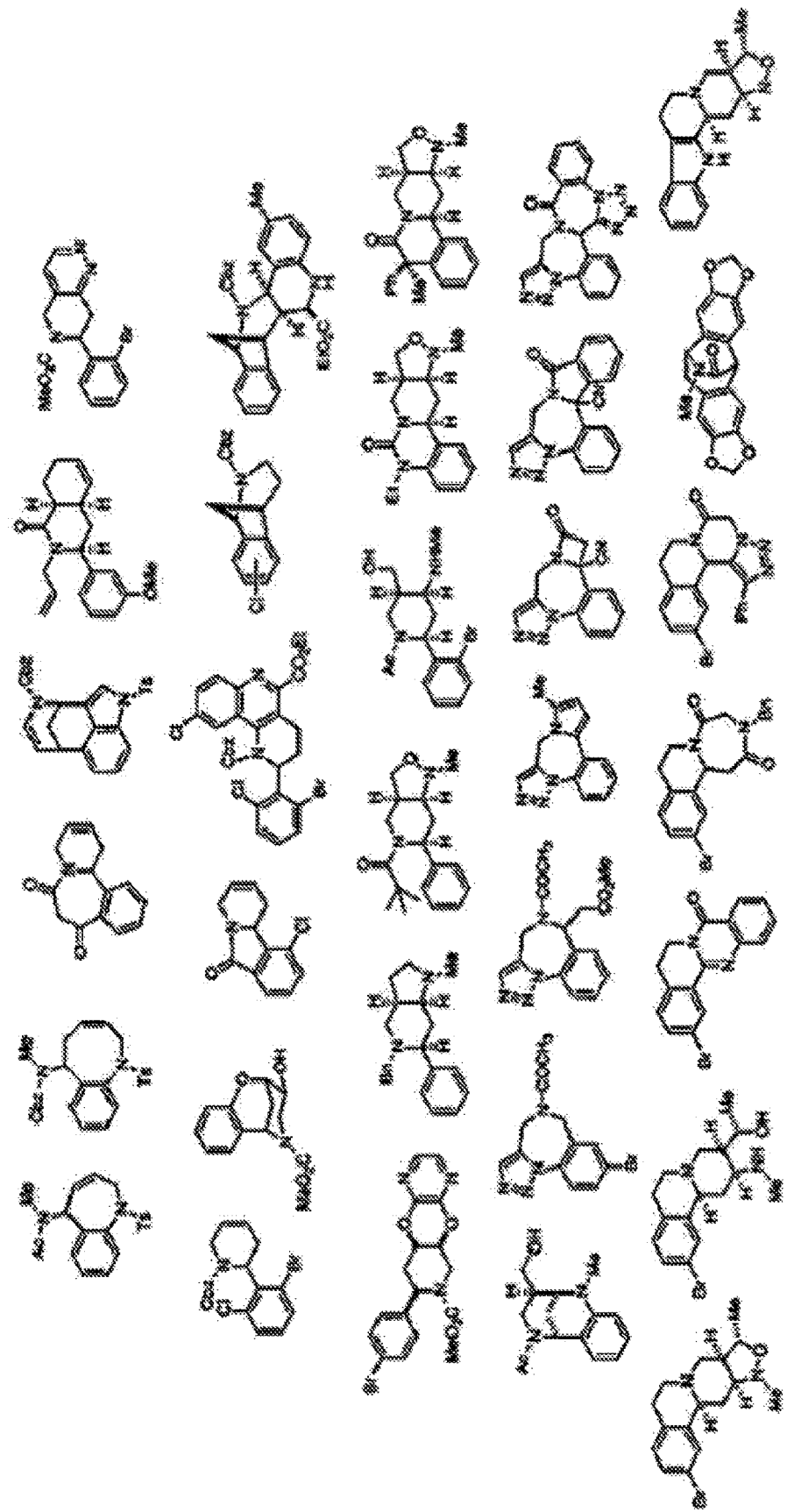
FIG. 1 Heterocyclic scaffolds.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene," by itself or as part of another substituent, means, unless otherwise stated, a divalent radical derived from an alkyne.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R$^1$, —C(O)NR$^1$, —NR'R—OR$^1$, —SR$^1$, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring.

A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R$^1$, where R' is a substituted or unsubstituted alkyl group as defined above. R' may have a specified number of carbons (e.g., "C$_1$-C$_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR$^1$, =O, =NR$^1$, —NR'R—SR$^1$, —halogen, —SiR'R"R'", —OC(O)R$^1$, —C(O)R$^1$, —CONR'R", —OC(O)NR 'R", —NR"C(O)R', —NR'—C(O)NR"R'", —NR"C(O)$_2$R$^1$, —NR—C(NR'R"R'")=NR'", —NR—C(NR'R")=NR'", —S(O)R$^1$, —S(O)$_2$R$^1$, —S(O)$_2$NR'R", —NRSO$_2$R$^1$, NR'NR"R'", ONR'R", NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR$^1$, —NR'R —SR$^1$, -halogen, —SiR'R"R'", —OC(O)R$^1$, —C(O)R$^1$, —CONR'R", —OC(O)NR'R", —NR"C(O)R$^1$, —NR'—C(O)NR"R'", —NR"C(O)$_2$R$^1$, —NR—C(NR'R"R'")=NR'", —NR—C(NR' R")=NR'", —S(O)R$^1$, —S(O)$_2$R$^1$, —S(O)$_2$NR'R", —NRSO$_2$R$^1$, NR'NR"R'", ONR'R", NR'C=(O)NR"NR'"R"", —CN, —NO$_2$, —R$^1$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3.

Alternatively, two of the substituents on adjacent atoms of the aryl or heteroaryl ring may optionally be replaced with a substituent of the formula—A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CHF$_2$, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC—(O)NHNH$_2$, —NHC=(O) NH$_2$, —NHSO$_2$H, —NHC=(O)H, —NHC(O)—OH, —NHOH, —OCF$_3$, —OCHF$_2$, —OCH$_2$F, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —$CHF_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC—(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —$CHF_2$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —$CHF_2$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol $\sim\!\!\sim\!\!\sim$ denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with Sigma 2 receptor activity. Certain methods described herein may treat diseases associated with progesterone receptor membrane component 1 activity. Certain methods described herein may treat diseases associated with progesterone receptor membrane component 1 activity by modulating the progesterone receptor membrane component 1. Certain methods described herein may treat diseases associated with Sigma 2 receptor activity by modulating the Sigma 2 receptor. For example, certain methods herein treat cancer. For example certain methods herein treat cancer by decreasing a symptom of cancer. Symptoms of cancer would be known or may be determined by a person of ordinary skill in the art. For example, certain methods herein treat a neurodegenerative disease (e.g., Alzheimer's disease, Parkinson's disease, Huntington's disease, frontotemporal dementia, or amyotrophic lateral sclerosis). For example certain methods herein treat a neurodegenerative disease by decreasing a symptom of a neurodegenerative disease.

Symptoms of a neurodegenerative disease would be known or may be determined by a person of ordinary skill in the art. For example, certain methods herein treat drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, or retinal neural degeneration. For example certain methods herein treat drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, or retinal neural degeneration by decreasing a symptom of drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, or retinal neural degeneration respectively. Symptoms of drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, or retinal neural degeneration would be known or may be determined by a person of ordinary skill in the art. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In embodiments, an effective amount is an amount of a compound effective for improving cognition (e.g., learning, understanding, comprehension) in a subject. In embodiments, an effective amount is an amount of a compound effective for increasing cognition (e.g., learning, understanding, comprehension) in a subject. In embodiments, an effective amount is an amount of a compound effective for enhancing cognition (e.g., learning, understanding, comprehension) in a subject.

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with Sigma 2 receptor activity may be treated with an agent (e.g. compound as described herein) effective for modulating Sigma 2 receptor activity. For example, a disease associated with progesterone receptor membrane component lactivity may be treated with an agent (e.g. compound as described herein) effective for modulating progesterone receptor membrane component 1 activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme (e.g., sigma 2 receptor, or progesterone receptor membrane component 1).

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule (e.g., sigma 2 receptor, or progesterone receptor membrane component 1). In embodiments, a modulator is an inhibitor (e.g., of sigma 2 receptor, or progesterone receptor membrane component 1). In embodiments, a modulator is an antagonist (e.g., of sigma 2 receptor, or progesterone receptor membrane component 1). In embodiments, a modulator is an activator (e.g., of sigma 2 receptor, or progesterone receptor membrane component 1). In embodiments, a modulator is an agonist (e.g., of sigma 2 receptor, or progesterone receptor membrane component 1).

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/ PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, *vinca* alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CIVIL), or multiple myeloma. In embodiments, the disease is cancer, a neurodegenerative disease, drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, or retinal neural degeneration. For example certain methods herein treat drug (e.g., ethanol, nicotine, cocaine, amphetamine, methamphetamine, an opiate, or an opioid) abuse, drug (e.g., ethanol, nicotine, cocaine, amphetamine, methamphetamine, an opiate, or an opioid) addiction, anxiety, depression, schizophrenia, epilepsy, migraine, neuropathic pain, amnesia, traumatic brain injury, inflammatory pain, stroke, a cardiovascular disease, multiple sclerosis, retinal neural degeneration, or an inflammatory disease. In embodiments the disease is pain (e.g., acute pain, inflammatory pain, acute inflammatory pain, chronic inflammatory pain, or neuropathic pain). In embodiments the disease is a psychiatric disease (e.g., anxiety, depression, schizophrenia, epilepsy, migraine, neuropathic pain, amnesia, traumatic brain injury, drug addiction, or drug abuse).

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non- Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or a leukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, a leukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticular, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

As used herein, the term "inflammatory disease" refers to a disease or condition characterized by aberrant inflammation (e.g. an increased level of inflammation compared to a control such as a healthy person not suffering from a disease). Examples of inflammatory diseases include post-operative cognitive dysfunction, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. Proteins associated with inflammation and inflammatory diseases (e.g. aberrant expression being a symptom or cause or marker of the disease) include interleukin-6 (IL-6), interleukin-8 (IL-8), interleukin-18 (IL-18), TNF-α (tumor necrosis factor-alpha), C-reactive protein (CRP), and inflammatory pain.

As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysmal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis; cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

As used herein, the term "psychiatric disease" refers to a disease or condition in which the mental or brain function of a subject becomes impaired. Examples of psychiatric diseases that may be treated with a compound, pharmaceutical composition, or method described herein include depression, major depression, chronic depression, atypical depression, bipolar depression, seasonal depression, anxiety, compulsive behavior, addiction, post-traumatic stress syndrome, major psychotic depression, stress disorders, cognitive impairment in depressed patients, chronic pain, postpartum psychosis, postpartum depression, neurological disorders in premature infants, migraine headaches, or psychotic depression.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of a disease associated with aberrant sigma 2 receptor activity or PGRMC1 activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "sigma receptor" refers to the sigma 1 receptor and/or sigma 2 receptor.

The term "sigma 1 receptor" or "S1t" or "61R" or "61R" or "a1" or "Sig1R" refers to a sigma receptor that is activated by tryptaminergic trace amines, select steroids (e.g., DHEA), and/or pregnenolone. The term "sigma 1 receptor" may refer to the nucleotide sequence or protein sequence of human sigma 1 receptor (e.g., Entrez 10280, Uniprot Q99720, RefSeq NM_005866, or RefSeq NP_005857). The term "sigma 1 receptor" includes both the wild-type form of the nucleotide sequences or proteins as well as any mutants thereof. In some embodiments, "sigma 1 receptor" is wild-type sigma 1 receptor. In some embodiments, "Sigma 1 receptor" is one or more mutant forms. The term "Sigma 1 receptor" XYZ refers to a nucleotide sequence or protein of a mutant Sigma 1 receptor wherein the Y numbered amino acid of Sigma 1 receptor that normally has an X amino acid in the wildtype, instead has a Z amino acid in the mutant. In embodiments, a Sigma 1 receptor is the human Sigma 1 receptor. In embodiments, the Sigma 1 receptor has the nucleotide sequence corresponding to reference number GI:532524979. In embodiments, the Sigma 1 receptor has the nucleotide sequence corresponding to RefSeq NM_005866.3. In embodiments, the Sigma 1 receptor has the protein sequence corresponding to reference number GI:5032117. In embodiments, the Sigma 1 receptor has the nucleotide sequence corresponding to RefSeq NP_005857.1. In embodiments, the Sigma 1 receptor has the following amino acid sequence:

```
                                        (SEQ ID NO: 1)
MQWAVGRRWAWAALLLAVAAVLTQVVWLWLGTQSFVFQREEIAQLARQYA

GLDHELAFSRLIVELRRLHPGHVLPDEELQWVFVNAGGWMGAMCLLHASL

SEYVLLFGTALGSRGHSGRYWAEISDTIISGTFHQWREGTTKSEVFYPGE

TVVHGPGEATAVEWGPNTWMVEYGRGVIPSTLAFALADTVFSTQDFLTLF

YTLRSYARGLRLELTTYLFGQDP
```

In embodiments, the Sigma 1 receptor is a mutant Sigma 1 receptor. In embodiments, the mutant Sigma 1 receptor is associated with a disease that is not associated with wildtype Sigma 1 receptor. In embodiments, the Sigma 1 receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

The term "sigma 2 receptor" or "S2R" or "$\sigma_2 R$" or "σ2R" or "σ2" or "Sig2R" refers to a sigma receptor located in lipid rafts, related to cytochromes, which may be coupled or reside on the PGRMC1 complex, EGFR, mTOR, caspases, or ion channels, and/or may bind select hormones or steroids. Sigma 2 receptor may bind 4-PPBP, SA 4503, ditolylguanidine, dimethyltryptamine, and/or siramesine. The term "sigma 2 receptor" includes both the wild-type form of the nucleotide sequences or proteins as well as any mutants thereof. In some embodiments, "sigma 2 receptor" is wild-type sigma 2 receptor. In some embodiments, "sigma 2 receptor" is one or more mutant forms.

The term "sigma 2 receptor modulator" is used in accordance with its well understood meaning in Chemistry and Biology and refers to a composition (e.g., compound) capable of modulating the activity of a sigma 2 receptor. In embodiments, a sigma 2 receptor modulator is a sigma 2 receptor inhibitor. In embodiments, the sigma 2 receptor modulator binds a sigma 2 receptor and modulates the activity or function of the sigma 2 receptor compared to a control (e.g., a control being the same experiment without administration of the compound). In embodiments, modulation of sigma 2 receptor activity is determined by an assay of binding and/or activity of sigma 2 receptor (e.g., an assay described herein, an assay described in an example herein, an assay used in the Psychoactive Drug Screening Program (PDSP) at Chapel Hill, N.C., or an assay described in website pdsp.med.unc.edu/PDSP %20Protocols %20II%202013-03-28.pdf).

The term "sigma 2 receptor inhibitor" is used in accordance with its well understood meaning in Chemistry and Biology and refers to a composition (e.g., compound) capable of reducing the activity of a sigma 2 receptor. In embodiments, a sigma 2 receptor inhibitor is a sigma 2 receptor antagonist. In embodiments, the sigma 2 receptor inhibitor binds a sigma 2 receptor and reduces the activity or function of the sigma 2 receptor compared to a control (e.g., a control being the same experiment without administration of the compound). In embodiments, reduction of sigma 2 receptor activity is determined by an assay of binding and/or activity of sigma 2 receptor (e.g., an assay described herein, an assay described in an example herein, an assay used in the Psychoactive Drug Screening Program (PDSP) at Chapel Hill, N.C., or an assay described in website pdsp.med.unc.edu/PDSP %20Protocols %20II %202013-03-28.pdf).

The term "progesterone receptor membrane component 1" or "PGRMC1" or "PRMC1" refers to the protein "progesterone receptor membrane component 1", which co-purifies with progesterone binding proteins in the liver and/or ovary under certain conditions. PGRMC1 binds heme and has structural similarity to motifs in cytochrome b5. PGRMC1 may bind and activate P450 proteins. The term "PGRMC1" may refer to the nucleotide sequence or protein sequence of human PGRMC1 (e.g., Entrez 10857, Uniprot O00264, RefSeq NM_006667, or RefSeq NP_006658). The term "PGRMC1" includes both the wild-type form of the nucleotide sequences or proteins as well as any mutants thereof. In some embodiments, "PGRMC1" is wild-type PGRMC1. In some embodiments, "PGRMC1" is one or more mutant forms. The term "PGRMC1" XYZ refers to a nucleotide sequence or protein of a mutant PGRMC1 wherein the Y numbered amino acid of PGRMC1 that normally has an X amino acid in the wildtype, instead has a Z amino acid in the mutant. In embodiments, a PGRMC1 is the human PGRMC1. In embodiments, the PGRMC1 has the nucleotide sequence corresponding to reference number GI:544063459. In embodiments, the PGRMC1 has the nucleotide sequence corresponding to RefSeq NM_006667.4. In embodiments, the PGRMC1 has the protein sequence corresponding to reference number GI:5729875. In embodiments, the PGRMC1 has the protein sequence corresponding to RefSeq NP_006658.1. In embodiments, the PGRMC1 has the following amino acid sequence:

(SEQ ID NO: 2)
MAAEDVVATGADPSDLESGGLLHEIFTSPLNLLLLGLCIFLLYKIVRGDQ

PAASGDSDDDEPPPLPRLKRRDFTPAELRREDGVQDPRILMAINGKVFDV

TKGRKFYGPEGPYGVFAGRDASRGLATFCLDKEALKDEYDDLSDLTAAQQ

ETLSDWESQFTFKYHHVGKLLKEGEEPTVYSDEEEPKDESARKND

"Analog" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

B. Compounds

In an aspect is provided a compound having the formula:

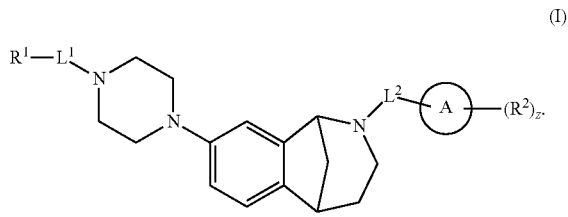

(I)

Ring A is cycloalkyl, heterocycloalkyl, aryl, or heteroaryl. $L^1$ is a bond or unsubstituted alkylene. $L^2$ is a bond, —SO$_2$—, —C(O)NH—, —NHC(O)—, —C(O)O—, —OC(O)—, —SO$_2$CH$_2$—, —C(O)NHCH$_2$—, —NHC(O)CH$_2$—C(O)OCH$_2$—, —OC(O)CH$_2$—, or unsubstituted alkylene. $R^1$ is a hydrogen, halogen, —CX$_3^1$, —CHX$_2^1$, —CH$_2$X$^1$, —CN, —NR$^7$R$^8$, —C(O)R$^9$, —C(O)OR$^9$, —C(O)NR$^7$R$^8$, —OR$^{10}$, —OC(O)OR$^9$, —OC(O)NR$^7$R$^8$, —OC(O)R$^9$, —C(S)R$^9$, —C(S)OR$^9$, —C(S)NR$^7$R$^8$, —SR$^{10}$, —OC(S)OR$^9$, —OC(S) NR$^7$R$^8$, —OC(S)R$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently a halogen, —CX$_3^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$_3^2$, —OCHX$_2^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents bonded to adjacent atoms may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl. z is an integer from 0 to 5. X, X¹, and X² are independently —Cl, —Br, —I, or —F.

In an aspect is provided a compound having the formula:

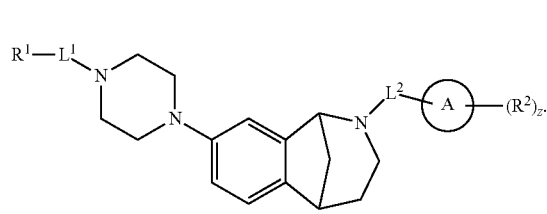

(I)

Ring A is cycloalkyl, heterocycloalkyl, aryl, or heteroaryl. L¹ is a bond or unsubstituted alkylene (e.g., branched alkylene, unbranched alkylene, branched alkenylene, unbranched alkenylene, branched alkynylene, or unbranched alkynylene). L² is a bond, —SO₂—, —C(O)NH—, —NHC(O)—, —C(O)O—, —OC(O)—, —SO₂CH₂—, —C(O)NHCH₂—, —NHC(O)CH₂—C(O)OCH₂—, —OC(O)CH₂—, or unsubstituted C₁-C₄ alkylene. R¹ is a hydrogen, halogen, —CX₃¹, —CHX₂¹, —CH₂X¹, —CN, —NR⁷R⁸, —C(O)R⁹, —C(O)OR⁹, —C(O)NR⁷R⁸, —OR¹⁰, —OC(O)OR⁹, —OC(O)NR⁷R⁸, —OC(O)R⁹, —C(S)R⁹, —C(S)OR⁹, —C(S)NR⁷R⁸, —SR¹⁰, —OC(S)OR⁹, —OC(S) NR⁷R⁸, —OC(S)R⁹, substituted or unsubstituted C₁-C₈ alkyl (e.g., —CH₂CH₂OH, —CH₂CH₂CH₂OH, branched alkyl, unbranched alkyl, branched alkenyl, unbranched alkenyl, branched alkynyl, or unbranched alkynyl), substituted or unsubstituted 2 to 8 membered heteroalkyl (e.g., —CH₂CH₂OCH₃, —CH₂CH₂CH₂OCH₃, branched heteroalkyl, unbranched heteroalkyl, branched heteroalkenyl, unbranched heteroalkenyl, branched heteroalkynyl, or unbranched heteroalkynyl), substituted or unsubstituted C₃-C₈ cycloalkyl, substituted or unsubstituted 3 to 6 membered heterocycloalkyl, substituted or unsubstituted phenyl, or substituted or unsubstituted 5 to 6 membered heteroaryl. R² is independently a halogen, —CX₃², —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)OH, —NHOH, —OCX₃², —OCHX₂², substituted or unsubstituted C₁-C₈ alkyl, substituted or unsubstituted 2 to 8 membered heteroalkyl, substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl; two R² substituents may optionally be joined to form a substituted or unsubstituted C₃-C₈ cycloalkyl, substituted or unsubstituted 3 to 8 membered heterocycloalkyl, substituted or unsubstituted phenyl, or substituted or unsubstituted 5 to 6 membered heteroaryl. R⁷, R⁸, R⁹, and R¹⁰ are independently hydrogen, halogen, —CX₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O) NHNH₂, —NHC═(O)NH₂, —NHSO₂H, —NHC═(O)H, —NHC(O)—OH, —NHOH, —OCX₃, —OCHX₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁷ and R⁸ substituents bonded to the same nitrogen atom may optionally be joined to form a substituted or unsubstituted heterocycloalkyl or substituted or unsubstituted heteroaryl. The symbol z is an integer from 0 to 5. The symbol X, X¹, and X² are independently —Cl, —Br, —I, or —F.

In embodiments, the compound has the formula:

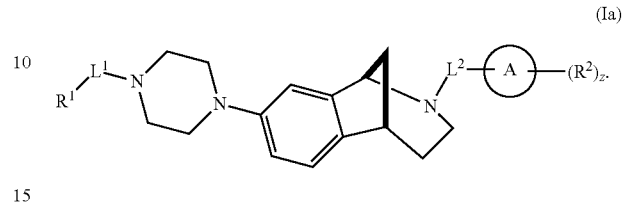

(Ia)

In embodiments, the compound has the formula:

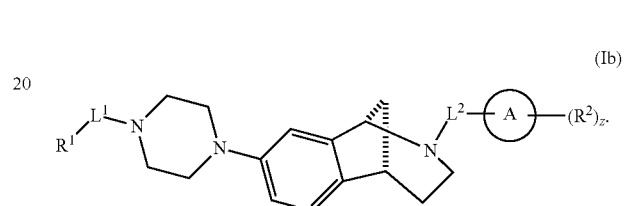

(Ib)

In embodiments, the compound has the formula:

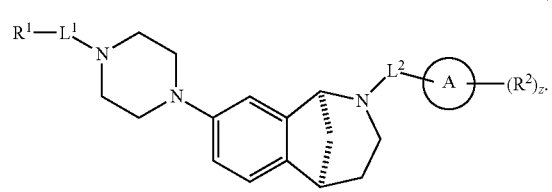

(Ib)

In embodiments, Ring A is C₃-C₁₀ cycloalkyl, 3 to 10 membered heterocycloalkyl, C₆-C₁₀ aryl, or 5 to 10 membered heteroaryl. In embodiments, Ring A is C₃-C₁₀ cycloalkyl. In embodiments, Ring A is 3 to 10 membered heterocycloalkyl. In embodiments, Ring A is C₆-C₁₀ aryl. In embodiments, Ring A is C₁₀ aryl. In embodiments, Ring A is C₉ aryl. In embodiments, Ring A is C₆ aryl. In embodiments, Ring A is 5 to 10 membered heteroaryl. In embodiments, Ring A is 5 to 9 membered heteroaryl. In embodiments, Ring A is 6 to 10 membered heteroaryl. In embodiments, Ring A is 6 to 9 membered heteroaryl. In embodiments, Ring A is 5 membered heteroaryl. In embodiments, Ring A is 6 membered heteroaryl. In embodiments, Ring A is 9 membered heteroaryl. In embodiments, Ring A is 10 membered heteroaryl. In embodiments, Ring A is C₃-C₈ cycloalkyl, 3 to 8 membered heterocycloalkyl, phenyl, or 5 to 6 membered heteroaryl. In embodiments, Ring A is phenyl. In embodiments, Ring A is C₃-C₈ cycloalkyl. In embodiments, Ring A is C₄-C₈ cycloalkyl. In embodiments, Ring A is C₃-C₇ cycloalkyl. In embodiments, Ring A is C₃-C₆ cycloalkyl. In embodiments, Ring A is C₄-C₆ cycloalkyl. In embodiments, Ring A is C₃ cycloalkyl. In embodiments, Ring A is C₄ cycloalkyl. In embodiments, Ring A is C₇ cycloalkyl. In embodiments, Ring A is C₈ cycloalkyl. In embodiments, Ring A is C₅-C₆ cycloalkyl. In embodiments, Ring A is C₅ cycloalkyl. In embodiments, Ring A is C₆ cycloalkyl. In embodiments, Ring A is C₅-C₆ cycloalkenyl. In embodiments, Ring A is C₅-C₆ cycloalkynyl. In embodiments, Ring A is $C_3$-$C_8$ cycloalkenyl. In embodiments, Ring A is $C_3$-$C_8$ cycloalkynyl. In embodiments, Ring A is 5 to 6 membered heterocycloalkyl. In embodiments, Ring A is 5 membered heterocycloalkyl. In embodiments, Ring A is 6 membered heterocycloalkyl. In embodiments, Ring A is 5 to 6 membered heteroaryl. In embodiments, Ring A is 5 membered heteroaryl. In embodiments, Ring A is 6 membered heteroaryl. In embodiments, Ring A is 3 to 8 membered heterocycloalkyl. In embodiments, Ring A is 3 to 6 membered heterocycloalkyl. In embodiments, Ring A is 3 to 7 membered heterocycloalkyl. In embodiments, Ring A is 4 to 6 membered heterocycloalkyl. In embodiments, Ring A is a fused ring cycloalkyl-cycloalkyl (e.g., combined rings of size $C_6$-$C_{12}$, $C_8$-$C_{10}$, or $C_9$-$C_{10}$). In embodiments, Ring A is a fused ring cycloalkyl-heterocycloalkyl (e.g., combined rings of size 6 to 12 member, 8 to 10 member, or 9 to 10 member). In embodiments, Ring A is a fused ring cycloalkyl-aryl (e.g., combined rings of size $C_7$-$C_{12}$, $C_8$-$C_{10}$, or $C_9$-$C_{10}$). In embodiments, Ring A is a fused ring cycloalkyl-heteroaryl (e.g., combined rings of size 6 to 12 member, 8 to 10 member, or 9 to 10 member). In embodiments, Ring A is a fused ring heterocycloalkyl-heterocycloalkyl (e.g., combined rings of size 6 to 12 member, 8 to 10 member, or 9 to 10 member). In embodiments, Ring A is a fused ring heterocycloalkyl-aryl (e.g., combined rings of size 7 to 12 member, 8 to 10 member, or 9 to 10 member). In embodiments, Ring A is a fused ring heterocycloalkyl-heteroaryl (e.g., combined rings of size 7 to 12 member, 8 to 10 member, or 9 to 10 member). In embodiments, Ring A is a fused ring aryl-aryl (e.g., combined rings of size $C_{10}$). In embodiments, Ring A is a fused ring aryl-heteroaryl (e.g., combined rings of size 9 to 10 member). In embodiments, Ring A is a fused ring heteroaryl-heteroaryl (e.g., combined rings of size 9 to 10 member).

In embodiments, Ring A is pyrrolidinyl. In embodiments, Ring A is tetrahydrofuranyl. In embodiments, Ring A is imidazolidinyl. In embodiments, Ring A is pyrazolidinyl. In embodiments, Ring A is oxazolidinyl. In embodiments, Ring A is isoxazolidinyl. In embodiments, Ring A is thiazolidinyl. In embodiments, Ring A is isothiazolidinyl. In embodiments, Ring A is dioxolanyl. In embodiments, Ring A is dithiolanyl. In embodiments, Ring A is piperidinyl. In embodiments, Ring A is oxanyl. In embodiments, Ring A is piperazinyl. In embodiments, Ring A is morpholinyl. In embodiments, Ring A is pyridinyl. In embodiments, Ring A is triazolyl. In embodiments, Ring A imidazolyl. In embodiments, Ring A is pyrazolyl. In embodiments, Ring A is oxazolyl. In embodiments, Ring A is isoxazolyl. In embodiments, Ring A is thiazolyl. In embodiments, Ring A is isothiazolyl. In embodiments, Ring A is pyrrolyl. In embodiments, Ring A is furanyl. In embodiments, Ring A is tetrazolyl. In embodiments, Ring A is triazolyl. In embodiments, Ring A is benzo[d][1,3]dioxolyl.

In embodiments, Ring A is phenyl. In embodiments, Ring A is pyridyl. In embodiments, Ring A is pyridazinyl. In embodiments, Ring A is pyrimidinyl. In embodiments, Ring A is pyrazinyl. In embodiments, Ring A is piperidinyl. In embodiments, Ring A is tetrahydropyranyl. In embodiments, Ring A is tetrahydrothiopyranyl. In embodiments, Ring A is cyclohexyl. In embodiments, Ring A is cyclopentyl. In embodiments, Ring A is cycloheptyl. In embodiments, Ring A is cyclobutyl. In embodiments, Ring A is cyclopropyl. In embodiments, Ring A is pyrrolyl. In embodiments, Ring A is furanyl. In embodiments, Ring A is thienyl. In embodiments, Ring A is pyrazolyl. In embodiments, Ring A is imidazolyl. In embodiments, Ring A is isoxazolyl. In embodiments, Ring A is oxazolyl. In embodiments, Ring A is isothiazolyl. In embodiments, Ring A is thiazolyl. In embodiments, Ring A is naphthyl. In embodiments, Ring A is quinolinyl. In embodiments, Ring A is isoquinolinyl. In embodiments, Ring A is indolyl. In embodiments, Ring A is benzimidazolyl. In embodiments, Ring A is indazolyl. In embodiments, Ring A is isoindolyl. In embodiments, Ring A is benzofuranyl. In embodiments, Ring A is benzo[c]thienyl. In embodiments, Ring A is 2,3-dihydro-1H-indenyl. In embodiments, Ring A is 1,2,3,4-tetrahydronaphthyl. In embodiments, Ring A is triazolyl. In embodiments, Ring A is uinoxalinyl. In embodiments, Ring A is quinazolinyl. In embodiments, Ring A is triazinyl. In embodiments, Ring A is cinnolinyl. In embodiments, Ring A is phthalazinyl. In embodiments, Ring A is benzoxazolyl. In embodiments, Ring A is benzisoxazolyl. In embodiments, Ring A is benzothiazolyl. In embodiments, Ring A is benzisothiazolyl. In embodiments, Ring A is benzo[d][1,2,3]triazolyl. In embodiments, Ring A is adamantyl.

In embodiments, $R^1$ is a hydrogen. In embodiments, $R^1$ is halogen. In embodiments, $R^1$ is —$CX_3^1$. In embodiments, $R^1$ is —$CHX_2^1$. In embodiments, $R^1$ is —$CH_2X^1$. In embodiments, $R^1$ is —CN. In embodiments, $R^1$ is —$NR^7R^8$. In embodiments, $R^1$ is —$C(O)R^9$. In embodiments, $R^1$ is —$C(O)OR^9$. In embodiments, $R^1$ is —$C(O)NR^7R^8$. In embodiments, $R^1$ is —$OR^{10}$. In embodiments, $R^1$ is —$OC(O)OR^9$. In embodiments, $R^1$ is —$OC(O)NR^7R^8$. In embodiments, $R^1$ is —$OC(O)R^9$. In embodiments, $R^1$ is —$C(S)R^9$. In embodiments, $R^1$ is —$C(S)OR^9$. In embodiments, $R^1$ is —$C(S)NR^7R^8$. In embodiments, $R^1$ is —$SR^{10}$. In embodiments, $R^1$ is —$OC(S)OR^9$. In embodiments, $R^1$ is —$OC(S)NR^7R^8$. In embodiments, $R^1$ is —$OC(S)R^9$. In embodiments, $R^1$ is substituted or unsubstituted $C_1$-$C_8$ alkyl (e.g., —$CH_2CH_2OH$, —$CH_2CH_2CH_2OH$, branched alkyl, unbranched alkyl, branched alkenyl, unbranched alkenyl, branched alkynyl, or unbranched alkynyl). In embodiments, $R^1$ is substituted or unsubstituted 2 to 8 membered heteroalkyl (e.g., —$CH_2CH_2OCH_3$, —$CH_2CH_2CH_2OCH_3$, branched heteroalkyl, unbranched heteroalkyl, branched heteroalkenyl, unbranched heteroalkenyl, branched heteroalkynyl, or unbranched heteroalkynyl). In embodiments, $R^1$ is substituted or unsubstituted $C_3$-$C_8$ cycloalkyl. In embodiments, $R^1$ is substituted or unsubstituted 3 to 6 membered heterocycloalkyl. In embodiments, $R^1$ is substituted or unsubstituted phenyl. In embodiments, $R^1$ is substituted or unsubstituted 5 to 6 membered heteroaryl. In embodiments, $R^1$ is substituted $C_1$-$C_8$ alkyl (e.g., branched alkyl, unbranched alkyl, branched alkenyl, unbranched alkenyl, branched alkynyl, or unbranched alkynyl). In embodiments, $R^1$ is substituted 2 to 8 membered heteroalkyl (e.g., branched heteroalkyl, unbranched heteroalkyl, branched heteroalkenyl, unbranched heteroalkenyl, branched heteroalkynyl, or unbranched heteroalkynyl). In embodiments, $R^1$ is substituted $C_3$-$C_8$ cycloalkyl. In embodiments, $R^1$ is substituted 3 to 6 membered heterocycloalkyl. In embodiments, $R^1$ is substituted phenyl. In embodiments, $R^1$ is substituted 5 to 6 membered heteroaryl. In embodiments, $R^1$ is unsubstituted $C_1$-$C_8$ alkyl (e.g., branched alkyl, unbranched alkyl, branched alkenyl, unbranched alkenyl, branched alkynyl, or unbranched alkynyl). In embodiments, $R^1$ is unsubstituted 2 to 8 membered heteroalkyl (e.g., branched heteroalkyl, unbranched heteroalkyl, branched heteroalkenyl, unbranched heteroalkenyl, branched heteroalkynyl, or unbranched heteroalkynyl). In embodiments, $R^1$ is unsubstituted $C_3$-$C_8$ cycloalkyl. In embodiments, $R^1$ is unsubstituted 3 to 6 membered heterocycloalkyl. In embodiments, $R^1$ is unsubstituted phenyl. In embodiments, $R^1$ is unsubstituted 5 to 6 membered heteroaryl.

In embodiments, $R^1$ is hydrogen, halogen, $-CX_3^1$, $-CHX_2^1$, $-CH_2X'$, $-CN$, $-NR^7R^8$, $-C(O)R^9$, $-C(O)OR^9$, $-C(O)NR^7R^8$, $-OR^{10}$, $-OC(O)NR^7R^8$, $-C(S)NR^7R^8$, $-SR^{10}$, substituted or unsubstituted $C_1$-$C_4$ alkyl, substituted or unsubstituted 2 to 4 membered heteroalkyl, substituted or unsubstituted $C_3$-$C_8$ cycloalkyl, or substituted or unsubstituted 4 to 6 membered heterocycloalkyl.

In embodiments, $R^1$ is hydrogen. In embodiments, $R^1$ is halogen. In embodiments, $R^1$ is $-CX_3^1$. In embodiments, $R^1$ is $-CHX_2^1$. In embodiments, $R^1$ is $-CH_2X^1$. In embodiments, $R^1$ is $-CN$. In embodiments, $R^1$ is $-NR^7R^8$. In embodiments, $R^1$ is $-C(O)R^9$. In embodiments, $R^1$ is $-C(O)OR^9$. In embodiments, $R^1$ is $-C(O)NR^7R^8$. In embodiments, $R^1$ is $-OR^{10}$. In embodiments, $R^1$ is $-OC(O)NR^7R^8$. In embodiments, $R^1$ is $-C(S)NR^7R^8$. In embodiments, $R^1$ is $-SR^{10}$. In embodiments, $R^1$ is halogen. In embodiments, $R^1$ is $-CF_3$. In embodiments, $R^1$ is $-CHF_2$. In embodiments, $R^1$ is $-CH_2F$. In embodiments, $R^1$ is $-CN$. In embodiments, $R^1$ is $-NH_2$. In embodiments, $R^1$ is $-C(O)H$. In embodiments, $R^1$ is $-C(O)OH$. In embodiments, $R^1$ is $-C(O)NH_2$. In embodiments, $R^1$ is $-OH$. In embodiments, $R^1$ is $-OC(O)NH_2$. In embodiments, $R^1$ is $-C(S)NH_2$. In embodiments, $R^1$ is $-SH$. In embodiments, $R^1$ is $-CF_3$. In embodiments, $R^1$ is $-CHF_2$. In embodiments, $R^1$ is $-CH_2F$.

In embodiments, $R^1$ is substituted or unsubstituted $C_1$-$C_4$ alkyl. In embodiments, $R^1$ is substituted or unsubstituted 2 to 4 membered heteroalkyl. In embodiments, $R^1$ is substituted or unsubstituted $C_3$-$C_8$ cycloalkyl. In embodiments, $R^1$ is substituted or unsubstituted 4 to 6 membered heterocycloalkyl. In embodiments, $R^1$ is substituted $C_1$-$C_4$ alkyl. In embodiments, $R^1$ is substituted 2 to 4 membered heteroalkyl. In embodiments, $R^1$ is substituted $C_3$-$C_8$ cycloalkyl. In embodiments, $R^1$ is substituted 4 to 6 membered heterocycloalkyl. In embodiments, $R^1$ is unsubstituted $C_1$-$C_4$ alkyl. In embodiments, $R^1$ is unsubstituted 2 to 4 membered heteroalkyl. In embodiments, $R^1$ is unsubstituted $C_3$-$C_8$ cycloalkyl. In embodiments, $R^1$ is unsubstituted 4 to 6 membered heterocycloalkyl. In embodiments, $R^1$ is substituted or unsubstituted $C_2$-$C_4$ alkyl. In embodiments, $R^1$ is substituted or unsubstituted 3 to 4 membered heteroalkyl. In embodiments, $R^1$ is substituted or unsubstituted $C_3$-$C_6$ cycloalkyl. In embodiments, $R^1$ is substituted or unsubstituted 5 to 6 membered heterocycloalkyl. In embodiments, $R^1$ is substituted $C_2$-$C_4$ alkyl. In embodiments, $R^1$ is substituted 3 to 4 membered heteroalkyl. In embodiments, $R^1$ is substituted $C_3$-$C_6$ cycloalkyl. In embodiments, $R^1$ is substituted 5 to 6 membered heterocycloalkyl. In embodiments, $R^1$ is unsubstituted $C_2$-$C_4$ alkyl. In embodiments, $R^1$ is unsubstituted 3 to 4 membered heteroalkyl. In embodiments, $R^1$ is unsubstituted $C_3$-$C_6$ cycloalkyl. In embodiments, $R^1$ is unsubstituted 5 to 6 membered heterocycloalkyl. In embodiments, $R^1$ is substituted or unsubstituted $C_3$-$C_4$ alkyl. In embodiments, $R^1$ is substituted or unsubstituted 4 membered heteroalkyl. In embodiments, $R^1$ is substituted or unsubstituted $C_5$-$C_6$ cycloalkyl. In embodiments, $R^1$ is substituted or unsubstituted 6 membered heterocycloalkyl. In embodiments, $R^1$ is substituted $C_3$-$C_4$ alkyl. In embodiments, $R^1$ is substituted 4 membered heteroalkyl. In embodiments, $R^1$ is substituted $C_5$-$C_6$ cycloalkyl. In embodiments, $R^1$ is substituted 6 membered heterocycloalkyl. In embodiments, $R^1$ is unsubstituted $C_3$-$C_4$ alkyl. In embodiments, $R^1$ is unsubstituted 4 membered heteroalkyl. In embodiments, $R^1$ is unsubstituted $C_5$-$C_6$ cycloalkyl. In embodiments, $R^1$ is unsubstituted 6 membered heterocycloalkyl. In embodiments, $R^1$ is substituted or unsubstituted $C_4$-$C_8$ cycloalkyl. In embodiments, $R^1$ is substituted $C_4$-$C_8$ cycloalkyl. In embodiments, $R^1$ is unsubstituted $C_4$-$C_8$ cycloalkyl. In embodiments, $R^1$ is substituted or unsubstituted $C_4$-$C_7$ cycloalkyl. In embodiments, $R^1$ is substituted $C_4$-$C_7$ cycloalkyl. In embodiments, $R^1$ is unsubstituted $C_4$-$C_7$ cycloalkyl. In embodiments, $R^1$ is substituted or unsubstituted $C_5$-$C_8$ cycloalkyl. In embodiments, $R^1$ is substituted $C_5$-$C_8$ cycloalkyl. In embodiments, $R^1$ is unsubstituted $C_5$-$C_8$ cycloalkyl. In embodiments, $R^1$ is substituted or unsubstituted $C_5$-$C_7$ cycloalkyl. In embodiments, $R^1$ is substituted $C_5$-$C_7$ cycloalkyl. In embodiments, $R^1$ is unsubstituted $C_5$-$C_7$ cycloalkyl. In embodiments, $R^1$ is substituted or unsubstituted $C_6$-$C_8$ cycloalkyl. In embodiments, $R^1$ is substituted $C_6$-$C_8$ cycloalkyl. In embodiments, $R^1$ is unsubstituted $C_6$-$C_8$ cycloalkyl.

In embodiments, $R^1$ is substituted or unsubstituted $C_4$ alkyl. In embodiments, $R^1$ is substituted or unsubstituted 3 membered heteroalkyl. In embodiments, $R^1$ is substituted or unsubstituted $C_6$ cycloalkyl. In embodiments, $R^1$ is substituted or unsubstituted 5 membered heterocycloalkyl. In embodiments, $R^1$ is substituted $C_4$ alkyl. In embodiments, $R^1$ is substituted 3 membered heteroalkyl. In embodiments, $R^1$ is substituted $C_6$ cycloalkyl. In embodiments, $R^1$ is substituted 5 membered heterocycloalkyl. In embodiments, $R^1$ is unsubstituted $C_4$ alkyl. In embodiments, $R^1$ is unsubstituted 3 membered heteroalkyl. In embodiments, $R^1$ is unsubstituted $C_6$ cycloalkyl. In embodiments, $R^1$ is unsubstituted 5 membered heterocycloalkyl. In embodiments, $R^1$ is substituted or unsubstituted $C_3$ alkyl. In embodiments, $R^1$ is substituted or unsubstituted $C_5$ cycloalkyl. In embodiments, $R^1$ is substituted $C_3$ alkyl. In embodiments, $R^1$ is substituted $C_5$ cycloalkyl. In embodiments, $R^1$ is unsubstituted $C_3$ alkyl. In embodiments, $R^1$ is unsubstituted $C_5$ cycloalkyl. In embodiments, $R^1$ is unsubstituted cyclopentyl. In embodiments, $R^1$ is unsubstituted cyclohexyl. In embodiments, $R^1$ is unsubstituted n-propyl. In embodiments, $R^1$ is unsubstituted $CH_2C(CH_2)CH_3$. In embodiments, $R^1$ is $-CH_2CH_2C(O)OCH_2CH_3$. In embodiments, $R^1$ is $-CH_2CH_2C(O)OCH_2CH_2CH_3$. In embodiments, $R^1$ is $-CH_2CH_2C(O)OCH(CH_3)_2$. In embodiments, $R^1$ is substituted or unsubstituted branched $C_3$-$C_5$ alkyl or substituted or unsubstituted 3 to 5 membered branched heteroalkyl. In embodiments, $R^1$ is substituted or unsubstituted $C_1$-$C_5$ alkyl, substituted or unsubstituted $C_2$-$C_5$ alkenyl, or substituted or unsubstituted $C_2$-$C_5$ alkynyl.

In embodiments, $R^1$ is an unsubstituted $C_1$-$C_3$ alkyl. In embodiments, $R^1$ is an unsubstituted $C_1$-$C_8$ alkyl. In embodiments, $R^1$ is an unsubstituted $C_1$-$C_7$ alkyl. In embodiments, $R^1$ is an unsubstituted $C_1$-$C_6$ alkyl. In embodiments, $R^1$ is an unsubstituted $C_1$-$C_5$ alkyl. In embodiments, $R^1$ is an unsubstituted $C_1$-$C_4$ alkyl. In embodiments, $R^1$ is an unsubstituted $C_2$-$C_8$ alkyl. In embodiments, $R^1$ is an unsubstituted $C_2$-$C_6$ alkyl. In embodiments, $R^1$ is an unsubstituted $C_2$-$C_4$ alkyl. In embodiments, $R^1$ is an unsubstituted $C_3$-$C_8$ alkyl. In embodiments, $R^1$ is an unsubstituted $C_3$-$C_6$ alkyl.

In embodiments, $R^1$ is a hydroxy substituted $C_1$-$C_3$ alkyl. In embodiments, $R^1$ is a hydroxy substituted $C_1$-$C_8$ alkyl. In embodiments, $R^1$ is a hydroxy substituted $C_1$-$C_7$ alkyl. In embodiments, $R^1$ is a hydroxy substituted $C_1$-$C_6$ alkyl. In embodiments, $R^1$ is a hydroxy substituted $C_1$-$C_5$ alkyl. In embodiments, $R^1$ is a hydroxy substituted $C_1$-$C_4$ alkyl. In embodiments, $R^1$ is a hydroxy substituted $C_2$-$C_8$ alkyl. In embodiments, $R^1$ is a hydroxy substituted $C_2$-$C_6$ alkyl. In embodiments, $R^1$ is a hydroxy substituted $C_2$-$C_4$ alkyl. In embodiments, $R^1$ is a hydroxy substituted $C_3$-$C_8$ alkyl. In embodiments, $R^1$ is a hydroxy substituted $C_3$-$C_6$ alkyl. In embodiments, $R^1$ is $-CH_2CH_2OH$. In embodiments, $R^1$ is $-CH_2CH_2CH_2OH$.

In embodiments, $R^1$ is a methoxy substituted $C_1$-$C_3$ alkyl. In embodiments, $R^1$ is a methoxy substituted $C_1$-$C_8$ alkyl. In embodiments, $R^1$ is a methoxy substituted $C_1$-$C_7$ alkyl. In embodiments, $R^1$ is a methoxy substituted $C_1$-$C_6$ alkyl. In embodiments, $R^1$ is a methoxy substituted $C_1$-$C_5$ alkyl. In embodiments, $R^1$ is a methoxy substituted $C_1$-$C_4$ alkyl. In embodiments, $R^1$ is a methoxy substituted $C_2$-$C_8$ alkyl. In embodiments, $R^1$ is a methoxy substituted $C_2$-$C_6$ alkyl. In embodiments, $R^1$ is a methoxy substituted $C_2$-$C_4$ alkyl. In embodiments, $R^1$ is a methoxy substituted $C_3$-$C_8$ alkyl. In embodiments, $R^1$ is a methoxy substituted $C_3$-$C_6$ alkyl. In embodiments, $R^1$ is —$CH_2CH_2OCH_3$. In embodiments, $R^1$ is —$CH_2CH_2CH_2OCH_3$.

In embodiments, $R^1$ is a ethoxy substituted $C_1$-$C_3$ alkyl. In embodiments, $R^1$ is a ethoxy substituted $C_1$-$C_8$ alkyl. In embodiments, $R^1$ is a ethoxy substituted $C_1$-$C_7$ alkyl. In embodiments, $R^1$ is a ethoxy substituted $C_1$-$C_6$ alkyl. In embodiments, $R^1$ is a ethoxy substituted $C_1$-$C_5$ alkyl. In embodiments, $R^1$ is a ethoxy substituted $C_1$-$C_4$ alkyl. In embodiments, $R^1$ is a ethoxy substituted $C_2$-$C_8$ alkyl. In embodiments, $R^1$ is a ethoxy substituted $C_2$-$C_6$ alkyl. In embodiments, $R^1$ is a ethoxy substituted $C_2$-$C_4$ alkyl. In embodiments, $R^1$ is a ethoxy substituted $C_3$-$C_8$ alkyl. In embodiments, $R^1$ is a ethoxy substituted $C_3$-$C_6$ alkyl.

In embodiments, $R^1$ is a propoxy substituted $C_1$-$C_3$ alkyl. In embodiments, $R^1$ is a propoxy substituted $C_1$-$C_8$ alkyl. In embodiments, $R^1$ is a propoxy substituted $C_1$-$C_7$ alkyl. In embodiments, $R^1$ is a propoxy substituted $C_1$-$C_6$ alkyl. In embodiments, $R^1$ is a propoxy substituted $C_1$-$C_5$ alkyl. In embodiments, $R^1$ is a propoxy substituted $C_1$-$C_4$ alkyl. In embodiments, $R^1$ is a propoxy substituted $C_2$-$C_8$ alkyl. In embodiments, $R^1$ is a propoxy substituted $C_2$-$C_6$ alkyl. In embodiments, $R^1$ is a propoxy substituted $C_2$-$C_4$ alkyl. In embodiments, $R^1$ is a propoxy substituted $C_3$-$C_8$ alkyl. In embodiments, $R^1$ is a propoxy substituted $C_3$-$C_6$ alkyl.

In embodiments, $R^1$ is a butoxy substituted $C_1$-$C_3$ alkyl. In embodiments, $R^1$ is a butoxy substituted $C_1$-$C_8$ alkyl. In embodiments, $R^1$ is a butoxy substituted $C_1$-$C_7$ alkyl. In embodiments, $R^1$ is a butoxy substituted $C_1$-$C_6$ alkyl. In embodiments, $R^1$ is a butoxy substituted $C_1$-$C_5$ alkyl. In embodiments, $R^1$ is a butoxy substituted $C_1$-$C_4$ alkyl. In embodiments, $R^1$ is a butoxy substituted $C_2$-$C_8$ alkyl. In embodiments, $R^1$ is a butoxy substituted $C_2$-$C_6$ alkyl. In embodiments, $R^1$ is a butoxy substituted $C_2$-$C_4$ alkyl. In embodiments, $R^1$ is a butoxy substituted $C_3$-$C_8$ alkyl. In embodiments, $R^1$ is a butoxy substituted $C_3$-$C_6$ alkyl.

In embodiments, $R^1$ is an unsubstituted $C_3$-$C_8$ alkenyl. In embodiments, $R^1$ is an unsubstituted $C_3$-$C_8$ alkynyl. In embodiments, $R^1$ is an unsubstituted $C_4$-$C_8$ alkenyl. In embodiments, $R^1$ is an unsubstituted $C_4$-$C_8$ alkynyl. In embodiments, $R^1$ is an unsubstituted $C_5$-$C_8$ alkenyl. In embodiments, $R^1$ is an unsubstituted $C_5$-$C_8$ alkynyl. In embodiments, $R^1$ is an unsubstituted $C_2$-$C_8$ alkenyl. In embodiments, $R^1$ is an unsubstituted $C_2$-$C_8$ alkynyl. In embodiments, $R^1$ is an unsubstituted $C_2$-$C_6$ alkenyl. In embodiments, $R^1$ is an unsubstituted $C_2$-$C_6$ alkynyl. In embodiments, $R^1$ is an unsubstituted $C_2$-$C_4$ alkenyl. In embodiments, $R^1$ is an unsubstituted $C_2$-$C_4$ alkynyl. In embodiments, $R^1$ is an unsubstituted $C_3$-$C_6$ alkenyl. In embodiments, $R^1$ is an unsubstituted $C_3$-$C_6$ alkynyl.

In embodiments, $R^1$ is an unsubstituted $C_2$-$C_8$ alkenyl, wherein the alkenyl includes only one unsaturated bond. In embodiments, $R^1$ is an unsubstituted $C_4$-$C_8$ alkenyl, wherein the alkenyl includes only two unsaturated bonds wherein one of the unsaturated bonds may be a triple bond. In embodiments, $R^1$ is an unsubstituted $C_6$-$C_8$ alkenyl; wherein the alkenyl includes only three unsaturated bonds wherein one or two of the unsaturated bonds may be a triple bond.

In embodiments, $R^1$ is unsubstituted $C_2$-$C_8$ alkynyl; wherein the alkynyl includes only one unsaturated bond. In embodiments, $R^1$ is unsubstituted $C_4$-$C_8$ alkynyl; wherein the alkynyl includes only two unsaturated bonds wherein one of the unsaturated bonds may be a double bond. In embodiments, $R^1$ is an unsubstituted $C_6$-$C_8$ alkynyl; wherein the alkynyl includes only three unsaturated bonds wherein one or two of the unsaturated bonds may be a double bond.

In embodiments wherein $R^1$ is an alkyl (e.g., substituted saturated/unsaturated alkyl of 3 or more carbons or unsubstituted saturated/unsaturated alkyl of 3 or more carbons), $R^1$ is a branched alkyl. In embodiments wherein $R^1$ is an alkyl (e.g., substituted saturated/unsaturated alkyl of 3 or more carbons or unsubstituted saturated/unsaturated alkyl of 3 or more carbons), $R^1$ is a straight chain alkyl. In embodiments wherein $R^1$ is a heteroalkyl (e.g., substituted saturated/unsaturated heteroalkyl of 3 or more members or unsubstituted saturated/unsaturated heteroalkyl of 3 or more members), $R^1$ is a branched heteroalkyl. In embodiments wherein $R^1$ is a heteroalkyl (e.g., substituted saturated/unsaturated heteroalkyl of 3 or more members or unsubstituted saturated/unsaturated heteroalkyl of 3 or more members), $R^1$ is a straight chain heteroalkyl.

In embodiments, $R^1$ is —$OR^{10}$, substituted or unsubstituted $C_1$-$C_6$ alkyl, substituted or unsubstituted 2 to 6 membered heteroalkyl, substituted or unsubstituted $C_3$-$C_8$ cycloalkyl, or substituted or unsubstituted 4 to 6 membered heterocycloalkyl.

In embodiments, $R^{10}$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^{10}$ is independently hydrogen. In embodiments, $R^{10}$ is independently substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{10}$ is independently substituted $C_1$-$C_8$ alkyl, substituted 2 to 8 membered heteroalkyl, substituted $C_3$-$C_8$ cycloalkyl, substituted 3 to 8 membered heterocycloalkyl, substituted phenyl, or substituted 5 to 6 membered heteroaryl. In embodiments, $R^{10}$ is independently unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted phenyl, or unsubstituted 5 to 6 membered heteroaryl. In embodiments, $R^{10}$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{10}$ is independently substituted $C_1$-$C_6$ alkyl, substituted 2 to 6 membered heteroalkyl, substituted $C_3$-$C_6$ cycloalkyl, substituted 3 to 6 membered heterocycloalkyl, substituted phenyl, or substituted 5 to 6 membered heteroaryl. In embodiments, $R^{10}$ is independently unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{10}$ is independently substituted or unsubstituted $C_1$-$C_4$ alkyl. In embodiments, $R^{10}$ is independently unsubstituted methyl. In embodiments, $R^{10}$ is independently unsubstituted ethyl. In embodiments, $R^{10}$ is independently unsubstituted propyl. In embodiments, $R^{10}$ is independently unsubstituted n-propyl. In embodiments, $R^{10}$ is independently unsubstituted isopropyl. In embodiments, $R^{10}$ is independently unsubstituted butyl. In embodiments, $R^{10}$ is independently unsubstituted n-butyl. In embodiments, $R^{10}$ is independently unsubstituted isobutyl. In embodiments, $R^{10}$ is independently unsubstituted tert-butyl. In embodiments, $R^{10}$ is independently unsubstituted cyclobutyl. In embodiments, $R^{10}$ is independently unsubstituted cyclopenyl. In embodiments, $R^{10}$ is independently unsubstituted cyclohexyl.

In embodiments, $L^1$-$R^1$ is as described in one of the compounds of table 1. In embodiments, $L^1$-$R^1$ is as described in one of the compounds of table 3. In embodiments, $L^1$-$R^1$ is as described in one of the compounds of table 4. In embodiments, $R^1$ is as described in one of the compounds of table 1. In embodiments, $R^1$ is as described in one of the compounds of table 3. In embodiments, $R^1$ is as described in one of the compounds of table 4.

In embodiments, $R^2$ is independently —F, —Cl, —Br, —I, —$CX_3^2$, —$CHX_3^2$, —$CH_2X^2$, —CN, —OH, —$NH_2$, —COOH, —$CONH_2$, —$NO_2$, —SH, —$OCX_3^2$, —$OCHX_2^2$, —$OCH_2X^2$, —$OCH_3$, —$OCH_2CH_3$, —OCH($CH_3$)$_2$, unsubstituted methyl, unsubstituted ethyl, unsubstituted isopropyl, or two $R^2$ substituents bonded to adjacent atoms are joined to form an unsubstituted 5 to 6 membered heterocycloalkyl or unsubstituted 5 to 6 membered heteroaryl. In embodiments, two $R^2$ substituents bonded to adjacent atoms are joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, two $R^2$ substituents bonded to adjacent atoms are joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^2$ is independently a halogen. In embodiments, $R^2$ is independently —$CX_3^2$. In embodiments, $R^2$ is independently —CN. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently —$SO_3H$. In embodiments, $R^2$ is independently —$SO_4H$. In embodiments, $R^2$ is independently —$SO_2NH_2$. In embodiments, $R^2$ is independently $NHNH_2$. In embodiments, $R^2$ is independently $ONH_2$. In embodiments, $R^2$ is independently NHC=(O)$NHNH_2$. In embodiments, $R^2$ is independently NHC=(O)$NH_2$. In embodiments, $R^2$ is independently —$NHSO_2H$. In embodiments, $R^2$ is independently —NHC=(O)H. In embodiments, $R^2$ is independently —NHC(O)OH. In embodiments, $R^2$ is independently —NHOH. In embodiments, $R^2$ is independently —$OCX_3^2$. In embodiments, $R^2$ is independently —$OCHX_2^2$. In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_6$ cycloalkyl. In embodiments, $R^2$ is independently substituted or unsubstituted 3 to 6 membered heterocycloalkyl. In embodiments, $R^2$ is independently substituted or unsubstituted phenyl. In embodiments, $R^2$ is independently substituted or unsubstituted 5 to 6 membered heteroaryl. In embodiments, $R^2$ is independently substituted $C_1$-$C_8$ alkyl. In embodiments, $R^2$ is independently substituted 2 to 8 membered heteroalkyl. In embodiments, $R^2$ is independently substituted $C_3$-$C_6$ cycloalkyl. In embodiments, $R^2$ is independently substituted 3 to 6 membered heterocycloalkyl. In embodiments, $R^2$ is independently substituted phenyl. In embodiments, $R^2$ is independently substituted 5 to 6 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_6$ cycloalkyl. In embodiments, $R^2$ is independently unsubstituted 3 to 6 membered heterocycloalkyl. In embodiments, $R^2$ is independently unsubstituted phenyl. In embodiments, $R^2$ is independently unsubstituted 5 to 6 membered heteroaryl. In embodiments, two $R^2$ substituents bonded to adjacent atoms may optionally be joined to form a substituted or unsubstituted $C_3$-$C_6$ cycloalkyl. In embodiments, two $R^2$ substituents bonded to adjacent atoms may optionally be joined to form a substituted or unsubstituted 3 to 6 membered heterocycloalkyl. In embodiments, two $R^2$ substituents bonded to adjacent atoms may optionally be joined to form a substituted or unsubstituted phenyl. In embodiments, two $R^2$ substituents bonded to adjacent atoms may optionally be joined to form a substituted or unsubstituted 5 to 6 membered heteroaryl.

In embodiments, $R^2$ is independently substituted or unsubstituted $C_1$-$C_6$ alkyl. In embodiments, $R^2$ is independently substituted or unsubstituted 2 to 6 membered heteroalkyl. In embodiments, $R^2$ is independently substituted or unsubstituted $C_5$-$C_6$ cycloalkyl. In embodiments, $R^2$ is independently substituted or unsubstituted 5 to 6 membered heterocycloalkyl. In embodiments, $R^2$ is independently substituted or unsubstituted 5 membered heteroaryl. In embodiments, $R^2$ is independently substituted or unsubstituted 6 membered heteroaryl. In embodiments, $R^2$ is independently substituted $C_1$-$C_6$ alkyl. In embodiments, $R^2$ is independently substituted 2 to 6 membered heteroalkyl. In embodiments, $R^2$ is independently substituted $C_5$-$C_6$ cycloalkyl. In embodiments, $R^2$ is independently substituted 5 membered heterocycloalkyl. In embodiments, $R^2$ is independently substituted 6 membered heteroaryl. In embodiments, $R^2$ is independently substituted 5 to 6 membered heteroaryl. In embodiments, $R^2$ is independently unsubstituted $C_1$-$C_6$ alkyl. In embodiments, $R^2$ is independently unsubstituted 2 to 6 membered heteroalkyl. In embodiments, $R^2$ is independently unsubstituted $C_5$-$C_6$ cycloalkyl. In embodiments, $R^2$ is independently unsubstituted 5 to 6 membered heterocycloalkyl. In embodiments, $R^2$ is independently unsubstituted 5 membered heteroaryl. In embodiments, $R^2$ is independently unsubstituted 6 membered heteroaryl.

In embodiments, $R^2$ is independently F. In embodiments, $R^2$ is independently —Cl. In embodiments, $R^2$ is independently —Br. In embodiments, $R^2$ is independently —I. In embodiments, $R^2$ is independently —$OCH_3$. In embodiments, $R^2$ is independently —$OCH_2CH_3$. In embodiments, $R^2$ is independently —OCH($CH_3$)$_2$. In embodiments, $R^2$ is independently unsubstituted methyl. In embodiments, $R^2$ is independently unsubstituted ethyl. In embodiments, $R^2$ is independently unsubstituted isopropyl. In embodiments, two $R^2$ substituents bonded to adjacent atoms are joined to form an unsubstituted 5 to 6 membered heterocycloalkyl. In embodiments, two $R^2$ substituents bonded to adjacent atoms are joined to form an unsubstituted 5 to 6 membered heteroaryl.

In embodiments, two $R^2$ substituents are joined to form a substituted or unsubstituted phenyl. In embodiments, two $R^2$ substituents are joined to form a substituted or unsubstituted pyridyl. In embodiments, two $R^2$ substituents are joined to form a substituted or unsubstituted pyridazinyl. In embodiments, two $R^2$ substituents are joined to form a substituted or unsubstituted pyrimidinyl. In embodiments, two $R^2$ substituents are joined to form a substituted or unsubstituted pyrazinyl. In embodiments, two $R^2$ substituents are joined to form a substituted or unsubstituted piperidinyl. In embodiments, two $R^2$ substituents are joined to form a substituted or unsubstituted tetrahydropyranyl. In embodiments, two $R^2$ substituents are joined to form a substituted or unsubstituted tetrahydrothiopyranyl. In embodiments, two $R^2$ substituents are joined to form a substituted or unsubstituted cyclohexyl. In embodiments, two $R^2$ substituents are joined to form a substituted or unsubstituted cyclopentyl. In embodiments, two $R^2$ substituents are joined to form a substituted or unsubstituted cycloheptyl. In embodiments, two $R^2$ substituents are joined to form a substituted or unsubstituted cyclobutyl. In embodiments, two $R^2$ substituents are joined to form a substituted or unsubstituted cyclopropyl. In embodiments, two $R^2$ substituents are joined to form a substituted or unsubstituted cyclohexenyl. In embodiments, two $R^2$ substituents are joined to form a substituted or unsubstituted cyclopentenyl. In embodiments, two $R^2$ substituents are joined to form a substituted or unsubstituted cycloheptenyl. In embodiments, two $R^2$ substituents are joined to form a substituted or unsubstituted cyclobutenyl. In embodiments, two $R^2$ substituents are joined to form a substituted or unsubstituted cyclopropenyl. In embodiments, two $R^2$ substituents are joined to form a substituted or unsubstituted pyrrolyl. In embodiments, two $R^2$ substituents are joined to form a substituted or unsubstituted furanyl. In embodiments, two $R^2$ substituents are joined to form a substituted or unsubstituted thienyl. In embodiments, two $R^2$ substituents are joined to form a substituted or unsubstituted pyrazolyl. In embodiments, two $R^2$ substituents are joined to form a substituted or unsubstituted imidazolyl. In embodiments, two $R^2$ substituents are joined to form a substituted or unsubstituted isoxazolyl. In embodiments, two $R^2$ substituents are joined to form a substituted or unsubstituted oxazolyl. In embodiments, two $R^2$ substituents are joined to form a substituted or unsubstituted isothiazolyl. In embodiments, two $R^2$ substituents are joined to form a substituted or unsubstituted thiazolyl. In embodiments, two $R^2$ substituents are joined to form a substituted or unsubstituted triazolyl. In embodiments, two $R^2$ substituents are joined to form a substituted or unsubstituted oxirenyl. In embodiments, two $R^2$ substituents are joined to form a substituted or unsubstituted oxetyl. In embodiments, two $R^2$ substituents are joined to form a substituted or unsubstituted dihydrofuranyl. In embodiments, two $R^2$ substituents are joined to form a substituted or unsubstituted dihydropyranyl. In embodiments, two $R^2$ substituents are joined to form a substituted or unsubstituted dihydrothiopyranyl. In embodiments, two $R^2$ substituents are joined to form a substituted or unsubstituted dihydrothienyl.

In embodiments, two $R^2$ substituents are joined to form an unsubstituted phenyl. In embodiments, two $R^2$ substituents are joined to form an unsubstituted pyridyl. In embodiments, two $R^2$ substituents are joined to form an unsubstituted pyridazinyl. In embodiments, two $R^2$ substituents are joined to form an unsubstituted pyrimidinyl. In embodiments, two $R^2$ substituents are joined to form an unsubstituted pyrazinyl. In embodiments, two $R^2$ substituents are joined to form an unsubstituted piperidinyl. In embodiments, two $R^2$ substituents are joined to form an unsubstituted tetrahydropyranyl. In embodiments, two $R^2$ substituents are joined to form an unsubstituted tetrahydrothiopyranyl. In embodiments, two $R^2$ substituents are joined to form an unsubstituted cyclohexyl. In embodiments, two $R^2$ substituents are joined to form an unsubstituted cyclopentyl. In embodiments, two $R^2$ substituents are joined to form an unsubstituted cycloheptyl. In embodiments, two $R^2$ substituents are joined to form an unsubstituted cyclobutyl. In embodiments, two $R^2$ substituents are joined to form an unsubstituted cyclopropyl. In embodiments, two $R^2$ substituents are joined to form an unsubstituted cyclohexenyl. In embodiments, two $R^2$ substituents are joined to form an unsubstituted cyclopentenyl. In embodiments, two $R^2$ substituents are joined to form an unsubstituted cycloheptenyl. In embodiments, two $R^2$ substituents are joined to form an unsubstituted cyclobutenyl. In embodiments, two $R^2$ substituents are joined to form an unsubstituted cyclopropenyl. In embodiments, two $R^2$ substituents are joined to form an unsubstituted pyrrolyl. In embodiments, two $R^2$ substituents are joined to form an unsubstituted furanyl. In embodiments, two $R^2$ substituents are joined to form an unsubstituted thienyl. In embodiments, two $R^2$ substituents are joined to form an unsubstituted pyrazolyl. In embodiments, two $R^2$ substituents are joined to form an unsubstituted imidazolyl. In embodiments, two $R^2$ substituents are joined to form an unsubstituted isoxazolyl. In embodiments, two $R^2$ substituents are joined to form an unsubstituted oxazolyl. In embodiments, two $R^2$ substituents are joined to form an unsubstituted isothiazolyl. In embodiments, two $R^2$ substituents are joined to form an unsubstituted thiazolyl. In embodiments, two $R^2$ substituents are joined to form an unsubstituted triazolyl. In embodiments, two $R^2$ substituents are joined to form an unsubstituted oxirenyl. In embodiments, two $R^2$ substituents are joined to form an unsubstituted oxetyl. In embodiments, two $R^2$ substituents are joined to form an unsubstituted dihydrofuranyl. In embodiments, two $R^2$ substituents are joined to form an unsubstituted dihydropyranyl. In embodiments, two $R^2$ substituents are joined to form an unsubstituted dihydrothiopyranyl. In embodiments, two $R^2$ substituents are joined to form an unsubstituted dihydrothienyl.

In embodiments, two $R^2$ substituents are joined to form a substituted phenyl. In embodiments, two $R^2$ substituents are joined to form a substituted pyridyl. In embodiments, two $R^2$ substituents are joined to form a substituted pyridazinyl. In embodiments, two $R^2$ substituents are joined to form a substituted pyrimidinyl. In embodiments, two $R^2$ substituents are joined to form a substituted pyrazinyl. In embodiments, two $R^2$ substituents are joined to form a substituted piperidinyl. In embodiments, two $R^2$ substituents are joined to form a substituted tetrahydropyranyl. In embodiments, two $R^2$ substituents are joined to form a substituted tetrahydrothiopyranyl. In embodiments, two $R^2$ substituents are joined to form a substituted cyclohexyl. In embodiments, two $R^2$ substituents are joined to form a substituted cyclopentyl. In embodiments, two $R^2$ substituents are joined to form a substituted cycloheptyl. In embodiments, two $R^2$ substituents are joined to form a substituted cyclobutyl. In embodiments, two $R^2$ substituents are joined to form a substituted cyclopropyl. In embodiments, two $R^2$ substituents are joined to form a substituted cyclohexenyl. In embodiments, two $R^2$ substituents are joined to form a substituted cyclopentenyl. In embodiments, two $R^2$ substituents are joined to form a substituted cycloheptenyl. In embodiments, two $R^2$ substituents are joined to form a substituted cyclobutenyl. In embodiments, two $R^2$ substituents are joined to form a substituted cyclopropenyl. In embodiments, two $R^2$ substituents are joined to form a substituted pyrrolyl. In embodiments, two $R^2$ substituents are joined to form a substituted furanyl. In embodiments, two $R^2$ substituents are joined to form a substituted thienyl. In embodiments, two $R^2$ substituents are joined to form a substituted pyrazolyl. In embodiments, two $R^2$ substituents are joined to form a substituted imidazolyl. In embodiments, two $R^2$ substituents are joined to form a substituted isoxazolyl. In embodiments, two $R^2$ substituents are joined to form a substituted oxazolyl. In embodiments, two $R^2$ substituents are joined to form a substituted isothiazolyl. In embodiments, two $R^2$ substituents are joined to form a substituted thiazolyl. In embodiments, two $R^2$ substituents are joined to form a substituted triazolyl. In embodiments, two $R^2$ substituents are joined to form a substituted oxirenyl. In embodiments, two $R^2$ substituents are joined to form a substituted oxetyl. In embodiments, two $R^2$ substituents are joined to form a substituted dihydrofuranyl. In embodiments, two $R^2$ substituents are joined to form a substituted dihydropyranyl. In embodiments, two $R^2$ substituents are joined to form a substituted dihydrothiopyranyl. In embodiments, two $R^2$ substituents are joined to form a substituted dihydrothienyl.

In embodiments, two $R^2$ substituents bonded to adjacent atoms are joined to form a substituted or unsubstituted phenyl. In embodiments, two $R^2$ substituents bonded to adjacent atoms are joined to form a substituted or unsubstituted pyridyl. In embodiments, two $R^2$ substituents bonded to adjacent atoms are joined to form a substituted or unsubstituted pyridazinyl. In embodiments, two $R^2$ substituents bonded to adjacent atoms are joined to form a substituted or unsubstituted pyrimidinyl. In embodiments, two $R^2$ substituents bonded to adjacent atoms are joined to form a substituted or unsubstituted pyrazinyl. In embodiments, two $R^2$ substituents bonded to adjacent atoms are joined to form a substituted or unsubstituted piperidinyl. In embodiments, two $R^2$ substituents bonded to adjacent atoms are joined to form a substituted or unsubstituted tetrahydropyranyl. In embodiments, two $R^2$ substituents bonded to adjacent atoms are joined to form a substituted or unsubstituted tetrahydrothiopyranyl. In embodiments, two $R^2$ substituents bonded to adjacent atoms are joined to form a substituted or unsubstituted cyclohexyl. In embodiments, two $R^2$ substituents bonded to adjacent atoms are joined to form a substituted or unsubstituted cyclopentyl. In embodiments, two $R^2$ substituents bonded to adjacent atoms are joined to form a substituted or unsubstituted cycloheptyl. In embodiments, two $R^2$ substituents bonded to adjacent atoms are joined to form a substituted or unsubstituted cyclobutyl. In embodiments, two $R^2$ substituents bonded to adjacent atoms are joined to form a substituted or unsubstituted cyclopropyl. In embodiments, two $R^2$ substituents bonded to adjacent atoms are joined to form a substituted or unsubstituted cyclohexenyl. In embodiments, two $R^2$ substituents bonded to adjacent atoms are joined to form a substituted or unsubstituted cyclopentenyl. In embodiments, two $R^2$ substituents bonded to adjacent atoms are joined to form a substituted or unsubstituted cycloheptenyl. In embodiments, two $R^2$ substituents bonded to adjacent atoms are joined to form a substituted or unsubstituted cyclobutenyl. In embodiments, two $R^2$ substituents bonded to adjacent atoms are joined to form a substituted or unsubstituted cyclopropenyl. In embodiments, two $R^2$ substituents bonded to adjacent atoms are joined to form a substituted or unsubstituted pyrrolyl. In embodiments, two $R^2$ substituents bonded to adjacent atoms are joined to form a substituted or unsubstituted furanyl. In embodiments, two $R^2$ substituents bonded to adjacent atoms are joined to form a substituted or unsubstituted thienyl. In embodiments, two $R^2$ substituents bonded to adjacent atoms are joined to form a substituted or unsubstituted pyrazolyl. In embodiments, two $R^2$ substituents bonded to adjacent atoms are joined to form a substituted or unsubstituted imidazolyl. In embodiments, two $R^2$ substituents bonded to adjacent atoms are joined to form a substituted or unsubstituted isoxazolyl. In embodiments, two $R^2$ substituents bonded to adjacent atoms are joined to form a substituted or unsubstituted oxazolyl. In embodiments, two $R^2$ substituents bonded to adjacent atoms are joined to form a substituted or unsubstituted isothiazolyl. In embodiments, two $R^2$ substituents bonded to adjacent atoms are joined to form a substituted or unsubstituted thiazolyl. In embodiments, two $R^2$ substituents bonded to adjacent atoms are joined to form a substituted or unsubstituted triazolyl. In embodiments, two $R^2$ substituents bonded to adjacent atoms are joined to form a substituted or unsubstituted oxirenyl. In embodiments, two $R^2$ substituents bonded to adjacent atoms are joined to form a substituted or unsubstituted oxetyl. In embodiments, two $R^2$ substituents bonded to adjacent atoms are joined to form a substituted or unsubstituted dihydrofuranyl. In embodiments, two $R^2$ substituents bonded to adjacent atoms are joined to form a substituted or unsubstituted dihydropyranyl. In embodiments, two $R^2$ substituents bonded to adjacent atoms are joined to form a substituted or unsubstituted dihydrothiopyranyl. In embodiments, two $R^2$ substituents bonded to adjacent atoms are joined to form a substituted or unsubstituted dihydrothienyl.

In embodiments, two $R^2$ substituents bonded to adjacent atoms are joined to form an unsubstituted phenyl. In embodiments, two $R^2$ substituents bonded to adjacent atoms are joined to form an unsubstituted pyridyl. In embodiments, two $R^2$ substituents bonded to adjacent atoms are joined to form an unsubstituted pyridazinyl. In embodiments, two $R^2$ substituents bonded to adjacent atoms are joined to form an unsubstituted pyrimidinyl. In embodiments, two $R^2$ substituents bonded to adjacent atoms are joined to form an unsubstituted pyrazinyl. In embodiments, two $R^2$ substituents bonded to adjacent atoms are joined to form an unsubstituted piperidinyl. In embodiments, two $R^2$ substituents bonded to adjacent atoms are joined to form an unsubstituted tetrahydropyranyl. In embodiments, two $R^2$ substituents bonded to adjacent atoms are joined to form an unsubstituted tetrahydrothiopyranyl. In embodiments, two $R^2$ substituents bonded to adjacent atoms are joined to form an unsubstituted cyclohexyl. In embodiments, two $R^2$ substituents bonded to adjacent atoms are joined to form an unsubstituted cyclopentyl. In embodiments, two $R^2$ substituents bonded to adjacent atoms are joined to form an unsubstituted cycloheptyl. In embodiments, two $R^2$ substituents bonded to adjacent atoms are joined to form an unsubstituted cyclobutyl. In embodiments, two $R^2$ substituents bonded to adjacent atoms are joined to form an unsubstituted cyclopropyl. In embodiments, two $R^2$ substituents bonded to adjacent atoms are joined to form an unsubstituted cyclohexenyl. In embodiments, two $R^2$ substituents bonded to adjacent atoms are joined to form an unsubstituted cyclopentenyl. In embodiments, two $R^2$ substituents bonded to adjacent atoms are joined to form an unsubstituted cycloheptenyl. In embodiments, two $R^2$ substituents bonded to adjacent atoms are joined to form an unsubstituted cyclobutenyl. In embodiments, two $R^2$ substituents bonded to adjacent atoms are joined to form an unsubstituted cyclopropenyl. In embodiments, two $R^2$ substituents bonded to adjacent atoms are joined to form an unsubstituted pyrrolyl. In embodiments, two $R^2$ substituents bonded to adjacent atoms are joined to form an unsubstituted furanyl. In embodiments, two $R^2$ substituents bonded to adjacent atoms are joined to form an unsubstituted thienyl. In embodiments, two $R^2$ substituents bonded to adjacent atoms are joined to form an unsubstituted pyrazolyl. In embodiments, two $R^2$ substituents bonded to adjacent atoms are joined to form an unsubstituted imidazolyl. In embodiments, two $R^2$ substituents bonded to adjacent atoms are joined to form an unsubstituted isoxazolyl. In embodiments, two $R^2$ substituents bonded to adjacent atoms are joined to form an unsubstituted oxazolyl. In embodiments, two $R^2$ substituents bonded to adjacent atoms are joined to form an unsubstituted isothiazolyl. In embodiments, two $R^2$ substituents bonded to adjacent atoms are joined to form an unsubstituted thiazolyl. In embodiments, two $R^2$ substituents bonded to adjacent atoms are joined to form an unsubstituted triazolyl. In embodiments, two $R^2$ substituents bonded to adjacent atoms are joined to form an unsubstituted oxirenyl. In embodiments, two $R^2$ substituents bonded to adjacent atoms are joined to form an unsubstituted oxetyl. In embodiments, two $R^2$ substituents bonded to adjacent atoms are joined to form an unsubstituted dihydrofuranyl. In embodiments, two $R^2$ substituents bonded to adjacent atoms are joined to form an unsubstituted dihydropyranyl. In embodiments, two $R^2$ substituents bonded to adjacent atoms are joined to form an unsubstituted dihydrothiopyranyl. In embodiments, two $R^2$ substituents bonded to adjacent atoms are joined to form an unsubstituted dihydrothienyl.

In embodiments, two $R^2$ substituents bonded to adjacent atoms are joined to form a substituted phenyl. In embodiments, two $R^2$ substituents bonded to adjacent atoms are joined to form a substituted pyridyl. In embodiments, two $R^2$ substituents bonded to adjacent atoms are joined to form a substituted pyridazinyl. In embodiments, two $R^2$ substituents bonded to adjacent atoms are joined to form a substituted pyrimidinyl. In embodiments, two $R^2$ substituents bonded to adjacent atoms are joined to form a substituted pyrazinyl. In embodiments, two $R^2$ substituents bonded to adjacent atoms are joined to form a substituted piperidinyl. In embodiments, two $R^2$ substituents bonded to adjacent atoms are joined to form a substituted tetrahydropyranyl. In embodiments, two $R^2$ substituents bonded to adjacent atoms are joined to form a substituted tetrahydrothiopyranyl. In embodiments, two $R^2$ substituents bonded to adjacent atoms are joined to form a substituted cyclohexyl. In embodiments, two $R^2$ substituents bonded to adjacent atoms are joined to form a substituted cyclopentyl. In embodiments, two $R^2$ substituents bonded to adjacent atoms are joined to form a substituted cycloheptyl. In embodiments, two $R^2$ substituents bonded to adjacent atoms are joined to form a substituted cyclobutyl. In embodiments, two $R^2$ substituents bonded to adjacent atoms are joined to form a substituted cyclopropyl. In embodiments, two $R^2$ substituents bonded to adjacent atoms are joined to form a substituted cyclohexenyl. In embodiments, two $R^2$ substituents bonded to adjacent atoms are joined to form a substituted cyclopentenyl. In embodiments, two $R^2$ substituents bonded to adjacent atoms are joined to form a substituted cycloheptenyl. In embodiments, two $R^2$ substituents bonded to adjacent atoms are joined to form a substituted cyclobutenyl. In embodiments, two $R^2$ substituents bonded to adjacent atoms are joined to form a substituted cyclopropenyl. In embodiments, two $R^2$ substituents bonded to adjacent atoms are joined to form a substituted pyrrolyl. In embodiments, two $R^2$ substituents bonded to adjacent atoms are joined to form a substituted furanyl. In embodiments, two $R^2$ substituents bonded to adjacent atoms are joined to form a substituted thienyl. In embodiments, two $R^2$ substituents bonded to adjacent atoms are joined to form a substituted pyrazolyl. In embodiments, two $R^2$ substituents bonded to adjacent atoms are joined to form a substituted imidazolyl. In embodiments, two $R^2$ substituents bonded to adjacent atoms are joined to form a substituted isoxazolyl. In embodiments, two $R^2$ substituents bonded to adjacent atoms are joined to form a substituted oxazolyl. In embodiments, two $R^2$ substituents bonded to adjacent atoms are joined to form a substituted isothiazolyl. In embodiments, two $R^2$ substituents bonded to adjacent atoms are joined to form a substituted thiazolyl. In embodiments, two $R^2$ substituents bonded to adjacent atoms are joined to form a substituted triazolyl. In embodiments, two $R^2$ substituents bonded to adjacent atoms are joined to form a substituted oxirenyl. In embodiments, two $R^2$ substituents bonded to adjacent atoms are joined to form a substituted oxetyl. In embodiments, two $R^2$ substituents bonded to adjacent atoms are joined to form a substituted dihydrofuranyl. In embodiments, two $R^2$ substituents bonded to adjacent atoms are joined to form a substituted dihydropyranyl. In embodiments, two $R^2$ substituents bonded to adjacent atoms are joined to form a substituted dihydrothiopyranyl. In embodiments, two $R^2$ substituents bonded to adjacent atoms are joined to form a substituted dihydrothienyl.

In embodiments, —$L^2$-Ring A—$(R^2)_z$ is

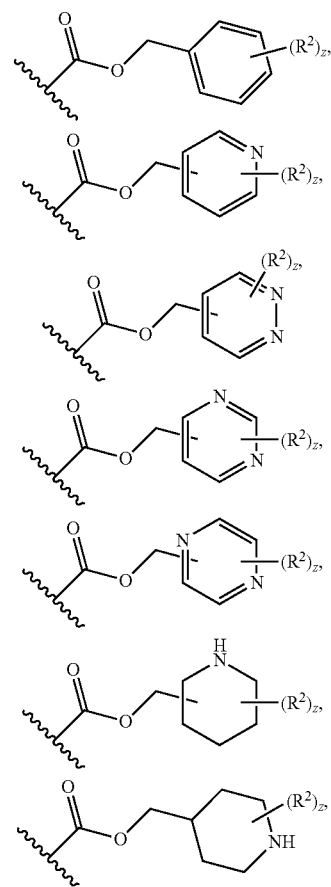

-continued
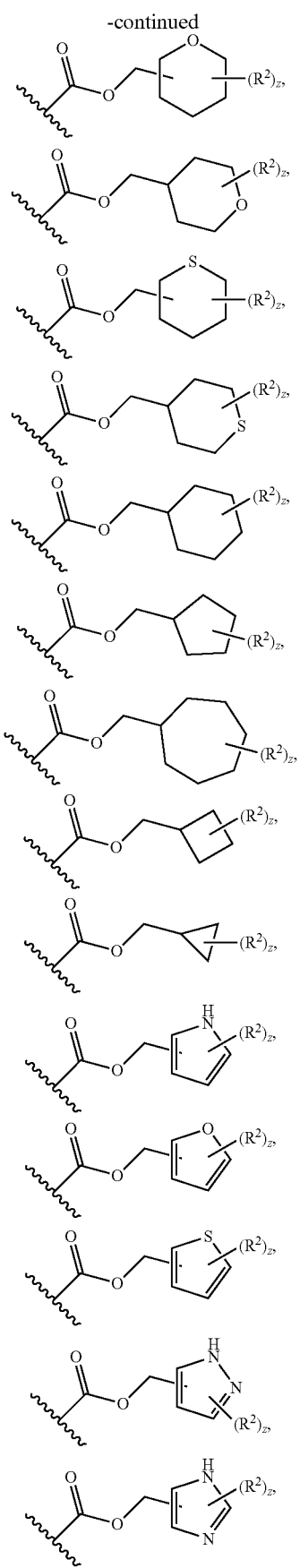
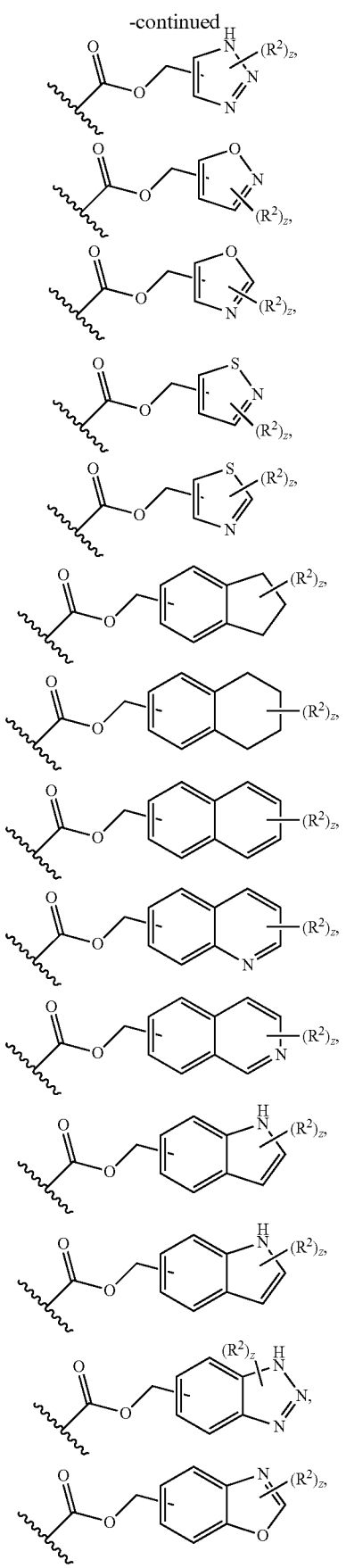

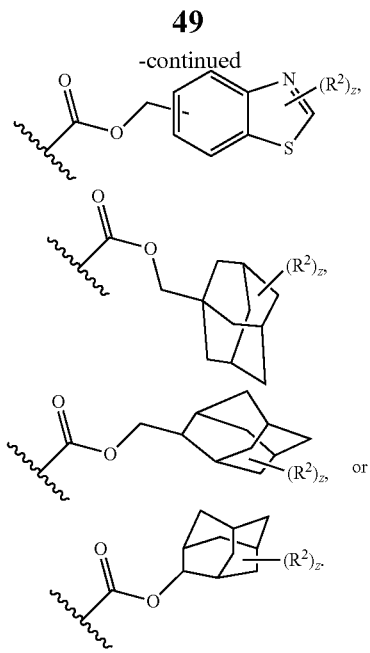
$R^2$ and z are as described herein.
In embodiments, —$L^2$-Ring A—$(R^2)_z$ is
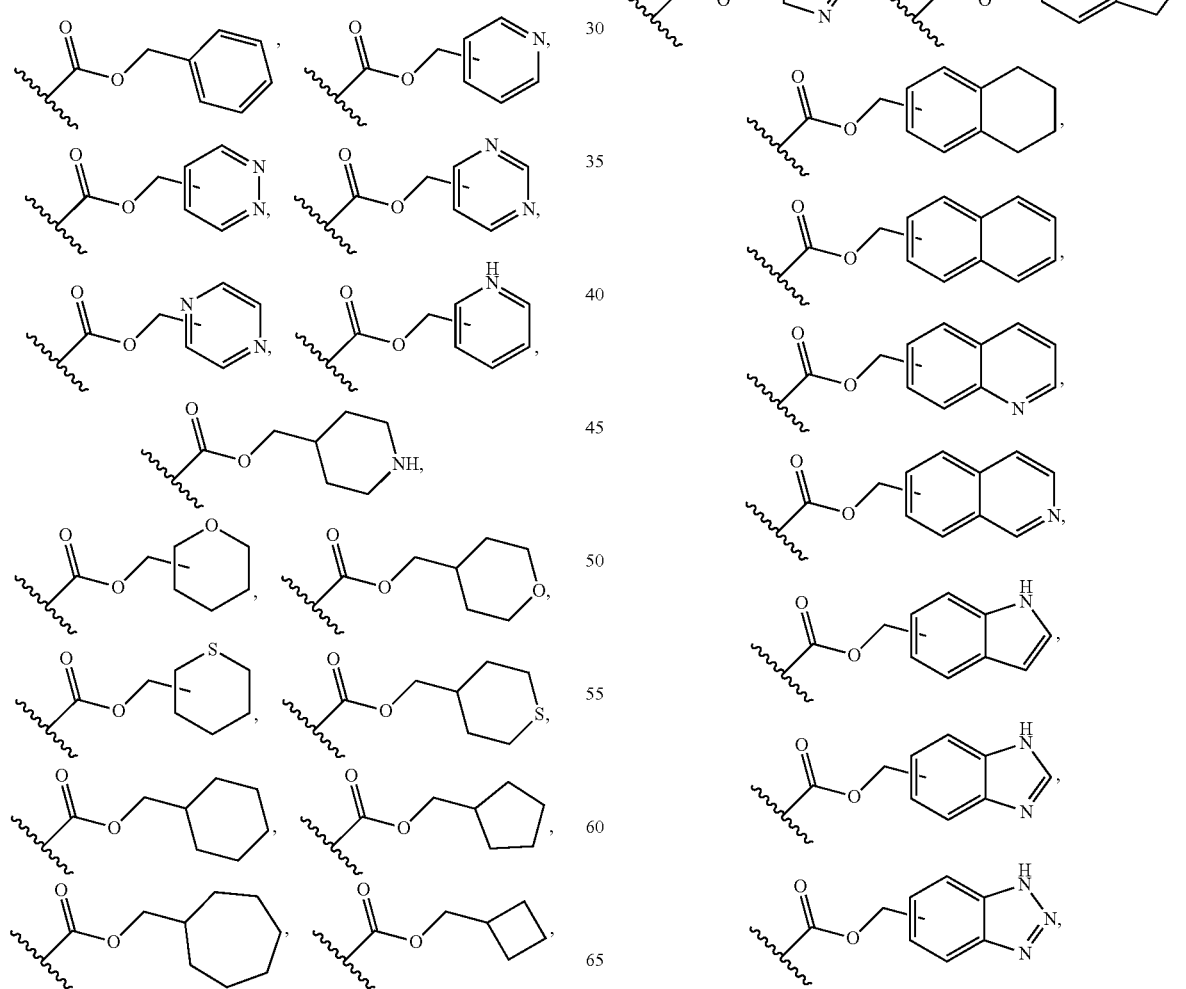

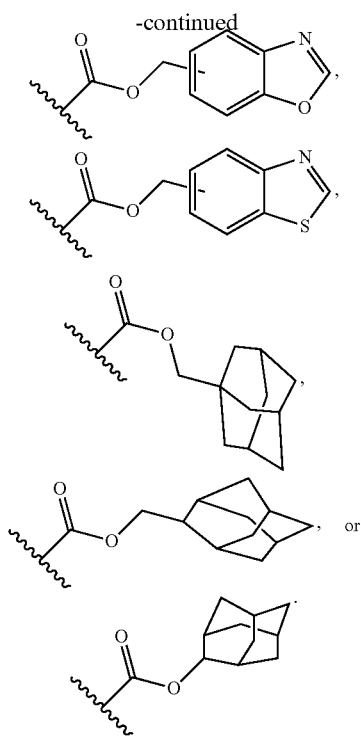

It is understood that in the immediately preceding embodiments, z is 0 and Ring A is not substituted with a non-hydrogen $R^2$.

In embodiments, —$L^2$-Ring A-$R^2$ is as described in one of the compounds of table 1. In embodiments, —$L^2$-Ring A-$R^2$ is as described in one of the compounds of table 3. In embodiments, —$L^2$-Ring A-$R^2$ is as described in one of the compounds of table 5. In embodiments, $R^2$ is as described in one of the compounds of table 1. In embodiments, $R^2$ is as described in one of the compounds of table 3. In embodiments, $R^2$ is as described in one of the compounds of table 5.

In embodiments, $L^1$ is a bond. In embodiments, $L^1$ is an unsubstituted $C_1$-$C_3$ alkylene. In embodiments, $L^1$ is an unsubstituted $C_1$-$C_{10}$ alkylene. In embodiments, $L^1$ is an unsubstituted $C_1$-$C_9$ alkylene. In embodiments, $L^1$ is an unsubstituted $C_1$-$C_8$ alkylene. In embodiments, $L^1$ is an unsubstituted $C_1$-$C_7$ alkylene. In embodiments, $L^1$ is an unsubstituted $C_1$-$C_6$ alkylene. In embodiments, $L^1$ is an unsubstituted $C_1$-$C_5$ alkylene. In embodiments, $L^1$ is an unsubstituted $C_1$-$C_4$ alkylene. In embodiments, $L^1$ is an unsubstituted $C_2$-$C_8$ alkylene. In embodiments, $L^1$ is an unsubstituted $C_2$-$C_6$ alkylene. In embodiments, $L^1$ is an unsubstituted $C_2$-$C_4$ alkylene. In embodiments, $L^1$ is an unsubstituted $C_3$-$C_8$ alkylene. In embodiments, $L^1$ is an unsubstituted $C_3$-$C_6$ alkylene. In embodiments, $L^1$ is —$CH_2$—. In embodiments, $L^1$ is —$CH_2CH_2$—. In embodiments, $L^1$ is —$CH_2CH_2CH_2$—. In embodiments, $L^1$ is —$CH_2CH_2CH_2CH_2$—. In embodiments, $L^1$ is —$CH_2 CH_2 CH_2 CH_2 CH_2$—.

In embodiments, $L^1$ is an unsubstituted $C_2$-$C_{10}$ alkenylene. In embodiments, $L^1$ is an unsubstituted $C_2$-$C_{10}$ alkynylene. In embodiments, $L^1$ is an unsubstituted $C_3$-$C_{10}$ alkenylene. In embodiments, $L^1$ is an unsubstituted $C_3$-$C_{10}$ alkynylene. In embodiments, $L^1$ is an unsubstituted $C_4$-$C_{10}$ alkenylene. In embodiments, $L^1$ is an unsubstituted $C_4$-$C_{10}$ alkynylene. In embodiments, $L^1$ is an unsubstituted $C_5$-$C_{10}$ alkenylene. In embodiments, $L^1$ is an unsubstituted $C_5$-$C_{10}$ alkynylene. In embodiments, $L^1$ is an unsubstituted $C_2$-$C_8$ alkenylene. In embodiments, $L^1$ is an unsubstituted $C_2$-$C_8$ alkynylene. In embodiments, $L^1$ is an unsubstituted $C_2$-$C_6$ alkenylene. In embodiments, $L^1$ is an unsubstituted $C_2$-$C_6$ alkynylene. In embodiments, $L^1$ is an unsubstituted $C_2$-$C_4$ alkenylene. In embodiments, $L^1$ is an unsubstituted $C_2$-$C_4$ alkynylene. In embodiments, $L^1$ is an unsubstituted $C_3$-$C_6$ alkenylene. In embodiments, $L^1$ is an unsubstituted $C_3$-$C_6$ alkynylene. In embodiments, $L^1$ is an unsubstituted $C_2$-$C_3$ alkenylene. In embodiments, $L^1$ is an unsubstituted $C_2$-$C_3$ alkynylene.

In embodiments, $L^1$ is an unsubstituted $C_2$-$C_{10}$ alkenylene, wherein the alkenylene includes only one unsaturated bond. In embodiments, $L^1$ is an unsubstituted $C_4$-$C_{10}$ alkenylene, wherein the alkenylene includes only two unsaturated bonds wherein one of the unsaturated bonds may be a triple bond. In embodiments, $L^1$ is an unsubstituted $C_6$-$C_{10}$ alkenylene; wherein the alkenylene includes only three unsaturated bonds wherein one or two of the unsaturated bonds may be a triple bond.

In embodiments, $L^1$ is unsubstituted $C_2$-$C_{10}$ alkynylene; wherein the alkynylene includes only one unsaturated bond. In embodiments, $L^1$ is unsubstituted $C_4$-$C_{10}$ alkynylene; wherein the alkynylene includes only two unsaturated bonds wherein one of the unsaturated bonds may be a double bond. In embodiments, $L^1$ is an unsubstituted $C_6$-$C_{10}$ alkynylene; wherein the alkynylene includes only three unsaturated bonds wherein one or two of the unsaturated bonds may be a double bond.

In embodiments wherein $L^1$ is an alkylene (e.g., unsubstituted saturated/unsaturated alkylene of 3 or more carbons), $L^1$ is a branched alkylene. In embodiments wherein $L^1$ is an alkylene (e.g., unsubstituted saturated/unsaturated alkylene of 3 or more carbons), $L^1$ is a straight chain alkylene.

In embodiments, $L^1$ is a bond, $R^1$ is —$OR^{10}$, substituted or unsubstituted $C_1$-$C_6$ alkyl, substituted or unsubstituted 2 to 6 membered heteroalkyl, substituted or unsubstituted $C_3$-$C_8$ cycloalkyl, or substituted or unsubstituted 4 to 6 membered heterocycloalkyl, and $R^{10}$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl. In embodiments, $L^1$ is an unsubstituted $C_1$-$C_3$ alkylene and $R^1$ is hydrogen, halogen, —$CX_3^1$, —$CHX_2^1$, —$CH_2X^1$, —CN, —$NR^7R^8$, —C(O)$R^9$, —C(O)O$R^9$, —C(O)$NR^7R^8$, —$OR^{10}$, —OC(O)$NR^7R^8$, —C(S)$NR^7R^8$, —$SR^{10}$, substituted or unsubstituted $C_1$-$C_4$ alkyl, substituted or unsubstituted 2 to 4 membered heteroalkyl, substituted or unsubstituted $C_3$-$C_6$ cycloalkyl, or substituted or unsubstituted 4 to 6 membered heterocycloalkyl. In embodiments, $L^1$ is a bond and $R^1$ is hydrogen, halogen, —$CX_3^1$, —$CHX_2^1$, —$CH_2X^1$, —CN, —$NR^7R^8$, —C(O)$R^9$, —C(O)O$R^9$, —C(O)$NR^7R^8$, $OR^{10}$ OC(O)$NR^7R^8$, —C(S)$NR^7R^8$, —$SR^{10}$, substituted or unsubstituted $C_1$-$C_4$ alkyl, substituted or unsubstituted 2 to 4 membered heteroalkyl, substituted or unsubstituted $C_3$-$C_6$ cycloalkyl, or substituted or unsubstituted 4 to 6 membered heterocycloalkyl.

In embodiments, $R^7$, $R^8$, $R^9$, and $R^{10}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC (O)—OH, —NHOH, —OCX$_3$, —OCHX$_2$, substituted or unsubstituted C$_1$-C$_{10}$ alkyl, substituted or unsubstituted 2 to 10 membered heteroalkyl, substituted or unsubstituted C$_3$-C$_{10}$ cycloalkyl, substituted or unsubstituted 3 to 10 membered heterocycloalkyl, substituted or unsubstituted C$_6$-C$_{10}$ aryl, or substituted or unsubstituted 5 to 10 membered heteroaryl; R$^7$ and R$^8$ substituents bonded to the same nitrogen atom may optionally be joined to form a substituted or unsubstituted 3 to 10 membered heterocycloalkyl or substituted or unsubstituted 5 to 10 membered heteroaryl. In embodiments, R$^7$, R$^8$, R$^9$, and R$^{10}$ are independently hydrogen, halogen, —CX$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$_3$, —OCHX$_2$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl; R$^7$ and R$^8$ substituents bonded to the same nitrogen atom may optionally be joined to form a substituted or unsubstituted 3 to 8 membered heterocycloalkyl or substituted or unsubstituted 5 to 6 membered heteroaryl. In embodiments, R$^7$, R$^8$, R$^9$, and R$^{10}$ are independently hydrogen, —CX$_3$, —CN, —COOH, —CONH$_2$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl; R$^7$ and R$^8$ substituents bonded to the same nitrogen atom may optionally be joined to form a substituted or unsubstituted 3 to 8 membered heterocycloalkyl or substituted or unsubstituted 5 to 6 membered heteroaryl. In embodiments, R$^7$, R$^8$, R$^9$, and R$^{10}$ are independently hydrogen, —CX$_3$, —CN, —COOH, —CONH$_2$, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; R$^7$ and R$^8$ substituents bonded to the same nitrogen atom may optionally be joined to form a substituted or unsubstituted 3 to 6 membered heterocycloalkyl. In embodiments, R$^7$, R$^8$, R$^9$, and R$^{10}$ are independently hydrogen, —CX$_3$, —CN, —COOH, —CONH$_2$, substituted or unsubstituted C$_1$-C$_4$ alkyl, substituted or unsubstituted 2 to 4 membered heteroalkyl, or substituted or unsubstituted C$_3$-C$_4$ cycloalkyl.

Each R$^7$, R$^8$, R$^9$, and R$^{10}$ may independently be hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCHF$_2$, —OCH$_2$F, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl. Each R$^7$, R$^8$, R$^9$, and R$^{10}$ may independently be hydrogen, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl. Each R$^7$, R$^8$, R$^9$, and R$^{10}$ may independently be hydrogen, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl. Each R$^7$, R$^8$, R$^9$, and R$^{10}$ may independently be hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. Each R$^7$, R$^8$, R$^9$, and R$^{10}$ may independently be hydrogen, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. Each R$^7$, R$^8$, R$^9$, and R$^{10}$ may independently be hydrogen, substituted or unsubstituted C$_1$-C$_4$ alkyl, substituted or unsubstituted 2 to 4 membered heteroalkyl, substituted or unsubstituted C$_4$-C$_6$ cycloalkyl, substituted or unsubstituted 4 to 6 membered heterocycloalkyl, substituted or unsubstituted phenyl, or substituted or unsubstituted 5 to 6 membered heteroaryl. Each R$^7$, R$^8$, R$^9$, and R$^{10}$ may independently be hydrogen, unsubstituted C$_1$-C$_4$ alkyl, unsubstituted 2 to 4 membered heteroalkyl, unsubstituted C$_4$-C$_6$ cycloalkyl, unsubstituted 4 to 6 membered heterocycloalkyl, unsubstituted phenyl, or unsubstituted 5 to 6 membered heteroaryl. Each R$^7$, R$^8$, R$^9$, and R$^{10}$ may independently be hydrogen, substituted or unsubstituted C$_1$-C$_3$ alkyl, substituted or unsubstituted 2 to 3 membered heteroalkyl, substituted or unsubstituted C$_5$-C$_6$ cycloalkyl, substituted or unsubstituted 5 to 6 membered heterocycloalkyl, substituted or unsubstituted phenyl, or substituted or unsubstituted 5 to 6 membered heteroaryl. Each R$^7$, R$^8$, R$^9$, and R$^{10}$ may independently be hydrogen, unsubstituted C$_1$-C$_3$ alkyl, unsubstituted 2 to 3 membered heteroalkyl, unsubstituted C$_5$-C$_6$ cycloalkyl, unsubstituted 5 to 6 membered heterocycloalkyl, unsubstituted phenyl, or unsubstituted 5 to 6 membered heteroaryl. Each R$^7$ and R$^8$ substituents bonded to the same nitrogen atom may be joined to form a substituted or unsubstituted 4 to 6 membered heterocycloalkyl or 5 to 6 membered heteroaryl. Each R$^7$ and R$^8$ substituents bonded to the same nitrogen atom may be joined to form an unsubstituted 4 to 6 membered heterocycloalkyl or 5 to 6 membered heteroaryl.

In embodiments, R$^7$, R$^8$, R$^9$, and R$^{10}$ are independently hydrogen, halogen, —CX$_3$, —CN, —COOH, —CONH$_2$, —OH, substituted or unsubstituted C$_1$-C$_5$ alkyl, substituted or unsubstituted 2 to 5 membered heteroalkyl, substituted or unsubstituted C$_3$-C$_8$ cycloalkyl, or substituted or unsubstituted 4 to 6 membered heterocycloalkyl.

In embodiments, R$^7$ is hydrogen. In embodiments, R$^7$ is halogen. In embodiments, R$^7$ is —CX$_3$. In embodiments, R$^7$ is —CN. In embodiments, R$^7$ is —OH. In embodiments, R$^7$ is —NH$_2$. In embodiments, R$^7$ is —COOH. In embodiments, R$^7$ is —CONH$_2$. In embodiments, R$^7$ is —NO$_2$. In embodiments, R$^7$ is —SH. In embodiments, R$^7$ is —SO$_3$H. In embodiments, R$^7$ is —SO$_4$H. In embodiments, R$^7$ is —SO$_2$NH$_2$. In embodiments, R$^7$ is NHNH$_2$. In embodiments, R$^7$ is ONH$_2$. In embodiments, R$^7$ is NHC=(O) NHNH$_2$. In embodiments, R$^7$ is NHC=(O) NH$_2$. In embodiments, R$^7$ is —NHSO$_2$H. In embodiments, R$^7$ is —NHC=(O)H. In embodiments, R$^7$ is —NHC(O)—OH. In embodiments, R$^7$ is —NHOH. In embodiments, R$^7$ is —OCX$_3$. In embodiments, R$^7$ is —OCHX$_2$. In embodiments, $R^7$ is substituted or unsubstituted $C_1$-$C_8$ alkyl. In embodiments, $R^7$ is substituted or unsubstituted 2 to 8 membered heteroalkyl. In embodiments, $R^7$ is substituted or unsubstituted $C_3$-$C_8$ cycloalkyl. In embodiments, $R^7$ is substituted or unsubstituted 3 to 6 membered heterocycloalkyl. In embodiments, $R^7$ is substituted or unsubstituted phenyl. In embodiments, $R^7$ is substituted or unsubstituted 5 to 6 membered heteroaryl. In embodiments, $R^7$ is unsubstituted $C_1$-$C_8$ alkyl. In embodiments, $R^7$ is unsubstituted 2 to 8 membered heteroalkyl. In embodiments, $R^7$ is unsubstituted $C_3$-$C_8$ cycloalkyl. In embodiments, $R^7$ is unsubstituted 3 to 6 membered heterocycloalkyl. In embodiments, $R^7$ is unsubstituted phenyl. In embodiments, $R^7$ is unsubstituted 5 to 6 membered heteroaryl. In embodiments, $R^7$ is unsubstituted methyl. In embodiments, $R^7$ is unsubstituted ethyl. In embodiments, $R^7$ is unsubstituted propyl. In embodiments, $R^7$ is unsubstituted isopropyl. In embodiments, $R^7$ is unsubstituted butyl. In embodiments, $R^7$ is unsubstituted tert-butyl.

In embodiments, $R^8$ is hydrogen. In embodiments, $R^8$ is halogen. In embodiments, $R^8$ is —$CX_3$. In embodiments, $R^8$ is —CN. In embodiments, $R^8$ is —OH. In embodiments, $R^8$ is —$NH_2$. In embodiments, $R^8$ is —COOH. In embodiments, $R^8$ is —$CONH_2$. In embodiments, $R^8$ is —$NO_2$. In embodiments, $R^8$ is —SH. In embodiments, $R^8$ is —$SO_3H$. In embodiments, $R^8$ is —$SO_4H$. In embodiments, $R^8$ is —$SO_2NH_2$. In embodiments, $R^8$ is $NHNH_2$. In embodiments, $R^8$ is $ONH_2$. In embodiments, $R^8$ is NHC=(O)$NHNH_2$. In embodiments, $R^8$ is NHC=(O) $NH_2$. In embodiments, $R^8$ is —$NHSO_2H$. In embodiments, $R^8$ is —NHC=(O)H. In embodiments, $R^8$ is —NHC(O)—OH. In embodiments, $R^8$ is —NHOH. In embodiments, $R^8$ is —$OCX_3$. In embodiments, $R^8$ is —$OCHX_2$. In embodiments, $R^8$ is substituted or unsubstituted $C_1$-$C_8$ alkyl. In embodiments, $R^8$ is substituted or unsubstituted 2 to 8 membered heteroalkyl. In embodiments, $R^8$ is substituted or unsubstituted $C_3$-$C_8$ cycloalkyl. In embodiments, $R^8$ is substituted or unsubstituted 3 to 6 membered heterocycloalkyl. In embodiments, $R^8$ is substituted or unsubstituted phenyl. In embodiments, $R^8$ is substituted or unsubstituted 5 to 6 membered heteroaryl. In embodiments, $R^8$ is unsubstituted $C_1$-$C_8$ alkyl. In embodiments, $R^8$ is unsubstituted 2 to 8 membered heteroalkyl. In embodiments, $R^8$ is unsubstituted $C_3$-$C_8$ cycloalkyl. In embodiments, $R^8$ is unsubstituted 3 to 6 membered heterocycloalkyl. In embodiments, $R^8$ is unsubstituted phenyl. In embodiments, $R^8$ is unsubstituted 5 to 6 membered heteroaryl. In embodiments, $R^8$ is unsubstituted methyl. In embodiments, $R^8$ is unsubstituted ethyl. In embodiments, $R^8$ is unsubstituted propyl. In embodiments, $R^8$ is unsubstituted isopropyl. In embodiments, $R^8$ is unsubstituted butyl. In embodiments, $R^8$ is unsubstituted tert-butyl.

In embodiments, $R^9$ is hydrogen. In embodiments, $R^9$ is halogen. In embodiments, $R^9$ is —$CX_3$. In embodiments, $R^9$ is —CN. In embodiments, $R^9$ is —OH. In embodiments, $R^9$ is —$NH_2$. In embodiments, $R^9$ is —COOH. In embodiments, $R^9$ is —$CONH_2$. In embodiments, $R^9$ is —$NO_2$. In embodiments, $R^9$ is —SH. In embodiments, $R^9$ is —$SO_3H$. In embodiments, $R^9$ is —$SO_4H$. In embodiments, $R^9$ is —$SO_2NH_2$. In embodiments, $R^9$ is $NHNH_2$. In embodiments, $R^9$ is $ONH_2$. In embodiments, $R^9$ is NHC=(O)$NHNH_2$. In embodiments, $R^9$ is NHC=(O) $NH_2$. In embodiments, $R^9$ is —$NHSO_2H$. In embodiments, $R^9$ is —NHC=(O)H. In embodiments, $R^9$ is —NHC(O)—OH. In embodiments, $R^9$ is —NHOH. In embodiments, $R^9$ is —$OCX_3$. In embodiments, $R^9$ is —$OCHX_2$. In embodiments, $R^9$ is substituted or unsubstituted $C_1$-$C_8$ alkyl. In embodiments, $R^9$ is substituted or unsubstituted 2 to 8 membered heteroalkyl. In embodiments, $R^9$ is substituted or unsubstituted $C_3$-$C_8$ cycloalkyl. In embodiments, $R^9$ is substituted or unsubstituted 3 to 6 membered heterocycloalkyl. In embodiments, $R^9$ is substituted or unsubstituted phenyl. In embodiments, $R^9$ is substituted or unsubstituted 5 to 6 membered heteroaryl. In embodiments, $R^9$ is unsubstituted $C_1$-$C_8$ alkyl. In embodiments, $R^9$ is unsubstituted 2 to 8 membered heteroalkyl. In embodiments, $R^9$ is unsubstituted $C_3$-$C_8$ cycloalkyl. In embodiments, $R^9$ is unsubstituted 3 to 6 membered heterocycloalkyl. In embodiments, $R^9$ is unsubstituted phenyl. In embodiments, $R^9$ is unsubstituted 5 to 6 membered heteroaryl. In embodiments, $R^9$ is unsubstituted methyl. In embodiments, $R^9$ is unsubstituted ethyl. In embodiments, $R^9$ is unsubstituted propyl. In embodiments, $R^9$ is unsubstituted isopropyl. In embodiments, $R^9$ is unsubstituted butyl. In embodiments, $R^9$ is unsubstituted tert-butyl.

In embodiments, $R^{10}$ is hydrogen. In embodiments, $R^{10}$ is halogen. In embodiments, $R^{10}$ is -$CX_3$. In embodiments, $R^{10}$ is —CN. In embodiments, $R^{10}$ is —OH. In embodiments, $R^{10}$ is —$NH_2$. In embodiments, $R^{10}$ is —COOH. In embodiments, $R^{10}$ is —$CONH_2$. In embodiments, $R^{10}$ is —$NO_2$. In embodiments, $R^{10}$ is —SH. In embodiments, $R^{10}$ is —$SO_3H$. In embodiments, $R^{10}$ is —$SO_4H$. In embodiments, $R^{10}$ is —$SO_2NH_2$. In embodiments, $R^{10}$ is $NHNH_2$. In embodiments, $R^{10}$ is $ONH_2$. In embodiments, $R^{10}$ is NHC=(O)$NHNH_2$. In embodiments, $R^{10}$ is NHC=(O) $NH_2$. In embodiments, $R^{10}$ is —$NHSO_2H$. In embodiments, $R^{10}$ is —NHC=(O)H. In embodiments, $R^{10}$ is —NHC(O)—OH. In embodiments, $R^{10}$ is —NHOH. In embodiments, $R^{10}$ is —$OCX_3$. In embodiments, $R^{10}$ is —$OCHX_2$. In embodiments, $R^{10}$ is substituted or unsubstituted $C_1$-$C_8$ alkyl. In embodiments, $R^{10}$ is substituted or unsubstituted 2 to 8 membered heteroalkyl. In embodiments, $R^{10}$ is substituted or unsubstituted $C_3$-$C_8$ cycloalkyl. In embodiments, $R^{10}$ is substituted or unsubstituted 3 to 6 membered heterocycloalkyl. In embodiments, $R^{10}$ is substituted or unsubstituted phenyl. In embodiments, $R^{10}$ is substituted or unsubstituted 5 to 6 membered heteroaryl. In embodiments, $R^{10}$ is unsubstituted $C_1$-$C_8$ alkyl. In embodiments, $R^{10}$ is unsubstituted 2 to 8 membered heteroalkyl. In embodiments, $R^{10}$ is unsubstituted $C_3$-$C_8$ cycloalkyl. In embodiments, $R^{10}$ is unsubstituted 3 to 6 membered heterocycloalkyl. In embodiments, $R^{10}$ is unsubstituted phenyl. In embodiments, $R^{10}$ is unsubstituted 5 to 6 membered heteroaryl. In embodiments, $R^{10}$ is unsubstituted methyl. In embodiments, $R^{10}$ is unsubstituted ethyl. In embodiments, $R^{10}$ is unsubstituted propyl. In embodiments, $R^{10}$ is unsubstituted isopropyl. In embodiments, $R^{10}$ is unsubstituted butyl. In embodiments, $R^{10}$ is unsubstituted tert-butyl.

In embodiments, $L^2$ is a bond. In embodiments, $L^2$ is —$SO_2$—. In embodiments, $L^2$ is —C(O)NH—. In embodiments, $L^2$ is —NHC(O)—. In embodiments, $L^2$ is —C(O)O—. In embodiments, $L^2$ is —OC(O)—. In embodiments, $L^2$ is —$SO_2CH_2$—. In embodiments, $L^2$ is —C(O)$NHCH_2$—. In embodiments, $L^2$ is —NHC(O)$CH_2$—. In embodiments, $L^2$ is —C(O)O$CH_2$—. In embodiments, $L^2$ is —OC(O)$CH_2$—. In embodiments, $L^2$ is unsubstituted $C_1$-$C_3$ alkylene. In embodiments, $L^2$ is unsubstituted $C_1$-$C_2$ alkylene. In embodiments, $L^2$ is unsubstituted methylene. In embodiments, $L^2$ is unsubstituted ethylene. In embodiments, $L^2$ is unsubstituted propylene. In embodiments, $L^2$ is unsubstituted isopropylene. In embodiments, $L^2$ is $C(CH_3)_2$—. In embodiments, $L^2$ is unsubstituted butylene. In embodiments, $L^2$ is unsubstituted $C_2$-$C_4$ alkenylene. In embodiments, $L^2$ is unsubstituted $C_2$-$C_3$ alkenylene. In embodiments, $L^2$ is unsubstituted $C_2$ alkenylene. In embodiments, $L^2$ is unsubstituted $C_3$ alkenylene. In embodiments, $L^2$ is unsubstituted $C_2$-$C_4$ alkynylene. In embodiments, $L^2$ is unsubstituted $C_2$-$C_3$ alkynylene. In embodiments, $L^2$ is unsubstituted $C_2$ alkynylene. In embodiments, $L^2$ is unsubstituted $C_3$ alkynylene. In embodiments, $L^2$ is —C(O)OCH$_2$CH$_2$—. In embodiments, $L^2$ is —C(O)OCH$_2$CH$_2$CH$_2$—. In embodiments, $L^2$ is —SO$_2$CH$_2$—. In embodiments, $L^2$ is —SO$_2$CH$_2$CH$_2$—. In embodiments, $L^2$ is —CH$_2$C(O)O—. In embodiments, $L^2$ is —CH$_2$C(O)OCH$_2$—. In embodiments, $L^2$ is —CH$_2$CH$_2$C(O)OCH$_2$—.

In embodiments, z is 1 or 2. In embodiments, z is 0. In embodiments, z is 1. In embodiments, z is 2. In embodiments, z is 3. In embodiments, z is 4. In embodiments, z is 5.

The symbol X may independently be Cl. The symbol X may independently be —Br. The symbol X may independently be —I. The symbol X may independently be —F.

The symbol $X^1$ may independently be Cl. The symbol $X^1$ may independently be —Br. The symbol $X^1$ may independently be —I. The symbol $X^1$ may independently be —F.

The symbol $X^2$ may independently be Cl. The symbol $X^2$ may independently be —Br. The symbol $X^2$ may independently be —I. The symbol $X^2$ may independently be —F.

In embodiments, the compound has the formula:

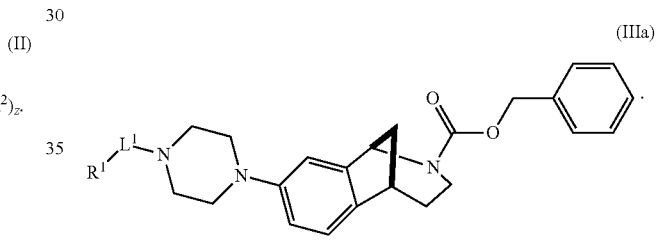

(II)

$R^1$, $R^2$, $L^1$, and z are as described herein.

In embodiments, the compound has the formula:

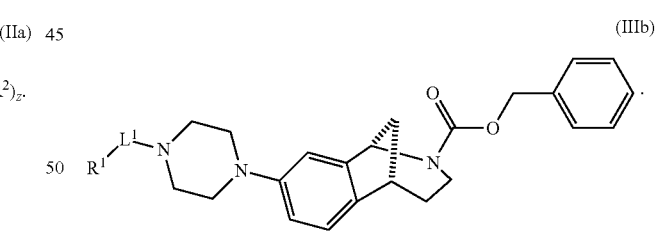

(IIa)

$R^1$, $R^2$, $L^1$, and z are as described herein.

In embodiments, the compound has the formula:

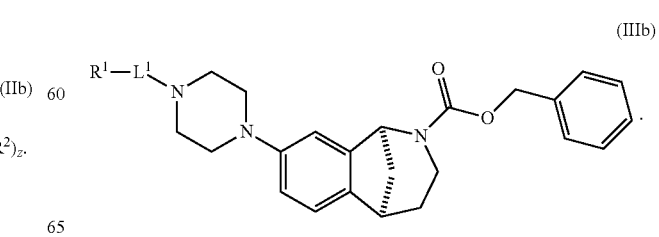

(IIb)

In embodiments, the compound has the formula:

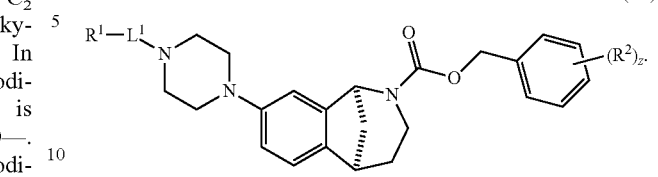

(IIb)

$R^1$, $R^2$, $L^1$, and z are as described herein.

In embodiments, the compound has the formula:

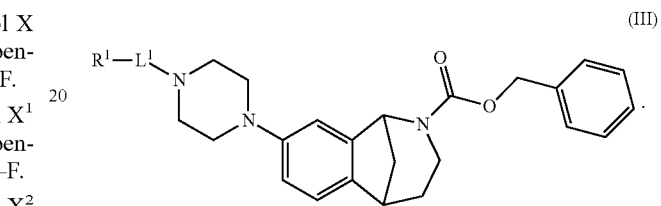

(III)

$R^1$ and $L^1$ are as described herein.

In embodiments, the compound has the formula:

(IIIa)

$R^1$ and $L^1$ are as described herein.

In embodiments, the compound has the formula:

(IIIb)

In embodiments, the compound has the formula:

(IIIb)

$R^1$ and $L^1$ are as described herein.

In embodiments, the compound has the formula:

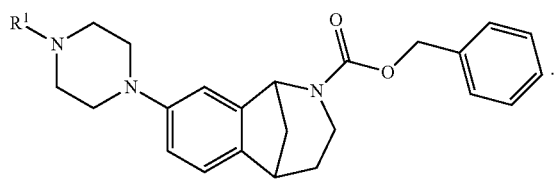
(IV)

R¹ is as described herein.
In embodiments, the compound has the formula:

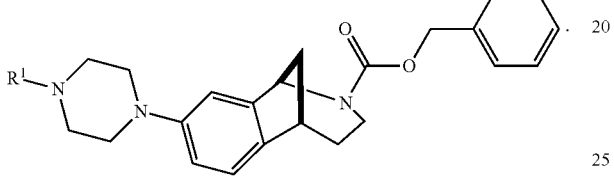
(IVa)

R¹ is as described herein.
In embodiments, the compound has the formula:

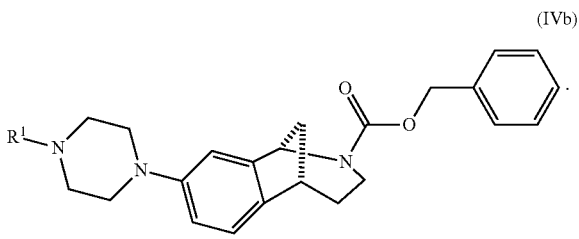
(IVb)

In embodiments, the compound has the formula:

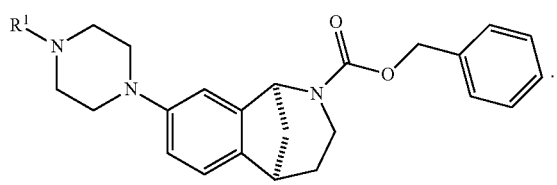
(IVb)

R¹ is as described herein.
In embodiments, the compound has the formula:

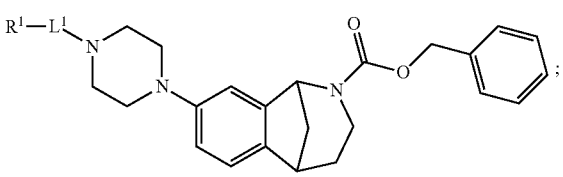

wherein L¹ and R¹ is as described herein. In embodiments, the compound has the formula:

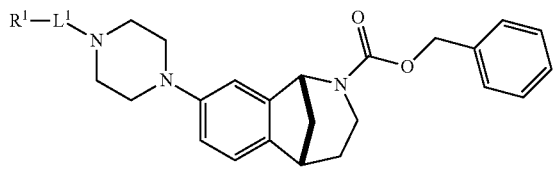

wherein L¹ and R¹ is as described herein. In embodiments, the compound has the formula:

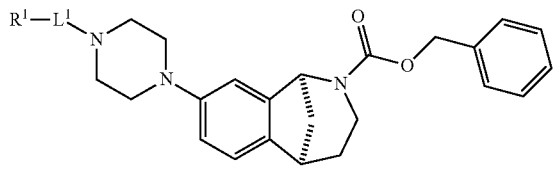

wherein L¹ and R¹ is as described herein.
In embodiments, the compound has the formula:

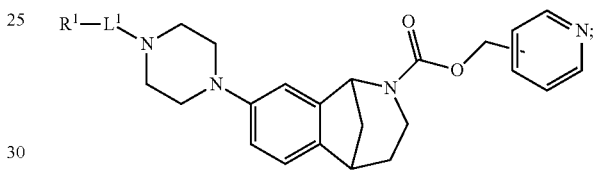

wherein L¹ and R¹ is as described herein. In embodiments, the compound has the formula:

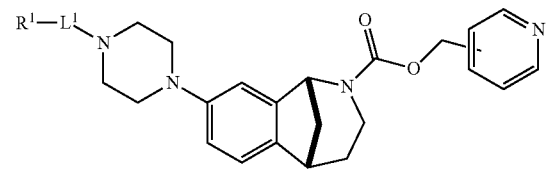

wherein L¹ and R¹ is as described herein. In embodiments, the compound has the formula:

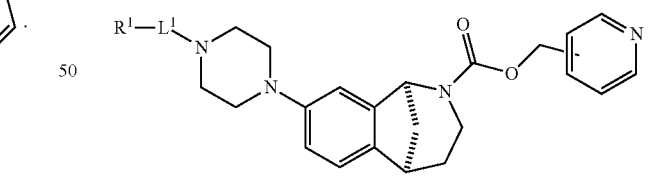

wherein L¹ and R¹ is as described herein.
In embodiments, the compound has the formula:

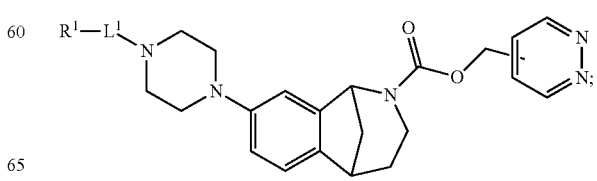

wherein L¹ and R¹ is as described herein. In embodiments, the compound has the formula:

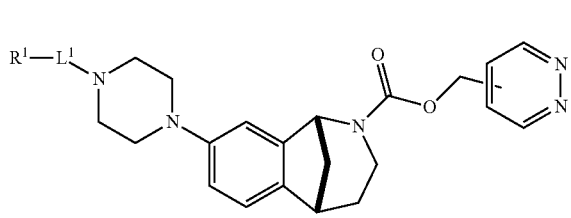

wherein L¹ and R¹ is as described herein. In embodiments, the compound has the formula:

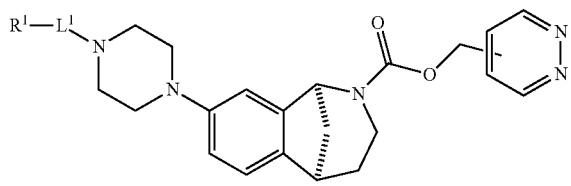

wherein L¹ and R¹ is as described herein.

In embodiments, the compound has the formula:

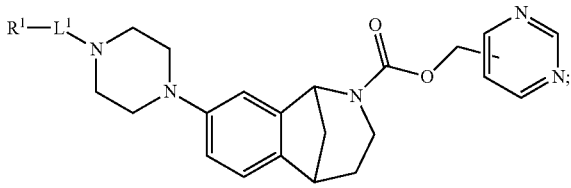

wherein L¹ and R¹ is as described herein. In embodiments, the compound has the formula:

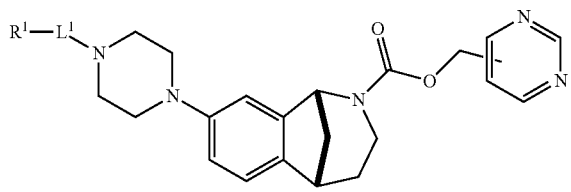

wherein L¹ and R¹ is as described herein. In embodiments, the compound has the formula:

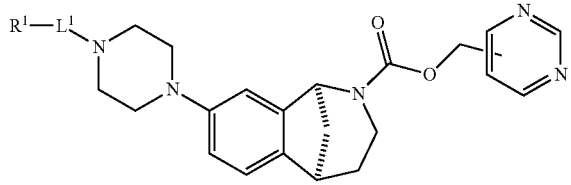

wherein L¹ and R¹ is as described herein.

In embodiments, the compound has the formula:

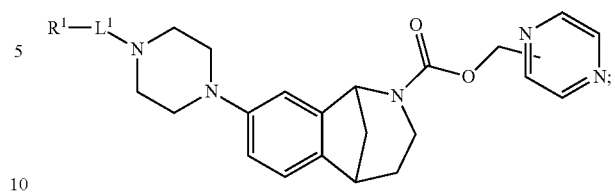

wherein L¹ and R¹ is as described herein. In embodiments, the compound has the formula:

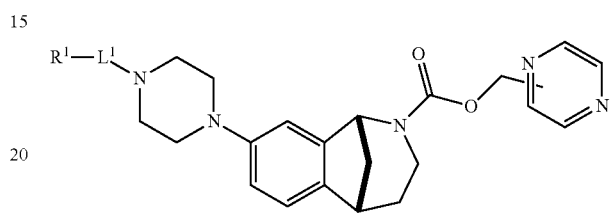

wherein L¹ and R¹ is as described herein. In embodiments, the compound has the formula:

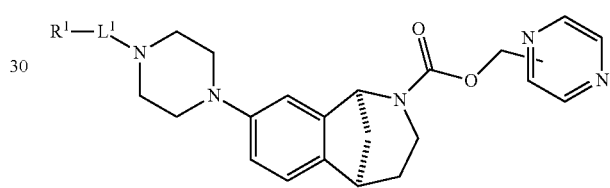

wherein L¹ and R¹ is as described herein.

In embodiments, the compound has the formula:

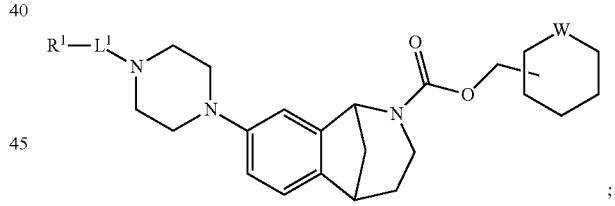

wherein L¹ and R¹ is as described herein. W is —NH—, —O—, or —S—. In embodiments, W is —NH—. In embodiments, W is —O—. In embodiments, W is —S—. In embodiments, the compound has the formula:

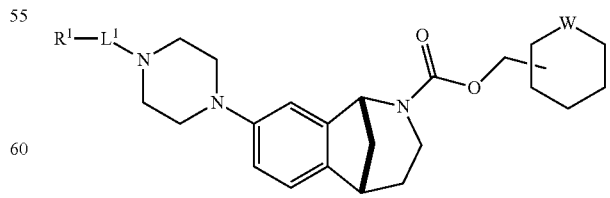

wherein L¹ and R¹ is as described herein. W is —NH—, —O—, or —S—. In embodiments, W is —NH—. In embodiments, W is —O—. In embodiments, W is —S—. In embodiments, the compound has the formula:

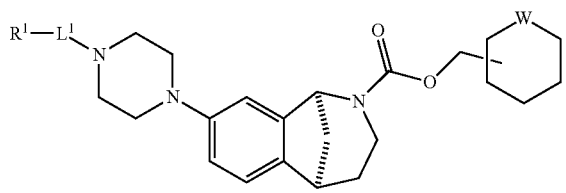

wherein L¹ and R¹ is as described herein. W is —NH—, —O—, or —S—. In embodiments, W is —NH—. In embodiments, W is —O—. In embodiments, W is —S—.

In embodiments, the compound has the formula:

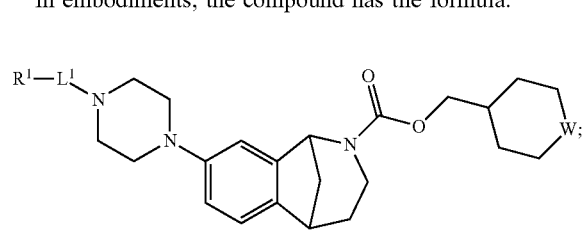

wherein L¹ and R¹ is as described herein. W is —NH—, —O—, or —S—. In embodiments, W is —NH—. In embodiments, W is —O—. In embodiments, W is —S—. In embodiments, the compound has the formula:

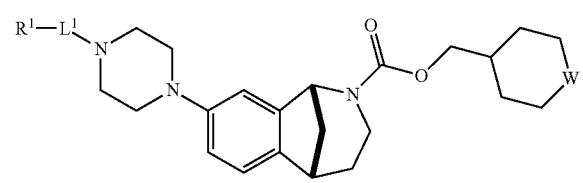

wherein L¹ and R¹ is as described herein. W is —NH—, —O—, or —S—. In embodiments, W is —NH—. In embodiments, W is —O—. In embodiments, W is —S—. In embodiments, the compound has the formula:

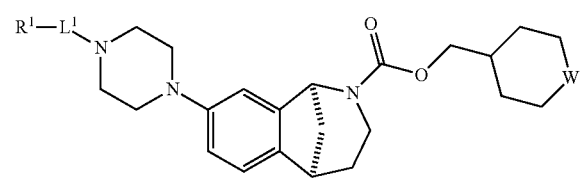

wherein L¹ and R¹ is as described herein. W is —NH—, —O—, or —S—. In embodiments, W is —NH—. In embodiments, W is —O—. In embodiments, W is S—.

In embodiments, the compound has the formula:

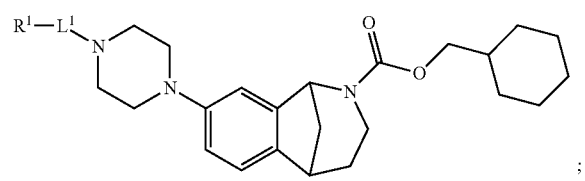

wherein L¹ and R¹ is as described herein. In embodiments, the compound has the formula:

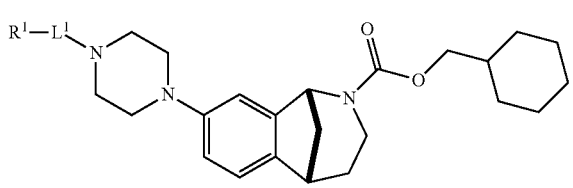

wherein L¹ and R¹ is as described herein. In embodiments, the compound has the formula:

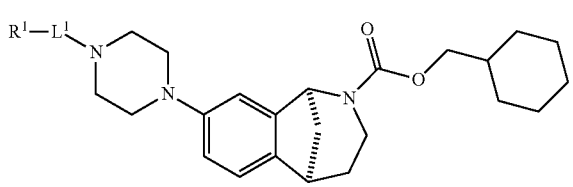

wherein L¹ and R¹ is as described herein.

In embodiments, the compound has the formula:

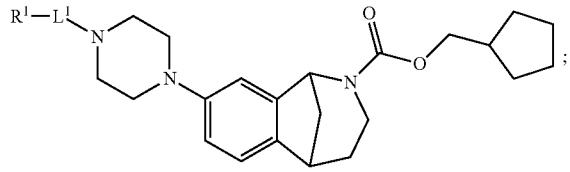

wherein L¹ and R¹ is as described herein. In embodiments, the compound has the formula:

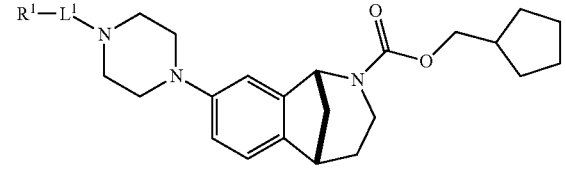

wherein L¹ and R¹ is as described herein. In embodiments, the compound has the formula:

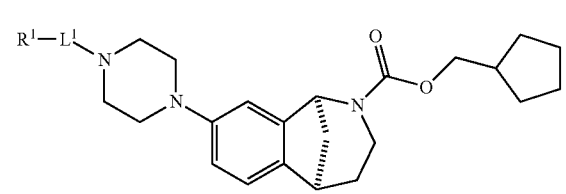

wherein L¹ and R¹ is as described herein.

In embodiments, the compound has the formula:

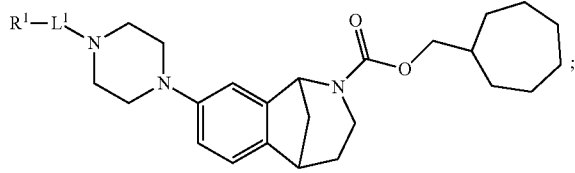

wherein $L^1$ and $R^1$ is as described herein. In embodiments, the compound has the formula:

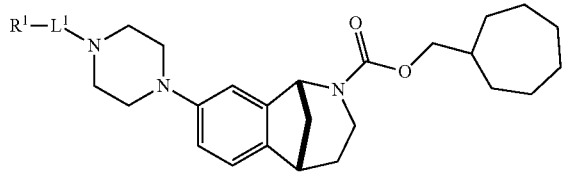

wherein $L^1$ and $R^1$ is as described herein. In embodiments, the compound has the formula:

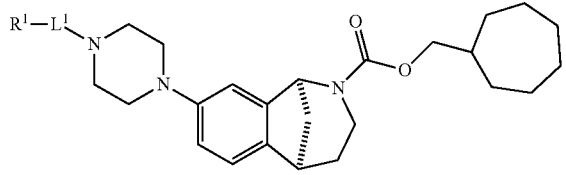

wherein $L^1$ and $R^1$ is as described herein.

In embodiments, the compound has the formula:

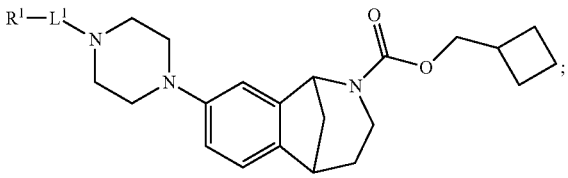

wherein $L^1$ and $R^1$ is as described herein. In embodiments, the compound has the formula:

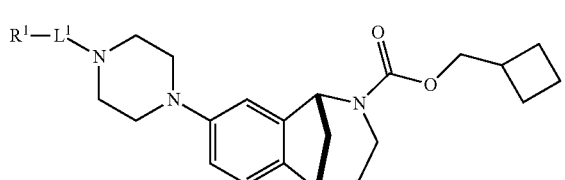

wherein $L^1$ and $R^1$ is as described herein. In embodiments, the compound has the formula:

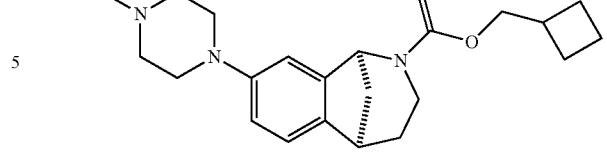

wherein $L^1$ and $R^1$ is as described herein.

In embodiments, the compound has the formula:

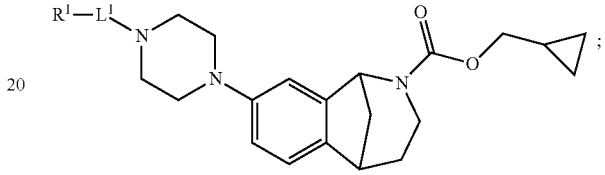

wherein $L^1$ and $R^1$ is as described herein. In embodiments, the compound has the formula:

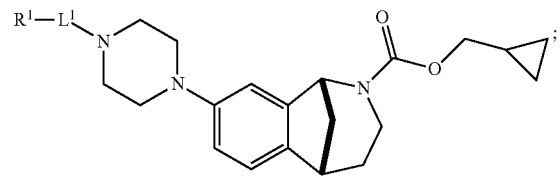

wherein $L^1$ and $R^1$ is as described herein. In embodiments, the compound has the formula:

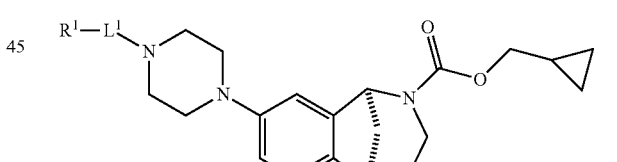

wherein $L^1$ and $R^1$ is as described herein.

In embodiments, the compound has the formula:

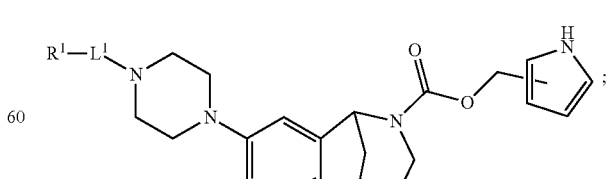

wherein $L^1$ and $R^1$ is as described herein. In embodiments, the compound has the formula:

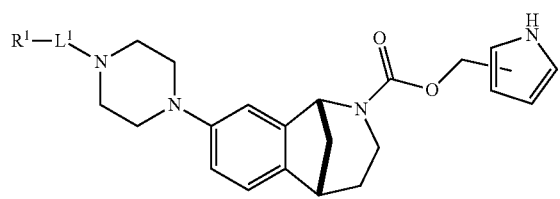

wherein L¹ and R¹ is as described herein. In embodiments, the compound has the formula:

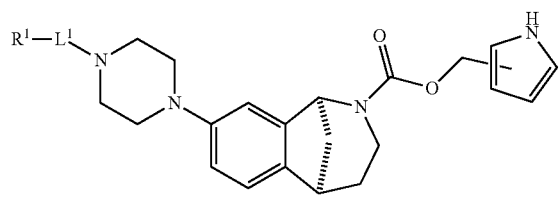

wherein L¹ and R¹ is as described herein.
In embodiments, the compound has the formula:

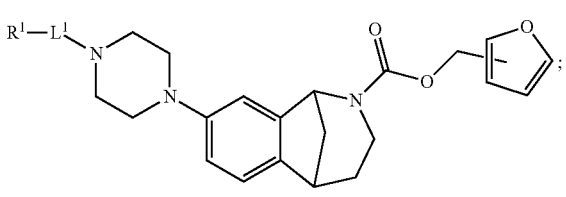

wherein L¹ and R¹ is as described herein. In embodiments, the compound has the formula:

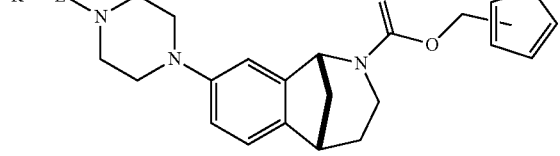

wherein L¹ and R¹ is as described herein.

In embodiments, the compound has the formula:

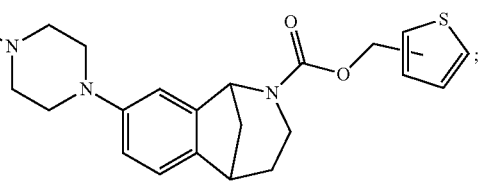

wherein L¹ and R¹ is as described herein. In embodiments, the compound has the formula:

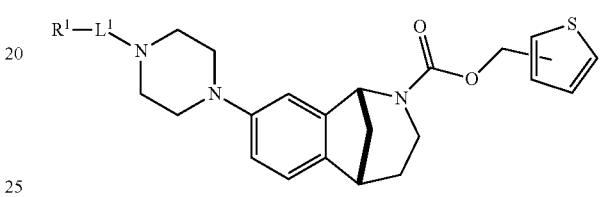

wherein L¹ and R¹ is as described herein. In embodiments, the compound has the formula:

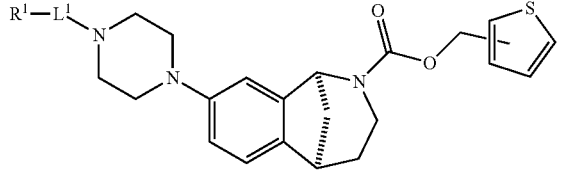

wherein L¹ and R¹ is as described herein.
In embodiments, the compound has the formula:

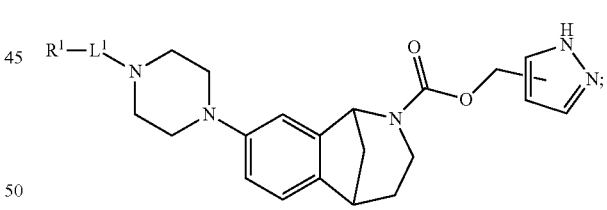

wherein L¹ and R¹ is as described herein. In embodiments, the compound has the formula:

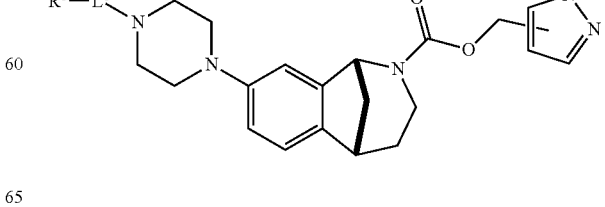

wherein L¹ and R¹ is as described herein. In embodiments, the compound has the formula:

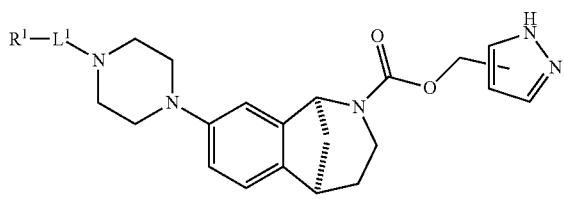

wherein L¹ and R¹ is as described herein.
In embodiments, the compound has the formula:

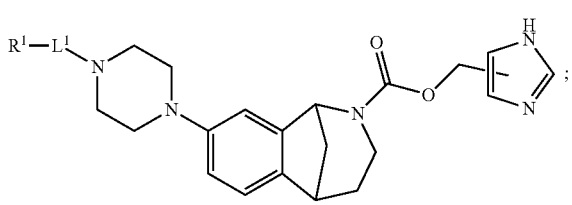

wherein L¹ and R¹ is as described herein. In embodiments, the compound has the formula:

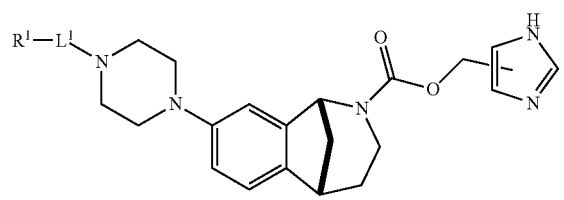

wherein L¹ and R¹ is as described herein. In embodiments, the compound has the formula:

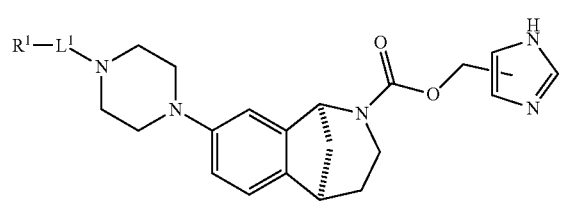

wherein L¹ and R¹ is as described herein.
In embodiments, the compound has the formula:

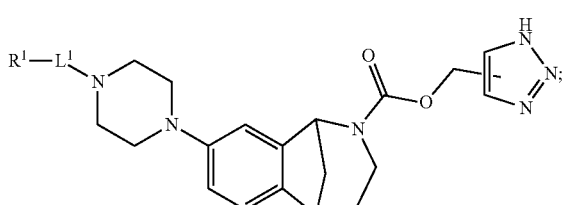

wherein L¹ and R¹ is as described herein. In embodiments, the compound has the formula:

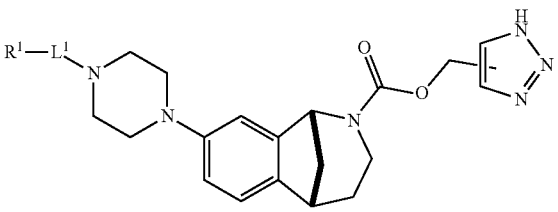

wherein L¹ and R¹ is as described herein. In embodiments, the compound has the formula:

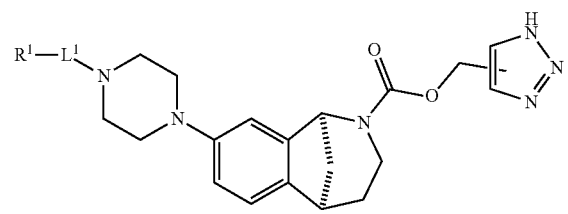

wherein L¹ and R¹ is as described herein.
In embodiments, the compound has the formula:

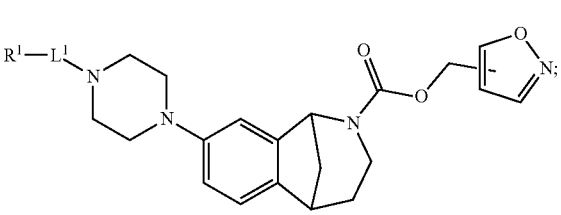

wherein L¹ and R¹ is as described herein. In embodiments, the compound has the formula:

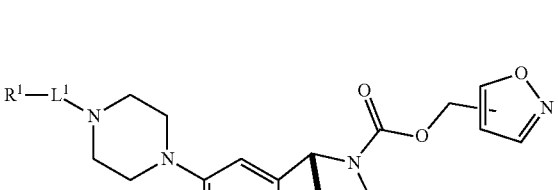

wherein L¹ and R¹ is as described herein. In embodiments, the compound has the formula:

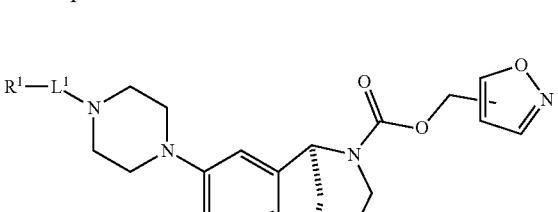

wherein L¹ and R¹ is as described herein.

In embodiments, the compound has the formula:

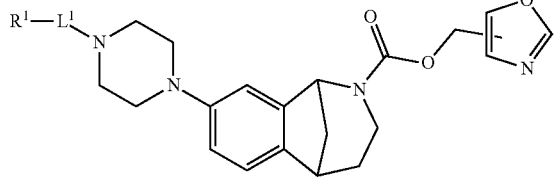

wherein $L^1$ and $R^1$ is as described herein. In embodiments, the compound has the formula:

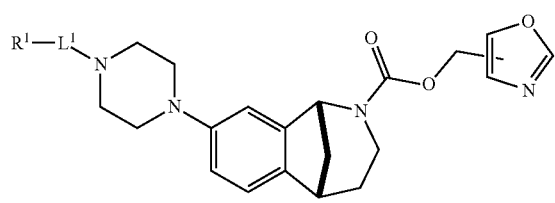

wherein $L^1$ and $R^1$ is as described herein. In embodiments, the compound has the formula:

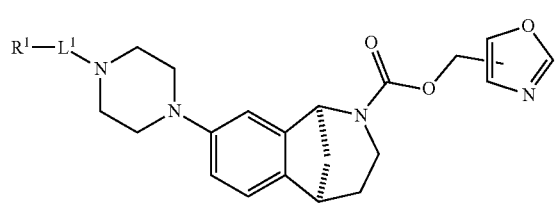

wherein $L^1$ and $R^1$ is as described herein.

In embodiments, the compound has the formula:

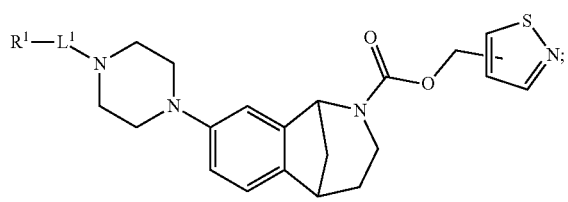

wherein $L^1$ and $R^1$ is as described herein. In embodiments, the compound has the formula:

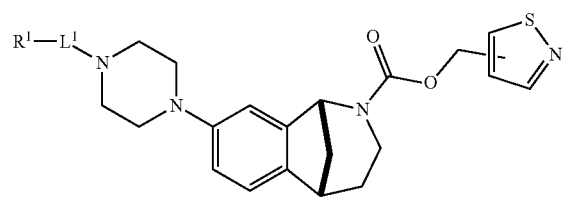

wherein $L^1$ and $R^1$ is as described herein. In embodiments, the compound has the formula:

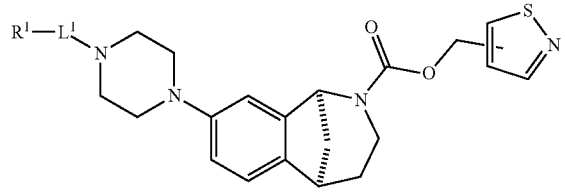

wherein $L^1$ and $R^1$ is as described herein.

In embodiments, the compound has the formula:

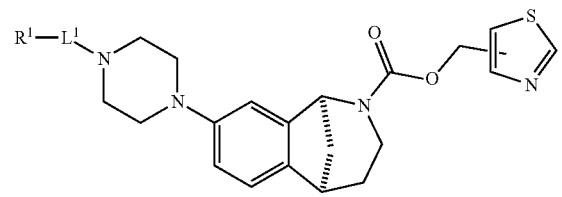

wherein $L^1$ and $R^1$ is as described herein. In embodiments, the compound has the formula:

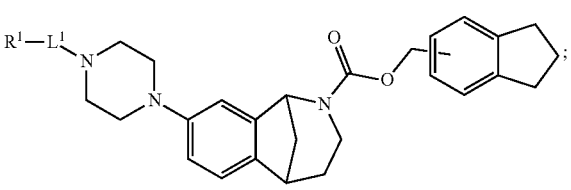

wherein $L^1$ and $R^1$ is as described herein.

In embodiments, the compound has the formula:

wherein $L^1$ and $R^1$ is as described herein.

In embodiments, the compound has the formula:

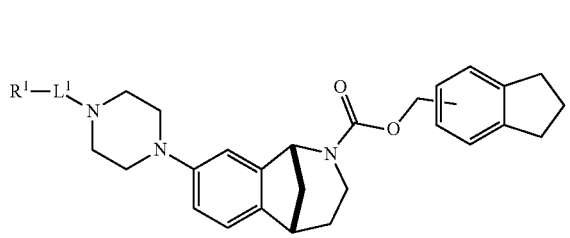

wherein $L^1$ and $R^1$ is as described herein. In embodiments, the compound has the formula:

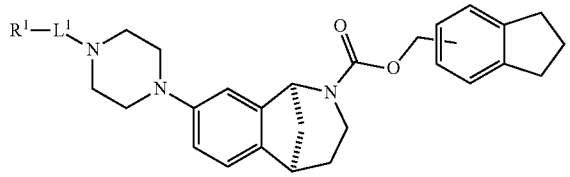

wherein $L^1$ and $R^1$ is as described herein.

In embodiments, the compound has the formula:

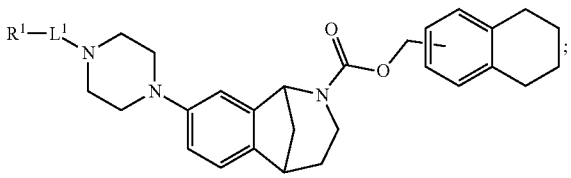

wherein $L^1$ and $R^1$ is as described herein.

In embodiments, the compound has the formula:

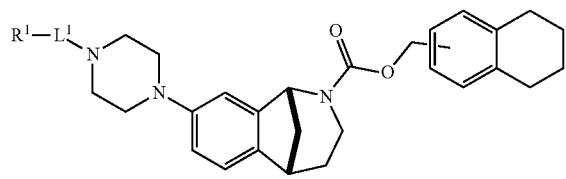

wherein $L^1$ and $R^1$ is as described herein. In embodiments, the compound has the formula:

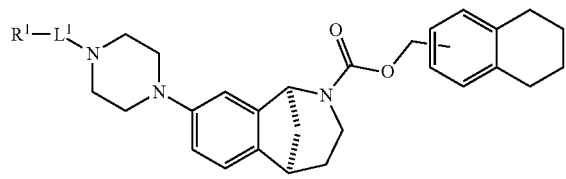

wherein $L^1$ and $R^1$ is as described herein.

In embodiments, the compound has the formula:

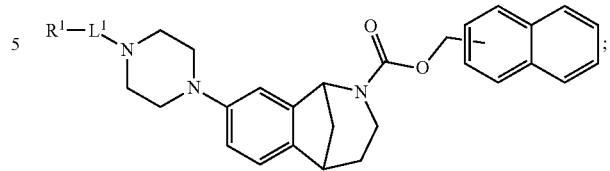

wherein $L^1$ and $R^1$ is as described herein.

In embodiments, the compound has the formula:

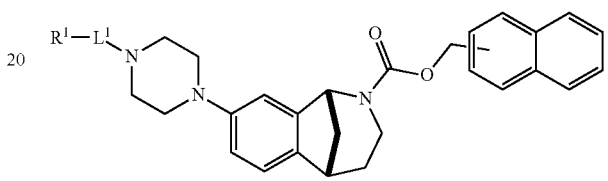

wherein $L^1$ and $R^1$ is as described herein. In embodiments, the compound has the formula:

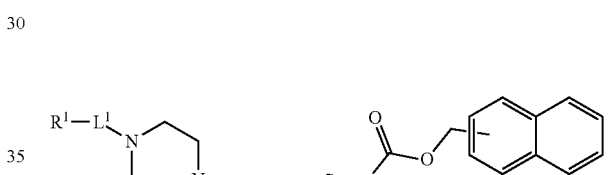

wherein $L^1$ and $R^1$ is as described herein.

In embodiments, the compound has the formula:

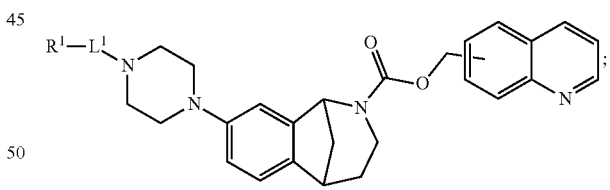

wherein $L^1$ and $R^1$ is as described herein.

In embodiments, the compound has the formula:

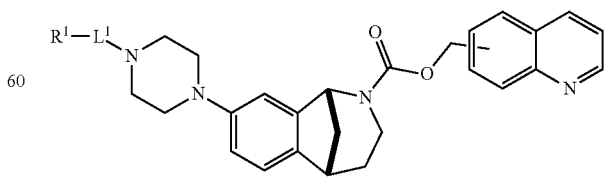

wherein $L^1$ and $R^1$ is as described herein. In embodiments, the compound has the formula:

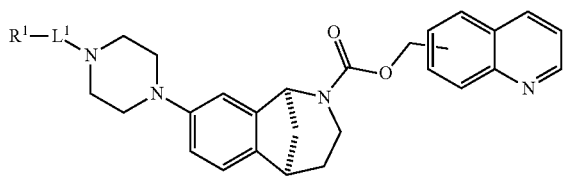

wherein $L^1$ and $R^1$ is as described herein.

In embodiments, the compound has the formula:

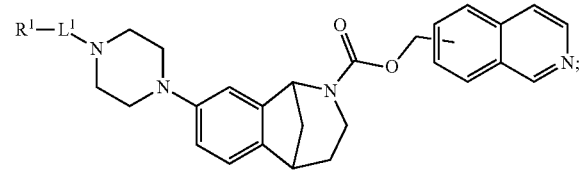

wherein $L^1$ and $R^1$ is as described herein.

In embodiments, the compound has the formula:

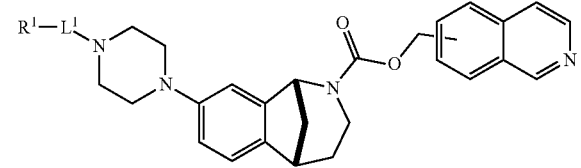

wherein $L^1$ and $R^1$ is as described herein.

In embodiments, the compound has the formula:

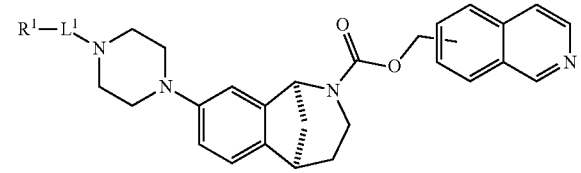

wherein $L^1$ and $R^1$ is as described herein.

In embodiments, the compound has the formula:

In embodiments, the compound has the formula:

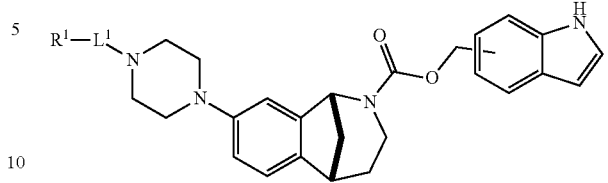

wherein $L^1$ and $R^1$ is as described herein. In embodiments, the compound has the formula:

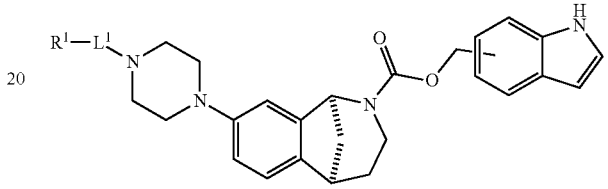

wherein $L^1$ and $R^1$ is as described herein.

In embodiments, the compound has the formula:

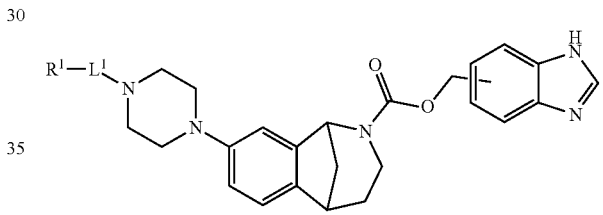

wherein $L^1$ and $R^1$ is as described herein.

In embodiments, the compound has the formula:

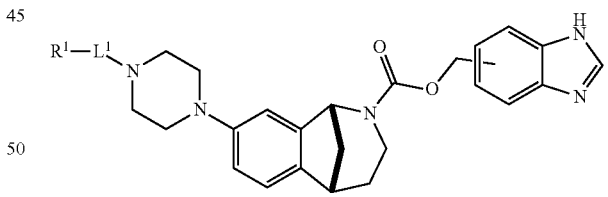

wherein $L^1$ and $R^1$ is as described herein. In embodiments, the compound has the formula:

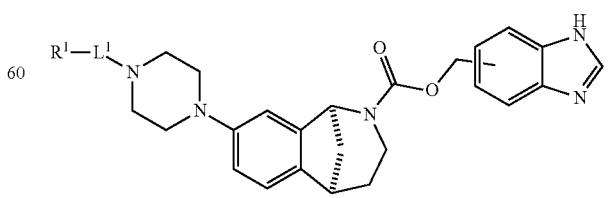

wherein $L^1$ and $R^1$ is as described herein.

In embodiments, the compound has the formula:

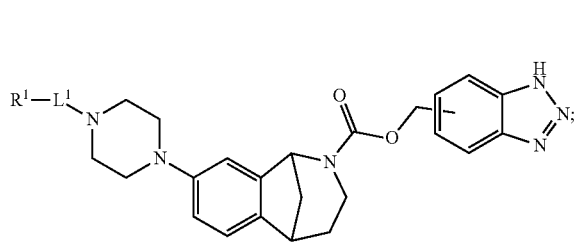

wherein L¹ and R¹ is as described herein.

In embodiments, the compound has the formula:

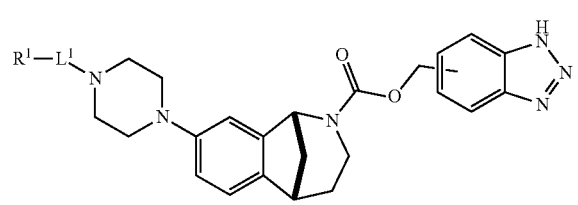

wherein L¹ and R¹ is as described herein. In embodiments, the compound has the formula:

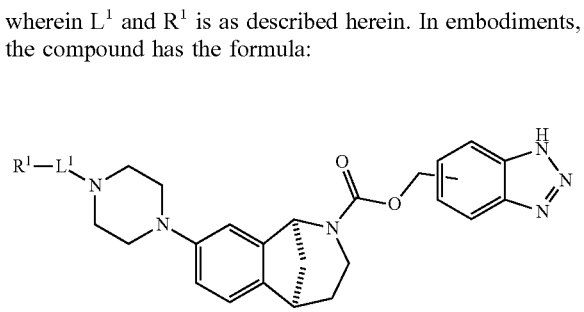

wherein L¹ and R¹ is as described herein.

In embodiments, the compound has the formula:

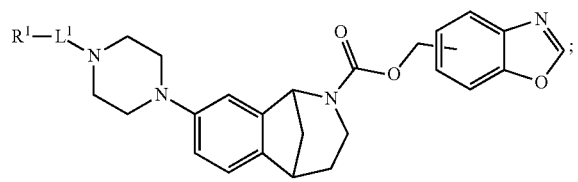

wherein L¹ and R¹ is as described herein.

In embodiments, the compound has the formula:

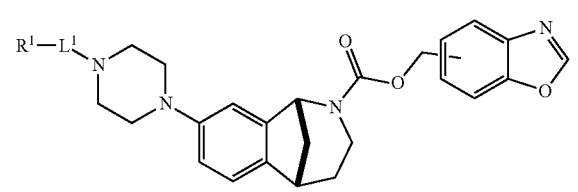

wherein L¹ and R¹ is as described herein. In embodiments, the compound has the formula:

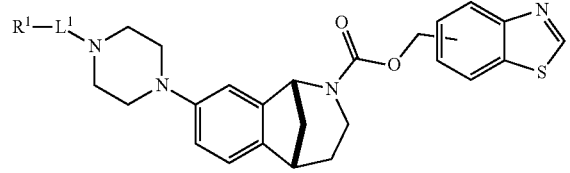

wherein L¹ and R¹ is as described herein.

In embodiments, the compound has the formula:

wherein L¹ and R¹ is as described herein.

In embodiments, the compound has the formula:

wherein L¹ and R¹ is as described herein.

In embodiments, the compound has the formula:

wherein L¹ and R¹ is as described herein. In embodiments, the compound has the formula:

wherein L¹ and R¹ is as described herein.

In embodiments, the compound has the formula:

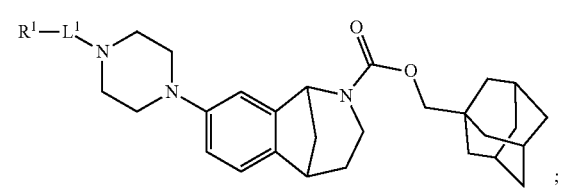

wherein L¹ and R¹ is as described herein. In embodiments, the compound has the formula:

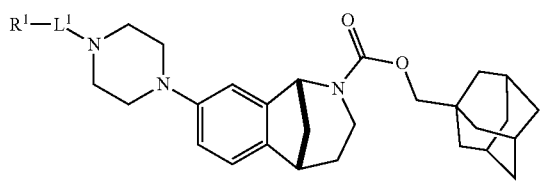

wherein L¹ and R¹ is as described herein. In embodiments, the compound has the formula:

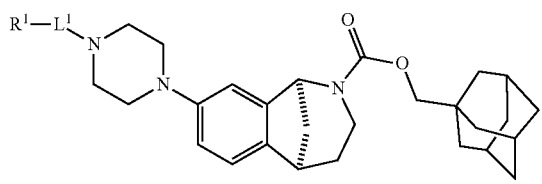

wherein L¹ and R¹ is as described herein.

In embodiments, the compound has the formula:

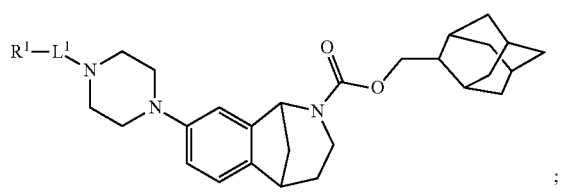

wherein L¹ and R¹ is as described herein. In embodiments, the compound has the formula:

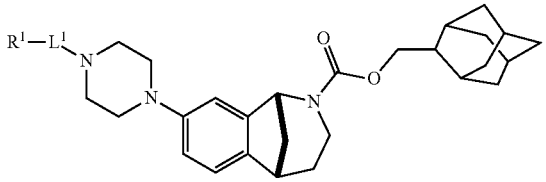

wherein L¹ and R¹ is as described herein. In embodiments, the compound has the formula:

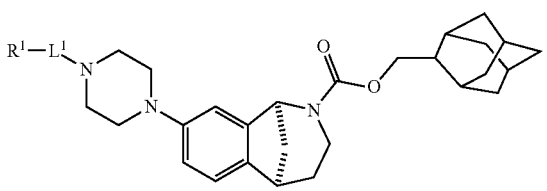

wherein L¹ and R¹ is as described herein.

In embodiments, the compound has the formula:

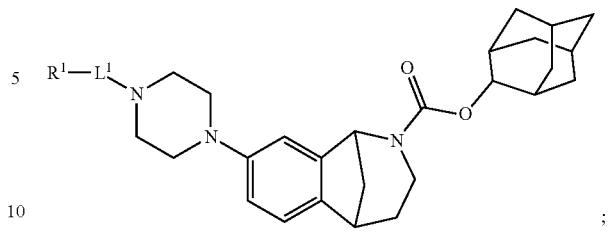

wherein L¹ and R¹ is as described herein. In embodiments, the compound has the formula:

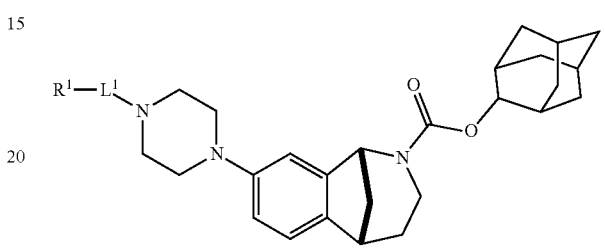

wherein L¹ and R¹ is as described herein. In embodiments, the compound has the formula:

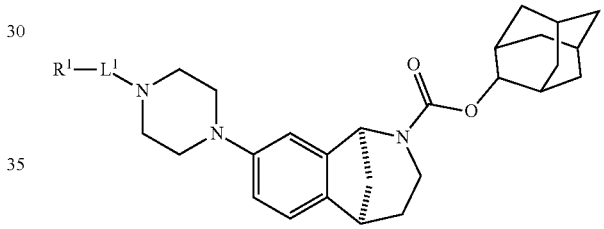

wherein L¹ and R¹ is as described herein.

In embodiments, the compound has the formula:

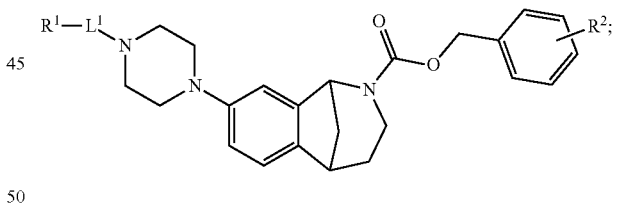

wherein L¹, R¹, and R² are as described herein. In embodiments, R² is halogen. In embodiments, R² is F. In embodiments, R² is Cl. In embodiments, R² is CH₃. In embodiments, R² is OCH₃. In embodiments, the compound has the formula:

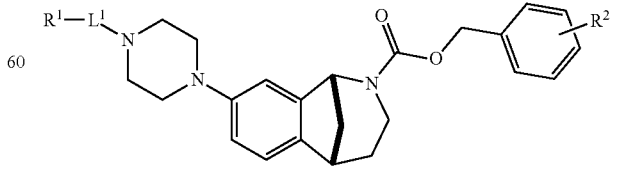

wherein L¹, R¹, and R² are as described herein. In embodiments, R² is halogen. In embodiments, R² is F. In embodiments, $R^2$ is Cl. In embodiments, $R^2$ is $CH_3$. In embodiments, $R^2$ is $OCH_3$. In embodiments, the compound has the formula:

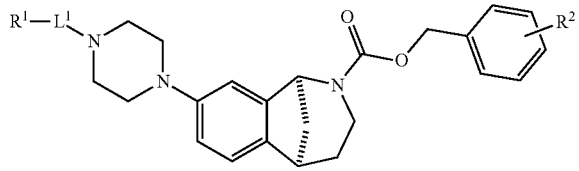

wherein $L^1$, $R^1$, and $R^2$ are as described herein. In embodiments, $R^2$ is halogen. In embodiments, $R^2$ is F. In embodiments, $R^2$ is Cl. In embodiments, $R^2$ is $CH_3$. In embodiments, $R^2$ is $OCH_3$.

In embodiments, the compound has the formula:

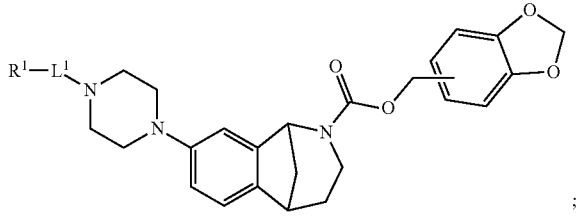

;

wherein $L^1$ and $R^1$ are as described herein.

In embodiments, the compound has the formula:

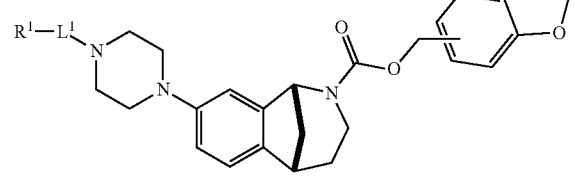

wherein $L^1$ and $R^1$ are as described herein.

In embodiments, the compound has the formula:

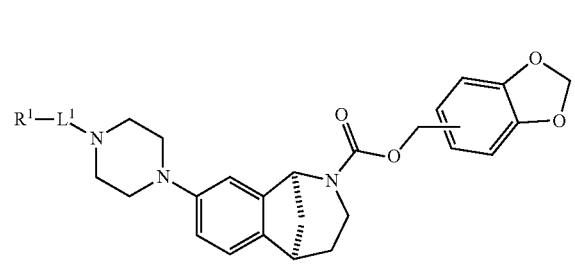

wherein $L^1$ and $R^1$ are as described herein.

In embodiments, the compound has the formula:

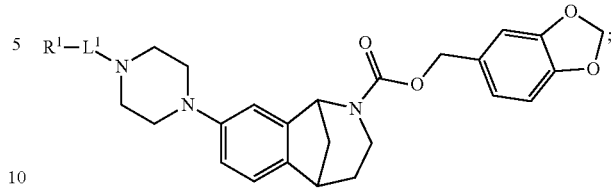

wherein $L^1$ and $R^1$ are as described herein.

In embodiments, the compound has the formula:

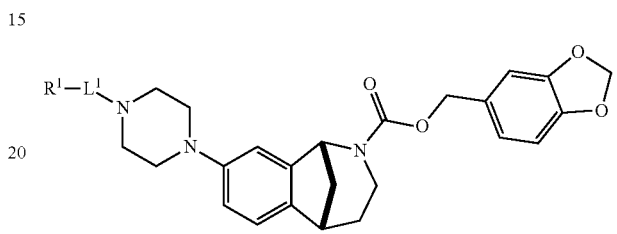

wherein $L^1$ and $R^1$ are as described herein.

In embodiments, the compound has the formula:

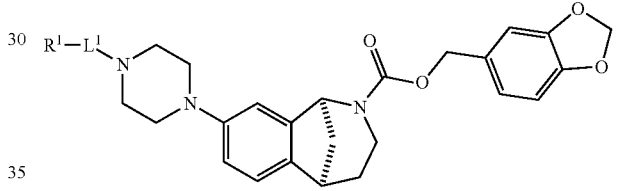

wherein $L^1$ and $R^1$ are as described herein.

In embodiments, the compound has the formula:

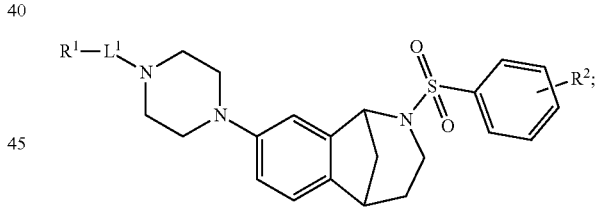

wherein $L^1$, $R^1$, and $R^2$ are as described herein.

In embodiments, $R^2$ is halogen. In embodiments, $R^2$ is F. In embodiments, $R^2$ is Cl. In embodiments, $R^2$ is $CH_3$. In embodiments, $R^2$ is $OCH_3$. In embodiments, the compound has the formula:

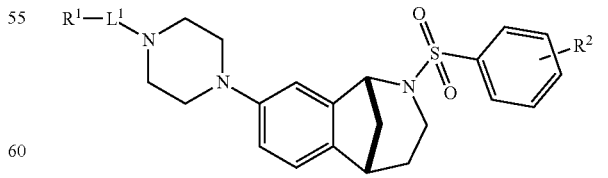

wherein $L^1$, $R^1$, and $R^2$ are as described herein.

In embodiments, $R^2$ is halogen. In embodiments, $R^2$ is F. In embodiments, $R^2$ is Cl. In embodiments, $R^2$ is $CH_3$. In embodiments, $R^2$ is $OCH_3$. In embodiments, the compound has the formula:

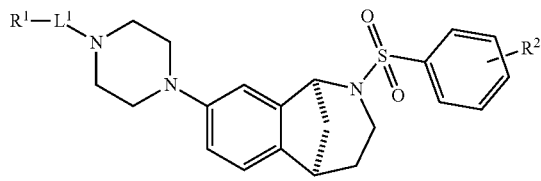

wherein $L^1$, $R^1$, and $R^2$ are as described herein.

In embodiments, $R^2$ is halogen. In embodiments, $R^2$ is F. In embodiments, $R^2$ is Cl. In embodiments, $R^2$ is $CH_3$. In embodiments, $R^2$ is $OCH_3$.

In embodiments, the compound has the formula:

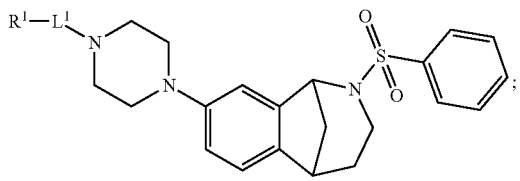

wherein $L^1$ and $R^1$ are as described herein. In embodiments, the compound has the formula:

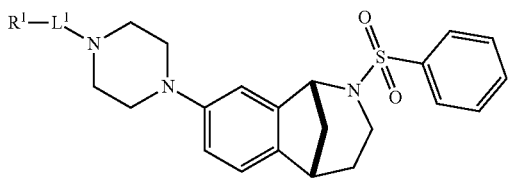

wherein $L^1$ and $R^1$ are as described herein. In embodiments, the compound has the formula:

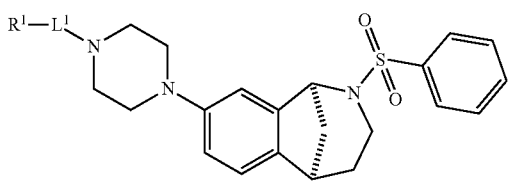

wherein $L^1$ and $R^1$ are as described herein.

In embodiments, the compound has the formula:

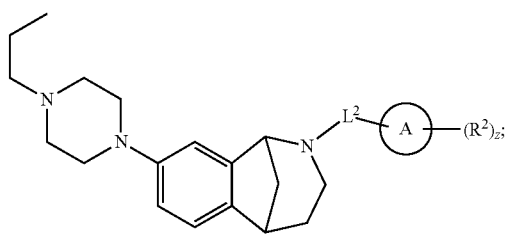

wherein $L^2$, z, Ring A, and $R^2$ are as described herein. In embodiments, the compound has the formula:

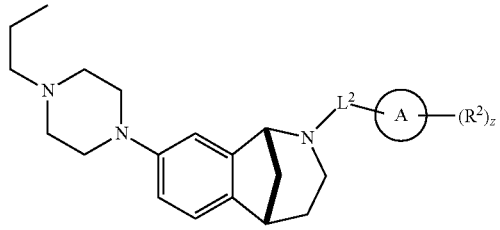

wherein $L^2$, z, Ring A, and $R^2$ are as described herein. In embodiments, the compound has the formula:

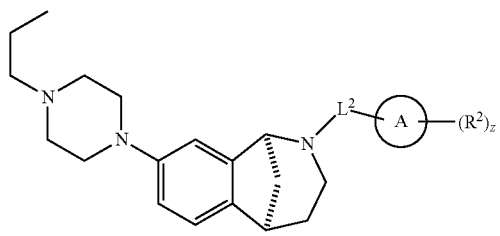

wherein $L^2$, z, Ring A, and $R^2$ are as described herein.
In embodiments, the compound has the formula:

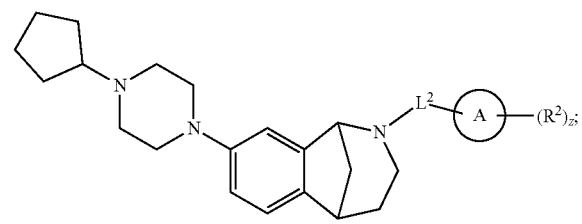

wherein $L^2$, z, Ring A, and $R^2$ are as described herein. In embodiments, the compound has the formula:

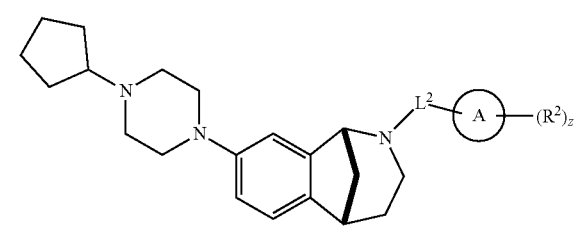

wherein $L^2$, z, Ring A, and $R^2$ are as described herein. In embodiments, the compound has the formula:

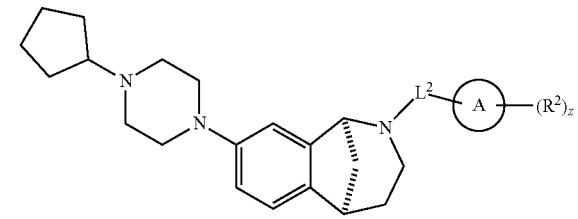

wherein $L^2$, z, Ring A, and $R^2$ are as described herein.

In embodiments, the compound has the formula:

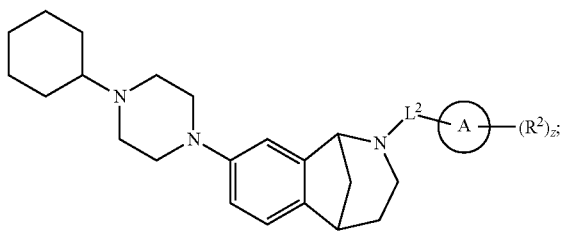

wherein $L^2$, z, Ring A, and $R^2$ are as described herein. In embodiments, the compound has the formula:

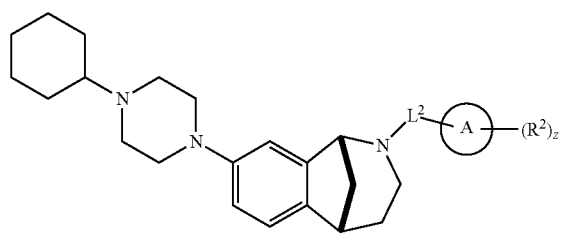

wherein $L^2$, z, Ring A, and $R^2$ are as described herein. In embodiments, the compound has the formula:

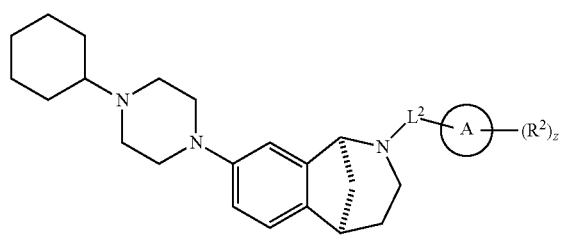

wherein $L^2$, z, Ring A, and $R^2$ are as described herein. In embodiments, the compound has the formula:

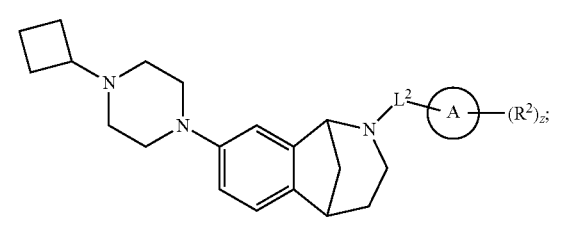

wherein $L^2$, z, Ring A, and $R^2$ are as described herein. In embodiments, the compound has the formula:

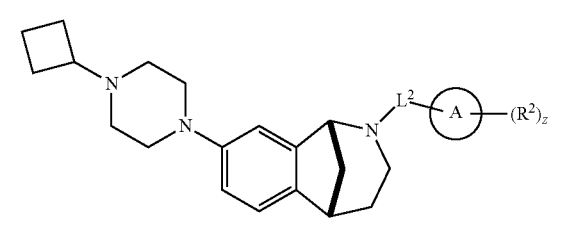

wherein $L^2$, z, Ring A, and $R^2$ are as described herein. In embodiments, the compound has the formula:

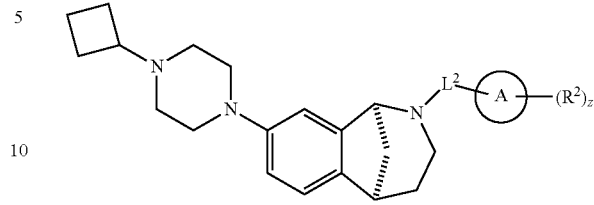

wherein $L^2$, z, Ring A, and $R^2$ are as described herein. In embodiments, the compound has the formula:

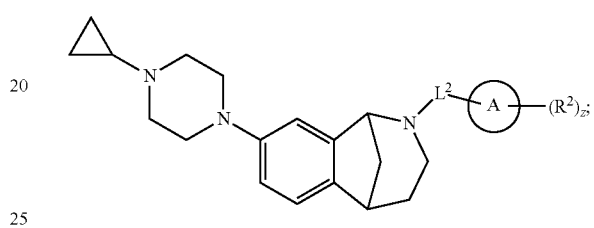

wherein $L^2$, z, Ring A, and $R^2$ are as described herein. In embodiments, the compound has the formula:

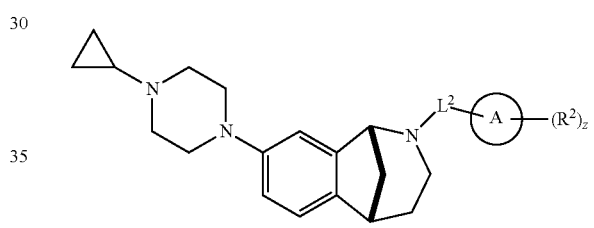

wherein $L^2$, z, Ring A, and $R^2$ are as described herein. In embodiments, the compound has the formula:

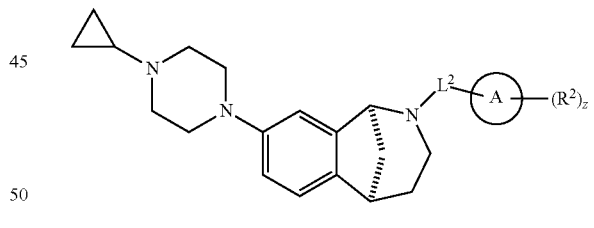

wherein $L^2$, z, Ring A, and $R^2$ are as described herein. In embodiments, the compound has the formula:

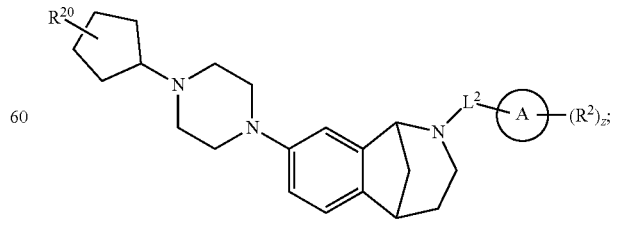

wherein $L^2$, z, Ring A, $R^2$ and $R^{20}$ are as described herein. In embodiments, the compound has the formula:

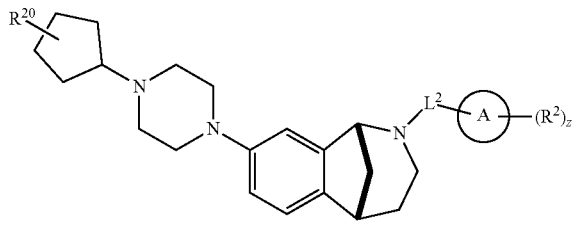

wherein $L^2$, z, Ring A, $R^2$, and $R^{20}$ are as described herein.
In embodiments, the compound has the formula:

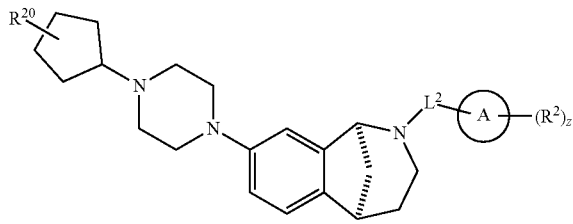

wherein $L^2$, z, Ring A, $R^2$, and $R^{20}$ are as described herein.
In embodiments, the compound has the formula:

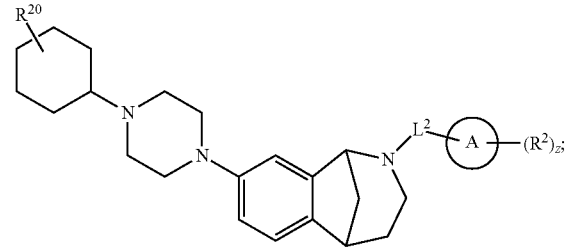

wherein $L^2$, z, Ring A, $R^2$, and $R^{20}$ are as described herein.
In embodiments, the compound has the formula:

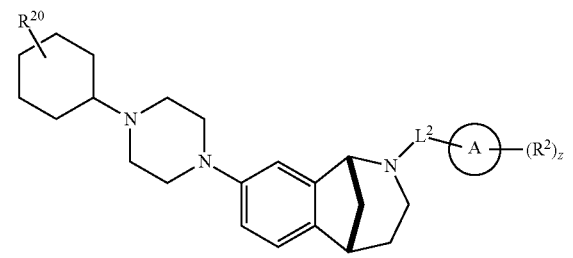

wherein $L^2$, z, Ring A, $R^2$, and $R^{20}$ are as described herein.
In embodiments, the compound has the formula:

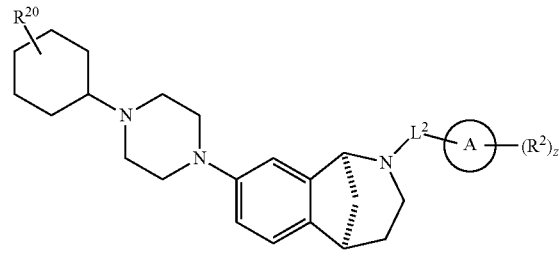

wherein $L^2$, z, Ring A, $R^2$, and $R^{20}$ are as described herein.
In embodiments, the compound has the formula:

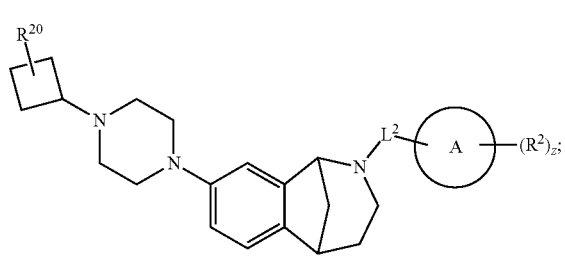

wherein $L^2$, z, Ring A, $R^2$, and $R^{20}$ are as described herein.
In embodiments, the compound has the formula:

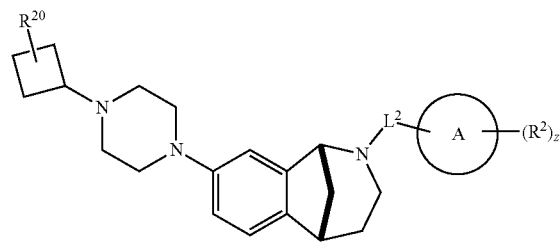

wherein $L^2$, z, Ring A, $R^2$, and $R^{20}$ are as described herein.
In embodiments, the compound has the formula:

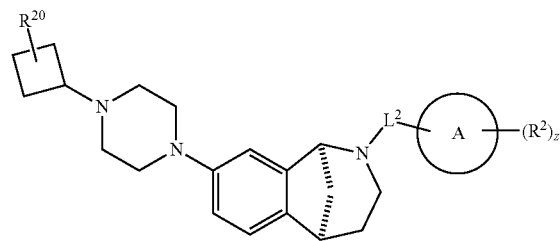

wherein $L^2$, z, Ring A, $R^2$, and $R^{20}$ are as described herein.

In embodiments, the compound has the formula:

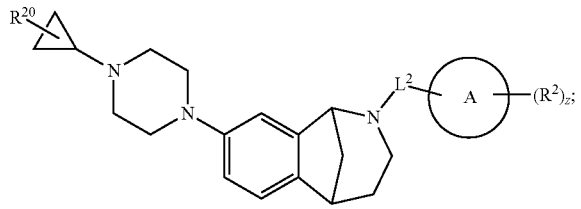

wherein L², z, Ring A, R², and R²⁰ are as described herein. In embodiments, the compound has the formula:

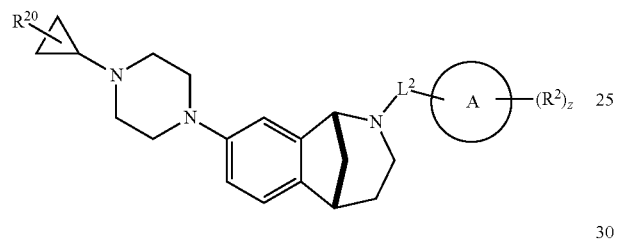

wherein L², z, Ring A, R², and R²⁰ are as described herein. In embodiments, the compound has the formula:

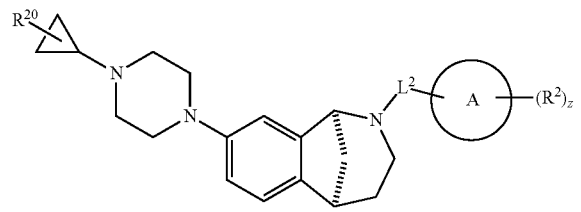

wherein L², z, Ring A, R², and R²⁰ are as described herein. In embodiments, the compound has the formula:

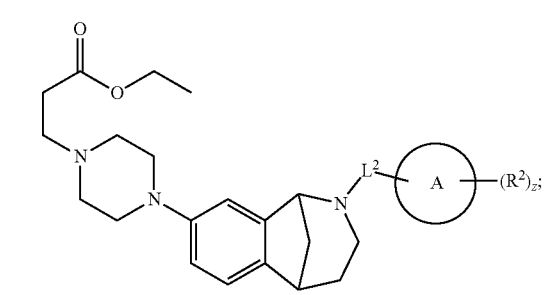

wherein L², z, Ring A, and R² are as described herein. In embodiments, the compound has the formula:

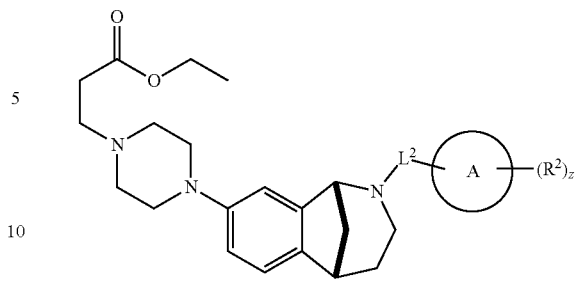

wherein L², z, Ring A, and R² are as described herein. In embodiments, the compound has the formula:

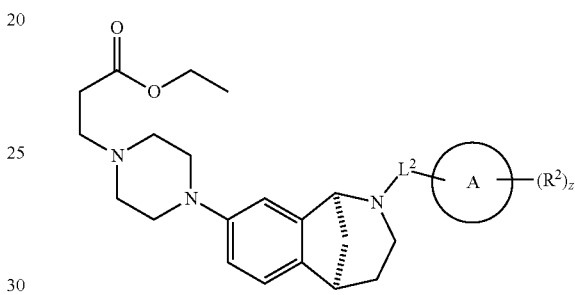

wherein L², z, Ring A, and R² are as described herein. In embodiments, the compound has the formula:

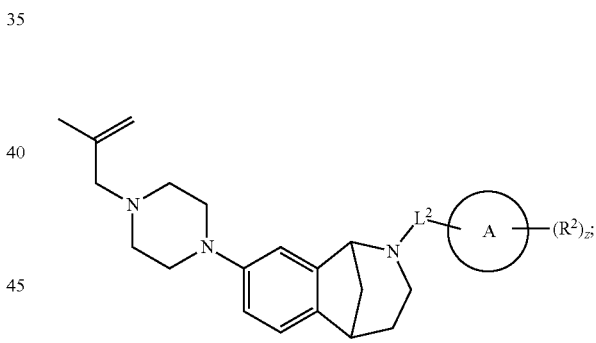

wherein L², z, Ring A, and R² are as described herein. In embodiments, the compound has the formula:

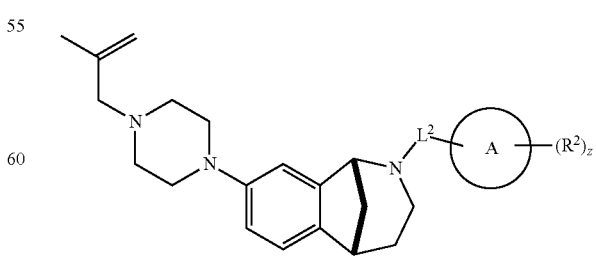

wherein L², z, Ring A, and R² are as described herein. In embodiments, the compound has the formula:

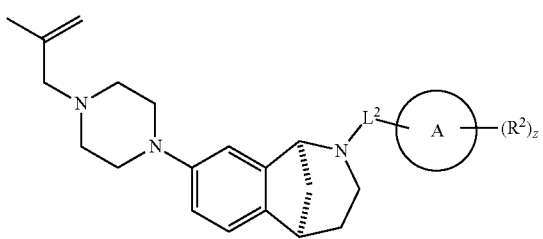

wherein $L^2$, z, Ring A, and $R^2$ are as described herein.
In embodiments, the compound has the formula:

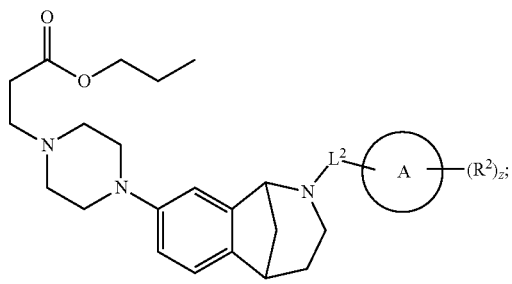

wherein $L^2$, z, Ring A, and $R^2$ are as described herein. In embodiments, the compound has the formula:

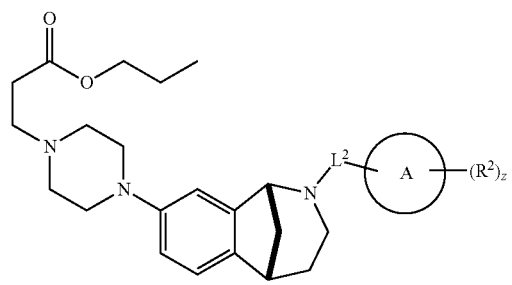

wherein $L^2$, z, Ring A, and $R^2$ are as described herein. In embodiments, the compound has the formula:

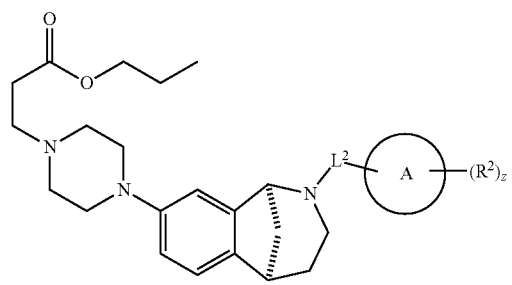

wherein $L^2$, z, Ring A, and $R^2$ are as described herein.

In embodiments, the compound has the formula:

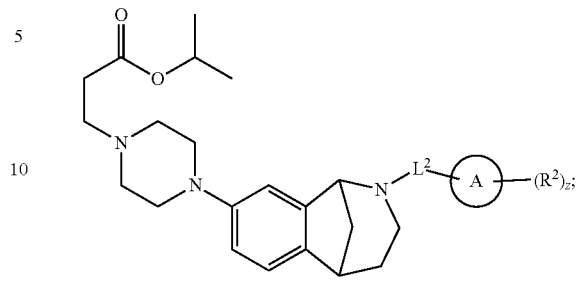

wherein $L^2$, z, Ring A, and $R^2$ are as described herein. In embodiments, the compound has the formula:

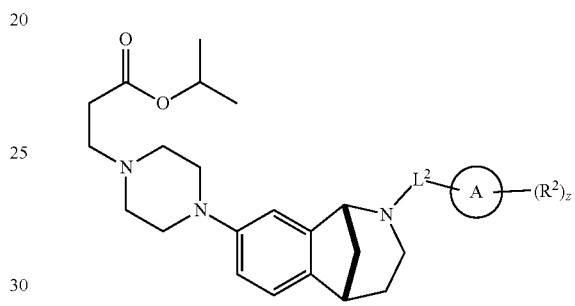

wherein $L^2$, z, Ring A, and $R^2$ are as described herein. In embodiments, the compound has the formula:

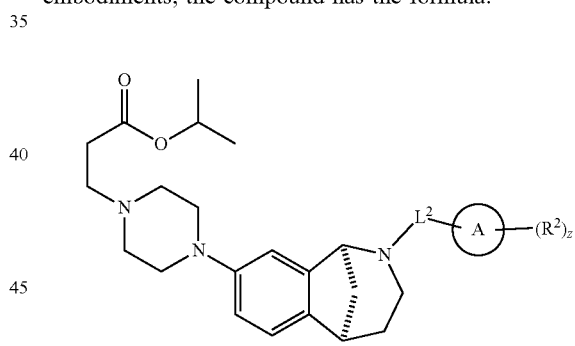

wherein $L^2$, z, Ring A, and $R^2$ are as described herein.

In embodiments, the compound has the formula:

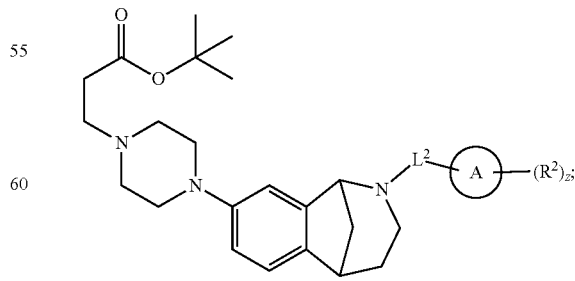

wherein $L^2$, z, Ring A, and $R^2$ are as described herein. In embodiments, the compound has the formula:

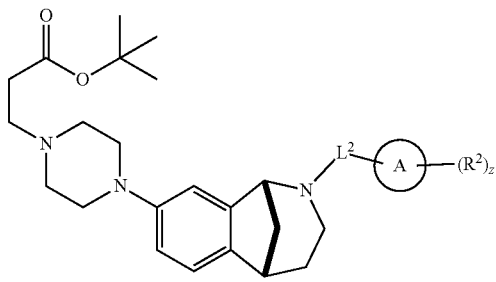

wherein $L^2$, z, Ring A, and $R^2$ are as described herein. In embodiments, the compound has the formula:

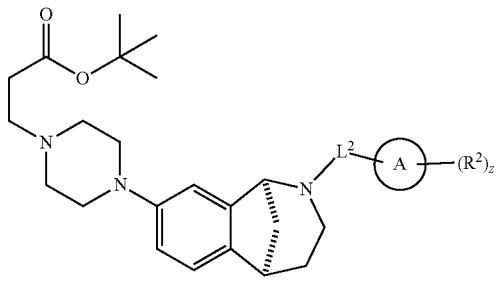

wherein $L^2$, z, Ring A, and $R^2$ are as described herein.

In embodiments, $R^1$ is independently hydrogen, halogen, $-CX_3^1$, $-CHX_2^1$, $-CH_2X^1$, $-OCX_3^1$, $-OCH_2X^1$, $-OCHX_2^1$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC=(O)NH_2$, $-NHSO_2H$, $-NHC=(O)H$, $-NHC(O)-OH$, $-NHOH$, $-OCHF_2$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^1$ is independently hydrogen, halogen, $-CX_3^1$, $-CHX_2^1$, $-CH_2X^1$, $-OCX_3^1$, $-OCH_2X^1$, $-OCHX_2^1$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC=(O)NH_2$, $-NHSO_2H$, $-NHC=(O)H$, $-NHC(O)-OH$, $-NHOH$, $-OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^1$ is independently $-F$, $-Cl$, $-Br$, or $-I$. In embodiments, $R^1$ is independently hydrogen. In embodiments, $R^1$ is independently unsubstituted methyl. In embodiments, $R^1$ is independently unsubstituted ethyl.

$R^{20}$ is independently oxo, halogen, $-CX_3^{20}$, $-CHX_2^{20}$, $-CH_2X^{20}$, $-OCX_3^{20}$, $-OCH_2X^{20}$, $-OCHX_2^{20}$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCHF_2$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered). In embodiments, $R^{20}$ is independently oxo, halogen, $-CX_3^{20}$, $-CHX_2^{20}$, $-CH_2X^{20}$, $-OCX_3^{20}$, $-OCH_2X^{20}$, $-OCHX_2^{20}$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20}$ is independently $-F$, $-Cl$, $-Br$, or $-I$. In embodiments, $R^{20}$ is independently hydrogen. In embodiments, $R^{20}$ is independently unsubstituted methyl. In embodiments, $R^{20}$ is independently unsubstituted ethyl.

$R^{21}$ is independently oxo, halogen, $-CX_3^{21}$, $-CHX_2^{21}$, $-CH_2X^{21}$, $-OCX_3^{21}$, $-OCH_2X^{21}$, $-OCHX_2^{21}$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). In embodiments, $R^{21}$ is independently oxo, halogen, $-CX_3^{21}$, $-CHX_2^{21}$, $-CH_2X^{21}$, $-OCX_3^{21}$, $-OCH_2X^{21}$, $-OCHX_2^{21}$, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21}$ is independently —F, —Cl, —Br, or —I. In embodiments, $R^{21}$ is independently hydrogen. In embodiments, $R^{21}$ is independently unsubstituted methyl. In embodiments, $R^{21}$ is independently unsubstituted ethyl.

$R^{22}$ is independently oxo, halogen, —$CX_3^{22}$, —$CHX_2^{22}$, —$CH_2X^{22}$, —$OCX_3^{22}$, —$OCH_2X^{22}$, —$OCHX_2^{22}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22}$ is independently —F, —Cl, —Br, or —I. In embodiments, $R^{22}$ is independently hydrogen. In embodiments, $R^{22}$ is independently unsubstituted methyl. In embodiments, $R^{22}$ is independently unsubstituted ethyl.

In embodiments, $R^2$ is independently hydrogen, oxo, halogen, —$CX_3^2$, —$CHX_2^2$, —$CH_2X^2$, —$OCX_3^2$, —$OCH_2X^2$, —$OCHX_2^2$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{23}$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 to 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 8 membered, 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). In embodiments, $R^2$ is independently hydrogen, halogen, —$CX_3^2$, —$CHX_2^2$, —$CH_2X^2$, —$OCX_3^2$, —$OCH_2X^2$, —$OCHX_2^2$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^2$ is independently —F, —Cl, —Br, or —I. In embodiments, $R^2$ is independently hydrogen. In embodiments, $R^2$ is independently unsubstituted methyl. In embodiments, $R^2$ is independently unsubstituted ethyl.

$R^{23}$ is independently oxo, halogen, —$CX_3^{23}$, —$CHX_2^{23}$, —$CH_2X^{23}$, —$OCX_3^{23}$, —$OCH_2X^{23}$, —$OCHX_2^{23}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{24}$—substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). In embodiments, $R^{23}$ is independently oxo, halogen, —$CX_3^{23}$, —$CHX_2^{23}$, —$CH_2X^{23}$, —$OCX_3^{23}$, —$OCH_2X^{23}$, —$OCHX_2^{23}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23}$ is independently —F, —Cl, —Br, or —I. In embodiments, $R^{23}$ is independently hydrogen. In embodiments, $R^{23}$ is independently unsubstituted methyl. In embodiments, $R^{23}$ is independently unsubstituted ethyl.

$R^{24}$ is independently oxo, halogen, —$CX_3^{24}$, —$CHX_2^{24}$, —$CH_2X^{24}$, —$OCX_3^{24}$, —$OCH_2X^{24}$, —$OCHX_2^{24}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). In embodiments, $R^{24}$ is independently oxo, halogen, —$CX_3^{24}$, —$CHX_2^{24}$, —$CH_2X^{24}$, —$OCX_3^{24}$, —$OCH_2X^{24}$, —$OCHX_2^{24}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24}$ is independently —F, —Cl, —Br, or —I. In embodiments, $R^{24}$ is independently hydrogen. In embodiments, $R^{24}$ is independently unsubstituted methyl. In embodiments, $R^{24}$ is independently unsubstituted ethyl.

$R^{25}$ is independently oxo, halogen, —$CX_3^{25}$, —$CHX_2^{25}$, —$CH_2X^{25}$, —$OCX_3^{25}$, —$OCH_2X^{25}$, —$OCHX_2^{25}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is independently —F, —Cl, —Br, or —I. In embodiments, $R^{25}$ is independently hydrogen. In embodiments, $R^{25}$ is independently unsubstituted methyl. In embodiments, $R^{25}$ is independently unsubstituted ethyl.

In embodiments, $R^7$ is independently hydrogen, halogen, —$CX_3^7$, —$CHX_2^7$, —$CH_2X^7$, —$OCX_3^7$, —$OCH_2X^7$, —$OCHX_2^7$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_4$-$C_6$, or $C_5$-$C_6$), $R^{38}$-substituted or unsubstituted heterocycloalkyl (e.g., 3 to 8 membered, 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered). In embodiments, $R^7$ is independently hydrogen, halogen, —$CX_3^7$, —$CHX_2^7$, —$CH_2X^7$, —$OCX_3^7$, —$OCH_2X^7$, —$OCHX_2^7$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^7$ is independently —F, —Cl, —Br, or —I. In embodiments, $R^7$ is independently hydrogen. In embodiments, $R^7$ is independently unsubstituted methyl. In embodiments, $R^7$ is independently unsubstituted ethyl. In embodiments, $R^7$ is independently hydrogen, —$CX_3^7$, —$CHX_2^7$, —$CH_2X^7$, —$CF_3$, —CN, —COOH, —$CONH_2$, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_3$-$C_6$, $C_4$-$C_6$, or $C_5$-$C_6$), $R^{38}$-substituted or unsubstituted heterocycloalkyl (e.g., 3 to 8 membered, 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered).

$R^{38}$ is independently oxo, halogen, —$CX_3^{38}$, —$CHX_2^{38}$, —$CH_2X^{38}$, —$OCX_3^{38}$, —$OCH_2X^{38}$, —$OCHX_2^{38}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 8 membered, 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). In embodiments, $R^{38}$ is independently oxo, halogen, —$CX_3^{38}$, —$CHX_2^{38}$, —$CH_2X^{38}$, —$OCX_3^{38}$, —$OCH_2X^{38}$, —$OCHX_2^{38}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38}$ is independently —F, —Cl, —Br, or —I. In embodiments, $R^{38}$ is independently hydrogen. In embodiments, $R^{38}$ is independently unsubstituted methyl. In embodiments, $R^{38}$ is independently unsubstituted ethyl.

$R^{39}$ is independently oxo, halogen, —$CX_3^{39}$, —$CHX_2^{39}$, —$CH_2X^{39}$, —$OCX_3^{39}$, —$OCH_2X^{39}$, —$OCHX_2^{39}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). In embodiments, $R^{39}$ is independently oxo, halogen, —$CX_3^{39}$, —$CHX_2^{39}$, —$CH_2X^{39}$, —$OCX_3^{39}$, —$OCH_2X^{39}$, —$OCHX_2^{39}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39}$ is independently —F, —Cl, —Br, or —I. In embodiments, $R^{39}$ is independently hydrogen. In embodiments, $R^{39}$ is independently unsubstituted methyl. In embodiments, $R^{39}$ is independently unsubstituted ethyl.

$R^{40}$ is independently oxo, halogen, —$CX_3^{40}$, —$CHX_2^{40}$, —$CH_2X^{40}$, —$OCX_3^{40}$, —$OCH_2X^{40}$, —$OCHX_2^{40}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40}$ is independently —F, —Cl, —Br, or —I. In embodiments, $R^{40}$ is independently hydrogen. In embodiments, $R^{40}$ is independently unsubstituted methyl. In embodiments, $R^{40}$ is independently unsubstituted ethyl.

In embodiments, $R^8$ is independently hydrogen, halogen, —$CX_3^8$, —$CHX_2^8$, —$CH_2X^8$, —$OCX_3^8$, —$OCH_2X^8$, —$OCHX_2^8$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., $C_6$-$C_{10}$ or phenyl), or $R^{41}$-substituted or unsubstituted heteroaryl (e.g., 5 to 10 membered, 5 to 9 membered, or 5 to 6 membered). In embodiments, $R^8$ is independently hydrogen, halogen, —$CX_3^8$, —$CHX_2^8$, —$CH_2X^8$, —$OCX_3^8$, —$OCH_2X^8$, —$OCHX_2^8$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^8$ is independently —F, —Cl, —Br, or —I. In embodiments, $R^8$ is independently hydrogen. In embodiments, $R^8$ is independently unsubstituted methyl. In embodiments, $R^8$ is independently unsubstituted ethyl. In embodiments, $R^8$ is independently hydrogen, —$CX_3^8$, —$CHX_2^8$, —$CH_2X^8$, —$CF_3$, —CN, —COOH, —$CONH_2$, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., $C_6$-$C_{10}$ or phenyl), or $R^{41}$-substituted or unsubstituted heteroaryl (e.g., 5 to 10 membered, 5 to 9 membered, or 5 to 6 membered).

$R^{41}$ is independently oxo, halogen, —$CX_3^{41}$, —$CHX_2^{41}$, —$CH_2X^{41}$, —$OCX_3^{41}$, —$OCH_2X^{41}$, —$OCHX_2^{41}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{42}$-substituted or unsubstituted alkyl (e.g., $C_1$-$C_8$, $C_1$-$C_6$, $C_1$-$C_4$, or $C_1$-$C_2$), $R^{42}$-substituted or unsubstituted heteroalkyl (e.g., 2 to 8 membered, 2 to 6 membered, 4 to 6 membered, 2 to 3 membered, or 4 to 5 membered), $R^{42}$-substituted or unsubstituted cycloalkyl (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., $C_6$-$C_{10}$ or phenyl), or $R^{42}$-substituted or unsubstituted heteroaryl (e.g., 5 to 10 membered, 5 to 9 membered, or 5 to 6 membered). In embodiments, $R^{41}$ is independently oxo, halogen, —$CX_3^{41}$, —$CHX_2^{41}$, —$CH_2X^{41}$, —$OCX_3^{41}$, —$OCH_2X^{41}$, —$OCHX_2^{41}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41}$ is independently —F, —Cl, —Br, or —I. In embodiments, $R^{41}$ is independently hydrogen. In embodiments, $R^{41}$ is independently unsubstituted methyl. In embodiments, $R^{41}$ is independently unsubstituted ethyl.

$R^{42}$ is independently oxo, halogen, —$CX_3^{42}$, —$CHX_2^{42}$, —$CH_2X^{42}$, —$OCX_3^{42}$, —$OCH_2X^{42}$, —$OCHX_2^{42}$, —$CF_3$, —CN, —OH, —$NH_2$, —COOH, —CONH$_2$, —NO$_2$, —SH, —SO$_3$H, —SO$_4$H, —SO$_2$NH$_2$, —NHNH$_2$, —NHC—(O)NHNH$_2$, —NHC═(O) NH$_2$, —NHSO$_2$H, —NHC═(O)H, —NHC(O)—OH, —NHOH, —OCF$_3$, —OCHF$_2$, —S(O)$_2$CHCH$_2$, —NHS(O)$_2$CHCH$_2$, R$^{43}$-substituted or unsubstituted alkyl (e.g., C$_1$-C$_8$, C$_1$-C$_6$, C$_1$-C$_4$, or C$_1$-C$_2$), R$^{43}$-substituted or unsubstituted heteroalkyl (e.g., 2 to 8 membered, 2 to 6 membered, 4 to 6 membered, 2 to 3 membered, or 4 to 5 membered), R$^{43}$-substituted or unsubstituted cycloalkyl (e.g., C$_3$-C$_8$, C$_3$-C$_6$, C$_4$-C$_6$, or C$_5$-C$_6$), R$^{43}$-substituted or unsubstituted heterocycloalkyl (e.g., 3 to 8 membered, 3 to 6 membered, 4 to 6 membered, 4 to 5 membered, or 5 to 6 membered), R$^{43}$-substituted or unsubstituted aryl (e.g., C$_6$-C$_{10}$ or phenyl), or R$^{43}$-substituted or unsubstituted heteroaryl (e.g., 5 to 10 membered, 5 to 9 membered, or 5 to 6 membered). In embodiments, R$^{42}$ is independently oxo, halogen, —CX$_3^{42}$, —CHX$_2^{42}$, —CH$_2$X$^{42}$, —OCX$_3^{42}$, —OCH$_2$X$^{42}$, —OCHX$_2^{42}$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —NHC—(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{42}$ is independently —F, —Cl, —Br, or —I. In embodiments, R$^{42}$ is independently hydrogen. In embodiments, R$^{42}$ is independently unsubstituted methyl. In embodiments, R$^{42}$ is independently unsubstituted ethyl.

R$^{43}$ is independently oxo, halogen, —CX$_3^{43}$, —CHX$_2^{43}$, —CH$_2$X$^{43}$, —OCX$_3^{43}$, —OCH$_2$X$^{43}$, —OCHX$_2^{43}$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{43}$ is independently —F, —Cl, —Br, or —I. In embodiments, R$^{43}$ is independently hydrogen. In embodiments, R$^{43}$ is independently unsubstituted methyl. In embodiments, R$^{43}$ is independently unsubstituted ethyl.

In embodiments, R$^9$ is independently hydrogen, halogen, —CX$_3^9$, —CHX$_2^9$, —CH$_2$X$^9$, —OCX$_3^9$, —OCH$_2$X$^9$, —OCHX$_2^9$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, R$^{44}$-substituted or unsubstituted alkyl (e.g., C$_1$-C$_8$, C$_1$-C$_6$, C$_1$-C$_4$, or C$_1$-C$_2$), R$^{44}$-substituted or unsubstituted heteroalkyl (e.g., 2 to 8 membered, 2 to 6 membered, 4 to 6 membered, 2 to 3 membered, or 4 to 5 membered), R$^{44}$-substituted or unsubstituted cycloalkyl (e.g., C$_3$-C$_8$, C$_4$-C$_6$, or C$_5$-C$_6$), R$^{44}$-substituted or unsubstituted heterocycloalkyl (e.g., 3 to 8 membered, 3 to 6 membered, 4 to 6 membered, 4 to 5 membered, or 5 to 6 membered), R$^{44}$-substituted or unsubstituted aryl (e.g., C$_6$-C$_{10}$ or phenyl), or R$^{44}$-substituted or unsubstituted heteroaryl (e.g., 5 to 10 membered, 5 to 9 membered, or 5 to 6 membered). In embodiments, R$^9$ is independently hydrogen, halogen, —CX$_3^9$, —CHX$_2^9$, —CH$_2$X$^9$, —OCX$_3^9$, —OCH$_2$X$^9$, —OCHX$_2^9$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^9$ is independently —F, —Cl, —Br, or —I. In embodiments, R$^9$ is independently hydrogen. In embodiments, R$^9$ is independently unsubstituted methyl. In embodiments, R$^9$ is independently unsubstituted ethyl. In embodiments, R$^9$ is independently hydrogen, —CX$_3^9$, —CHX$_2^9$, —CH$_2$X$^9$, —CF$_3$, —CN, —COOH, —CONH$_2$, R$^{44}$-substituted or unsubstituted alkyl (e.g., C$_1$-C$_8$, C$_1$-C$_6$, C$_1$-C$_4$, or C$_1$-C$_2$), R$^{44}$-substituted or unsubstituted heteroalkyl (e.g., 2 to 8 membered, 2 to 6 membered, 4 to 6 membered, 2 to 3 membered, or 4 to 5 membered), R$^{44}$-substituted or unsubstituted cycloalkyl (e.g., C$_3$-C$_8$, C$_3$-C$_6$, C$_4$-C$_6$, or C$_5$-C$_6$), R$^{44}$-substituted or unsubstituted heterocycloalkyl (e.g., 3 to 8 membered, 3 to 6 membered, 4 to 6 membered, 4 to 5 membered, or 5 to 6 membered), R$^{44}$-substituted or unsubstituted aryl (e.g., C$_6$-C$_{10}$ or phenyl), or R$^{44}$-substituted or unsubstituted heteroaryl (e.g., 5 to 10 membered, 5 to 9 membered, or 5 to 6 membered).

R$^{44}$ is independently oxo, halogen, —CX$_3^{44}$, —CHX$_2^{44}$, —CH$_2$X$^{44}$, —OCX$_3^{44}$, —OCH$_2$X$^{44}$, —OCHX$_2^{44}$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC—(O)NHNH$_2$, —NHC═(O) NH$_2$, —NHSO$_2$H, —NHC═(O)H, —NHC(O)—OH, —NHOH, —OCF$_3$, —OCHF$_2$, R$^{45}$-substituted or unsubstituted alkyl (e.g., C$_1$-C$_8$, C$_1$-C$_6$, C$_1$-C$_4$, or C$_1$-C$_2$), R$^{45}$-substituted or unsubstituted heteroalkyl (e.g., 2 to 8 membered, 2 to 6 membered, 4 to 6 membered, 2 to 3 membered, or 4 to 5 membered), R$^{45}$-substituted or unsubstituted cycloalkyl (e.g., C$_3$-C$_8$, C$_3$-C$_6$, C$_4$-C$_6$, or C$_5$-C$_6$), R$^{45}$-substituted or unsubstituted heterocycloalkyl (e.g., 3 to 8 membered, 3 to 6 membered, 4 to 6 membered, 4 to 5 membered, or 5 to 6 membered), R$^{45}$-substituted or unsubstituted aryl (e.g., C$_6$-C$_{10}$ or phenyl), or R$^{45}$-substituted or unsubstituted heteroaryl (e.g., 5 to 10 membered, 5 to 9 membered, or 5 to 6 membered). In embodiments, R$^{44}$ is independently oxo, halogen, —CX$_3^{44}$, —CHX$_2^{44}$, —CH$_2$X$^{44}$, —OCX$_3^{44}$, —OCH$_2$X$^{44}$, —OCHX$_2^{44}$, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC—(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{44}$ is independently —F, —Cl, —Br, or —I. In embodiments, $R^{44}$ is independently hydrogen. In embodiments, $R^{44}$ is independently unsubstituted methyl. In embodiments, $R^{44}$ is independently unsubstituted ethyl.

$R^{45}$ is independently oxo, halogen, —$CX_3^{45}$, —$CHX_2^{45}$, —$CH_2X^{45}$, —$OCX_3^{45}$, —$OCH_2X^{45}$, —$OCHX_2^{45}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{46}$— substituted or unsubstituted alkyl (e.g., $C_1$-$C_8$, $C_1$-$C_6$, $C_1$-$C_4$, or $C_1$-$C_2$), $R^{46}$-substituted or unsubstituted heteroalkyl (e.g., 2 to 8 membered, 2 to 6 membered, 4 to 6 membered, 2 to 3 membered, or 4 to 5 membered), $R^{46}$-substituted or unsubstituted cycloalkyl (e.g., $C_3$-$C_8$, $C_3$-$C_6$, $C_3$-$C_6$, $C_4$-$C_6$, or $C_5$-$C_6$), $R^{46}$-substituted or unsubstituted heterocycloalkyl (e.g., 3 to 8 membered, 3 to 6 membered, 4 to 6 membered, 4 to 5 membered, or 5 to 6 membered), $R^{46}$-substituted or unsubstituted aryl (e.g., $C_6$-$C_{10}$ or phenyl), or $R^{46}$-substituted or unsubstituted heteroaryl (e.g., 5 to 10 membered, 5 to 9 membered, or 5 to 6 membered). In embodiments, $R^{45}$ is independently oxo, halogen, —$CX_3^{45}$, —$CHX_2^{45}$, —$CH_2X^{45}$, —$OCX_3^{45}$, —$OCH_2X^{45}$, —$OCHX_2^{45}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{45}$ is independently —F, —Cl, —Br, or —I. In embodiments, $R^{45}$ is independently hydrogen. In embodiments, $R^{45}$ is independently unsubstituted methyl. In embodiments, $R^{45}$ is independently unsubstituted ethyl.

$R^{46}$ is independently oxo, halogen, —$CX_3^{46}$, —$CHX_2^{46}$, —$CH_2X^{46}$, —$OCX_3^{46}$, —$OCH_2X^{46}$, —$OCHX_2^{46}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{46}$ is independently —F, —Cl, —Br, or —I. In embodiments, $R^{46}$ is independently hydrogen. In embodiments, $R^{46}$ is independently unsubstituted methyl. In embodiments, $R^{46}$ is independently unsubstituted ethyl.

In embodiments, $R^{10}$ is independently hydrogen, halogen, —$CX_3^{10}$, —$CHX_2^{10}$, —$CH_2X^{10}$, —$OCX_3^{10}$, —$OCH_2X^{10}$, —$OCHX_2^{10}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{47}$-substituted or unsubstituted alkyl (e.g., $C_1$-$C_8$, $C_1$-$C_4$, or $C_1$-$C_2$), $R^{47}$-substituted or unsubstituted heteroalkyl (e.g., 2 to 8 membered, 2 to 6 membered, 4 to 6 membered, 2 to 3 membered, or 4 to 5 membered), $R^{47}$-substituted or unsubstituted cycloalkyl (e.g., $C_3$-$C_8$, $C_4$-$C_6$, or $C_5$-$C_6$), $R^{47}$-substituted or unsubstituted heterocycloalkyl (e.g., 3 to 8 membered, 3 to 6 membered, 4 to 6 membered, 4 to 5 membered, or 5 to 6 membered), $R^{47}$-substituted or unsubstituted aryl (e.g., $C_6$-$C_{10}$ or phenyl), or $R^{47}$-substituted or unsubstituted heteroaryl (e.g., 5 to 10 membered, 5 to 9 membered, or 5 to 6 membered). In embodiments, $R^{10}$ is independently hydrogen, halogen, —$CX_3^{10}$, —$CHX_2^{10}$, —$CH_2X^{10}$, —$OCX_3^{10}$, —$OCH_2X^{10}$, —$OCHX_2^{10}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{10}$ is independently —F, —Cl, —Br, or —I. In embodiments, $R^{10}$ is independently hydrogen. In embodiments, $R^{10}$ is independently unsubstituted methyl. In embodiments, $R^{10}$ is independently unsubstituted ethyl. In embodiments, $R^{10}$ is independently hydrogen, —$CX_3^{10}$, —$CHX_2^{10}$, —$CH_2X^{10}$, —$CF_3$, —CN, —COOH, —$CONH_2$, $R^{47}$-substituted or unsubstituted alkyl (e.g., $C_1$-$C_8$, $C_1$-$C_6$, $C_1$-$C_6$, $C_1$-$C_4$, or $C_1$-$C_2$), $R^{47}$-substituted or unsubstituted heteroalkyl (e.g., 2 to 8 membered, 2 to 6 membered, 4 to 6 membered, 2 to 3 membered, or 4 to 5 membered), $R^{47}$-substituted or unsubstituted cycloalkyl (e.g., $C_3$-$C_8$, $C_3$-$C_6$, $C_4$-$C_6$, or $C_5$-$C_6$), $R^{47}$-substituted or unsubstituted heterocycloalkyl (e.g., 3 to 8 membered, 3 to 6 membered, 4 to 6 membered, 4 to 5 membered, or 5 to 6 membered), $R^{47}$-substituted or unsubstituted aryl (e.g., $C_6$-$C_{10}$ or phenyl), or $R^{47}$-substituted or unsubstituted heteroaryl (e.g., 5 to 10 membered, 5 to 9 membered, or 5 to 6 membered).

$R^{47}$ is independently oxo, halogen, —$CX_3^{47}$, —$CHX_2^{47}$, —$CH_2X^{47}$, —$OCX_3^{47}$, —$OCH_2X^{47}$, —$OCHX_2^{47}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{48}$-substituted or unsubstituted alkyl (e.g., $C_1$-$C_8$, $C_1$-$C_6$, $C_1$-$C_4$, or $C_1$-$C_2$), $R^{48}$-substituted or unsubstituted heteroalkyl (e.g., 2 to 8 membered, 2 to 6 membered, 4 to 6 membered, 2 to 3 membered, or 4 to 5 membered), $R^{48}$-substituted or unsubstituted cycloalkyl (e.g., $C_3$-$C_8$, $C_3$-$C_6$, $C_4$-$C_6$, or $C_5$-$C_6$), $R^{48}$-substituted or unsubstituted heterocycloalkyl (e.g., 3 to 8 membered, 3 to 6 membered, 4 to 6 membered, 4 to 5 membered, or 5 to 6 membered), $R^{48}$-substituted or unsubstituted aryl (e.g., $C_6$-$C_{10}$ or phenyl), or $R^{48}$-substituted or unsubstituted heteroaryl (e.g., 5 to 10 membered, 5 to 9 membered, or 5 to 6 membered). In embodiments, $R^{47}$ is independently oxo,
halogen, —$CX_3^{47}$, —$CHX_2^{47}$, —$CH_2X^{47}$, —$OCX_3^{47}$, —$OCH_2X^{47}$, —$OCHX_2^{47}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{47}$ is independently —F, —Cl, —Br, or —I. In embodiments, $R^{47}$ is independently hydrogen. In embodiments, $R^{47}$ is independently unsubstituted methyl. In embodiments, $R^{47}$ is independently unsubstituted ethyl.

$R^{48}$ is independently oxo,
halogen, —$CX_3^{48}$, —$CHX_2^{48}$, —$CH_2X^{48}$, —$OCX_3^{48}$, —$OCH_2X^{48}$, —$OCHX_2^{48}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{49}$-substituted or unsubstituted alkyl (e.g., $C_1$-$C_8$, $C_1$-$C_6$, $C_1$-$C_4$, or $C_1$-$C_2$), $R^{49}$-substituted or unsubstituted heteroalkyl (e.g., 2 to 8 membered, 2 to 6 membered, 4 to 6 membered, 2 to 3 membered, or 4 to 5 membered), $R^{49}$-substituted or unsubstituted cycloalkyl (e.g., $C_3$-$C_8$, $C_3$-$C_6$, $C_4$-$C_6$, or $C_5$-$C_6$), $R^{49}$-substituted or unsubstituted heterocycloalkyl (e.g., 3 to 8 membered, 3 to 6 membered, 4 to 6 membered, 4 to 5 membered, or 5 to 6 membered), $R^{49}$-substituted or unsubstituted aryl (e.g., $C_6$-$C_{10}$ or phenyl), or $R^{49}$-substituted or unsubstituted heteroaryl (e.g., 5 to 10 membered, 5 to 9 membered, or 5 to 6 membered). In embodiments, $R^{48}$ is independently oxo,
halogen, —$CX_3^{48}$, —$CHX_2^{48}$, —$CH_2X^{48}$, —$OCX_3^{48}$, —$OCH_2X^{48}$, —$OCHX_2^{48}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{48}$ is independently —F, —Cl, —Br, or —I. In embodiments, $R^{48}$ is independently hydrogen. In embodiments, $R^{48}$ is independently unsubstituted methyl. In embodiments, $R^{48}$ is independently unsubstituted ethyl.

$R^{49}$ is independently oxo,
halogen, —$CX_3^{49}$, —$CHX_2^{49}$, —$CH_2X^{49}$, —$OCX_3^{49}$, —$OCH_2X^{49}$, —$OCHX_2^{49}$, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{49}$ is independently —F, —Cl, —Br, or —I. In embodiments, $R^{49}$ is independently hydrogen. In embodiments, $R^{49}$ is independently unsubstituted methyl. In embodiments, $R^{49}$ is independently unsubstituted ethyl.

In embodiments, $R^{22}$, $R^{25}$, $R^{40}$, $R^{43}$, $R^{46}$ and $R^{49}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$, $R^{25}$, $R^{40}$, $R^{43}$, and $R^{49}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$, $R^{25}$, $R^{40}$, $R^{43}$, $R^{46}$, and $R^{49}$ are independently oxo,
halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, —$L^1$-$R^1$ is

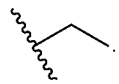

In embodiments, —$L^1$-$R^1$ is

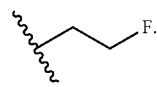 [SMILES: *CCF]

In embodiments, —$L^1$-$R^1$ is

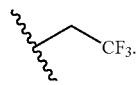

In embodiments, —L¹-R¹ is
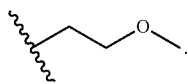 [SMILES: *CCOC]
In embodiments, —L¹-R¹ is
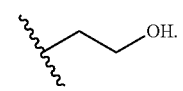
In embodiments, —L¹-R¹ is
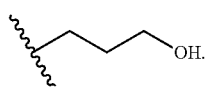 [SMILES: *CCCO]
In embodiments, —L¹-R¹ is
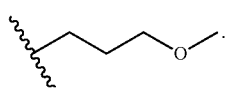 [SMILES: *CCCOC]
In embodiments, —L¹-R¹ is
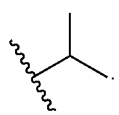
In embodiments, —L¹-R¹ is
In embodiments, —L¹-R¹ is
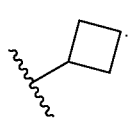
In embodiments, —L¹-R¹ is
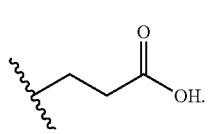 [SMILES: *CCC(=O)O]
In embodiments, —L¹-R¹ is
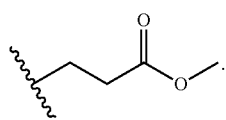 [SMILES: *CCC(=O)OC]
In embodiments, —L¹-R¹ is
In embodiments, —L¹-R¹ is
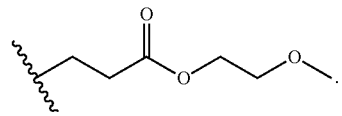 [SMILES: *CCC(=O)OCCOC]
In embodiments, —L¹-R¹ is
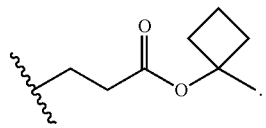 [SMILES: *CCC(=O)OC1(C)CCC1]
In embodiments, —L¹-R¹ is
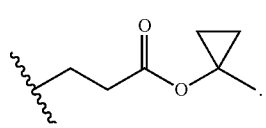 [SMILES: *CCC(=O)OC1(C)CC1]
In embodiments, —L¹-R¹ is
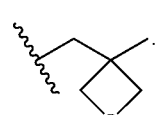
In embodiments, —L¹-R¹ is
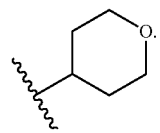 [SMILES: *C1CCOCC1]

In embodiments, —L¹-R¹ is

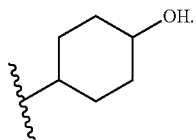 [SMILES: *C1CCC(O)CC1]

In embodiments, —L¹-R¹ is

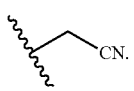

In embodiments, —L¹-R¹ is

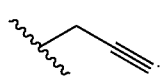

In embodiments, —L¹-R¹ is

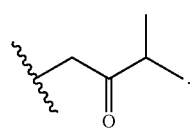 [SMILES: *CC(=O)C(C)C]

In embodiments, —L¹-R¹ is

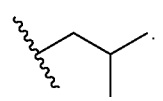

In embodiments, —L¹-R¹ is

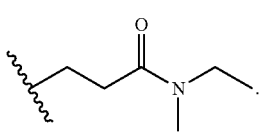 [SMILES: *CCC(=O)N(C)CC]

In embodiments, —L¹-R¹ is

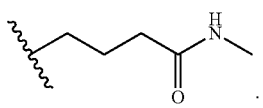 [SMILES: *CCCC(=O)NC]

In embodiments, —L¹-R¹ is

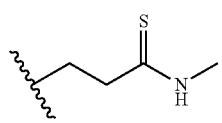

In embodiments, —L¹-R¹ is

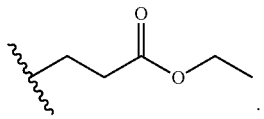 [SMILES: *CCC(=O)OCC]

In embodiments, —L¹-R¹ is

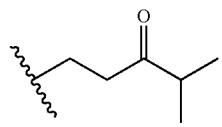

In embodiments, L¹ is a bond and R¹ is unsubstituted ethyl. In embodiments, L¹ is a bond and R¹ is unsubstituted propyl. In embodiments, L¹ is a bond and R¹ is unsubstituted n-propyl. In embodiments, L¹ is a bond and R¹ is unsubstituted isopropyl. In embodiments, L¹ is a bond and R¹ is unsubstituted butyl. In embodiments, L¹ is a bond and R¹ is unsubstituted n-butyl. In embodiments, L¹ is a bond and R¹ is unsubstituted isobutyl. In embodiments, L¹ is a bond and R¹ is unsubstituted tert-butyl. In embodiments, L¹ is a bond and R¹ is trifluoromethyl. In embodiments, L¹ is a bond and R¹ is trichloromethyl. In embodiments, L¹ is a bond and R¹ is unsubstituted methoxy. In embodiments, L¹ is a bond and R¹ is unsubstituted ethoxy. In embodiments, L¹ is a bond and R¹ is trifluoromethoxy. In embodiments, L¹ is a bond and R¹ is —OH. In embodiments, L¹ is a bond and R¹ is unsubstituted cyclopropyl. In embodiments, L¹ is a bond and R¹ is unsubstituted cyclobutyl. In embodiments, L¹ is a bond and R¹ is unsubstituted cyclopentyl. In embodiments, L¹ is a bond and R¹ is unsubstituted cyclohexyl. In embodiments, L¹ is a bond and R¹ is unsubstituted cycloheptyl. In embodiments, L¹ is a bond and R¹ is unsubstituted oxetanyl. In embodiments, L¹ is a bond and R¹ is methyl-substituted oxetanyl. In embodiments, L¹ is a bond and R¹ is unsubstituted piperidinyl. In embodiments, L¹ is a bond and R¹ is unsubstituted oxanyl. In embodiments, L¹ is a bond and R¹ is unsubstituted tetrahydropyranyl. In embodiments, L¹ is a bond and R¹ is unsubstituted cyclohexyl. In embodiments, L¹ is a bond and R¹ is hydroxyl substituted cyclohexyl. In embodiments, L¹ is a bond and R¹ is —CN. In embodiments, L¹ is a bond and R¹ is unsubstituted ethynyl. In embodiments, L¹ is a bond and R¹ is —C(O)CH(CH₃)₂. In embodiments, L¹ is a bond and R¹ is —CH(CH₃)₂. In embodiments, L¹ is a bond and R¹ is —COOH. In embodiments, L¹ is a bond and R¹ is —C(O)OMe. In embodiments, L¹ is a bond and R¹ is —C(O)OEt. In embodiments, L¹ is a bond and R¹ is —C(O)OCH(CH₃)₂. In embodiments, L¹ is a bond and R¹ is —C(O)OCH₂CH₂OCH₃. In embodiments, L¹ is a bond and R¹ is —C(O)OCH₂CH₂OCH₂CH₃. In embodiments, L¹ is a bond and R¹ is —C(O)O(methyl substituted cyclobutyl). In embodiments, L¹ is a bond and R¹ is —C(O)O(methyl substituted cyclopropyl). In embodiments, L¹ is a bond and R¹ is —C(O)N(CH₃)(CH₂CH₃). In embodiments, L¹ is a bond and R¹ is —C(O)N(CH₃)(CH₃). In embodiments, L¹ is a bond and R¹ is —OC(O)NH(CH₃). In embodiments, L¹ is a bond and R¹ is OC(O)N(CH₃)(CH₃). In embodiments, L¹ is a bond and R¹ is —OC(O)N(CH₂CH₃)(CH₂CH₃). In embodiments, L¹ is a bond and R¹ is —C(S)N(CH₃)(CH₂CH₃). In embodiments, L¹ is a bond and R¹ is —C(S)N(CH₃)(CH₃). In embodiments, L¹ is a bond and R¹ is —C(S)NH(CH₃). In embodiments, L¹ is a bond and R¹ is —C(S)N(CH₂CH₃)(CH₂CH₃). In embodiments, L¹ is a bond and R¹ is —CH₂CH₂CH₃. In embodiments, L¹ is a bond and R¹ is —C(O)OCH₂CH₃. In embodiments, L¹ is a bond and R¹ is —C(O)OCH₂CH₃. In embodiments, L¹ is a bond and R¹ is —CH₂C(CH₂)(CH₃). In embodiments, L¹ is a bond and R¹ is —C(CH₂)(CH₃). In embodiments, L¹ is a bond and R¹ is —C(CH₂)(CH₂CH₃). In embodiments, L¹ is a bond and R¹ is —C(CHCH₃)(CH₃). In embodiments, L¹ is a bond and R¹ is —C(C(CH₃)₂)(CH₃).

In embodiments, L¹ is an unsubstituted methylene and R¹ is unsubstituted methyl. In embodiments, L¹ is an unsubstituted methylene and R¹ is unsubstituted ethyl. In embodiments, L¹ is an unsubstituted methylene and R¹ is unsubstituted propyl. In embodiments, L¹ is an unsubstituted methylene and R¹ is unsubstituted isopropyl. In embodiments, L¹ is an unsubstituted methylene and R¹ is unsubstituted butyl. In embodiments, L¹ is an unsubstituted methylene and R¹ is unsubstituted isobutyl. In embodiments, L¹ is an unsubstituted methylene and R¹ is unsubstituted tert-butyl. In embodiments, L¹ is an unsubstituted methylene and R¹ is trifluoromethyl. In embodiments, L¹ is an unsubstituted methylene and R¹ is trichloromethyl. In embodiments, L¹ is an unsubstituted methylene and R¹ is unsubstituted methoxy. In embodiments, L¹ is an unsubstituted methylene and R¹ is unsubstituted ethoxy. In embodiments, L¹ is an unsubstituted methylene and R¹ is trifluoromethoxy. In embodiments, L¹ is an unsubstituted methylene and R¹ is —OH. In embodiments, L¹ is an unsubstituted methylene and R¹ is unsubstituted cyclopropyl. In embodiments, L¹ is an unsubstituted methylene and R¹ is unsubstituted cyclobutyl. In embodiments, L¹ is an unsubstituted methylene and R¹ is unsubstituted cyclopentyl. In embodiments, L¹ is an unsubstituted methylene and R¹ is unsubstituted oxetanyl. In embodiments, L¹ is an unsubstituted methylene and R¹ is methyl-substituted oxetanyl. In embodiments, L¹ is an unsubstituted methylene and R¹ is unsubstituted piperidinyl. In embodiments, L¹ is an unsubstituted methylene and R¹ is unsubstituted oxanyl. In embodiments, L¹ is an unsubstituted methylene and R¹ is unsubstituted tetrahydropyranyl. In embodiments, L¹ is an unsubstituted methylene and R¹ is unsubstituted cyclohexyl. In embodiments, L¹ is an unsubstituted methylene and R¹ is hydroxyl substituted cyclohexyl. In embodiments, L¹ is an unsubstituted methylene and R¹ is —CN. In embodiments, L¹ is an unsubstituted methylene and R¹ is unsubstituted ethynyl. In embodiments, L¹ is an unsubstituted methylene and R¹ is —C(O)CH(CH₃)₂. In embodiments, L¹ is an unsubstituted methylene and R¹ is —CH(CH₃)₂. In embodiments, L¹ is an unsubstituted methylene and R¹ is —COOH. In embodiments, L¹ is an unsubstituted methylene and R¹ is —C(O)OMe. In embodiments, L¹ is an unsubstituted methylene and R¹ is —C(O)OEt. In embodiments, L¹ is an unsubstituted methylene and R¹ is —C(O)OCH(CH₃)₂. In embodiments, L¹ is an unsubstituted methylene and R¹ is —C(O)OCH₂CH₂OCH₃. In embodiments, L¹ is an unsubstituted methylene and R¹ is —C(O)OCH₂CH₂OCH₂CH₃. In embodiments, L¹ is an unsubstituted methylene and R¹ is —C(O)O(methyl substituted cyclobutyl). In embodiments, L¹ is an unsubstituted methylene and R¹ is C(O)O(methyl substituted cyclopropyl). In embodiments, L¹ is an unsubstituted methylene and R¹ is —C(O)N(CH₃)(CH₂CH₃). In embodiments, L¹ is an unsubstituted methylene and R¹ is —C(O)N(CH₃)(CH₃). In embodiments, L¹ is an unsubstituted methylene and R¹ is —OC(O)NH(CH₃). In embodiments, L¹ is an unsubstituted methylene and R¹ is —OC(O)N(CH₃)(CH₃). In embodiments, L¹ is an unsubstituted methylene and R¹ is —OC(O)N(CH₂CH₃)(CH₂CH₃). In embodiments, L¹ is an unsubstituted methylene and R¹ is —C(S)N(CH₃)(CH₂CH₃). In embodiments, L¹ is an unsubstituted methylene and R¹ is —C(S)N(CH₃)(CH₃). In embodiments, L¹ is an unsubstituted methylene and R¹ is —C(S)NH(CH₃). In embodiments, L¹ is an unsubstituted methylene and R¹ is —C(S)N(CH₂CH₃)(CH₂CH₃). In embodiments, L¹ is an unsubstituted methylene and R¹ is —CH₂CH₂CH₃. In embodiments, L¹ is an unsubstituted methylene and R¹ is —C(O)OCH₂CH₂CH₃. In embodiments, L¹ is an unsubstituted methylene and R¹ is —C(O)OCH₂CH₃. In embodiments, L¹ is an unsubstituted methylene and R¹ is —CH₂C(CH₂)(CH₃). In embodiments, L¹ is an unsubstituted methylene and R¹ is —C(CH₂)(CH₃). In embodiments, L¹ is an unsubstituted methylene and R¹ is —C(CH₂)(CH₂CH₃). In embodiments, L¹ is an unsubstituted methylene and R¹ is —C(CHCH₃)(CH₃). In embodiments, L¹ is an unsubstituted methylene and R¹ is —C(C(CH₃)₂)(CH₃).

In embodiments, L¹ is an unsubstituted ethylene and R¹ is unsubstituted methyl. In embodiments, L¹ is an unsubstituted ethylene and R¹ is unsubstituted ethyl. In embodiments, L¹ is an unsubstituted ethylene and R¹ is unsubstituted propyl. In embodiments, L¹ is an unsubstituted ethylene and R¹ is unsubstituted isopropyl. In embodiments, L¹ is an unsubstituted ethylene and R¹ is unsubstituted butyl. In embodiments, L¹ is an unsubstituted ethylene and R¹ is unsubstituted isobutyl. In embodiments, L¹ is an unsubstituted ethylene and R¹ is unsubstituted tert-butyl. In embodiments, L¹ is an unsubstituted ethylene and R¹ is trifluoromethyl. In embodiments, L¹ is an unsubstituted ethylene and R¹ is trichloromethyl. In embodiments, L¹ is an unsubstituted ethylene and R¹ is unsubstituted methoxy. In embodiments, L¹ is an unsubstituted ethylene and R¹ is unsubstituted ethoxy. In embodiments, L¹ is an unsubstituted ethylene and R¹ is trifluoromethoxy. In embodiments, L¹ is an unsubstituted ethylene and R¹ is —OH. In embodiments, L¹ is an unsubstituted ethylene and R¹ is unsubstituted cyclopropyl. In embodiments, L¹ is an unsubstituted ethylene and R¹ is unsubstituted cyclobutyl. In embodiments, L¹ is an unsubstituted ethylene and R¹ is unsubstituted cyclopentyl. In embodiments, L¹ is an unsubstituted ethylene and R¹ is unsubstituted oxetanyl. In embodiments, L¹ is an unsubstituted ethylene and R¹ is methyl-substituted oxetanyl. In embodiments, L¹ is an unsubstituted ethylene and R¹ is unsubstituted piperidinyl. In embodiments, L¹ is an unsubstituted ethylene and R¹ is unsubstituted oxanyl. In embodiments, L¹ is an unsubstituted ethylene and R¹ is unsubstituted tetrahydropyranyl. In embodiments, L¹ is an unsubstituted ethylene and R¹ is unsubstituted cyclohexyl. In embodiments, L¹ is an unsubstituted ethylene and R¹ is hydroxyl substituted cyclohexyl. In embodiments, L¹ is an unsubstituted ethylene and R¹ is —CN. In embodiments, L¹ is an unsubstituted ethylene and R¹ is unsubstituted ethynyl. In embodiments, L¹ is an unsubstituted ethylene and R¹ is —C(O)CH(CH₃)₂. In embodiments, L¹ is an unsubstituted ethylene and R¹ is —CH(CH₃)₂. In embodiments, L¹ is an unsubstituted ethylene and R¹ is —COOH. In embodiments, L¹ is an unsubstituted ethylene and R¹ is —C(O)OMe. In embodiments, L¹ is an unsubstituted ethylene and R¹ is —C(O)OEt. In embodiments, L¹ is an unsubstituted ethylene and R¹ is —C(O)OCH(CH₃)₂. In embodiments, L¹ is an unsubstituted ethylene and R¹ is —C(O)OCH₂CH₂OCH₃. In embodiments, L¹ is an unsubstituted ethylene and R¹ is —C(O)OCH₂CH₂OCH₂CH₃. In embodiments, L¹ is an unsubstituted ethylene and R¹ is —C(O)O(methyl substituted cyclobutyl). In embodiments, L¹ is an unsubstituted ethylene and R¹ is C(O)O(methyl substituted cyclopropyl).

In embodiments, L¹ is an unsubstituted ethylene and R¹ is —C(O)N(CH₃)(CH₂CH₃). In embodiments, L¹ is an unsubstituted ethylene and R¹ is —C(O)N(CH₃)(CH₃). In embodiments, L¹ is an unsubstituted ethylene and R¹ is —OC(O)NH(CH₃). In embodiments, L¹ is an unsubstituted ethylene and R¹ is —OC(O)N(CH₃)(CH₃). In embodiments, L¹ is an unsubstituted ethylene and R¹ is —OC(O)N(CH₂CH₃)(CH₂CH₃). In embodiments, L¹ is an unsubstituted ethylene and R¹ is —C(S)N(CH₃)(CH₂CH₃). In embodiments, L¹ is an unsubstituted ethylene and R¹ is —C(S)N(CH₃)(CH₃). In embodiments, L¹ is an unsubstituted ethylene and R¹ is —C(S)NH(CH₃). In embodiments, L¹ is an unsubstituted ethylene and R¹ is —C(S)N(CH₂CH₃)(CH₂CH₃). In embodiments, L¹ is an unsubstituted ethylene and R¹ is —CH₂CH₂CH₃. In embodiments, L¹ is an unsubstituted ethylene and R¹ is —C(O)OCH₂CH₂CH₃. In embodiments, L¹ is an unsubstituted ethylene and R¹ is —C(O)OCH₂CH₃. In embodiments, L¹ is an unsubstituted ethylene and R¹ is —CH₂C(CH₂)(CH₃). In embodiments, L¹ is an unsubstituted ethylene and R¹ is —C(CH₂)(CH₃). In embodiments, L¹ is an unsubstituted ethylene and R¹ is —C(CH₂)(CH₂CH₃). In embodiments, L¹ is an unsubstituted ethylene and R¹ is —C(CHCH₃)(CH₃). In embodiments, L¹ is an unsubstituted ethylene and R¹ is —C(C(CH₃)₂)(CH₃).

In embodiments, L¹ is an unsubstituted propylene and R¹ is unsubstituted methyl. In embodiments, L¹ is an unsubstituted propylene and R¹ is unsubstituted ethyl. In embodiments, L¹ is an unsubstituted propylene and R¹ is unsubstituted propyl. In embodiments, L¹ is an unsubstituted propylene and R¹ is unsubstituted isopropyl. In embodiments, L¹ is an unsubstituted propylene and R¹ is unsubstituted butyl. In embodiments, L¹ is an unsubstituted propylene and R¹ is unsubstituted isobutyl. In embodiments, L¹ is an unsubstituted propylene and R¹ is unsubstituted tert-butyl. In embodiments, L¹ is an unsubstituted propylene and R¹ is trifluoromethyl. In embodiments, L¹ is an unsubstituted propylene and R¹ is trichloromethyl. In embodiments, L¹ is an unsubstituted propylene and R¹ is unsubstituted methoxy. In embodiments, L¹ is an unsubstituted propylene and R¹ is unsubstituted ethoxy. In embodiments, L¹ is an unsubstituted propylene and R¹ is trifluoromethoxy. In embodiments, L¹ is an unsubstituted propylene and R¹ is —OH. In embodiments, L¹ is an unsubstituted propylene and R¹ is unsubstituted cyclopropyl. In embodiments, L¹ is an unsubstituted propylene and R¹ is unsubstituted cyclobutyl. In embodiments, L¹ is an unsubstituted propylene and R¹ is unsubstituted cyclopentyl. In embodiments, L¹ is an unsubstituted propylene and R¹ is unsubstituted oxetanyl. In embodiments, L¹ is an unsubstituted propylene and R¹ is methyl-substituted oxetanyl. In embodiments, L¹ is an unsubstituted propylene and R¹ is unsubstituted piperidinyl. In embodiments, L¹ is an unsubstituted propylene and R¹ is unsubstituted oxanyl. In embodiments, L¹ is an unsubstituted propylene and R¹ is unsubstituted tetrahydropyranyl. In embodiments, L¹ is an unsubstituted propylene and R¹ is unsubstituted cyclohexyl. In embodiments, L¹ is an unsubstituted propylene and R¹ is hydroxyl substituted cyclohexyl. In embodiments, L¹ is an unsubstituted propylene and R¹ is —CN. In embodiments, L¹ is an unsubstituted propylene and R¹ is unsubstituted ethynyl. In embodiments, L¹ is an unsubstituted propylene and R¹ is —C(O)CH(CH₃)₂. In embodiments, L¹ is an unsubstituted propylene and R¹ is —CH(CH₃)₂. In embodiments, L¹ is an unsubstituted propylene and R¹ is —COOH. In embodiments, L¹ is an unsubstituted propylene and R¹ is —C(O)OMe. In embodiments, L¹ is an unsubstituted propylene and R¹ is —C(O)OEt. In embodiments, L¹ is an unsubstituted propylene and R¹ is —C(O)OCH(CH₃)₂. In embodiments, L¹ is an unsubstituted propylene and R¹ is —C(O)OCH₂CH₂OCH₃. In embodiments, L¹ is an unsubstituted propylene and R¹ is —C(O)OCH₂CH₂OCH₂CH₃. In embodiments, L¹ is an unsubstituted propylene and R¹ is C(O)O(methyl substituted cyclobutyl). In embodiments, L¹ is an unsubstituted propylene and R¹ is C(O)O(methyl substituted cyclopropyl). In embodiments, L¹ is an unsubstituted propylene and R¹ is —C(O)N(CH₃)(CH₂CH₃). In embodiments, L¹ is an unsubstituted propylene and R¹ is —C(O)N(CH₃)(CH₃). In embodiments, L¹ is an unsubstituted propylene and R¹ is —OC(O)NH(CH₃). In embodiments, L¹ is an unsubstituted propylene and R¹ is OC(O)N(CH₃)(CH₃). In embodiments, L¹ is an unsubstituted propylene and R¹ is —OC(O)N(CH₂CH₃)(CH₂CH₃). In embodiments, L¹ is an unsubstituted propylene and R¹ is —C(S)N(CH₃)(CH₂CH₃). In embodiments, L¹ is an unsubstituted propylene and R¹ is —C(S)N(CH₃)(CH₃). In embodiments, L¹ is an unsubstituted propylene and R¹ is —C(S)NH(CH₃). In embodiments, L¹ is an unsubstituted propylene and R¹ is —C(S)N(CH₂CH₃)(CH₂CH₃). In embodiments, L¹ is an unsubstituted propylene and R¹ is —CH₂CH₂CH₃. In embodiments, L¹ is an unsubstituted propylene and R¹ is —C(O)OCH₂CH₂CH₃. In embodiments, L¹ is an unsubstituted propylene and R¹ is —C(O)OCH₂CH₃. In embodiments, L¹ is an unsubstituted propylene and R¹ is —CH₂C(CH₂)(CH₃). In embodiments, L¹ is an unsubstituted propylene and R¹ is —C(CH₂)(CH₃). In embodiments, L¹ is an unsubstituted propylene and R¹ is C(CH₂)(CH₂CH₃). In embodiments, L¹ is an unsubstituted propylene and R¹ is —C(CHCH₃)(CH₃). In embodiments, L¹ is an unsubstituted propylene and R¹ is C(C(CH₃)₂)(CH₃).

In embodiments, L¹ is an unsubstituted n-propylene and R¹ is unsubstituted methyl. In embodiments, L¹ is an unsubstituted n-propylene and R¹ is unsubstituted ethyl. In embodiments, L¹ is an unsubstituted n-propylene and R¹ is unsubstituted propyl. In embodiments, L¹ is an unsubstituted n-propylene and R¹ is unsubstituted isopropyl. In embodiments, L¹ is an unsubstituted n-propylene and R¹ is unsubstituted butyl. In embodiments, L¹ is an unsubstituted n-propylene and R¹ is unsubstituted isobutyl. In embodiments, L¹ is an unsubstituted n-propylene and R¹ is unsubstituted tert-butyl. In embodiments, L¹ is an unsubstituted n-propylene and R¹ is trifluoromethyl. In embodiments, L¹ is an unsubstituted n-propylene and R¹ is trichloromethyl. In embodiments, L¹ is an unsubstituted n-propylene and R¹ is unsubstituted methoxy. In embodiments, L¹ is an unsubstituted n-propylene and R¹ is unsubstituted ethoxy. In embodiments, L¹ is an unsubstituted n-propylene and R¹ is trifluoromethoxy. In embodiments, L¹ is an unsubstituted n-propylene and R¹ is —OH. In embodiments, L¹ is an unsubstituted n-propylene and R¹ is unsubstituted cyclopropyl. In embodiments, L¹ is an unsubstituted n-propylene and R¹ is unsubstituted cyclobutyl. In embodiments, L¹ is an unsubstituted n-propylene and R¹ is unsubstituted cyclopentyl. In embodiments, L¹ is an unsubstituted n-propylene and R¹ is unsubstituted oxetanyl. In embodiments, L¹ is an unsubstituted n-propylene and R¹ is methyl-substituted oxetanyl. In embodiments, L¹ is an unsubstituted n-propylene and R¹ is unsubstituted piperidinyl. In embodiments, L¹ is an unsubstituted n-propylene and R¹ is unsubstituted oxanyl. In embodiments, L¹ is an unsubstituted n-propylene and R¹ is unsubstituted tetrahydropyranyl. In embodiments, L¹ is an unsubstituted n-propylene and R¹ is unsubstituted cyclohexyl. In embodiments, L¹ is an unsubstituted n-propylene and R¹ is hydroxyl substituted cyclohexyl. In embodiments, L¹ is an unsubstituted n-propylene and R¹ is —CN. In embodiments, $L^1$ is an unsubstituted n-propylene and $R^1$ is unsubstituted ethynyl. In embodiments, $L^1$ is an unsubstituted n-propylene and $R^1$ is —C(O)CH(CH$_3$)$_2$. In embodiments, $L^1$ is an unsubstituted n-propylene and $R^1$ is —CH(CH$_3$)$_2$. In embodiments, $L^1$ is an unsubstituted n-propylene and $R^1$ is —COOH. In embodiments, $L^1$ is an unsubstituted n-propylene and $R^1$ is —C(O)OMe. In embodiments, $L^1$ is an unsubstituted n-propylene and $R^1$ is —C(O)OEt. In embodiments, $L^1$ is an unsubstituted n-propylene and $R^1$ is —C(O)OCH(CH$_3$)$_2$. In embodiments, $L^1$ is an unsubstituted n-propylene and $R^1$ is —C(O)OCH$_2$CH$_2$OCH$_3$. In embodiments, $L^1$ is an unsubstituted n-propylene and $R^1$ is —C(O)OCH$_2$CH$_2$OCH$_2$CH$_3$. In embodiments, $L^1$ is an unsubstituted n-propylene and $R^1$ is —C(O)O(methyl substituted cyclobutyl). In embodiments, $L^1$ is an unsubstituted n-propylene and $R^1$ is —C(O)O (methyl substituted cyclopropyl). In embodiments, $L^1$ is an unsubstituted n-propylene and $R^1$ is —C(O)N(CH$_3$)(CH$_2$CH$_3$). In embodiments, $L^1$ is an unsubstituted n-propylene and $R^1$ is —C(O)N(CH$_3$)(CH$_3$). In embodiments, $L^1$ is an unsubstituted n-propylene and $R^1$ is —OC(O)NH(CH$_3$). In embodiments, $L^1$ is an unsubstituted n-propylene and $R^1$ is —OC(O)N(CH$_3$)(CH$_3$). In embodiments, $L^1$ is an unsubstituted n-propylene and $R^1$ is —OC(O)N(CH$_2$CH$_3$)(CH$_2$CH$_3$). In embodiments, $L^1$ is an unsubstituted n-propylene and $R^1$ is —C(S)N(CH$_3$)(CH$_2$CH$_3$). In embodiments, $L^1$ is an unsubstituted n-propylene and $R^1$ is —C(S)N(CH$_3$)(CH$_3$). In embodiments, $L^1$ is an unsubstituted n-propylene and $R^1$ is —C(S)NH(CH$_3$). In embodiments, $L^1$ is an unsubstituted n-propylene and $R^1$ is —C(S)N(CH$_2$CH$_3$)(CH$_2$CH$_3$). In embodiments, $L^1$ is an unsubstituted n-propylene and $R^1$ is —CH$_2$CH$_2$CH$_3$. In embodiments, $L^1$ is an unsubstituted n-propylene and $R^1$ is —C(O)OCH$_2$CH$_2$CH$_3$. In embodiments, $L^1$ is an unsubstituted n-propylene and $R^1$ is —C(O)OCH$_2$CH$_3$. In embodiments, $L^1$ is an unsubstituted n-propylene and $R^1$ is CH$_2$C(CH$_2$)(CH$_3$). In embodiments, $L^1$ is an unsubstituted n-propylene and $R^1$ is —C(CH$_2$)(CH$_3$). In embodiments, $L^1$ is an unsubstituted n-propylene and $R^1$ is —C(CH$_2$)(CH$_2$CH$_3$). In embodiments, $L^1$ is an unsubstituted n-propylene and $R^1$ is —C(CHCH$_3$)(CH$_3$). In embodiments, $L^1$ is an unsubstituted n-propylene and $R^1$ is —C(C(CH$_3$)$_2$)(CH$_3$).

In embodiments, $L^1$ is an unsubstituted n-butylene and $R^1$ is unsubstituted methyl. In embodiments, $L^1$ is an unsubstituted n-butylene and $R^1$ is unsubstituted ethyl. In embodiments, $L^1$ is an unsubstituted n-butylene and $R^1$ is unsubstituted propyl. In embodiments, $L^1$ is an unsubstituted n-butylene and $R^1$ is unsubstituted isopropyl. In embodiments, $L^1$ is an unsubstituted n-butylene and $R^1$ is unsubstituted butyl. In embodiments, $L^1$ is an unsubstituted n-butylene and $R^1$ is unsubstituted isobutyl. In embodiments, $L^1$ is an unsubstituted n-butylene and $R^1$ is unsubstituted tert-butyl. In embodiments, $L^1$ is an unsubstituted n-butylene and $R^1$ is trifluoromethyl. In embodiments, $L^1$ is an unsubstituted n-butylene and $R^1$ is trichloromethyl. In embodiments, $L^1$ is an unsubstituted n-butylene and $R^1$ is unsubstituted methoxy. In embodiments, $L^1$ is an unsubstituted n-butylene and $R^1$ is unsubstituted ethoxy. In embodiments, $L^1$ is an unsubstituted n-butylene and $R^1$ is trifluoromethoxy. In embodiments, $L^1$ is an unsubstituted n-butylene and $R^1$ is —OH. In embodiments, $L^1$ is an unsubstituted n-butylene and $R^1$ is unsubstituted cyclopropyl. In embodiments, $L^1$ is an unsubstituted n-butylene and $R^1$ is unsubstituted cyclobutyl. In embodiments, $L^1$ is an unsubstituted n-butylene and $R^1$ is unsubstituted cyclopentyl. In embodiments, $L^1$ is an unsubstituted n-butylene and $R^1$ is unsubstituted oxetanyl. In embodiments, $L^1$ is an unsubstituted n-butylene and $R^1$ is methyl-substituted oxetanyl. In embodiments, $L^1$ is an unsubstituted n-butylene and $R^1$ is unsubstituted piperidinyl. In embodiments, $L^1$ is an unsubstituted n-butylene and $R^1$ is unsubstituted oxanyl. In embodiments, $L^1$ is an unsubstituted n-butylene and $R^1$ is unsubstituted tetrahydropyranyl. In embodiments, $L^1$ is an unsubstituted n-butylene and $R^1$ is unsubstituted cyclohexyl. In embodiments, $L^1$ is an unsubstituted n-butylene and $R^1$ is hydroxyl substituted cyclohexyl. In embodiments, $L^1$ is an unsubstituted n-butylene and $R^1$ is —CN. In embodiments, $L^1$ is an unsubstituted n-butylene and $R^1$ is unsubstituted ethynyl. In embodiments, $L^1$ is an unsubstituted n-butylene and $R^1$ is —C(O)CH(CH$_3$)$_2$. In embodiments, $L^1$ is an unsubstituted n-butylene and $R^1$ is —CH(CH$_3$)$_2$. In embodiments, $L^1$ is an unsubstituted n-butylene and $R^1$ is —COOH. In embodiments, $L^1$ is an unsubstituted n-butylene and $R^1$ is —C(O)OMe. In embodiments, $L^1$ is an unsubstituted n-butylene and $R^1$ is —C(O)OEt. In embodiments, $L^1$ is an unsubstituted n-butylene and $R^1$ is —C(O)OCH(CH$_3$)$_2$. In embodiments, $L^1$ is an unsubstituted n-butylene and $R^1$ is —C(O)OCH$_2$CH$_2$OCH$_3$. In embodiments, $L^1$ is an unsubstituted n-butylene and $R^1$ is C(O)OCH$_2$CH$_2$OCH$_2$CH$_3$. In embodiments, $L^1$ is an unsubstituted n-butylene and $R^1$ is —C(O)O(methyl substituted cyclobutyl). In embodiments, $L^1$ is an unsubstituted n-butylene and $R^1$ is C(O)O(methyl substituted cyclopropyl). In embodiments, $L^1$ is an unsubstituted n-butylene and $R^1$ is —C(O)N(CH$_3$)(CH$_2$CH$_3$). In embodiments, $L^1$ is an unsubstituted n-butylene and $R^1$ is —C(O)N(CH$_3$)(CH$_3$). In embodiments, $L^1$ is an unsubstituted n-butylene and $R^1$ is —OC(O)NH(CH$_3$). In embodiments, $L^1$ is an unsubstituted n-butylene and $R^1$ is —OC(O)N(CH$_3$)(CH$_3$). In embodiments, $L^1$ is an unsubstituted n-butylene and $R^1$ is —OC(O)N(CH$_2$CH$_3$)(CH$_2$CH$_3$). In embodiments, $L^1$ is an unsubstituted n-butylene and $R^1$ is —C(S)N(CH$_3$)(CH$_2$CH$_3$). In embodiments, $L^1$ is an unsubstituted n-butylene and $R^1$ is —C(S)N(CH$_3$)(CH$_3$). In embodiments, $L^1$ is an unsubstituted n-butylene and $R^1$ is —C(S)NH(CH$_3$).

In embodiments, $L^1$ is an unsubstituted n-butylene and $R^1$ is —C(S)N(CH$_2$CH$_3$)(CH$_2$CH$_3$). In embodiments, $L^1$ is an unsubstituted n-butylene and $R^1$ is —CH$_2$CH$_2$CH$_3$. In embodiments, $L^1$ is an unsubstituted n-butylene and $R^1$ is —C(O)OCH$_2$CH$_2$CH$_3$. In embodiments, $L^1$ is an unsubstituted n-butylene and $R^1$ is —C(O)OCH$_2$CH$_3$. In embodiments, $L^1$ is an unsubstituted n-butylene and $R^1$ is —CH$_2$C(CH$_2$)(CH$_3$). In embodiments, $L^1$ is an unsubstituted n-butylene and $R^1$ is —C(CH$_2$)(CH$_3$). In embodiments, $L^1$ is an unsubstituted n-butylene and $R^1$ is —C(CH$_2$)(CH$_2$CH$_3$). In embodiments, $L^1$ is an unsubstituted n-butylene and $R^1$ is C(CHCH$_3$)(CH$_3$). In embodiments, $L^1$ is an unsubstituted n-butylene and $R^1$ is —C(C(CH$_3$)$_2$)(CH$_3$).

In embodiments, $L^2$ is C(O)OCH$_2$— and ring A is phenyl and $R^2$ is halo. In embodiments, $L^2$ is C(O)OCH$_2$— and ring A is phenyl and $R^2$ is chloro. In embodiments, $L^2$ is C(O)OCH$_2$— and Ring A is phenyl and $R^2$ is fluoro. In embodiments, $L^2$ is C(O)OCH$_2$— and Ring A is phenyl and $R^2$ is iodo. In embodiments, $L^2$ is C(O)OCH$_2$— and Ring A is phenyl and $R^2$ is bromo. In embodiments, $L^2$ is C(O)OCH$_2$— and Ring A is phenyl and $R^2$ is CH$_3$. In embodiments, $L^2$ is C(O)OCH$_2$— and Ring A is phenyl and $R^2$ is CH$_2$CH$_3$. In embodiments, $L^2$ is C(O)OCH$_2$— and Ring A is phenyl and $R^2$ is OCH$_3$. In embodiments, $L^2$ is C(O)OCH$_2$— and Ring A is phenyl and $R^2$ is OCH$_2$CH$_3$. In embodiments, $L^2$ is C(O)OCH$_2$— and Ring A is phenyl and $R^2$ is CF$_3$. In embodiments, $L^2$ is C(O)OCH$_2$— and Ring A is benzo[d][1,3]dioxolyl and z is 0. In embodiments, $L^2$ is C(O)OCH$_2$— and Ring A is phenyl and z is 0.

In embodiments, $L^2$ is $SO_2$— and Ring A is phenyl and $R^2$ is halo. In embodiments, $L^2$ is $SO_2$— and Ring A is phenyl and $R^2$ is chloro. In embodiments, $L^2$ is $SO_2$— and Ring A is phenyl and $R^2$ is fluoro. In embodiments, $L^2$ is $SO_2$— and Ring A is phenyl and $R^2$ is iodo. In embodiments, $L^2$ is $SO_2$— and Ring A is phenyl and $R^2$ is bromo. In embodiments, $L^2$ is $SO_2$— and Ring A is phenyl and $R^2$ is $CH_3$. In embodiments, $L^2$ is $SO_2$— and Ring A is phenyl and $R^2$ is $CH_2CH_3$. In embodiments, $L^2$ is $SO_2$— and Ring A is phenyl and $R^2$ is $OCH_3$. In embodiments, $L^2$ is $SO_2$— and Ring A is phenyl and $R^2$ is $OCH_2CH_3$. In embodiments, $L^2$ is $SO_2$— and Ring A is phenyl and $R^2$ is $CF_3$. In embodiments, $L^2$ is $SO_2$— and Ring A is benzo[d][1,3]dioxolyl and z is 0. In embodiments, $L^2$ is $SO_2$— and Ring A is phenyl and z is 0.

In embodiments, $L^2$ is $C(O)OCH_2$— and Ring A is pyridinyl. In embodiments, $L^2$ is $C(O)OCH_2$— and Ring A is pyrimidinyl. In embodiments, $L^2$ is $C(O)OCH_2$— and Ring A is thiophenyl. In embodiments, $L^2$ is $C(O)OCH_2$— and Ring A is thienyl. In embodiments, $L^2$ is $C(O)OCH_2$— and Ring A is furanyl. In embodiments, $L^2$ is $C(O)OCH_2$— and Ring A is indolyl. In embodiments, $L^2$ is $C(O)OCH_2$— and Ring A is benzoxadiazolyl. In embodiments, $L^2$ is —$C(O)OCH_2$— and Ring A is benzodioxolyl. In embodiments, $L^2$ is $C(O)OCH_2$— and Ring A is benzodioxanyl. In embodiments, $L^2$ is $C(O)OCH_2$— and Ring A is thianaphthanyl. In embodiments, $L^2$ is $C(O)OCH_2$— and Ring A is pyrrolopyridinyl. In embodiments, $L^2$ is $C(O)OCH_2$— and Ring A is indazolyl. In embodiments, $L^2$ is $C(O)OCH_2$— and Ring A is quinolinyl. In embodiments, $L^2$ is $C(O)OCH_2$— and Ring A is quinoxalinyl. In embodiments, $L^2$ is $C(O)OCH_2$— and Ring A is pyridopyrazinyl. In embodiments, $L^2$ is $C(O)OCH_2$— and Ring A is quinazolinonyl. In embodiments, $L^2$ is $C(O)OCH_2$— and Ring A is benzoisoxazolyl. In embodiments, $L^2$ is $C(O)OCH_2$— and Ring A is imidazopyridinyl. In embodiments, $L^2$ is $C(O)OCH_2$— and Ring A is benzofuranyl. In embodiments, $L^2$ is $C(O)OCH_2$— and Ring A is benzothienyl. In embodiments, $L^2$ is $C(O)OCH_2$— and Ring A is benzothiophenyl. In embodiments, $L^2$ is $C(O)OCH_2$— and Ring A is phenyl. In embodiments, $L^2$ is $C(O)OCH_2$— and Ring A is naphthyl. In embodiments, $L^2$ is $C(O)OCH_2$— and Ring A is biphenyl. In embodiments, $L^2$ is $C(O)OCH_2$— and Ring A is pyrrolyl. In embodiments, $L^2$ is —$C(O)OCH_2$— and Ring A is pyrazolyl. In embodiments, $L^2$ is —$C(O)OCH_2$— and Ring A is imidazolyl. In embodiments, $L^2$ is —$C(O)OCH_2$— and Ring A is pyrazinyl. In embodiments, $L^2$ is —$C(O)OCH_2$— and Ring A is oxazolyl. In embodiments, $L^2$ is —$C(O)OCH_2$— and Ring A is isoxazolyl. In embodiments, $L^2$ is —$C(O)OCH_2$— and Ring A is thiazolyl. In embodiments, $L^2$ is —$C(O)OCH_2$— and Ring A is furylthienyl. In embodiments, $L^2$ is —$C(O)OCH_2$— and Ring A is pyridyl. In embodiments, $L^2$ is —$C(O)OCH_2$— and Ring A is pyrimidyl. In embodiments, $L^2$ is —$C(O)OCH_2$— and Ring A is benzothiazolyl. In embodiments, $L^2$ is —$C(O)OCH_2$— and Ring A is purinyl. In embodiments, $L^2$ is —$C(O)OCH_2$— and Ring A is benzimidazolyl. In embodiments, $L^2$ is —$C(O)OCH_2$— and Ring A is isoquinolyl. In embodiments, $L^2$ is —$C(O)OCH_2$— and Ring A is thiadiazolyl. In embodiments, $L^2$ is —$C(O)OCH_2$— and Ring A is oxadiazolyl. In embodiments, $L^2$ is —$C(O)OCH_2$— and Ring A is pyrrolyl. In embodiments, $L^2$ is —$C(O)OCH_2$— and Ring A is diazolyl. In embodiments, $L^2$ is —$C(O)OCH_2$— and Ring A is triazolyl. In embodiments, $L^2$ is —$C(O)OCH_2$— and Ring A is tetrazolyl. In embodiments, $L^2$ is —$C(O)OCH_2$— and Ring A is benzothiadiazolyl. In embodiments, $L^2$ is —$C(O)OCH_2$— and Ring A is isothiazolyl. In embodiments, $L^2$ is —$C(O)OCH_2$— and Ring A is pyrazolopyrimidinyl. In embodiments, $L^2$ is —$C(O)OCH_2$— and Ring A is pyrrolopyrimidinyl. In embodiments, $L^2$ is —$C(O)OCH_2$— and Ring A is benzotriazolyl. In embodiments, $L^2$ is —$C(O)OCH_2$— and Ring A is benzoxazolyl. In embodiments, $L^2$ is —$C(O)OCH_2$— and Ring A is quinolyl. In embodiments, $L^2$ is —$C(O)OCH_2$— and Ring A is benzo[d][1,3]dioxolyl.

In embodiments, the compound has a greater binding affinity for sigma 2 receptor over sigma 1 receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for sigma 1 receptor).

In embodiments, the compound has a greater binding affinity for sigma 2 receptor over serotonin transporter (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for serotonin transporter).

In embodiments, the compound has a greater binding affinity for sigma 2 receptor over norepinephrine transporter (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for norepinephrine transporter).

In embodiments, the compound has a greater binding affinity for sigma 2 receptor over dopamine transporter (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for dopamine transporter).

In embodiments, the compound has a greater binding affinity for sigma 2 receptor over serotonin receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for serotonin receptor).

In embodiments, the compound has a greater binding affinity for sigma 2 receptor over dopamine receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for dopamine receptor).

In embodiments, the compound has a greater binding affinity for sigma 2 receptor over nicotinic acetylcholine receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for nicotinic acetylcholine receptor).

In embodiments, the compound has a greater binding affinity for sigma 2 receptor over muscarinic acetylcholine receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for muscarinic acetylcholine receptor).

In embodiments, the compound has a greater binding affinity for sigma 2 receptor over opioid receptor (e.g., binds sigma 2 receptor with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for opioid receptor).

In embodiments, the compound has a greater binding affinity for progesterone receptor membrane component 1 over sigma 1 receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for sigma 1 receptor).

In embodiments, the compound has a greater binding affinity for progesterone receptor membrane component 1 over serotonin transporter (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for serotonin transporter).

In embodiments, the compound has a greater binding affinity for progesterone receptor membrane component 1 over norepinephrine transporter (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for norepinephrine transporter).

In embodiments, the compound has a greater binding affinity for progesterone receptor membrane component 1 over dopamine transporter (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for dopamine transporter).

In embodiments, the compound has a greater binding affinity for progesterone receptor membrane component 1 over serotonin receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for serotonin receptor).

In embodiments, the compound has a greater binding affinity for progesterone receptor membrane component 1 over dopamine receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for dopamine receptor).

In embodiments, the compound has a greater binding affinity for progesterone receptor membrane component 1 over nicotinic acetylcholine receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for nicotinic acetylcholine receptor).

In embodiments, the compound has a greater binding affinity for progesterone receptor membrane component 1 over muscarinic acetylcholine receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for muscarinic acetylcholine receptor).

In embodiments, the compound has a greater binding affinity for progesterone receptor membrane component 1 over opioid receptor (e.g., binds progesterone receptor membrane component 1 with 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold the affinity for opioid receptor).

In embodiments, the compound is

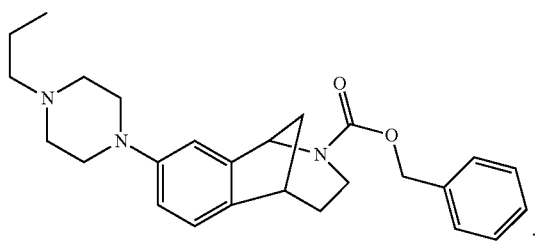 [SMILES: CCCN1CCN(c2ccc3c(c2)C2CC3CCN2C(=O)OCc2ccccc2)CC1]

In embodiments, the compound is

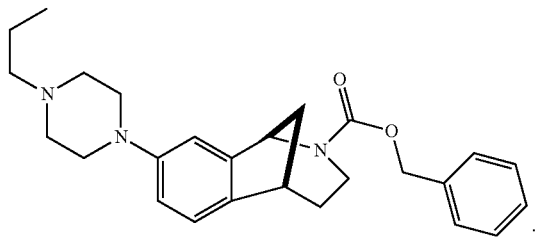

In embodiments, the compound is

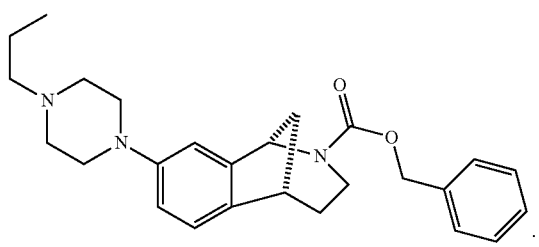

In embodiments, the compound is
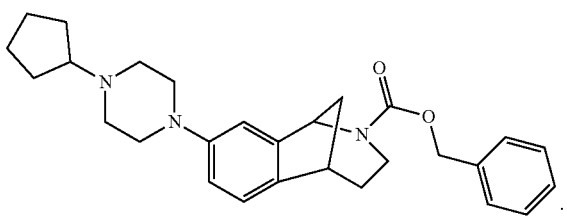 [SMILES: O=C(OCc1ccccc1)N1CCC2CC1c1cc(N3CCN(C4CCCC4)CC3)ccc12]
In embodiments, the compound is
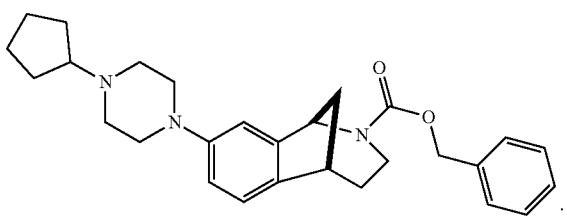
In embodiments, the compound is
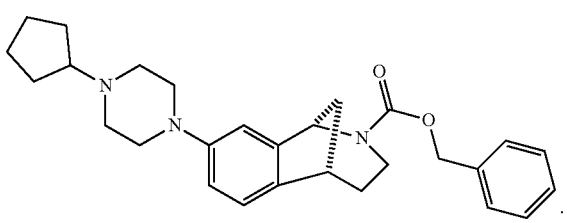
In embodiments, the compound is
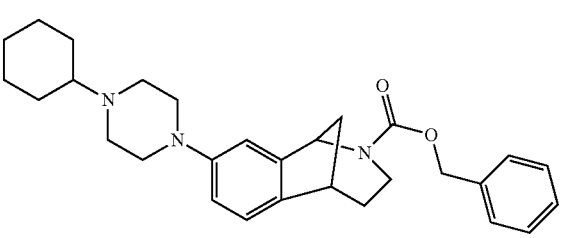
In embodiments, the compound is
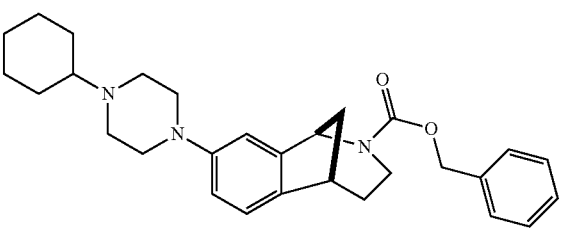
In embodiments, the compound is
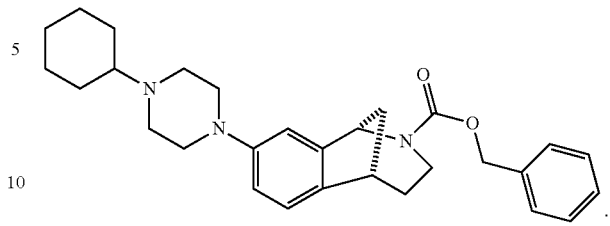
In embodiments, the compound is
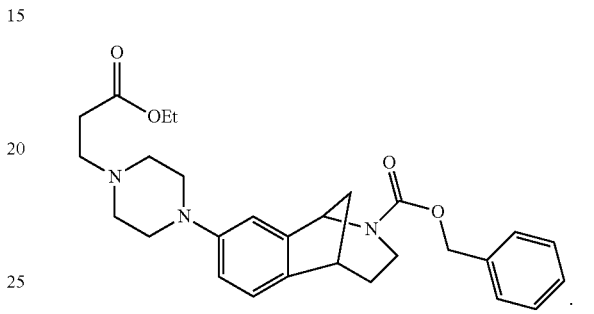
In embodiments, the compound is
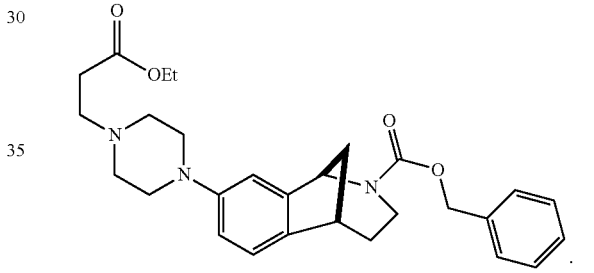
In embodiments, the compound is
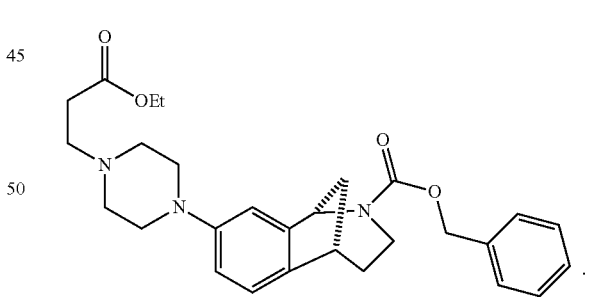
In embodiments, the compound is
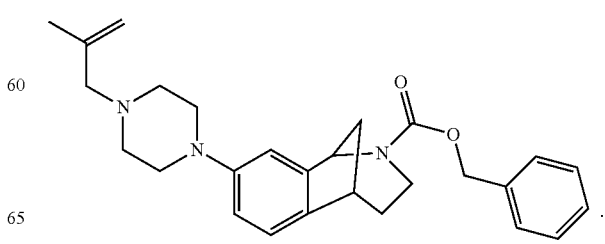

In embodiments, the compound is
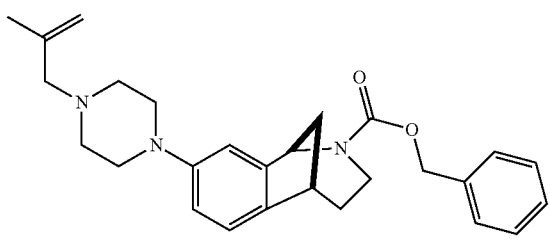
In embodiments, the compound is
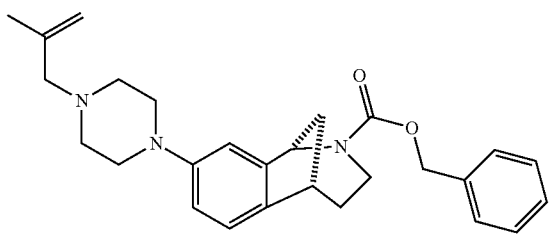
In embodiments, the compound is
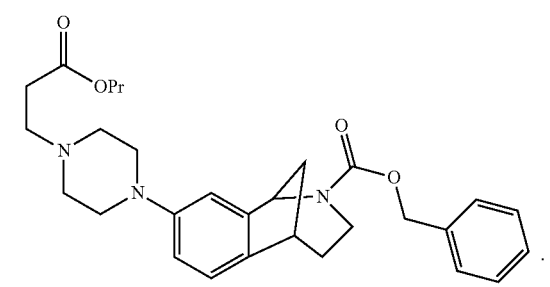
In embodiments, the compound is
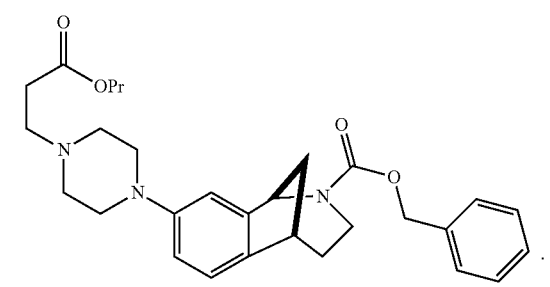
In embodiments, the compound is
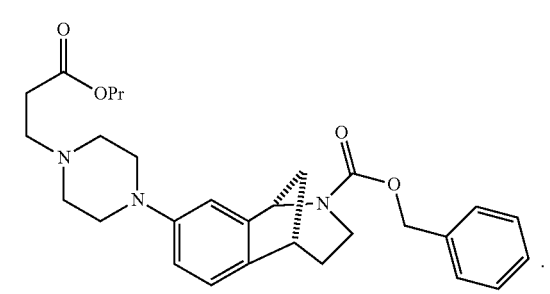
In embodiments, the compound is
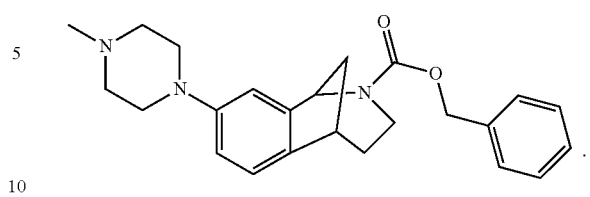
In embodiments, the compound is
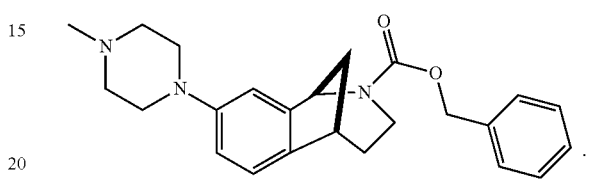
In embodiments, the compound is
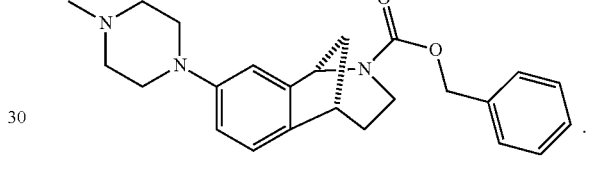
In embodiments, the compound is
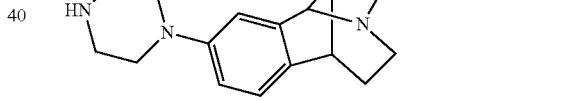
In embodiments, the compound is
In embodiments, the compound is
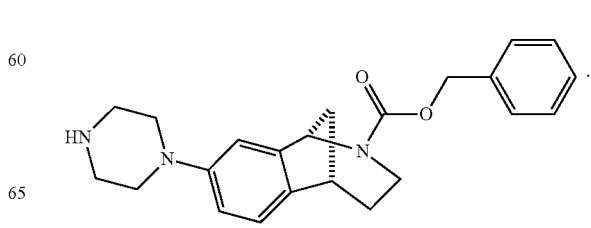

In embodiments, the compound is
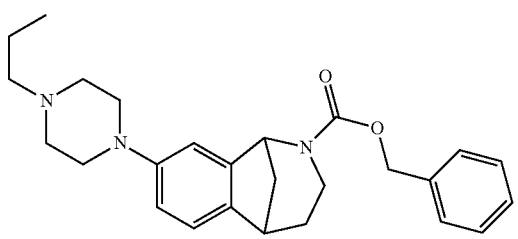
In embodiments, the compound is
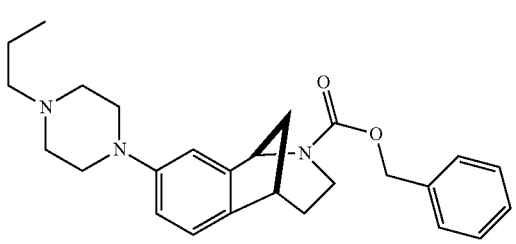
In embodiments, the compound is
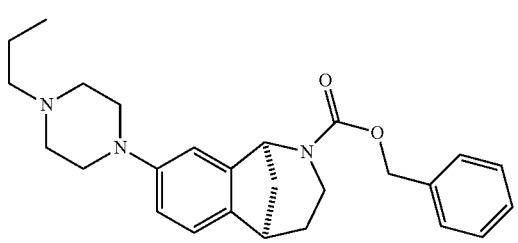
In embodiments, the compound is
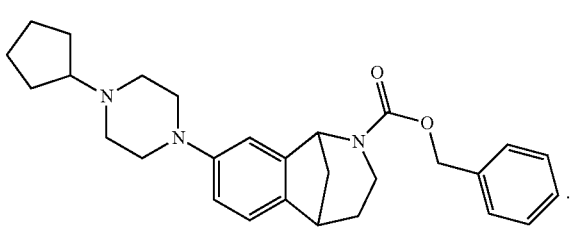 [SMILES: O=C(OCc1ccccc1)N1CCC2CC1c1cc(N3CCN(C4CCCC4)CC3)ccc12]
In embodiments, the compound is
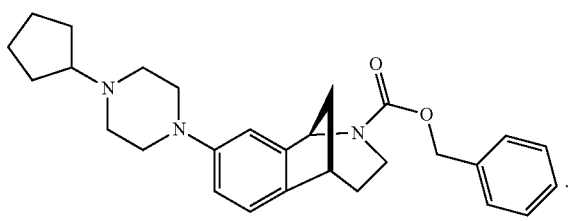 [SMILES: O=C(OCc1ccccc1)N1CC[C@@H]2C[C@@H]1c1cc(N3CCN(C4CCCC4)CC3)ccc12]
In embodiments, the compound is
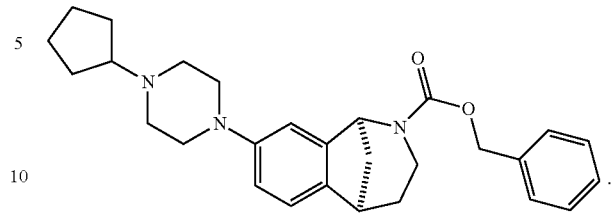
In embodiments, the compound is
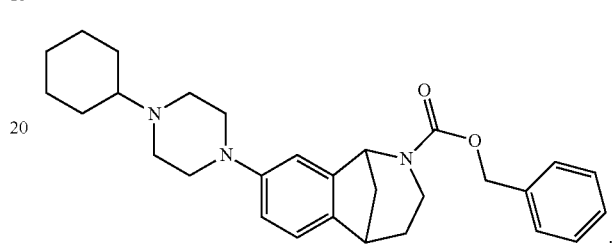
In embodiments, the compound is
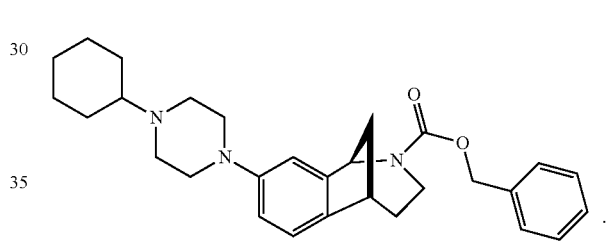
In embodiments, the compound is
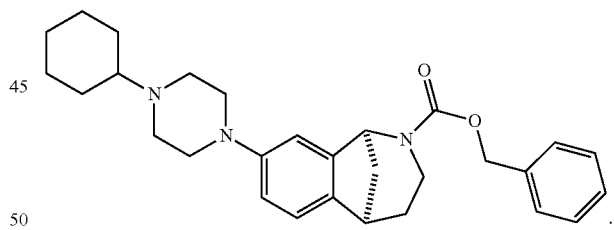
In embodiments, the compound is
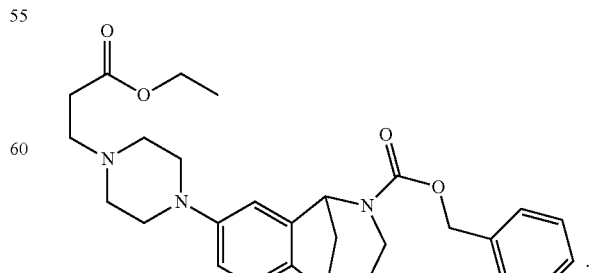

In embodiments, the compound is
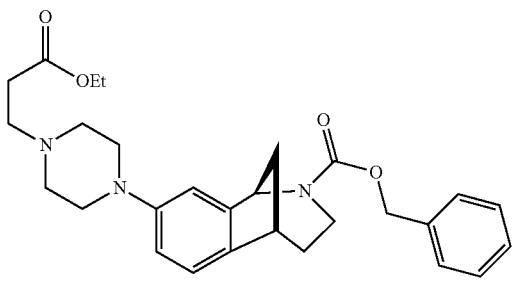
In embodiments, the compound is
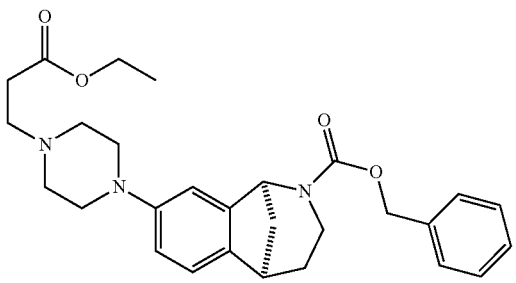
In embodiments, the compound is
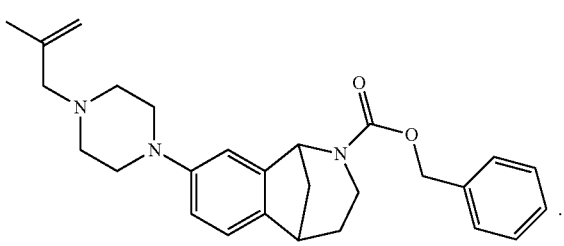 [SMILES: C=C(C)CN1CCN(c2ccc3c(c2)C2CC3CCN2C(=O)OCc2ccccc2)CC1]
In embodiments, the compound is
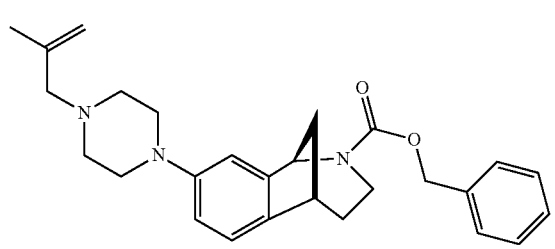
In embodiments, the compound is
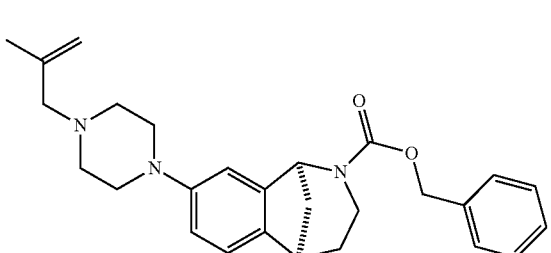
In embodiments, the compound is
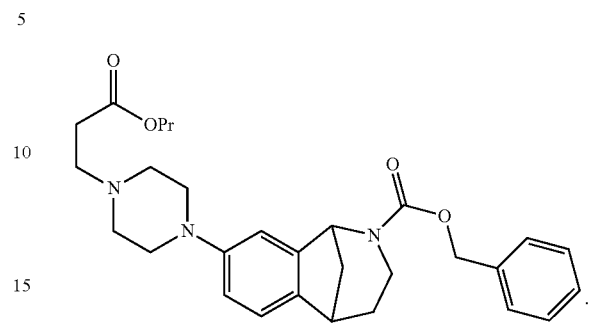
In embodiments, the compound is
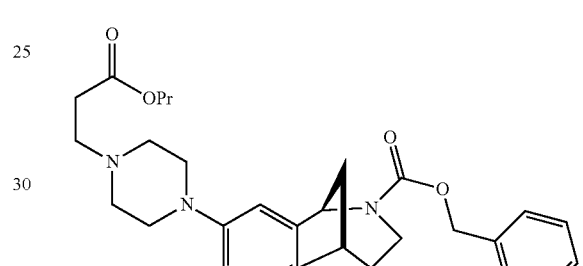
In embodiments, the compound is
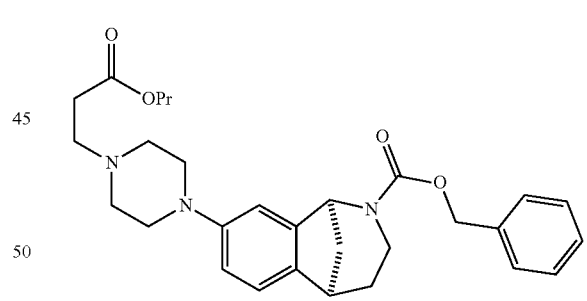
In embodiments, the compound is
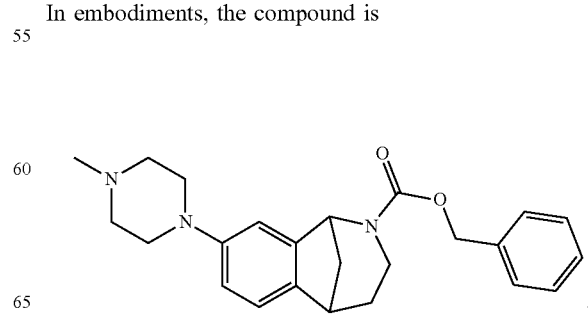

In embodiments, the compound is

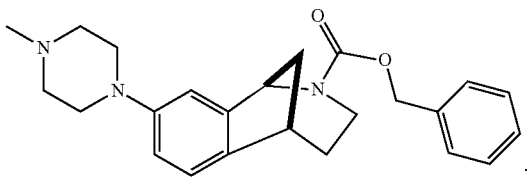

In embodiments, the compound is

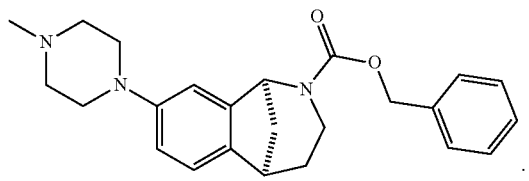

In embodiments, the compound is

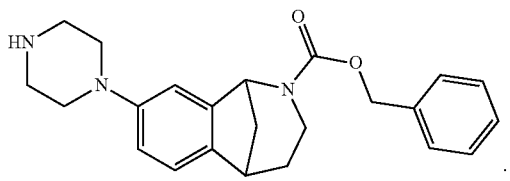 [SMILES: O=C(OCc1ccccc1)N1CCC2CC1c1cc(N3CCNCC3)ccc12]

In embodiments, the compound is

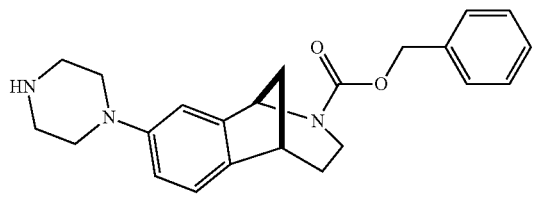

In embodiments, the compound is

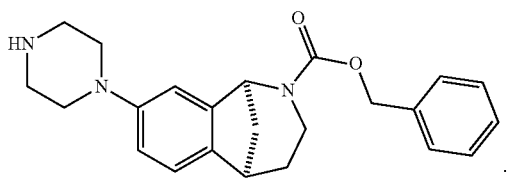

In embodiments, the compound is a compound described herein, including in an aspect, embodiment, example, table, figure, scheme, or claim. In embodiments, the compound is a compound described in table 1. In embodiments, the compound is a compound described in table 3. In embodiments, the compound is a compound described in table 4. In embodiments, the compound is a compound described in table 5. In embodiments, the compound is a compound described in table 6. In embodiments, the compound is a compound described in table 7.

In embodiments, $L^1$-$R^1$ is not unsubstituted methyl. In embodiments, $R^1$ is not hydrogen, unsubstituted methyl, —C(O)$R^9$, or —C(S)N$R^7R^8$, when $L^1$ is a bond. In embodiments, $R^1$ is not hydrogen, unsubstituted methyl, —C(O)$R^9$, or —C(S)N$R^7R^8$, when $L^1$ is a bond. In embodiments, $R^1$ is not hydrogen when $L^1$ is a bond. In embodiments, $R^1$ is not unsubstituted methyl when $L^1$ is a bond. In embodiments, $R^1$ is not —C(O)$R^9$ when $L^1$ is a bond. In embodiments, $R^1$ is not —C(S)N$R^7R^8$, when $L^1$ is a bond. In embodiments, $L^{1}$-$R^1$ is not-$CH_2CH$=$CH_2$.

In embodiments, $R^7$ is not hydrogen. In embodiments, $R^7$ is not halogen. In embodiments, $R^7$ is not —$CX_3$. In embodiments, $R^7$ is not —CN. In embodiments, $R^7$ is not —OH. In embodiments, $R^7$ is not —$NH_2$. In embodiments, $R^7$ is not —COOH. In embodiments, $R^7$ is not —$CONH_2$. In embodiments, $R^7$ is not —$NO_2$. In embodiments, $R^7$ is not —SH. In embodiments, $R^7$ is not —$SO_3H$. In embodiments, $R^7$ is not —$SO_4H$. In embodiments, $R^7$ is not —$SO_2NH_2$. In embodiments, $R^7$ is not $NHNH_2$. In embodiments, $R^7$ is not $ONH_2$. In embodiments, $R^7$ is not NHC=(O)$NHNH_2$. In embodiments, $R^7$ is not NHC=(O) $NH_2$. In embodiments, $R^7$ is not —$NHSO_2H$. In embodiments, $R^7$ is not —NHC=(O)H. In embodiments, $R^7$ is not —NHC(O)—OH. In embodiments, $R^7$ is not —NHOH. In embodiments, $R^7$ is not —$OCX_3$. In embodiments, $R^7$ is not —$OCHX_2$. In embodiments, $R^7$ is not substituted or unsubstituted $C_1$-$C_8$ alkyl. In embodiments, $R^7$ is not substituted or unsubstituted 2 to 8 membered heteroalkyl. In embodiments, $R^7$ is not substituted or unsubstituted $C_3$-$C_8$ cycloalkyl. In embodiments, $R^7$ is not substituted or unsubstituted 3 to 6 membered heterocycloalkyl. In embodiments, $R^7$ is not substituted or unsubstituted phenyl. In embodiments, $R^7$ is not substituted or unsubstituted 5 to 6 membered heteroaryl. In embodiments, $R^7$ is not unsubstituted $C_1$-$C_8$ alkyl. In embodiments, $R^7$ is not unsubstituted 2 to 8 membered heteroalkyl. In embodiments, $R^7$ is not unsubstituted $C_3$-$C_8$ cycloalkyl. In embodiments, $R^7$ is not unsubstituted 3 to 6 membered heterocycloalkyl. In embodiments, $R^7$ is not unsubstituted phenyl. In embodiments, $R^7$ is not unsubstituted 5 to 6 membered heteroaryl.

In embodiments, $R^8$ is not hydrogen. In embodiments, $R^8$ is not halogen. In embodiments, $R^8$ is not —$CX_3$. In embodiments, $R^8$ is not —CN. In embodiments, $R^8$ is not —OH. In embodiments, $R^8$ is not —$NH_2$. In embodiments, $R^8$ is not —COOH. In embodiments, $R^8$ is not —$CONH_2$. In embodiments, $R^8$ is not —$NO_2$. In embodiments, $R^8$ is not —SH. In embodiments, $R^8$ is not —$SO_3H$. In embodiments, $R^8$ is not —$SO_4H$. In embodiments, $R^8$ is not —$SO_2NH_2$. In embodiments, $R^8$ is not $NHNH_2$. In embodiments, $R^8$ is not $ONH_2$. In embodiments, $R^8$ is not NHC=(O)$NHNH_2$. In embodiments, $R^8$ is not NHC=(O) $NH_2$. In embodiments, $R^8$ is not —$NHSO_2H$. In embodiments, $R^8$ is not —NHC=(O)H. In embodiments, $R^8$ is not —NHC(O)—OH. In embodiments, $R^8$ is not —NHOH. In embodiments, $R^8$ is not —$OCX_3$. In embodiments, $R^8$ is not —$OCHX_2$. In embodiments, $R^8$ is not substituted or unsubstituted $C_1$-$C_8$ alkyl. In embodiments, $R^8$ is not substituted or unsubstituted 2 to 8 membered heteroalkyl. In embodiments, $R^8$ is not substituted or unsubstituted $C_3$-$C_8$ cycloalkyl. In embodiments, $R^8$ is not substituted or unsubstituted 3 to 6 membered heterocycloalkyl. In embodiments, $R^8$ is not substituted or unsubstituted phenyl. In embodiments, $R^8$ is not substituted or unsubstituted 5 to 6 membered heteroaryl. In embodiments, $R^8$ is not unsubstituted $C_1$-$C_8$ alkyl. In embodiments, $R^8$ is not unsubstituted 2 to 8 membered heteroalkyl. In embodiments, $R^8$ is not unsubstituted $C_3$-$C_8$ cycloalkyl. In embodiments, $R^8$ is not unsubstituted 3 to 6 membered heterocycloalkyl. In embodiments, $R^8$ is not unsubstituted phenyl. In embodiments, $R^8$ is not unsubstituted 5 to 6 membered heteroaryl. In embodiments, $R^9$ is not hydrogen. In embodiments, $R^9$ is not halogen. In embodiments, $R^9$ is not —$CX_3$. In embodiments, $R^9$ is not —CN. In embodiments, $R^9$ is not —OH. In embodiments, $R^9$ is not —$NH_2$. In embodiments, $R^9$ is not —COOH. In embodiments, $R^9$ is not —$CONH_2$. In embodiments, $R^9$ is not —$NO_2$. In embodiments, $R^9$ is not —SH. In embodiments, $R^9$ is not —$SO_3H$. In embodiments, $R^9$ is not —$SO_4H$. In embodiments, $R^9$ is not —$SO_2NH_2$. In embodiments, $R^9$ is not $NHNH_2$. In embodiments, $R^9$ is not $ONH_2$. In embodiments, $R^9$ is not —NHC=(O)$NHNH_2$. In embodiments, $R^9$ is not NHC=(O) $NH_2$. In embodiments, $R^9$ is not —$NHSO_2H$. In embodiments, $R^9$ is not —NHC=(O)H. In embodiments, $R^9$ is not —NHC(O)—OH. In embodiments, $R^9$ is not —NHOH. In embodiments, $R^9$ is not —$OCX_3$. In embodiments, $R^9$ is not —$OCHX_2$. In embodiments, $R^9$ is not substituted or unsubstituted $C_1$-$C_8$ alkyl. In embodiments, $R^9$ is not substituted or unsubstituted 2 to 8 membered heteroalkyl. In embodiments, $R^9$ is not substituted or unsubstituted $C_3$-$C_8$ cycloalkyl. In embodiments, $R^9$ is not substituted or unsubstituted 3 to 6 membered heterocycloalkyl. In embodiments, $R^9$ is not substituted or unsubstituted phenyl. In embodiments, $R^9$ is not substituted or unsubstituted 5 to 6 membered heteroaryl. In embodiments, $R^9$ is not unsubstituted $C_1$-$C_8$ alkyl. In embodiments, $R^9$ is not unsubstituted 2 to 8 membered heteroalkyl. In embodiments, $R^9$ is not unsubstituted $C_3$-$C_8$ cycloalkyl. In embodiments, $R^9$ is not unsubstituted 3 to 6 membered heterocycloalkyl. In embodiments, $R^9$ is not unsubstituted phenyl. In embodiments, $R^9$ is not unsubstituted 5 to 6 membered heteroaryl.

In embodiments, the compound is not

In embodiments, the compound is not

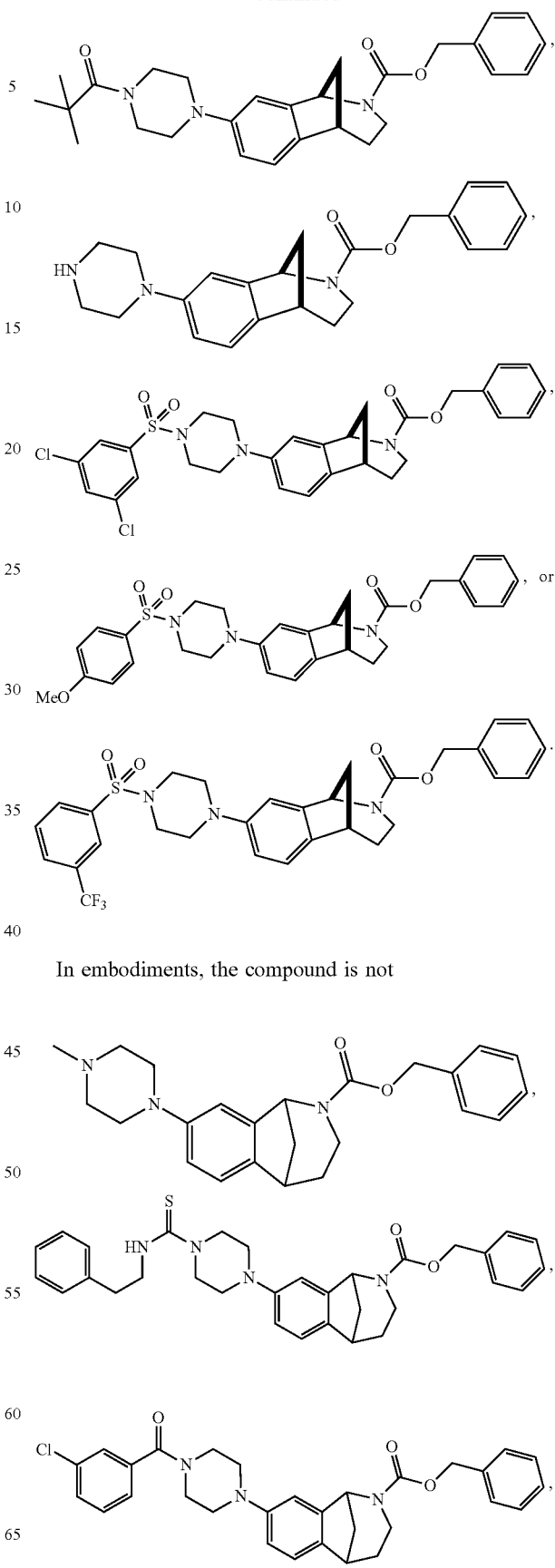

-continued
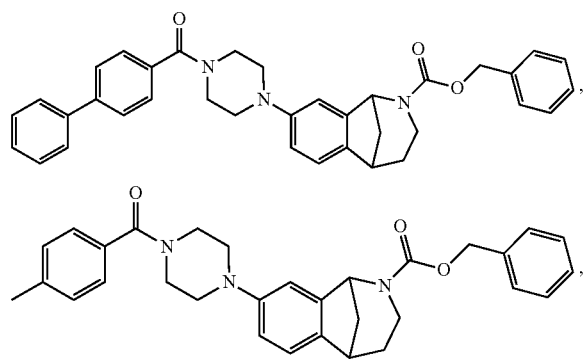
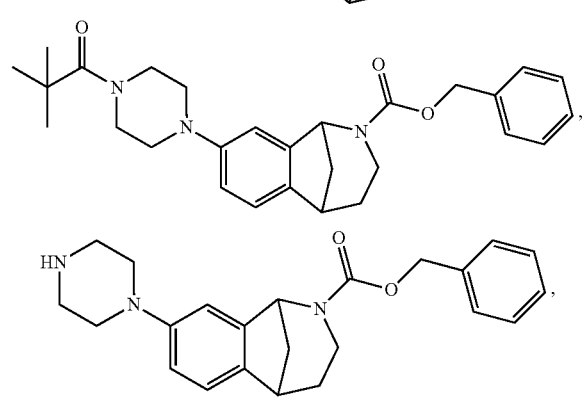
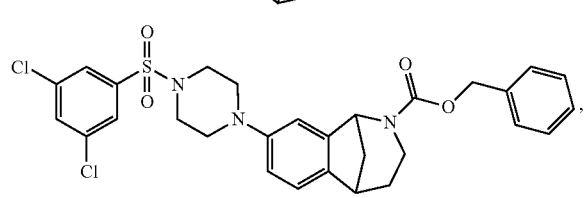
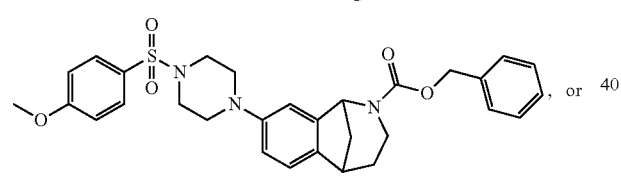
, or
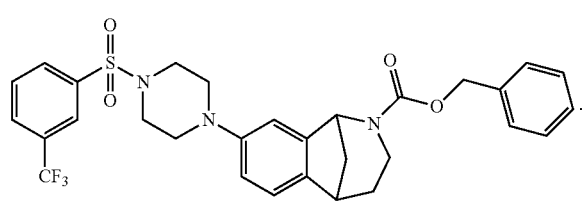
.
In embodiments, the compound is not a compound described in WO2015009742.
In embodiments, the compound is not
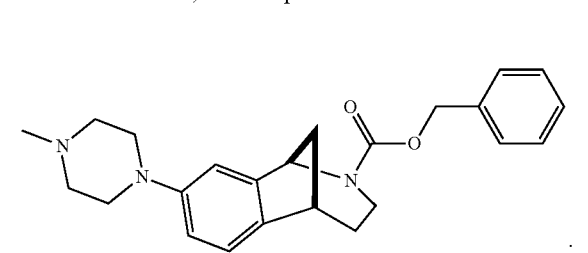
In embodiments, the compound is not
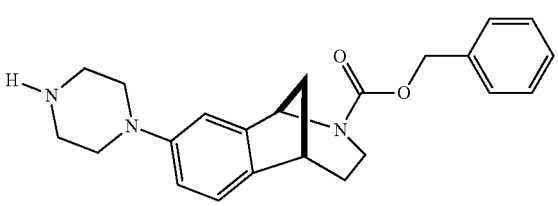
In embodiments, the compound is not
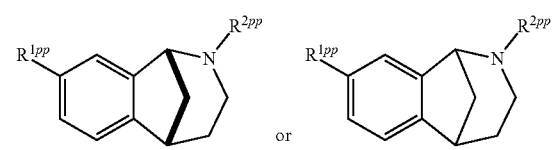
| $R^{1pp}$ | $R^{2pp}$ |
|---|---|
| 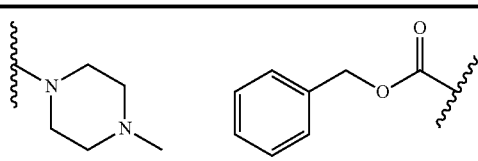 | |
| 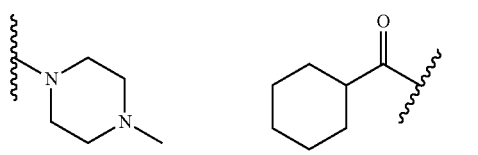 | |
| 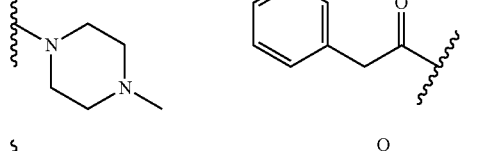 | |
| 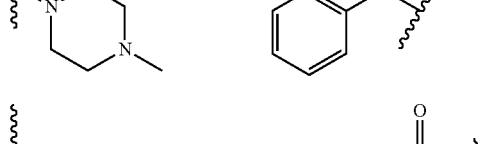 | |
| 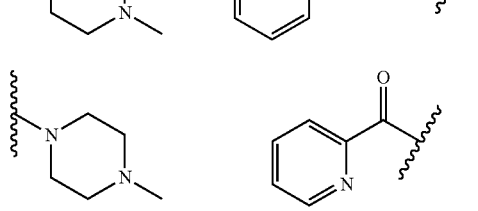 | |

137
-continued
| $R^{1pp}$ | $R^{2pp}$ |
|---|---|
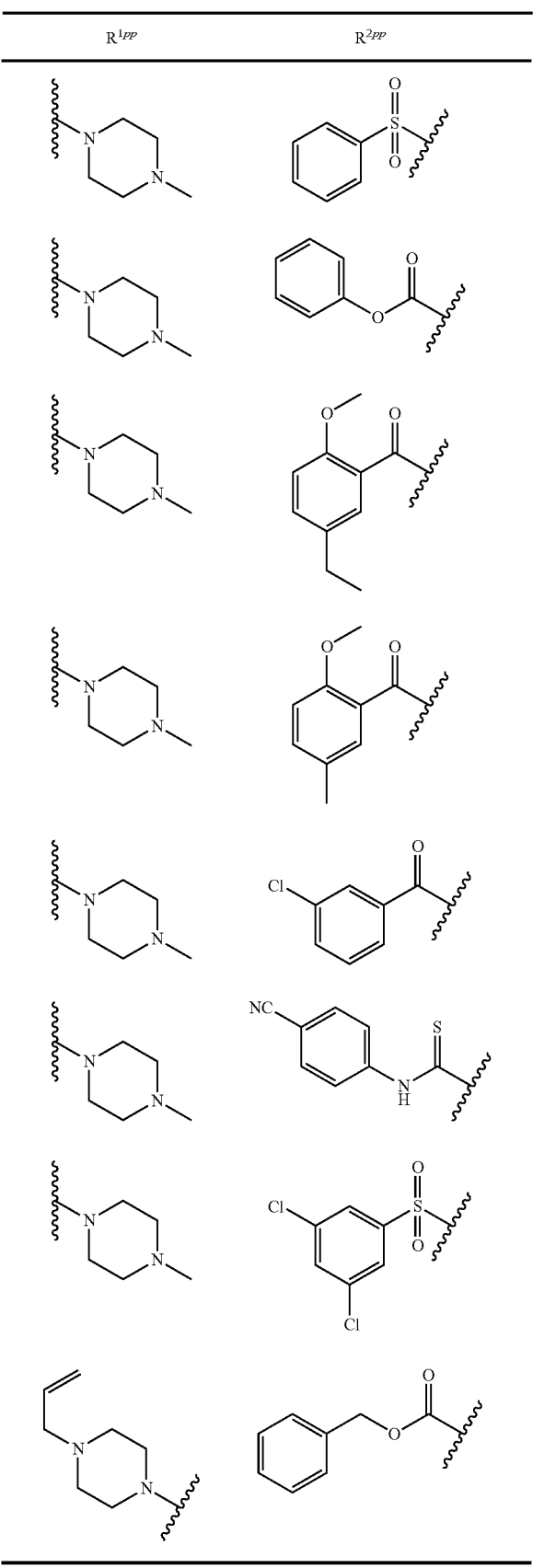
138
In embodiments, the compound is not
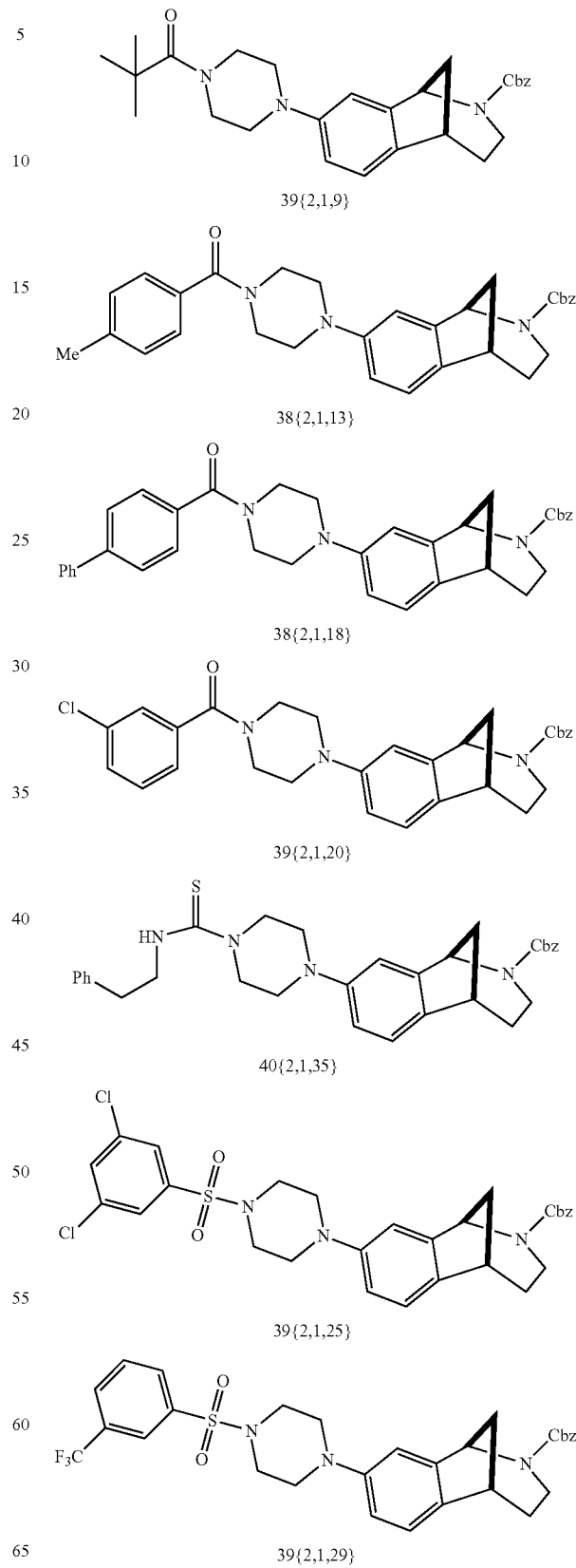

139
-continued

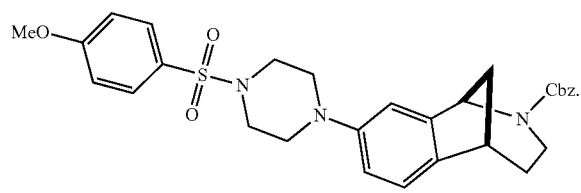

39{2,1,30}

In embodiments, the compound is not

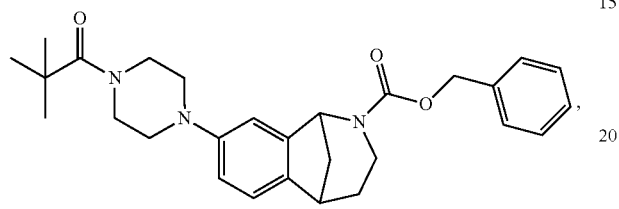

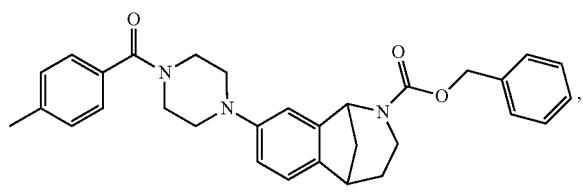

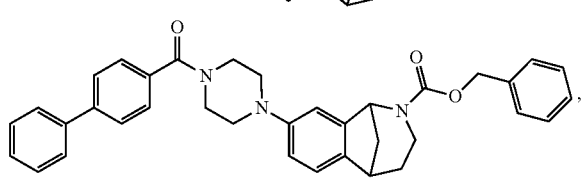

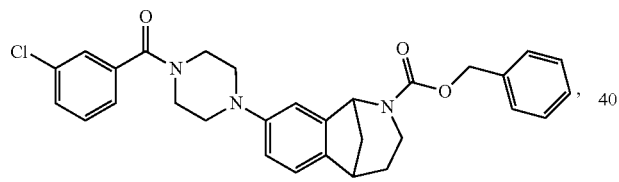

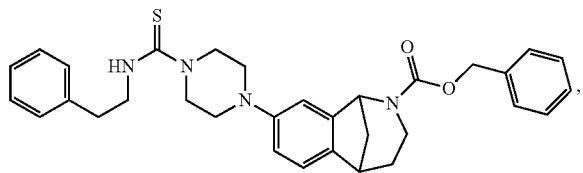

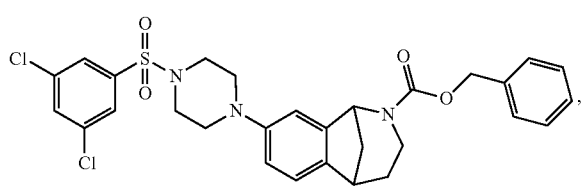

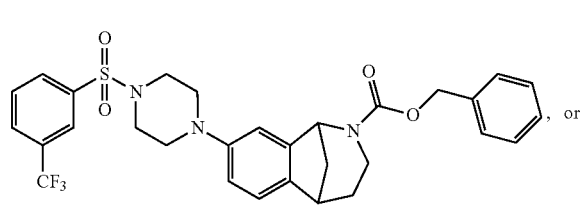, or

140
-continued

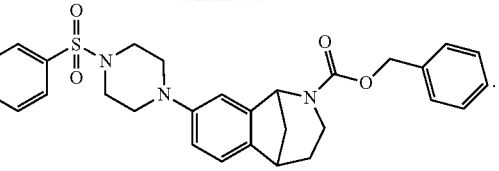

In embodiments, the compound is not

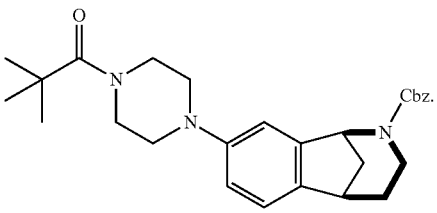

In embodiments, the compound is not

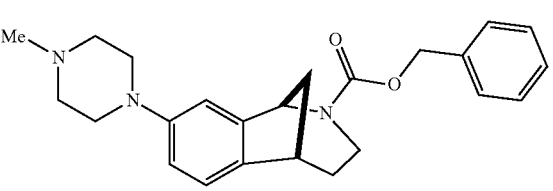

In embodiments, the compound is not:

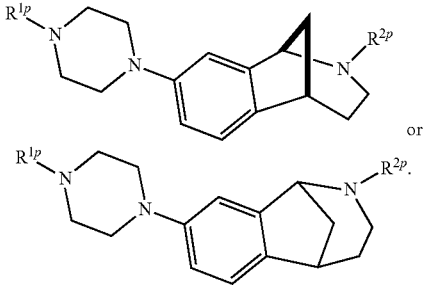

$R^{1p}$ is independently hydrogen, halogen, —$CX^p_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC=(O)NH_2$, —$NHSO_2H$, —NHC=(O)H, —NHC(O)—OH, —NHOH, —$OCX^p_3$, —$OCHX^p_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{2p}$ is hydrogen, halogen, —$CX^{1p}_3$, —$CHX^{1p}_2$, —$CH_2X^{1p}$, —CN, —$NR^{7p}R^{8'}$, —$C(O)R^{9p}$, —$C(O)OR^{9p}$, —$C(O)NR^{7p}R^{8p}$, —$OR^{10p}$, —$OC(O)OR^{9p}$, —$OC(O)NR^{7p}R^{8p}$, —$OC(O)R^{9p}$, —C(S) $R^{9p}$, —$C(S)OR^{9p}$, —$C(S)NR^{7p}R^{8p}$, —$SR^{10p}$, —OC(S) $OR^{9p}$, —$OC(S)NR^{7p}R^{8p}$, —$OC(S)R^{9p}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{7p}$, $R^{8p}$, $R^{9p}$, and $R^{10p}$ are independently hydrogen, halogen, —$CX^P_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^P_3$, —$OCHX^P_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^{7p}$ and $R^{8p}$ substituents bonded to the same nitrogen atom may optionally be joined to form a substituted or unsubstituted 3 to 6 membered heterocycloalkyl or substituted or unsubstituted 5 to 6 membered heteroaryl. The symbol z is an integer from 0 to 5. The symbols $X^p$ and $X^{1p}$ are independently —Cl, —Br, —I, or —F.

In embodiments, $R^{1p}$ is independently hydrogen, halogen, —$CX^P_3$, —CN, —OH, —$NH_2$, —COOH, —$CONH_2$, —$NO_2$, —SH, —$SO_2Cl$, —$SO_3H$, —$SO_4H$, —$SO_2NH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^P_3$, —$OCHX^P_2$, unsubstituted alkyl, unsubstituted heteroalkyl, unsubstituted cycloalkyl, unsubstituted heterocycloalkyl, unsubstituted aryl or unsubstituted heteroaryl. In embodiments, $R^{1p}$ is unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1p}$ is unsubstituted $C_1$-$C_6$ alkyl. In embodiments, $R^{1p}$ is unsubstituted $C_1$-$C_5$ alkyl. In embodiments, $R^{1p}$ is unsubstituted $C_1$-$C_4$ alkyl. In embodiments, $R^{1p}$ is unsubstituted $C_1$-$C_3$ alkyl. In embodiments, $R^{1p}$ is unsubstituted $C_1$-$C_2$ alkyl. In embodiments, $R^{1p}$ is unsubstituted $C_2$-$C_6$ alkyl. In embodiments, $R^{1p}$ is unsubstituted $C_3$-$C_6$ alkyl. In embodiments, $R^{1p}$ is unsubstituted $C_4$-$C_6$ alkyl.

In embodiments, $R^{2p}$ is independently substituted or unsubstituted $C_1$-$C_6$ alkyl, substituted or unsubstituted 2 to 6 membered heteroalkyl, substituted or unsubstituted $C_4$-$C_6$ cycloalkyl, substituted or unsubstituted 4 to 6 membered heterocycloalkyl, substituted or unsubstituted phenyl, or substituted or unsubstituted 5 to 6 membered heteroaryl. In embodiments, $R^{2p}$ is substituted or unsubstituted 3 to 6 membered heteroalkyl. In embodiments, $R^{2p}$ is substituted or unsubstituted 4 to 6 membered heteroalkyl.

In embodiments, $R^{2p}$ is hydrogen, $R^{3p}$-substituted or unsubstituted cycloalkyl, $R^{3p}$-substituted or unsubstituted heterocycloalkyl, $R^{3p}$-substituted or unsubstituted aryl, or $R^{3p}$-substituted or unsubstituted heteroaryl. In embodiments, $R^2$ is independently hydrogen, $R^{3p}$-substituted or unsubstituted $C_4$-$C_6$ cycloalkyl, $R^{3p}$-substituted or unsubstituted 4 to 6 membered heterocycloalkyl, $R^{3p}$-substituted or unsubstituted phenyl, or $R^{3p}$-substituted or unsubstituted 5 to 6 membered heteroaryl. In embodiments, $R^{2p}$ is independently hydrogen. In embodiments, $R^2$ is independently $R^{3p}$-substituted or unsubstituted $C_4$-$C_6$ cycloalkyl. In embodiments, $R^{2p}$ is independently $R^{3p}$-substituted or unsubstituted 4 to 6 membered heterocycloalkyl. In embodiments, $R^{2p}$ is independently $R^{3p}$-substituted or unsubstituted phenyl. In embodiments, $R^{2p}$ is independently $R^{3p}$-substituted or unsubstituted 5 to 6 membered heteroaryl. In embodiments, $R^{2p}$ is independently unsubstituted $C_4$-$C_6$ cycloalkyl. In embodiments, $R^{2p}$ is unsubstituted 4 to 6 membered heterocycloalkyl. In embodiments, $R^{2p}$ is unsubstituted phenyl. In embodiments, $R^2$ is unsubstituted 5 to 6 membered heteroaryl. In embodiments, $R^{2p}$ is independently $R^{3p}$-substituted or unsubstituted cycloalkyl or independently $R^{3p}$-substituted heterocycloalkyl. In embodiments, $R^{2p}$ is independently $R^{3p}$-substituted phenyl or independently $R^{3p}$-substituted 5 to 6 membered heteroaryl.

$R^{3p}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^{3p}$ substituents may optionally be joined to form a substituted or unsubstitued cycloalkyl, substituted or unsubstituted heterocycloalkyl, substituted or unsubstituted aryl, or substituted or unsubstituted heteroaryl.

In embodiments, $R^{3p}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{3p}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{4p}$-substituted or unsubstituted alkyl, $R^{4p}$-substituted or unsubstituted heteroalkyl, $R^{4p}$-substituted or unsubstituted cycloalkyl, $R^{4p}$-substituted or unsubstituted heterocycloalkyl, $R^{4p}$-substituted or unsubstituted aryl, or $R^{4p}$-substituted or unsubstituted heteroaryl. In embodiments, two adjacent $R^{3p}$ substituents may optionally be joined to form an $R^{4p}$-substituted or unsubstituted cycloalkyl, $R^{4p}$-substituted or unsubstituted heterocycloalkyl, $R^{4p}$-substituted or unsubstituted aryl, or $R^{4p}$-substituted or unsubstituted heteroaryl. In embodiments, $R^{3p}$ is independently $R^{4p}$-substituted or unsubstituted cycloalkyl, $R^{4p}$-substituted or unsubstituted heterocycloalkyl. In embodiments, $R^{3p}$ is independently $R^{4p}$-substituted or unsubstituted phenyl or $R^{4p}$-substituted or unsubstituted 5 to 6 membered heteroaryl.

$R^{4p}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{4p}$ is independently hydrogen, unsubstituted $C_1$-$C_6$ alkyl, unsubstituted 2 to 6 membered heteroalkyl. In embodiments, $R^{4p}$ is independently unsubstituted 3 to 6 membered heteroalkyl. In embodiments, $R^{4p}$ is independently unsubstituted 4 to 6 membered heteroalkyl. In embodiments, $R^{4p}$ is independently halogen, oxo, —$CF_3$, —CCl$_3$, —CN, —S(O)CH$_3$, —OH, —NH$_2$, —COOH, —CONH$_2$, —NO$_2$, —C(O)CH$_3$, —CH$_2$CH$_3$, —CH$_2$CH$_2$OH, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

Each R$^{7p}$, R$^{8p}$, R$^{9p}$, and R$^{10p}$ may independently be hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl. Each R$^{7p}$, R$^{8p}$, R$^{9p}$, and R$^{10p}$ may independently be hydrogen, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl. Each R$^{7p}$, R$^{8p}$, R$^{9p}$, and R$^{10p}$ may independently be hydrogen, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl. Each R$^{7p}$, R$^{8p}$, R$^{9p}$, and R$^{10p}$ may independently be hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. Each R$^{7p}$, R$^{8p}$, R$^{9p}$, and R$^{10p}$ may independently be hydrogen, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. Each R$^{7p}$, R$^{8p}$, R$^{9p}$, and R$^{10p}$ may independently be hydrogen, substituted or unsubstituted C$_1$-C$_4$ alkyl, substituted or unsubstituted 2 to 4 membered heteroalkyl, substituted or unsubstituted C$_4$-C$_6$ cycloalkyl, substituted or unsubstituted 4 to 6 membered heterocycloalkyl, substituted or unsubstituted phenyl, or substituted or unsubstituted 5 to 6 membered heteroaryl. Each R$^{7p}$, R$^{8p}$, R$^{9p}$, and R$^{10p}$ may independently be hydrogen, unsubstituted C$_1$-C$_4$ alkyl, unsubstituted 2 to 4 membered heteroalkyl, unsubstituted C$_4$-C$_6$ cycloalkyl, unsubstituted 4 to 6 membered heterocycloalkyl, unsubstituted phenyl, or unsubstituted 5 to 6 membered heteroaryl. Each R$^{7p}$, R$^{8p}$, R$^{9p}$, and R$^{10p}$ may independently be hydrogen, substituted or unsubstituted C$_1$-C$_3$ alkyl, substituted or unsubstituted 2 to 3 membered heteroalkyl, substituted or unsubstituted C$_5$-C$_6$ cycloalkyl, substituted or unsubstituted 5 to 6 membered heterocycloalkyl, substituted or unsubstituted phenyl, or substituted or unsubstituted 5 to 6 membered heteroaryl. Each R$^{7p}$, R$^{8p}$, R$^{9p}$, and R$^{10p}$ may independently be hydrogen, unsubstituted C$_1$-C$_3$ alkyl, unsubstituted 2 to 3 membered heteroalkyl, unsubstituted C$_5$-C$_6$ cycloalkyl, unsubstituted 5 to 6 membered heterocycloalkyl, unsubstituted phenyl, or unsubstituted 5 to 6 membered heteroaryl. Each R$^7$ and R$^{8p}$ substituents bonded to the same nitrogen atom may be joined to form a substituted or unsubstituted 4 to 6 membered heterocycloalkyl or 5 to 6 membered heteroaryl. Each R$^7$ and R$^{8p}$ substituents bonded to the same nitrogen atom may be joined to form an unsubstituted 4 to 6 membered heterocycloalkyl or unsubstituted 5 to 6 membered heteroaryl.

In embodiments, R$^{7p}$, R$^{8p}$, R$^{9p}$, and R$^{10p}$ are independently hydrogen, halogen, —CX$^p_3$, —CN, —COOH, —CONH$_2$, —OH, substituted or unsubstituted C$_1$-C$_5$ alkyl, substituted or unsubstituted 2 to 5 membered heteroalkyl, substituted or unsubstituted C$_3$-C$_8$ cycloalkyl, or substituted or unsubstituted 4 to 6 membered heterocycloalkyl. In embodiments, R$^{7p}$, R$^{8p}$, R$^{9p}$, and R$^{10p}$ are independently hydrogen, —CX$^p_3$, —COOH, —CONH$_2$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl.

In embodiments, R$^{7p}$ is hydrogen. In embodiments, R$^{7p}$ is halogen. In embodiments, R$^{7p}$ is CX$_3$. In embodiments, R$^{7p}$ is CN. In embodiments, R$^{7p}$ is OH. In embodiments, R$^{7p}$ is NH$_2$. In embodiments, R$^{7p}$ is COOH. In embodiments, R$^{7p}$ is CONH$_2$. In embodiments, R$^{7p}$ is NO$_2$. In embodiments, R$^{7p}$ is SH. In embodiments, R$^{7p}$ is SO$_3$H. In embodiments, R$^{7p}$ is SO$_4$H. In embodiments, R$^{7p}$ is SO$_2$NH$_2$. In embodiments, R$^{7p}$ is NHNH$_2$. In embodiments, R$^{7p}$ is ONH$_2$. In embodiments, R$^{7p}$ is NHC=(O)NHNH$_2$. In embodiments, R$^{7p}$ is NHC=(O) NH$_2$. In embodiments, R$^{7p}$ is NHSO$_2$H. In embodiments, R$^{7p}$ is NHC=(O)H. In embodiments, R$^{7p}$ is NHC(O)—OH. In embodiments, R$^{7p}$ is NHOH. In embodiments, R$^{7p}$ is —OCX$_3$. In embodiments, R$^{7p}$ is OCHX$_2^1$. In embodiments, R$^{7p}$ is substituted or unsubstituted C$_1$-C$_8$ alkyl. In embodiments, R$^{7p}$ is substituted or unsubstituted 2 to 8 membered heteroalkyl. In embodiments, R$^{7p}$ is substituted or unsubstituted C$_3$-C$_8$ cycloalkyl. In embodiments, R$^{7p}$ is substituted or unsubstituted 3 to 6 membered heterocycloalkyl. In embodiments, R$^{7p}$ is substituted or unsubstituted phenyl. In embodiments, R$^{7p}$ is substituted or unsubstituted 5 to 6 membered heteroaryl. In embodiments, R$^{7p}$ is unsubstituted C$_1$-C$_8$ alkyl. In embodiments, R$^{7p}$ is unsubstituted 2 to 8 membered heteroalkyl. In embodiments, R$^{7p}$ is unsubstituted C$_3$-C$_8$ cycloalkyl. In embodiments, R$^{7p}$ is unsubstituted 3 to 6 membered heterocycloalkyl. In embodiments, R$^{7p}$ is unsubstituted phenyl. In embodiments, R$^{7p}$ is unsubstituted 5 to 6 membered heteroaryl. In embodiments, R$^{7p}$ is unsubstituted methyl. In embodiments, R$^{7p}$ is unsubstituted ethyl. In embodiments, R$^{7p}$ is unsubstituted propyl. In embodiments, R$^{7p}$ is unsubstituted isopropyl. In embodiments, R$^{7p}$ is unsubstituted butyl. In embodiments, R$^{7p}$ is unsubstituted tert-butyl.

In embodiments, R$^{8p}$ is hydrogen. In embodiments, R$^{8p}$ is halogen. In embodiments, R$^{8p}$ is CX$^p_3$. In embodiments, R$^{8p}$ is CN. In embodiments, R$^{8p}$ is OH. In embodiments, R$^{8p}$ is NH$_2$. In embodiments, R$^{8p}$ is COOH. In embodiments, R$^{8p}$ is CONH$_2$. In embodiments, R$^{8p}$ is NO$_2$. In embodiments, R$^{8p}$ is SH. In embodiments, R$^{8p}$ is SO$_3$H. In embodiments, R$^{8p}$ is SO$_4$H. In embodiments, R$^{8p}$ is SO$_2$NH$_2$. In embodiments, R$^{8p}$ is NHNH$_2$. In embodiments, R$^{8p}$ is ONH$_2$. In embodiments, R$^{8p}$ is NHC=(O)NHNH$_2$. In embodiments, R$^{8p}$ is NHC=(O) NH$_2$. In embodiments, R$^{8p}$ is NHSO$_2$H. In embodiments, R$^{8p}$ is NHC=(O)H. In embodiments, R$^{8p}$ is NHC(O)—OH. In embodiments, R$^{8p}$ is NHOH. In embodiments, R$^{8p}$ is —OCX$_3$. In embodiments, R$^{8p}$ is OCHX$_2^1$. In embodiments, R$^{8p}$ is substituted or unsubstituted C$_1$-C$_8$ alkyl. In embodiments, R$^{8p}$ is substituted or unsubstituted 2 to 8 membered heteroalkyl. In embodiments, R$^{8p}$ is substituted or unsubstituted $C_3$-$C_8$ cycloalkyl. In embodiments, $R^{8p}$ is substituted or unsubstituted 3 to 6 membered heterocycloalkyl. In embodiments, $R^{8p}$ is substituted or unsubstituted phenyl. In embodiments, $R^{8p}$ is substituted or unsubstituted 5 to 6 membered heteroaryl. In embodiments, $R^{8p}$ is unsubstituted $C_1$-$C_8$ alkyl. In embodiments, $R^{8p}$ is unsubstituted 2 to 8 membered heteroalkyl. In embodiments, $R^{8p}$ is unsubstituted $C_3$-$C_8$ cycloalkyl. In embodiments, $R^{8p}$ is unsubstituted 3 to 6 membered heterocycloalkyl. In embodiments, $R^{8p}$ is unsubstituted phenyl. In embodiments, $R^{8p}$ is unsubstituted 5 to 6 membered heteroaryl. In embodiments, $R^{8p}$ is unsubstituted methyl. In embodiments, $R^{8p}$ is unsubstituted ethyl. In embodiments, $R^{8p}$ is unsubstituted propyl. In embodiments, $R^{8p}$ is unsubstituted isopropyl. In embodiments, $R^{8p}$ is unsubstituted butyl. In embodiments, $R^{8p}$ is unsubstituted tert-butyl.

In embodiments, $R^{9p}$ is hydrogen. In embodiments, $R^{9p}$ is halogen. In embodiments, $R^{9p}$ is $CX^p_3$. In embodiments, $R^{9p}$ is CN. In embodiments, $R^{9p}$ is OH. In embodiments, $R^{9p}$ is $NH_2$. In embodiments, $R^{9p}$ is COOH. In embodiments, $R^{9p}$ is $CONH_2$. In embodiments, $R^{9p}$ is $NO_2$. In embodiments, $R^{9p}$ is SH. In embodiments, $R^{9p}$ is $SO_3H$. In embodiments, $R^{9p}$ is $SO_4H$. In embodiments, $R^{9p}$ is $SO_2NH_2$. In embodiments, $R^{9p}$ is $NHNH_2$. In embodiments, $R^{9p}$ is $ONH_2$. In embodiments, $R^{9p}$ is $NHC=(O)NHNH_2$. In embodiments, $R^{9p}$ is $NHC=(O) NH_2$. In embodiments, $R^{9p}$ is $NHSO_2H$. In embodiments, $R^{9p}$ is $NHC=(O)H$. In embodiments, $R^{9p}$ is $NHC(O)$—OH. In embodiments, $R^{9p}$ is NHOH. In embodiments, $R^{9p}$ is —$OCX_3$. In embodiments, $R^{9p}$ is $OCHX_2^1$. In embodiments, $R^{9p}$ is substituted or unsubstituted $C_1$-$C_8$ alkyl. In embodiments, $R^{9p}$ is substituted or unsubstituted 2 to 8 membered heteroalkyl. In embodiments, $R^{9p}$ is substituted or unsubstituted $C_3$-$C_8$ cycloalkyl. In embodiments, $R^{9p}$ is substituted or unsubstituted 3 to 6 membered heterocycloalkyl. In embodiments, $R^{9p}$ is substituted or unsubstituted phenyl. In embodiments, $R^{9p}$ is substituted or unsubstituted 5 to 6 membered heteroaryl. In embodiments, $R^{9p}$ is unsubstituted $C_1$-$C_8$ alkyl. In embodiments, $R^{9p}$ is unsubstituted 2 to 8 membered heteroalkyl. In embodiments, $R^{9p}$ is unsubstituted $C_3$-$C_8$ cycloalkyl. In embodiments, $R^{9p}$ is unsubstituted 3 to 6 membered heterocycloalkyl. In embodiments, $R^{8p}$ is unsubstituted phenyl. In embodiments, $R^{8p}$ is unsubstituted 5 to 6 membered heteroaryl. In embodiments, $R^{8p}$ is unsubstituted methyl. In embodiments, $R^{8p}$ is unsubstituted ethyl. In embodiments, $R^{8p}$ is unsubstituted propyl. In embodiments, $R^{8p}$ is unsubstituted isopropyl. In embodiments, $R^{8p}$ is unsubstituted butyl. In embodiments, $R^{8p}$ is unsubstituted tert-butyl.

In embodiments, $R^{10p}$ is hydrogen. In embodiments, $R^{10p}$ is halogen. In embodiments, $R^{10p}$ is $CX^p_3$. In embodiments, $R^{10p}$ is —CN. In embodiments, $R^{10p}$ is OH. In embodiments, $R^{10p}$ is —$NH_2$. In embodiments, $R^{10p}$ is COOH. In embodiments, $R^{10p}$ is $CONH_2$. In embodiments, $R^{10p}$ is $NO_2$. In embodiments, $R^{10p}$ is SH. In embodiments, $R^{10p}$ is $SO_3H$. In embodiments, $R^{10p}$ is $SO_4H$. In embodiments, $R^{10p}$ is $SO_2NH_2$. In embodiments, $R^{10p}$ is $NHNH_2$. In embodiments, $R^{10p}$ is $ONH_2$. In embodiments, $R^{10p}$ is $NHC=(O)NHNH_2$. In embodiments, $R^{10p}$ is $NHC=(O) NH_2$. In embodiments, $R^{10p}$ is $NHSO_2H$. In embodiments, $R^{10p}$ is $NHC=(O)H$. In embodiments, $R^{10p}$ is $NHC(O)$—OH. In embodiments, $R^{10p}$ is NHOH. In embodiments, $R^{10p}$ is —$OCX_3$. In embodiments, $R^{10p}$ is $OCHX^p_2$. In embodiments, $R^{10p}$ is substituted or unsubstituted $C_1$-$C_8$ alkyl. In embodiments, $R^{10p}$ is substituted or unsubstituted 2 to 8 membered heteroalkyl. In embodiments, $R^{10p}$ is substituted or unsubstituted $C_3$-$C_8$ cycloalkyl. In embodiments, $R^{10p}$ is substituted or unsubstituted 3 to 6 membered heterocycloalkyl. In embodiments, $R^{10p}$ is substituted or unsubstituted phenyl. In embodiments, $R^{10p}$ is substituted or unsubstituted 5 to 6 membered heteroaryl. In embodiments, $R^{10p}$ is unsubstituted $C_1$-$C_8$ alkyl. In embodiments, $R^{10p}$ is unsubstituted 2 to 8 membered heteroalkyl. In embodiments, $R^{10p}$ is unsubstituted $C_3$-$C_8$ cycloalkyl. In embodiments, $R^{10p}$ is unsubstituted 3 to 6 membered heterocycloalkyl. In embodiments, $R^{10p}$ is unsubstituted phenyl. In embodiments, $R^{10p}$ is unsubstituted 5 to 6 membered heteroaryl. In embodiments, $R^{10p}$ is unsubstituted methyl. In embodiments, $R^{10p}$ is unsubstituted ethyl. In embodiments, $R^{10p}$ is unsubstituted propyl. In embodiments, $R^{10p}$ is unsubstituted isopropyl. In embodiments, $R^{10p}$ is unsubstituted butyl. In embodiments, $R^{10p}$ is unsubstituted tert-butyl.

In embodiments, the compound is not:

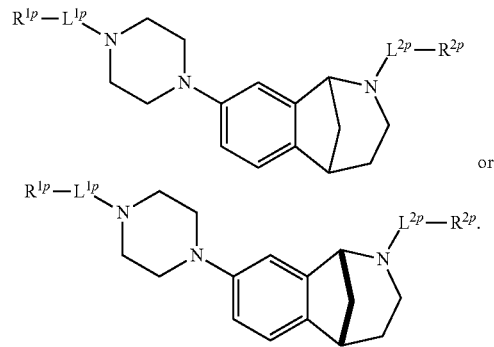

In embodiments, the compound is not:

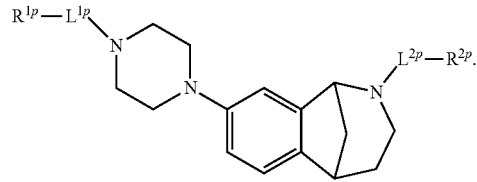

In embodiments, the compound is not:

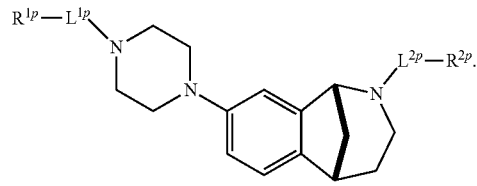

$L^{1p}$ is a bond, —C(O)—, —$S(O)_2$—, substituted or unsubstituted methylene, or substituted or unsubstituted 2 to 4 membered heteroalkylene. In embodiments, $L^{1p}$ is a bond. In embodiments, $L^{1p}$ is C(O)—. In embodiments, $L^{1p}$ is —$S(O)_2$—. In embodiments, $L^{1p}$ is unsubstituted methylene. In embodiments, $L^{1p}$ is $C(S)NHCH_2CH_2$—. In embodiments, $L^{1p}$ is substituted 2 to 4 membered heteroalkylene. In embodiments, $L^{1p}$ is unsubstituted 2 to 4 membered heteroalkylene. In embodiments, $L^{1p}$ is thioxo substituted 2 to 4 membered heteroalkylene.

In embodiments, $R^{1p}$ is independently substituted alkyl. In embodiments, $R^{1p}$ is independently substituted $C_1$-$C_6$ alkyl. In embodiments, $R^{1p}$ is independently substituted $C_1$-$C_4$ alkyl. In embodiments, $R^{1p}$ is independently oxo substituted alkyl. In embodiments, $R^{1p}$ is independently oxo substituted $C_1$-$C_6$ alkyl. In embodiments, $R^{1p}$ is independently oxo substituted $C_1$-$C_5$ alkyl. In embodiments, $R^{1p}$ is independently unsubstituted alkyl. In embodiments, $R^{1p}$ is independently unsubstituted $C_1$-$C_6$ alkyl. In embodiments, $R^{1p}$ is independently unsubstituted $C_1$-$C_4$ alkyl. In embodiments, $R^{1p}$ is independently unsubstituted methyl. In embodiments, $R^{1p}$ is independently unsubstituted tert-butyl. In embodiments, $R^{1p}$ is independently substituted 2 to 4 membered heteroalkylene. In embodiments, $R^{1p}$ is independently thioxo substituted 2 to 4 membered heteroalkylene. In embodiments, $R^{1p}$ is independently thioxo, phenyl substituted 2 to 4 membered heteroalkylene.

In embodiments, $R^{1p}$ is independently substituted or unsubstituted aryl. In embodiments, $R^{1p}$ is independently substituted or unsubstituted phenyl. In embodiments, $R^{1p}$ is independently substituted phenyl. In embodiments, $R^{1p}$ is independently unsubstituted phenyl. In embodiments, $R^{1p}$ is independently unsubstituted diphenyl. In embodiments, $R^{1p}$ is independently phenyl substituted with halogen. In embodiments, $R^{1p}$ is independently phenyl substituted with unsubstituted methyl. In embodiments, $R^{1p}$ is independently phenyl substituted with unsubstituted $C_1$-$C_3$ alkyl. In embodiments, $R^{1p}$ is independently phenyl substituted with unsubstituted methoxy. In embodiments, $R^{1p}$ is independently phenyl substituted with $CX^p{}_3$. In embodiments, $R^{1p}$ is independently phenyl substituted with $CF_3$. In embodiments, $R^{1p}$ is independently phenyl substituted with unsubstituted phenyl.

$L^{2p}$ is a bond, —$SO_2$—, —C(O)O—, —C(O)—, —$SO_2CH_2$—, —C(S)NH—, —C(O)$OCH_2$—, —C(O)$CH_2$—, —C(O)$CH_2CH_2$—, or unsubstituted $C_1$-$C_4$ alkylene. In embodiments, $L^{2p}$ is a bond. In embodiments, $L^{2p}$ is —$SO_2$—. In embodiments, $L^{2p}$ is —C(O)O—. In embodiments, $L^{2p}$ is —C(O)—. In embodiments, $L^{2p}$ is —$SO_2CH_2$—. In embodiments, $L^{2p}$ is —C(S)NH—. In embodiments, $L^{2p}$ is —C(O)$OCH_2$—. In embodiments, $L^{2p}$ is —C(O)$CH_2$—. In embodiments, $L^{2p}$ is —C(O)$CH_2CH_2$—. In embodiments, $L^{2p}$ is unsubstituted $C_1$-$C_4$ alkylene.

In embodiments, $R^{2p}$ is independently substituted or unsubstituted $C_1$-$C_8$ alkyl, substituted or unsubstituted 2 to 8 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{2p}$ is independently unsubstituted $C_1$-$C_8$ alkyl. In embodiments, $R^{2p}$ is independently unsubstituted $C_1$-$C_4$ alkyl. In embodiments, $R^{2p}$ is independently unsubstituted $C_1$-$C_2$ alkyl. In embodiments, $R^{2p}$ is independently unsubstituted $C_2$-$C_4$ alkenyl. In embodiments, $R^{2p}$ is independently unsubstituted ethenyl. In embodiments, $R^{2p}$ is independently substituted or unsubstituted 5 to 6 membered heteroaryl. In embodiments, $R^{2p}$ is independently unsubstituted 5 to 6 membered heteroaryl. In embodiments, $R^{2p}$ is independently unsubstituted 6 membered heteroaryl. In embodiments, $R^{2p}$ is independently unsubstituted pyridyl. In embodiments, $R^{2p}$ is independently substituted or unsubstituted phenyl. In embodiments, $R^{2p}$ is independently unsubstituted phenyl. In embodiments, $R^{2p}$ is independently substituted phenyl. In embodiments, $R^{2p}$ is independently methoxy substituted phenyl. In embodiments, $R^{2p}$ is independently ethoxy substituted phenyl. In embodiments, $R^{2p}$ is independently phenyl independently substituted with unsubstituted 2 to 3 membered alkoxy. In embodiments, $R^{2p}$ is phenyl independently substituted with unsubstituted $C_1$-$C_4$ alkyl. In embodiments, $R^{2p}$ is phenyl independently substituted with unsubstituted $C_1$-$C_2$ alkyl. In embodiments, $R^{2p}$ is phenyl independently substituted with halogen. In embodiments, $R^{2p}$ is phenyl independently substituted with unsubstituted —CN. In embodiments, $R^{2p}$ is independently substituted or unsubstituted $C_3$-$C_6$ cycloalkyl. In embodiments, $R^{2p}$ is independently unsubstituted $C_3$-$C_6$ cycloalkyl. In embodiments, $R^{2p}$ is independently unsubstituted $C_5$-$C_6$ cycloalkyl.

In embodiments, —$L^{2p}$-$R^{2p}$ is independently

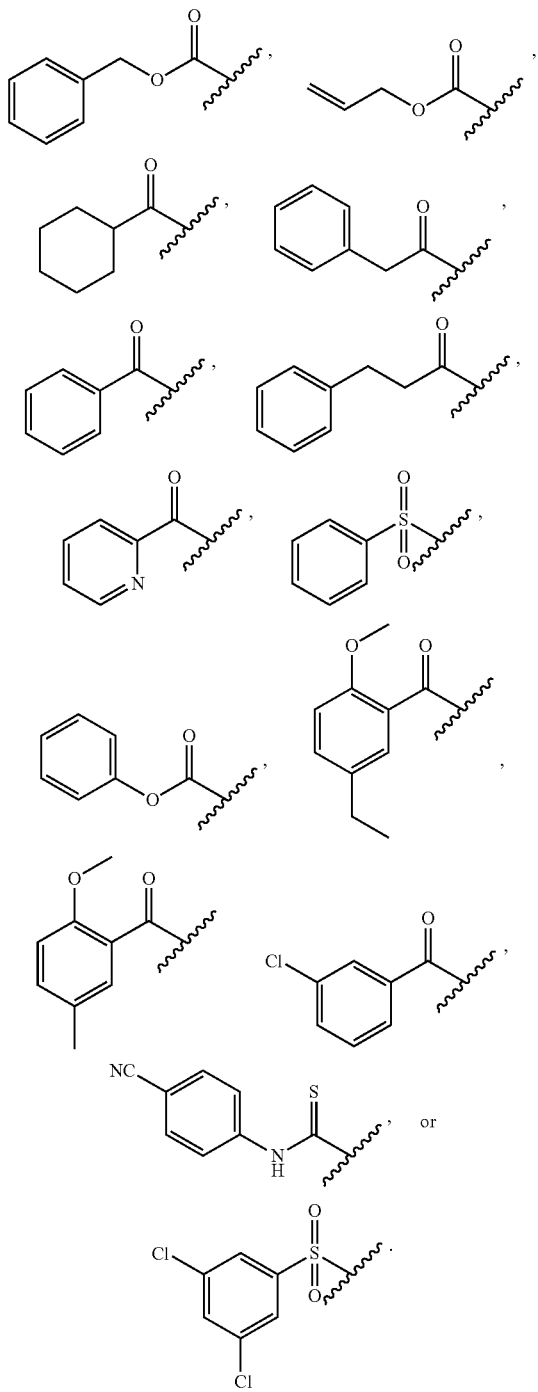

It will be understood that a compound depicted with the general structure

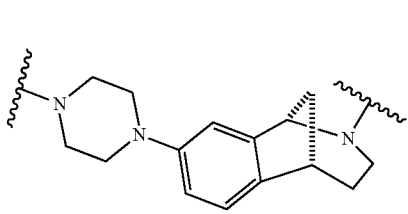

may equivalently be depicted with the general structure

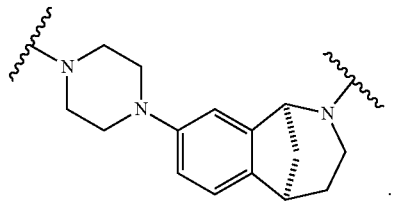 [SMILES: *N1CCN(c2ccc3c(c2)[C@@H]2C[C@H]3CCN2*)CC1]

It will be understood that a compound depicted with the general structure

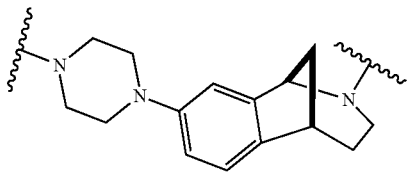

may equivalently be depicted with the general structure

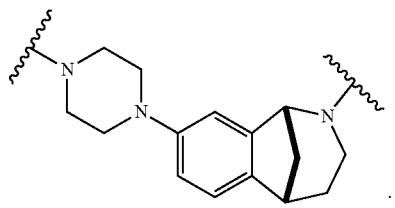 [SMILES: *N1CCN(c2ccc3c(c2)[C@H]2C[C@@H]3CCN2*)CC1]

It will be understood that a compound depicted with the general structure

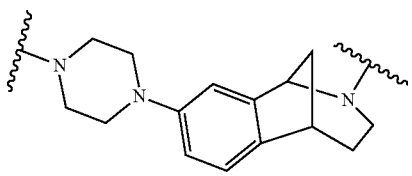 [SMILES: *N1CCN(c2ccc3c(c2)C2CC3CCN2*)CC1]

may equivalently be depicted with the general structure

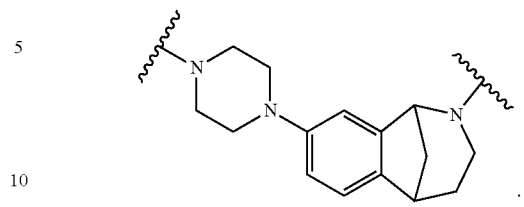

C. Pharmaceutical Compositions

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In embodiments of the pharmaceutical compositions, the compound, or pharmaceutically acceptable salt thereof, is included in a therapeutically effective amount. In embodiments of the pharmaceutical compositions, the compound is included in a drug-eluting stent.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an anti-cancer agent. In embodiments, the second agent is an anti-inflammatory disease agent. In embodiments, the second agent is an anti-neurodegenerative disease agent. In embodiments, the second agent is an anti-cardiovascular disease agent. In embodiments, the second agent is an analgesic agent. In embodiments, the second agent is an agent for treating a psychiatric disease.

D. Methods of Treatment

In an aspect is provided a method of treating a disease including administering an effective amount of a compound as described herein. In an aspect is provided a compound as described herein for use as a medicament (e.g., for treatment of a disease). In an aspect is provided a compound as describe herein for use in the treatment of a disease (e.g., including administering an effective amount of a compound as described herein).

In embodiments, the method does not induce increases in intracellular calcium concentration (e.g. compared to control (e.g., the same method without administering the compound). In embodiments, the method reduces the level of IL-1β (e.g. compared to control). In embodiments, the method reduces the level of TNFα (e.g. compared to control). In embodiments, the method reduces the level of CD14 (e.g., compared to control). In embodiments, the method reduces the level of IL-1β (e.g. compared to control) in the brain of a subject. In embodiments, the method reduces the level of TNFα (e.g. compared to control) in the brain of a subject. In embodiments, the method reduces the level of CD14 (e.g., compared to control) in the brain of a subject. In embodiments, the method reduces the levels of long term depression (e.g., compared to control). In embodiments, the method reduces the levels of long term depression in neurons (e.g., compared to control). In embodiments, the method reduces the levels of neuronal long term depression (e.g., compared to control) n. In embodiments, the method reduces the levels of long term depression of hippocampal neurons (e.g., compared to control). In embodiments, the method reduces the levels of hippocampal long term depression (e.g., compared to control).

In embodiments, the disease is cancer. In embodiments, the disease is an autoimmune disease. In embodiments, the disease is an inflammatory disease. In embodiments, the disease is a neurodegenerative disease. In embodiments, the disease is a psychiatric disease. In embodiments, the disease is pain. In embodiments, the disease is a cardiovascular disease. In embodiments, the disease is traumatic brain injury.

In an aspect is provided a method of treating cancer in a subject in need thereof, the method including administering an effective amount of a compound described herein. In embodiments, the cancer is brain cancer. In embodiments, the cancer is neuroblastoma. In embodiments, the cancer is glioblastoma. In embodiments, the cancer is glioma. In embodiments, the cancer is oligodendroglioma. In embodiments, the cancer is Anaplastic astrocytoma, Astrocytoma, Central neurocytoma, Choroid plexus carcinoma, Choroid plexus papilloma, Choroid plexus tumor, Dysembryoplastic neuroepithelial tumour, Ependymal tumor, ependymoma, Fibrillary astrocytoma, Giant-cell glioblastoma, Glioblastoma multiforme, Gliomatosis cerebri, Gliosarcoma, Hemangiopericytoma, Medulloblastoma, Medulloepithelioma, Meningeal carcinomatosis, meningioma, Neuroblastoma, Neurocytoma, Oligoastrocytoma, Oligodendroglioma, Optic nerve sheath meningioma, Pediatric ependymoma, Pilocytic astrocytoma, Pinealoblastoma, Pineocytoma, Pleomorphic anaplastic neuroblastoma, Pleomorphic xanthoastrocytoma, Primary central nervous system lymphoma, Sphenoid wing meningioma, Subependymal giant cell astrocytoma, Subependymoma, or Trilateral retinoblastoma.

In an aspect is provided a method to treating a neurodegenerative disease in a subject in need thereof, the method including administering an effective amount of a compound described herein.

In embodiments, the neurodegenerative disease is Alzheimer's disease, Parkinson's disease, Huntington's disease, progressive supranuclear palsy, frontotemporal dementia, or amyotrophic lateral sclerosis. In embodiments, the neurodegenerative disease is Alzheimer's disease. In embodiments, the neurodegenerative disease is Parkinson's disease. In embodiments, the neurodegenerative disease is Huntington's disease. In embodiments, the neurodegenerative disease is progressive supranuclear palsy. In embodiments, the neurodegenerative disease is amyotrophic lateral sclerosis. In embodiments, the neurodegenerative disease is frontotemporal dementia. In embodiments, the method increases survival of neurons (e.g. compared to control). In embodiments, the method increases survival of neurons in a subject with amyotrophic lateral sclerosis (e.g., compared to control). In embodiments, the method increases survival of motor neurons (e.g. compared to control). In embodiments, the method increases survival of motor neurons in a subject with amyotrophic lateral sclerosis (e.g., compared to control).

In an aspect is provided a method of treating drug abuse in a subject in need thereof, the method including administering an effective amount of a compound described herein.

In an aspect is provided a method of treating drug addiction in a subject in need thereof, the method including administering an effective amount of a compound described herein.

In embodiments, the drug is ethanol, nicotine, cocaine, amphetamine, methamphetamine, an opiate, or an opioid.

In an aspect is provided a method of treating a psychiatric disease in a subject in need thereof, the method including administering an effective amount of a compound described herein.

In an aspect is provided a method of treating anxiety, depression, schizophrenia, or epilepsy in a subject in need thereof, the method including administering an effective amount of a compound described herein.

In an aspect is provided a method of treating pain in a subject in need thereof, the method including administering an effective amount of a compound described herein.

In an aspect is provided a method of treating migraine or neuropathic pain in a subject in need thereof, the method including administering an effective amount of a compound described herein.

In an aspect is provided a method to treating an inflammatory disease in a subject in need thereof, the method including administering an effective amount of a compound described herein. In embodiments, the inflammatory disease is associated with brain inflammation.

In an aspect is provided a method to treating a cardiovascular disease in a subject in need thereof, the method including administering an effective amount of a compound described herein.

In an aspect is provided a method of treating amnesia, traumatic brain injury, inflammatory pain, stroke, a cardiovascular disease, multiple sclerosis, or retinal neural degeneration in a subject in need thereof, the method including administering an effective amount of a compound described herein. In an aspect is provided a method of treating traumatic brain injury in a subject in need thereof, the method including administering an effective amount of a compound described herein. In embodiments, the traumatic brain injury is blast traumatic brain injury. In embodiments, the traumatic brain injury is blast-induced traumatic brain injury. In embodiments, the traumatic brain injury is open head injury. In embodiments, the traumatic brain injury is closed head injury. In embodiments, the traumatic brain injury is deceleration injury. In embodiments, the traumatic brain injury is chemical injury. In embodiments, the traumatic brain injury is toxic injury. In embodiments, the traumatic brain injury is hypoxia-induced injury. In embodiments, the traumatic brain injury is associated with hypoxia. In embodiments, the traumatic brain injury is associated with a tumor. In embodiments, the traumatic brain injury is cancer associated injury. In embodiments, the traumatic brain injury is associated with an infectious agent. In embodiments, the traumatic brain injury is associated with stroke. In embodiments, the traumatic brain injury is associated with diffuse axonal injury. In embodiments, the traumatic brain injury is associated with encephalitis. In embodiments, the traumatic brain injury is associated with meningitis.

In an aspect is provided a method of modulating a sigma 2 receptor, the method including contacting a sigma 2 receptor with a compound described herein, thereby modulating the sigma 2 receptor.

In an aspect is provided a method of modulating progesterone receptor membrane component 1, the method including contacting a progesterone receptor membrane component 1 with a compound described herein, thereby modulating the progesterone receptor membrane component 1.

In embodiments, the modulating is inhibiting. In embodiments, the modulating is antagonizing. In embodiments, the modulating is activating. In embodiments, the modulating is agonizing.

In an aspect is provided a method of improving (e.g., compared to control, for example the same method without administering the compound) cognition in a subject, the method including administering an effective amount of a compound described herein to the subject.

In another aspect is provided a method of improving (e.g., compared to control, for example the same method without administering the compound) cognition in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for improving cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in improving cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a method of increasing (e.g., compared to control, for example the same method without administering the compound) cognition in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for increasing cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in increasing cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a method of enhancing (e.g., compared to control, for example the same method without administering the compound) cognition in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for enhancing cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in enhancing cognition in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In embodiments, the subject is suffering from a disease impairing cognition. In embodiments, the subject is not suffering from a disease impairing cognition. In embodiments, the method or use includes improving, enhancing, or increasing the subject's cognition beyond the subject's cognition in the absence of the compound. In embodiments, cognition is the ability to learn, understand, remember, or perform a mental function.

In an aspect is provided a method of treating traumatic brain injury in a subject in need thereof, including administering an effective amount of a Sigma 2 Receptor modulator (e.g., inhibitor) to the subject. In embodiments, the Sigma 2 Receptor modulator (e.g., inhibitor) is a compound described herein or in PCT/US14/46730; Mach, R. H.; Zheng, C.; Hawkins, W. G. "The σ2 Receptor: A Novel Protein for the Imaging and Treatment of Cancer." *J. Med. Chem.* 2013, 56, 7137-7160; Huang, Y. S.; Lu, H. L.; Zhang, L. J.; Wu, Z. "Sigma-2 receptor ligands and their perspectives in cancer diagnosis and therapy." Med. Res. Rev. 2014, 34, 532-566; or Guo, L.; Zhen, X. "Sigma-2 receptor ligands: neurobiological effects." *Curr. Med. Chem.* 2015, 22, 989-1003, all of which are incorporated herein by reference in their entirety for all purposes. In embodiments, the Sigma 2 Receptor modulator (e.g., inhibitor) is a compound described herein. In embodiments, the Sigma 2 Receptor modulator (e.g., inhibitor) is a compound described in PCT/US14/46730, which is incorporated herein in its entirety for all purposes. In embodiments, the Sigma 2 Receptor modulator (e.g., inhibitor) modulates (e.g., reduces) the level of Sigma 2 Receptor activity compared to a control (e.g., same method except without administration of the Sigma 2 Receptor modulator (e.g., inhibitor)). In embodiments, the Sigma 2 Receptor modulator (e.g., inhibitor) modulates (e.g., reduces) the level of Sigma 2 Receptor activity by at least 1, 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 91, 92, 93, 94, 95, 96, 97, 98, or 99%, compared to control. In embodiments, the Sigma 2 Receptor modulator (e.g., inhibitor) modulates (e.g., reduces) the level of Sigma 2 Receptor activity by about 1, 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 91, 92, 93, 94, 95, 96, 97, 98, or 99%, compared to control. In embodiments, the Sigma 2 Receptor modulator (e.g., inhibitor) modulates (e.g., reduces) the level of Sigma 2 Receptor activity by 1, 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 91, 92, 93, 94, 95, 96, 97, 98, or 99%, compared to control. In embodiments, the Sigma 2 Receptor modulator (e.g., inhibitor) modulates (e.g., reduces) the level of Sigma 2 Receptor activity by about 1, 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 91, 92, 93, 94, 95, 96, 97, 98, or 99%, compared to control, as measured by an assay method described herein (e.g., the receptor binding assay for Sigma 2 Receptor described in the Example section herein, for example in Example 14). In embodiments, the Sigma 2 Receptor modulator (e.g., inhibitor) modulates (e.g., reduces) the level of Sigma 2 Receptor activity by about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000-fold (e.g., compared to control) (e.g., as measured by an assay method described herein, for example, the receptor binding assay for Sigma 2 Receptor described in the Example section herein, such as in Example 14). In embodiments, the Sigma 2 Receptor modulator (e.g., inhibitor)

modulates (e.g., reduces) the level of Sigma 2 Receptor activity by at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000-fold (e.g., compared to control) (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has an inhibitory constant (Ki) for Sigma 2 Receptor of about $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or $10^{-14}$ M (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has an inhibitory constant (Ki) for Sigma 2 Receptor of at least $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or $10^{-14}$ M (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has an inhibitory constant (Ki) for Sigma 2 Receptor of $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{40}$ M, $10^{-11}$ M, $10^{12}$ M, $10^{13}$ M, or $10^{-14}$ M (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has a half maximal inhibitory concentration (IC50) for Sigma 2 Receptor activity of about $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{40}$ M, $10^{-11}$ M, $10^{12}$ M, $10^{13}$ M, or $10^{-14}$ M (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has a half maximal inhibitory concentration (IC50) for Sigma 2 Receptor activity of at least $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or $10^{-14}$ M (e.g., as measured by an assay method described herein, for example, the receptor binding assay for Sigma 2 Receptor described in the Example section herein, such as in Example 14). In embodiments, the Sigma 2 Receptor modulator (e.g., inhibitor) has a half maximal inhibitory concentration (IC50) for Sigma 2 Receptor activity of $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or $10^{-14}$ M (e.g., as measured by an assay method described herein, for example, the receptor binding assay for Sigma 2 Receptor described in the Example section herein, such as in Example 14). In embodiments, the method improves cognition following traumatic brain injury (e.g., compared to control). In embodiments, the method improves spatial memory following traumatic brain injury (e.g., compared to control). In embodiments, the method improves long term memory following traumatic brain injury (e.g., compared to control). In embodiments, the method improves short term memory following traumatic brain injury (e.g., compared to control).

In embodiments, the disease is a disease described herein and the compound is a compound described herein.

E. Detection and Diagnostics Methods and Compositions

Provided herein are compounds for use as diagnostic tools or for methods of diagnosis. The methods of diagnosis provided herein can be combined with other methods of diagnosis well known in the art. Non-limiting examples of other methods of diagnosis include detection of previously known disease biomarkers, including protein and nucleic acid biomarker detection, radiography, co-axial tomography (CAT) scans, positron emission tomography (PET), radionuclide scanning, and magnetic resonance imaging.

In an aspect is provided a radiolabeled compound, or pharmaceutically acceptable salt thereof, as described herein, including embodiments (e.g. in an aspect, embodiment, example, figure, table, or claim). In embodiments, the radiolabeled compound may be used in methods of identification and/or characterization of diseases or proteins. In embodiments, the protein is sigma 2 receptor. In embodiments, the protein is progesterone receptor membrane component 1. In embodiments, a radiolabeled compound physiologically maps sigma 2 receptors. In embodiments, a radiolabeled compound physiologically maps progesterone receptor membrane component 1. In embodiments, the radiolabeled compound includes $^{18}$F. In embodiments, the radiolabeled compound includes $^{11}$C. In embodiments, the radiolabeled compound includes $^{125}$I. In embodiments, the radiolabeled compound includes $^{3}$H. In embodiments, the compound is enriched in the radiolabel beyond the natural abundancy of the radiolabel.

In an aspect is provided a compound, or pharmaceutically acceptable salt thereof, as described herein, including embodiments (e.g. in an aspect, embodiment, example, figure, table, or claim) connected (e.g., bonded, non-covalently associated, covalently bonded) to a detectable agent. In embodiments, the compound connected to the detectable agent may be used in a method of detecting a protein (e.g., photoaffinity labeling). In embodiments, the detectable agent is a photochemically reactive species covalently attached to the compound. In embodiments, the photochemically reactive species is a compound including a nitrene, carbene, ketone, cation, and/or radical.

The detectable agent may be a moiety when bonded to the compound. Among the detectable agent are imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. Enzymes that may be used as imaging agents in accordance with the embodiments of the disclosure include, but are not limited to, horseradish peroxidase, alkaline phosphatase, acid phosphatase, glucose oxidase, β-galactosidase, β-glucuronidase or β-lactamase. Such enzymes may be used in combination with a chromogen, a fluorogenic compound or a luminogenic compound to generate a detectable signal.

In an aspect is provided a radiolabeled compound, or pharmaceutically acceptable salt thereof, as described herein, including embodiments (e.g. in an aspect, embodiment, example, figure, table, or claim) for use in sigma 2 receptor binding assays (e.g., for determining $IC_{50}$s and $K_i$s of test ligands). In an aspect is provided a radiolabeled compound, or pharmaceutically acceptable salt thereof, as described herein, including embodiments (e.g. in an aspect, embodiment, example, figure, table, or claim) for use in progesterone receptor membrane component 1 binding assays. In embodiments, the radiolabeled compound contains tritium.

Radioactive substances that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

In an aspect is provided a method of detecting a sigma 2 receptor in an individual including: (a) administering to the individual an effective amount of a detectable compound described herein; (b) allowing the detectable compound described herein to bind to a sigma 2 receptor within the individual thereby forming a detectable compound-sigma 2 receptor complex; and (c) detecting the detectable compound-sigma 2 receptor complex in the individual. A detectable compound may be a compound described herein that includes a radiolabel (detectable atom such as $^{18}$F, $^{32}$P, $^{33}$P, $^{11}$C, $^{15}$O, $^{13}$C, $^{13}$N, $^{17}$O, $^{14}$C, $^{3}$H) or a conjugate of a compound described herein and a detectable agent. In embodiments, the detection includes protein or nucleic acid detection, radiography, co-axial tomography (CAT) scan, positron emission tomography (PET), radionuclide scanning, or magnetic resonance imaging.

In an aspect is provided a method of detecting a sigma 2 receptor including: (a) administering to a sample a detectable compound described herein; (b) allowing the detectable compound described herein to bind to a sigma 2 receptor within the sample, thereby forming a detectable compound-sigma 2 receptor complex; and (c) detecting the detectable compound-sigma 2 receptor complex in the sample. In embodiments, a detectable compound is a compound described herein that includes a radiolabel (detectable atom such as $^{18}$F, $^{32}$P, $^{33}$P, $^{11}$C, $^{15}$O, $^{13}$C, $^{13}$N, $^{17}$O, $^{14}$C, $^{3}$H) or a conjugate of a compound described herein and a detectable agent. In embodiments, the detection includes protein or nucleic acid detection, radiography, co-axial tomography (CAT) scan, positron emission tomography (PET), radionuclide scanning, or magnetic resonance imaging. In embodiments, the sample is taken from a subject. In embodiments, the sample is a cell culture. In embodiments, the sample is a tissue. In embodiments, the sample is an animal.

In an aspect is provided a method of detecting a progesterone receptor membrane component 1 in an individual including: (a) administering to the individual an effective amount of a detectable compound described herein; (b) allowing the detectable compound described herein to bind to a progesterone receptor membrane component 1 within the individual thereby forming a detectable compound-progesterone receptor membrane component 1 complex; and (c) detecting the detectable compound-progesterone receptor membrane component 1 complex in the individual. In embodiments, a detectable compound is a compound described herein that includes a radiolabel (detectable atom such as $^{18}$F, $^{32}$P, $^{33}$P, $^{11}$C, $^{15}$O, $^{13}$C, $^{13}$N, $^{17}$O, $^{14}$C, $^{3}$H) or a conjugate of a compound described herein and a detectable agent. In embodiments, the detection includes protein or nucleic acid detection, radiography, co-axial tomography (CAT) scan, positron emission tomography (PET), radionuclide scanning, or magnetic resonance imaging.

In an aspect is provided a method of detecting a progesterone receptor membrane component 1 including: (a) administering to a sample a detectable compound described herein; (b) allowing the detectable compound described herein to bind to a sig progesterone receptor membrane component 1 within the sample, thereby forming a detectable compound-progesterone receptor membrane component 1 complex; and (c) detecting the detectable compound-progesterone receptor membrane component 1 complex in the sample. In embodiments, a detectable compound is a compound described herein that includes a radiolabel (detectable atom such as $^{18}$F, $^{32}$P, $^{33}$P, $^{11}$C, $^{15}$O, $^{13}$C, $^{13}$N, $^{17}$O, $^{14}$C, $^{3}$H) or a conjugate of a compound described herein and a detectable agent. In embodiments, the detection includes protein or nucleic acid detection, radiography, co-axial tomography (CAT) scan, positron emission tomography (PET), radionuclide scanning, or magnetic resonance imaging. In embodiments, the sample is taken from a subject. In embodiments, the sample is a cell culture. In embodiments, the sample is a tissue. In embodiments, the sample is an animal.

A "detectable agent" is a composition detectable by spectroscopic, photochemical, biochemical, immunochemical, chemical, magnetic resonance imaging, or other physical means. For example, useful labels include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

F. Further Embodiments

P1. A compound having the formula:

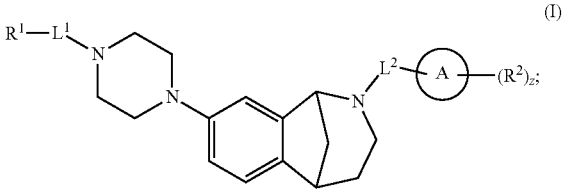

Ring A is $C_5$-$C_6$ cycloalkyl, 5 to 6 membered heterocycloalkyl, phenyl, or 5 to 6 membered heteroaryl; $L^1$ is a bond or unsubstituted $C_1$-$C_{10}$ alkylene; $L^2$ is a bond, —$SO_2$—, —C(O)NH—, —NHC(O)—, —C(O)O—, —OC(O)—, —$SO_2CH_2$—, —C(O)$NHCH_2$—, —NHC(O)$CH_2$—, —C(O)$OCH_2$—, —OC(O)$CH_2$—, or unsubstituted $C_1$-$C_3$ alkylene; $R^1$ is a hydrogen, halogen, —$CX_3^1$, —$CHX_2^1$, —$CH_2X^1$, —CN, —$NR^7R^8$, —C(O)$R^9$, —C(O)$OR^9$, —C(O)$NR^7R^8$, —$OR^{10}$, —OC(O)$OR^9$, —OC(O)$NR^7R^8$, —OC(O)$R^9$, —C(S)$R^9$, —C(S)$OR^9$, —C(S)$NR^7R^8$, —$SR^{10}$, —OC(S)$OR^9$, —OC(S)$NR^7R^8$, —OC(S)$R^9$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^2$ is independently a halogen, —$CX_3^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX_3^2$, —$OCHX_2^2$, substituted or unsubstituted $C_1$-$C_8$ alkyl, substituted or unsubstituted 2 to 8 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two $R^2$ substituents bonded to adjacent atoms may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^7$, $R^8$, $R^9$, and $R^{10}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX_3$, —$OCHX_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^7$ and $R^8$ substituents bonded to the same nitrogen atom may optionally be joined to form a substituted or unsubstituted 3 to 6 membered heterocycloalkyl or substituted or unsubstituted 5 to 6 membered heteroaryl; z is an integer from 0 to 5; and X, $X^1$, and $X^2$ are independently —Cl, —Br, —I, or —F.

P2. The compound of embodiment P1, wherein the compound has the formula:

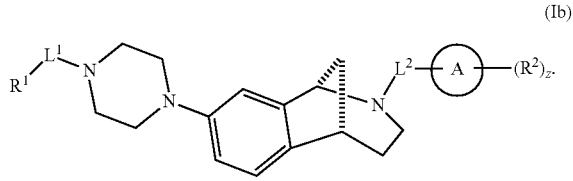

(Ia)

P3. The compound of embodiment P1, wherein the compound has the formula:

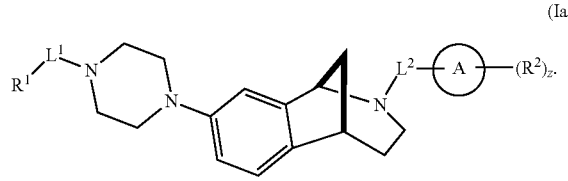

(Ib)

P4. The compound of one of embodiments P1 to P3, wherein $L^1$-$R^1$ is not unsubstituted methyl.

P5. The compound of one of embodiments P1 to P3, wherein $R^1$ is not hydrogen, unsubstituted methyl, —C(O)$R^9$, or —C(S)$NR^7R^8$, when $L^1$ is a bond.

P6. The compound of one of embodiments P1 to P3, wherein the compound is not

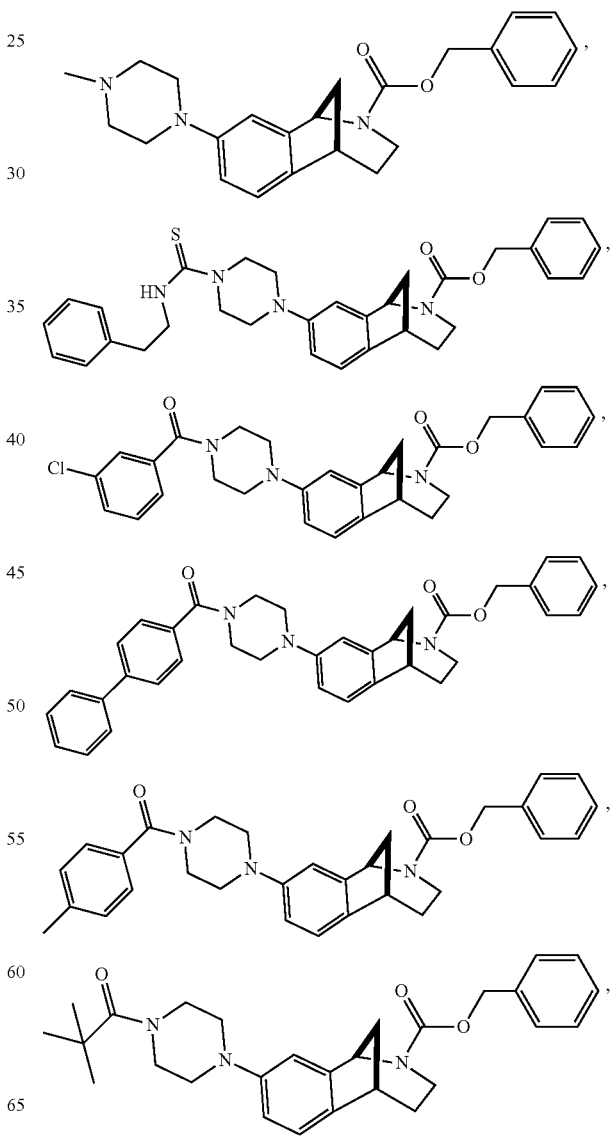

-continued

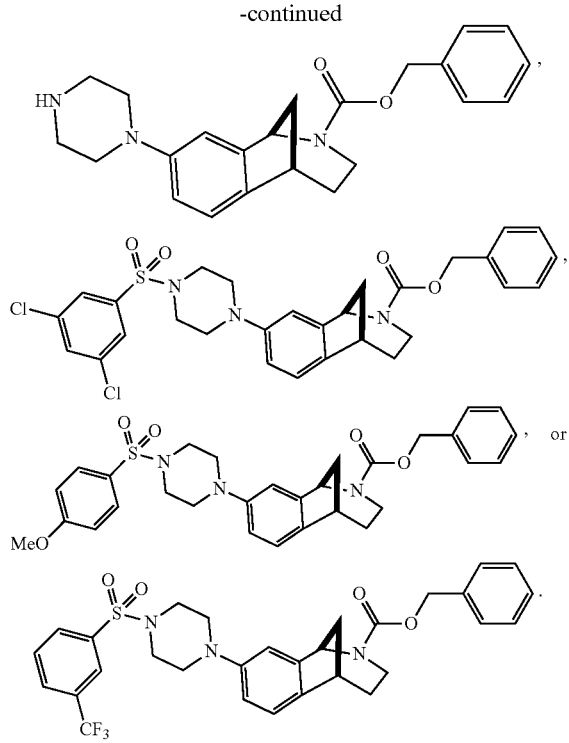

P7. The compound of one of embodiments P1 to P6, wherein Ring A is phenyl.

P8. The compound of one of embodiments P1 to P7, wherein $R^2$ is independently —F, —Cl, —Br, —I, —$CX_3^2$, —CN, —OH, —$NH_2$, —COOH, —$CONH_2$, —$NO_2$, —SH, —$OCX_3^2$, —$OCHX_2^2$, —$OCH_3$, —$OCH_2CH_3$, —$OCH(CH_3)_2$, unsubstituted methyl, unsubstituted ethyl, unsubstituted isopropyl, or two $R^2$ substituents bonded to adjacent atoms are joined to form an unsubstituted 5 to 6 membered heterocycloalkyl or unsubstituted 5 to 6 membered heteroaryl.

P9. The compound of one of embodiments P1 to P8, wherein z is 1 or 2.

P10. The compound of one of embodiments P1 to P8, wherein z is 0.

P11. The compound of one of embodiments P1 to P10, wherein $L^2$ is —$SO_2$—.

P12. The compound of one of embodiments P1 to P10, wherein $L^2$ is —$C(O)OCH_2$—.

P13. The compound of one of embodiments P1 to P12, wherein $L^1$ is a bond; and $R^1$ is —$OR^{10}$, substituted or unsubstituted $C_1$-$C_6$ alkyl, substituted or unsubstituted 2 to 6 membered heteroalkyl, substituted or unsubstituted $C_3$-$C_8$ cycloalkyl, and substituted or unsubstituted 4 to 6 membered heterocycloalkyl; and $R^{10}$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

P14. The compound of one of embodiments P1 to P12, wherein $L^1$ is an unsubstituted $C_1$-$C_3$ alkylene; and $R^1$ is hydrogen, halogen, —$CX_3^1$, —$CHX_2^1$, —$CH_2X^1$, —CN, —$NR^7R^8$, —$C(O)R^9$, —$C(O)OR^9$, —$C(O)NR^7R^8$, —$OR^{10}$, —$OC(O)NR^7R^8$, —$C(S)NR^7R^8$, —Se, substituted or unsubstituted $C_1$-$C_4$ alkyl, substituted or unsubstituted 2 to 4 membered heteroalkyl, substituted or unsubstituted $C_3$-$C_6$ cycloalkyl, or substituted or unsubstituted 4 to 6 membered heterocycloalkyl.

P15. The compound of one of embodiments P1 to P12, wherein $L^1$ is an unsubstituted $C_1$-$C_3$ alkylene; and $R^1$ is substituted or unsubstituted branched $C_3$-$C_5$ alkyl or substituted or unsubstituted 3 to 5 membered branched heteroalkyl.

P16. The compound of one of embodiments P1 to P12, wherein $L^1$ is an unsubstituted $C_1$-$C_3$ alkylene; and $R^1$ is substituted or unsubstituted $C_1$-$C_5$ alkyl, substituted or unsubstituted $C_2$-$C_5$ alkenyl, or substituted or unsubstituted $C_2$-$C_5$ alkynyl.

P17. The compound of one of embodiments P1 to P12, wherein $L^1$ is a bond; and $R^1$ is —$CH_2CH_2OH$, —$CH_2CH_2CH_2OH$, —$CH_2CH_2OCH_3$, or —$CH_2CH_2CH_2OCH_3$.

P18. The compound of one of embodiments P1 to P17, wherein $R^7$, $R^8$, $R^9$, and $R^{10}$ are independently hydrogen, halogen, —$CX_3$, —CN, —COOH, —$CONH_2$, —OH, substituted or unsubstituted $C_1$-$C_5$ alkyl, substituted or unsubstituted 2 to 5 membered heteroalkyl, substituted or unsubstituted $C_3$-$C_8$ cycloalkyl, or substituted or unsubstituted 4 to 6 membered heterocycloalkyl.

P19. A pharmaceutical composition comprising a pharmaceutically acceptable excipient and a compound of one of embodiments P1 to P18, or a pharmaceutically acceptable salt thereof.

P20. A method of treating cancer in a subject in need thereof, the method comprising administering an effective amount of a compound of one of embodiments P1 to P18.

P21. A method of improving cognition in a subject, the method comprising administering an effective amount of a compound of one of embodiments P1 to P18.

P22. A method to treating a neurodegenerative disease in a subject in need thereof, the method comprising administering an effective amount of a compound of one of embodiments P1 to P18.

P23. The method of embodiment P22, wherein the neurodegenerative disease is Alzheimer's disease, Parkinson's disease, Huntington's disease, progressive supranuclear palsy, or amyotrophic lateral sclerosis.

P24. A method of treating drug abuse in a subject in need thereof, the method comprising administering an effective amount of a compound of one of embodiments P1 to P18.

P25. A method of embodiment P24, wherein the drug is ethanol, nicotine, cocaine, amphetamine, methamphetamine, an opiate, or an opioid.

P26. A method of treating anxiety, depression, schizophrenia, or epilepsy in a subject in need thereof, the method comprising administering an effective amount of a compound of one of embodiments P1 to P18.

P27. A method of treating migraine or neuropathic pain in a subject in need thereof, the method comprising administering an effective amount of a compound of one of embodiments P1 to P18.

P28. A method of treating amnesia, traumatic brain injury, inflammatory pain, stroke, a cardiovascular disease, multiple sclerosis, or retinal neural degeneration in a subject in need thereof, the method comprising administering an effective amount of a compound of one of embodiments P1 to P18.

P29. A method of modulating a sigma 2 receptor, the method comprising contacting a sigma 2 receptor with a compound of one of embodiments P1 to P18, thereby modulating said sigma 2 receptor.

P30. A method of modulating progesterone receptor membrane component 1, the method comprising contacting a progesterone receptor membrane component 1 with a compound of one of embodiments P1 to P18, thereby modulating said progesterone receptor membrane component 1.

P31. The method of one of embodiments P29 to P30, wherein the modulating is inhibiting.

P32. The method of one of embodiments P29 to P30, wherein the modulating is antagonizing.

P33. The method of one of embodiments P29 to P30, wherein the modulating is activating.

P34. The method of one of embodiments P29 to P30, wherein the modulating is agonizing.

G. Additional Embodiments

1. A compound having the formula:

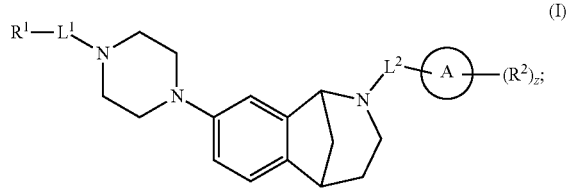

(I)

Ring A is cycloalkyl, heterocycloalkyl, aryl, or heteroaryl; $L^1$ is a bond or unsubstituted alkylene; $L^2$ is a bond, —SO$_2$—, —C(O)NH—, —NHC(O)—, —C(O)O—, —OC(O)—, —SO$_2$CH$_2$—, —C(O)NHCH$_2$—, —NHC(O)CH$_2$—C(O)OCH$_2$—, —OC(O)CH$_2$—, or unsubstituted alkylene; $R^1$ is a hydrogen, halogen, —CX$_3^1$, —CHX$_2^1$, —CH$_2$X$^1$, —CN, —NR$^7$R$^8$, —C(O)R$^9$, —C(O)OR$^9$, —C(O)NR$^7$R$^8$, —OR$^{10}$, —OC(O)OR$^9$, —OC(O)NR$^7$R$^8$, —OC(O)R$^9$, —C(S)R$^9$, —C(S)OR$^9$, —C(S)NR$^7$R$^8$, —SR$^{10}$, —OC(S)OR$^9$, —OC(S) NR$^7$R$^8$, —OC(S)R$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently a halogen, —CX$_3^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$_3^2$, —OCHX$_2^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents bonded to adjacent atoms may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; z is an integer from 0 to 5; and X, $X^1$, and $X^2$ are independently —Cl, —Br, —I, or —F.

2. The compound of embodiment 1, wherein the compound has the formula:

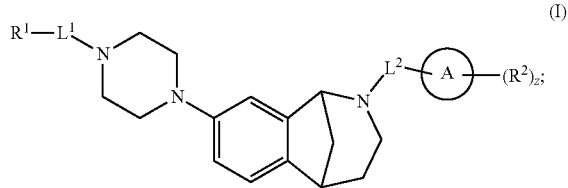

(I)

Ring A is $C_5$-$C_6$ cycloalkyl, 5 to 6 membered heterocycloalkyl, phenyl, or 5 to 6 membered heteroaryl; $L^1$ is a bond or unsubstituted $C_1$-$C_{10}$ alkylene; $L^2$ is a bond, —SO$_2$—, —C(O)NH—, —NHC(O)—, —C(O)O—, —OC(O)—, —SO$_2$CH$_2$—, —C(O)NHCH$_2$—, —NHC(O)CH$_2$—C(O)OCH$_2$—, —OC(O)CH$_2$—, or unsubstituted $C_1$-$C_3$ alkylene; $R^1$ is a hydrogen, halogen, —CX$_3^1$, —CHX$_2^1$, —CH$_2$X$^1$, —CN, —NR$^7$R$^8$, —C(O)R$^9$, —C(O)OR$^9$, —C(O)NR$^7$R$^8$, —OR$^{10}$, —OC(O)OR$^9$, —OC(O)NR$^7$R$^8$, —OC(O)R$^9$, —C(S)R$^9$, —C(S)OR$^9$, —C(S)NR$^7$R$^8$, —SR$^{10}$, —OC(S)OR$^9$, —OC(S) NR$^7$R$^8$, —OC(S)R$^9$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^2$ is independently a halogen, —CX$_3^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)OH, —NHOH, —OCX$_3^2$, —OCHX$_2^2$, substituted or unsubstituted $C_1$-$C_8$ alkyl, substituted or unsubstituted 2 to 8 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two $R^2$ substituents bonded to adjacent atoms may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^7$, $R^8$, $R^9$, and $R^{10}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCX$_3$, —OCHX$_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^7$ and $R^8$ substituents bonded to the same nitrogen atom may optionally be joined to form a substituted or unsubstituted 3 to 6 membered heterocycloalkyl or substituted or unsubstituted 5 to 6 membered heteroaryl; z is an integer from 0 to 5; and X, $X^1$, and $X^2$ are independently —Cl, —Br, —I, or —F.

3. The compound of one of embodiments 1 to 2, wherein the compound has the formula:

(Ia)
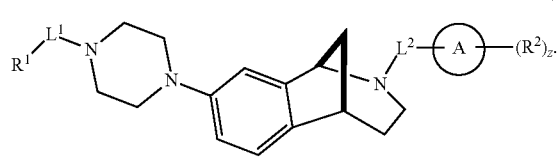
4. The compound of one of embodiments 1 to 2, wherein the compound has the formula:
(Ib)
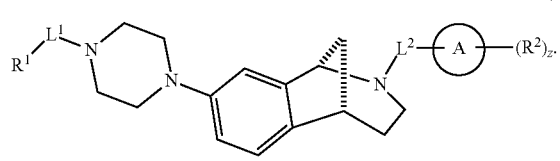
5. The compound of one of embodiments 1 to 4, wherein L¹-R¹ is not unsubstituted methyl.
6. The compound of one of embodiments 1 to 4, wherein R¹ is not hydrogen, unsubstituted methyl, —C(O)R⁹, or —C(S)NR⁷R⁸, when L¹ is a bond.
7. The compound of one of embodiments 1 to 4, wherein the compound is not
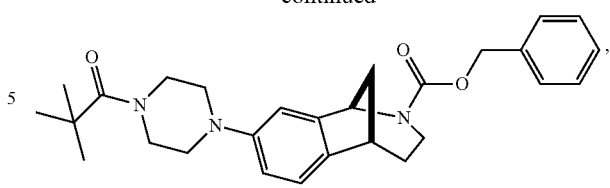
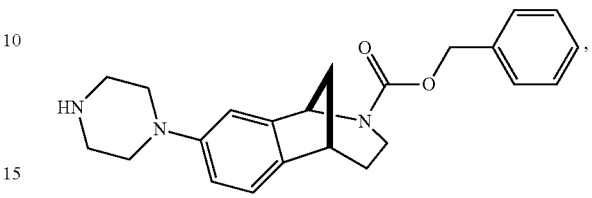
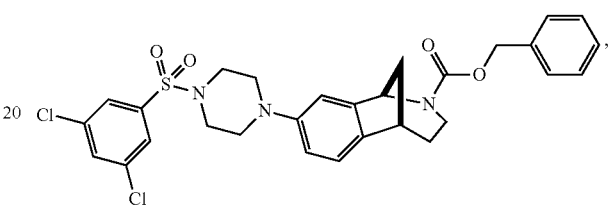
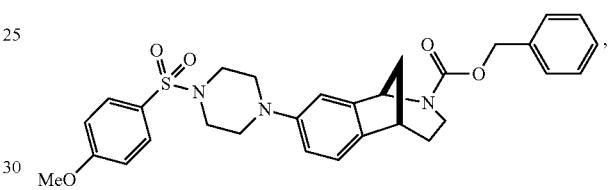
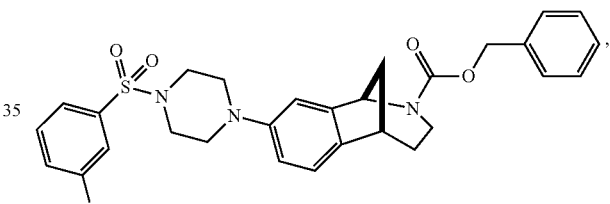
-continued
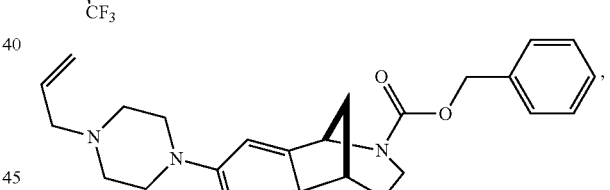
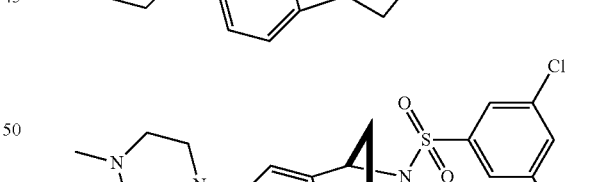
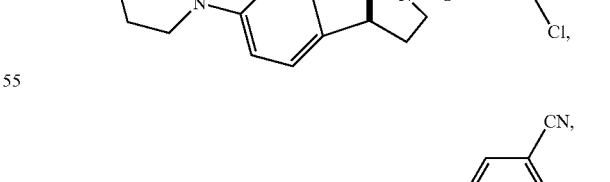
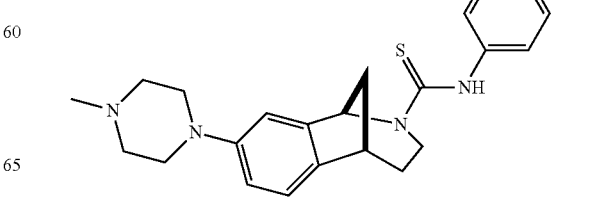

167
-continued
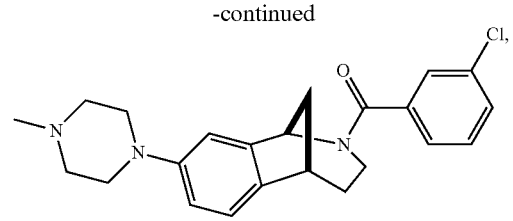
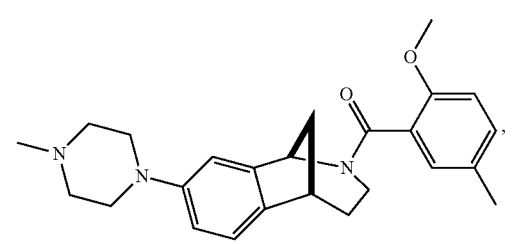
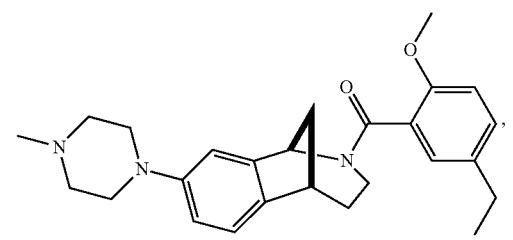
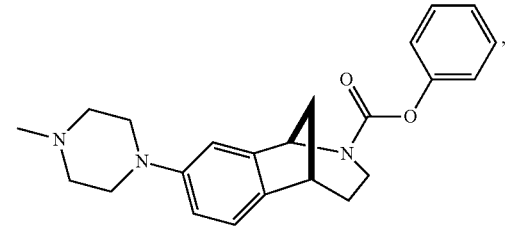
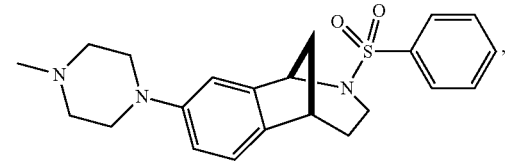
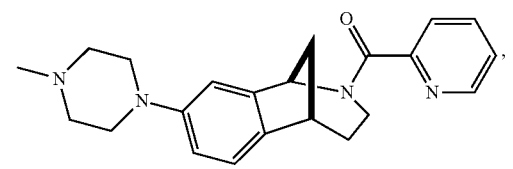
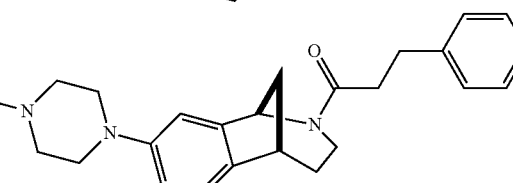
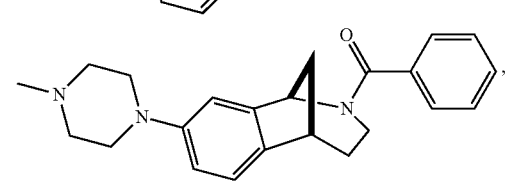
168
-continued
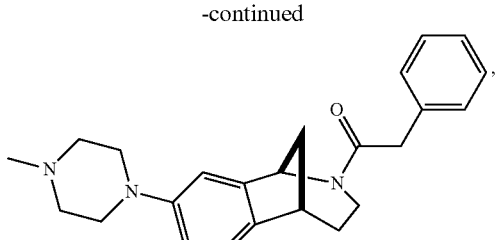
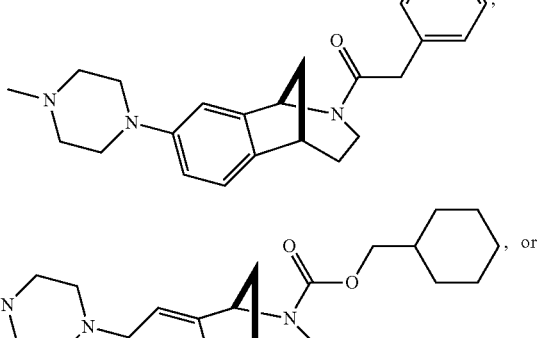, or
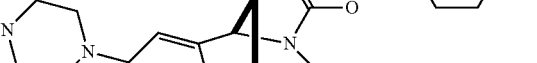
8. The compound of one of embodiments 1 to 4, wherein the compound is not
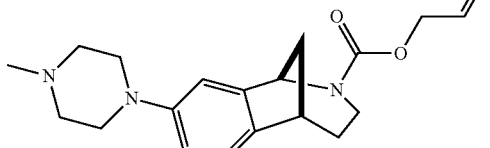
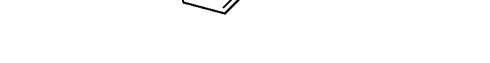
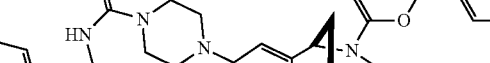

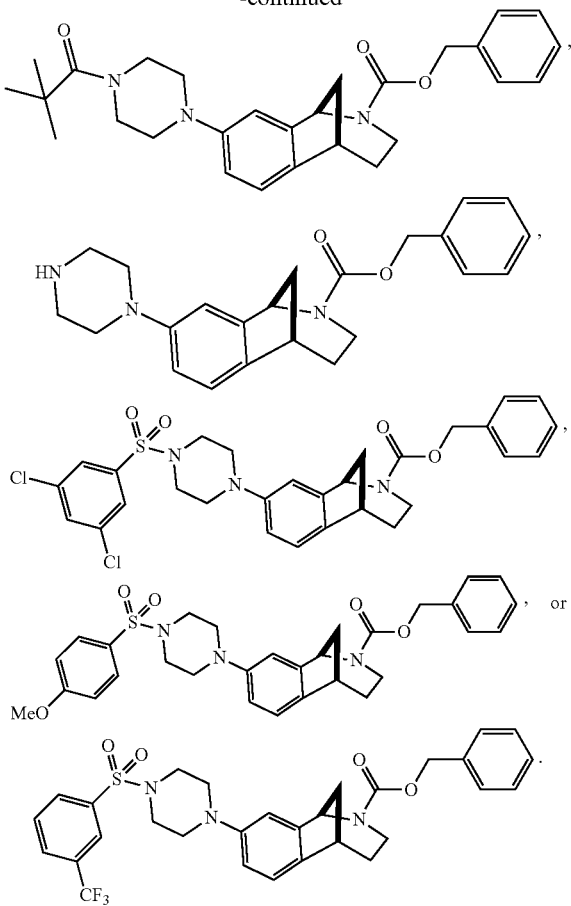

9. The compound of one of embodiments 1 to 8, wherein Ring A is phenyl.

10. The compound of one of embodiments 1 to 9, wherein $R^2$ is independently F, —Cl, —Br, —I, —$CX_3^2$, —CN, —OH, —$NH_2$, —COOH, —$CONH_2$, —$NO_2$, —SH, —$OCX_3^2$, —$OCHX_2^2$, —$OCH_3$, —$OCH_2CH_3$, —$OCH(CH_3)_2$, unsubstituted methyl, unsubstituted ethyl, unsubstituted isopropyl, or two $R^2$ substituents bonded to adjacent atoms are joined to form an unsubstituted 5 to 6 membered heterocycloalkyl or unsubstituted 5 to 6 membered heteroaryl.

11. The compound of one of embodiments 1 to 10, wherein z is 1 or 2.

12. The compound of one of embodiments 1 to 10, wherein z is 0.

13. The compound of one of embodiments 1 to 12, wherein $L^2$ is —$SO_2$—.

14. The compound of one of embodiments 1 to 12, wherein $L^2$ is —C(O)$OCH_2$—.

15. The compound of one of embodiments 1 to 14, wherein $L^1$ is a bond; and $R^1$ is —$OR^{10}$, substituted or unsubstituted $C_1$-$C_6$ alkyl, substituted or unsubstituted 2 to 6 membered heteroalkyl, substituted or unsubstituted $C_3$-$C_8$ cycloalkyl, and substituted or unsubstituted 4 to 6 membered heterocycloalkyl; and $R^{10}$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

16. The compound of one of embodiments 1 to 14, wherein $L^1$ is an unsubstituted $C_1$-$C_3$ alkylene; and $R^1$ is hydrogen, halogen, —$CX_3^1$, —$CHX_2^1$, —$CH_2X^1$, —CN, —$NR^7R^8$, —C(O)$R^9$, —C(O)$OR^9$, —C(O)$NR^7R^8$, —$OR^{10}$, —OC(O)$NR^7R^8$, —C(S)$NR^7R^8$, —$SR^{10}$, substituted or unsubstituted $C_1$-$C_4$ alkyl, substituted or unsubstituted 2 to 4 membered heteroalkyl, substituted or unsubstituted $C_3$-$C_6$ cycloalkyl, or substituted or unsubstituted 4 to 6 membered heterocycloalkyl.

17. The compound of one of embodiments 1 to 14, wherein $L^1$ is an unsubstituted $C_1$-$C_3$ alkylene; and $R^1$ is substituted or unsubstituted branched $C_3$-$C_5$ alkyl or substituted or unsubstituted 3 to 5 membered branched heteroalkyl.

18. The compound of one of embodiments 1 to 14, wherein $L^1$ is an unsubstituted $C_1$-$C_3$ alkylene; and $R^1$ is substituted or unsubstituted $C_1$-$C_5$ alkyl, substituted or unsubstituted $C_2$-$C_5$ alkenyl, or substituted or unsubstituted $C_2$-$C_5$ alkynyl.

19. The compound of one of embodiments 1 to 14, wherein $L^1$ is a bond; and $R^1$ is —$CH_2CH_2OH$, —$CH_2CH_2CH_2OH$, —$CH_2CH_2OCH_3$, or —$CH_2CH_2CH_2OCH_3$.

20. The compound of one of embodiments 1 to 19, wherein $R^7$, $R^8$, $R^9$, and $R^{10}$ are independently hydrogen, halogen, —$CX_3$, —CN, —COOH, —$CONH_2$, —OH, substituted or unsubstituted $C_1$-$C_5$ alkyl, substituted or unsubstituted 2 to 5 membered heteroalkyl, substituted or unsubstituted $C_3$-$C_8$ cycloalkyl, or substituted or unsubstituted 4 to 6 membered heterocycloalkyl.

21. The compound of embodiment 1 having the formula:

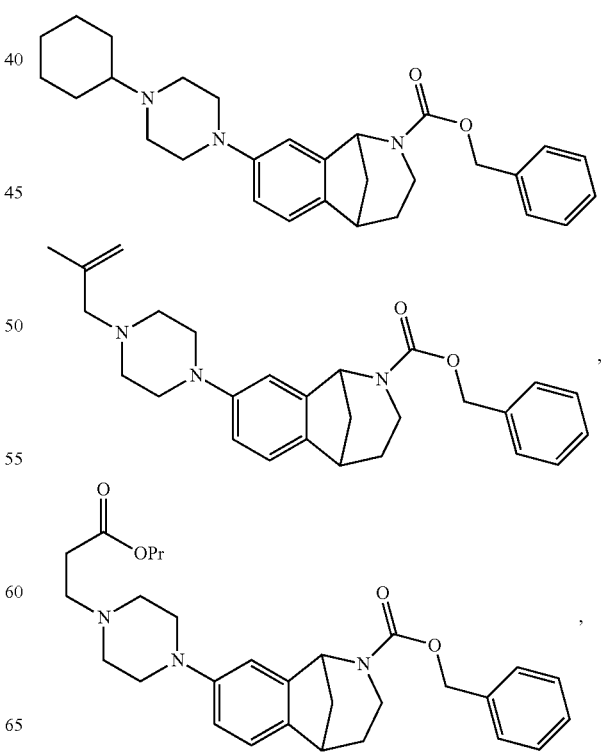

171
-continued
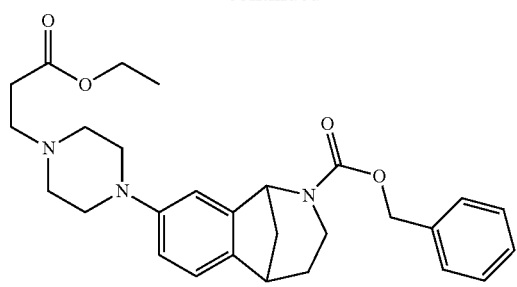
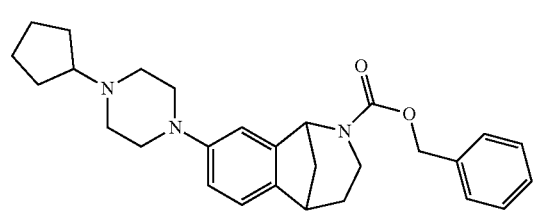
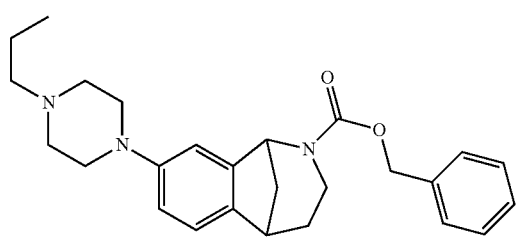
22. The compound of embodiment 1 having the formula:
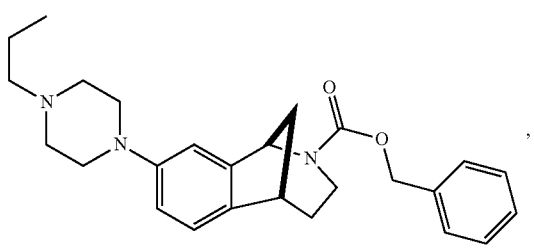
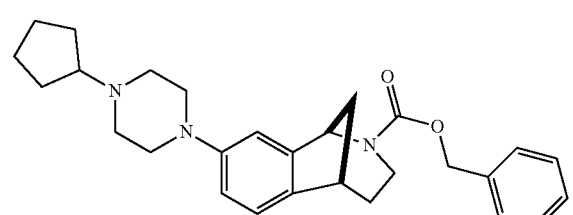
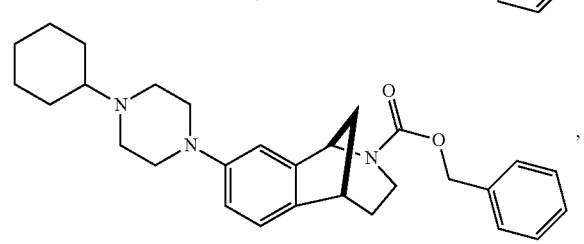
172
-continued
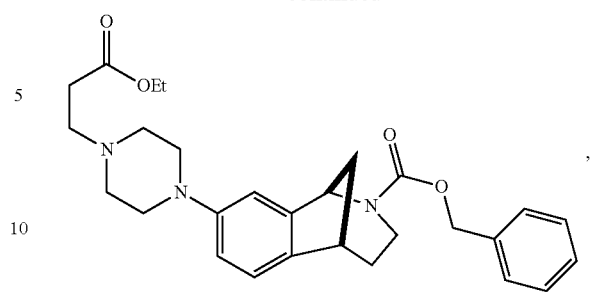
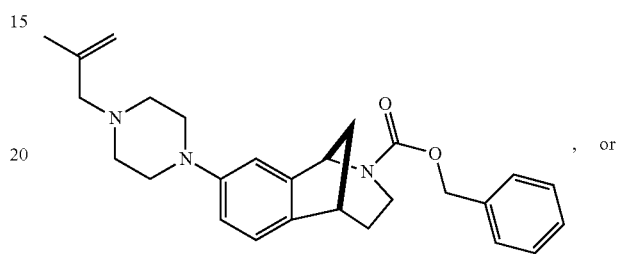
, or
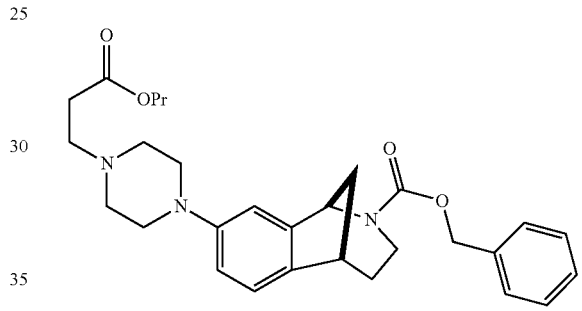
23. The compound of embodiment 1 having the formula:
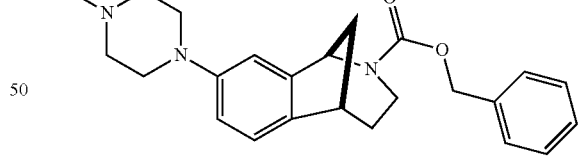
24. The compound of embodiment 1 having the formula:
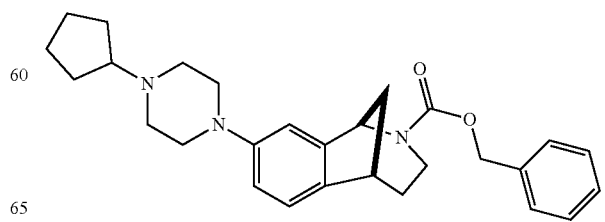

25. The compound of embodiment 1 having the formula:

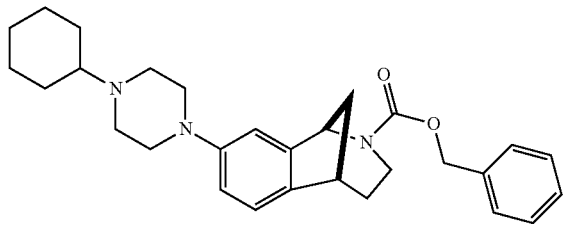

26. The compound of embodiment 1 having the formula:

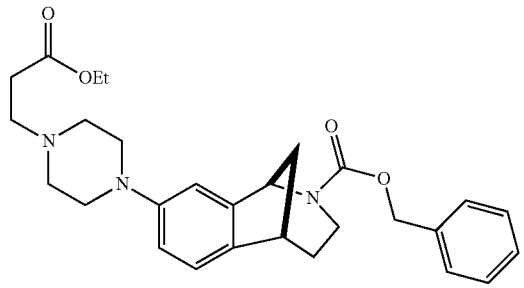

27. The compound of embodiment 1 having the formula:

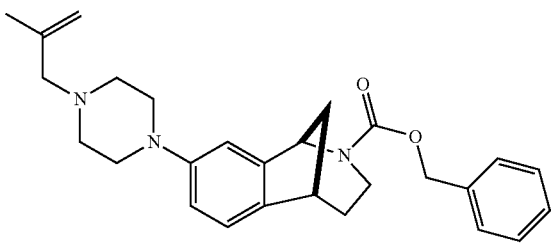

28. The compound of embodiment 1 having the formula:

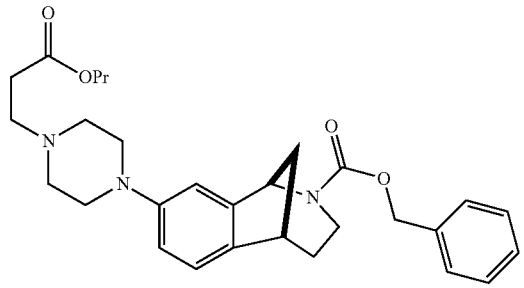

29. The compound of embodiment 1 having the formula:

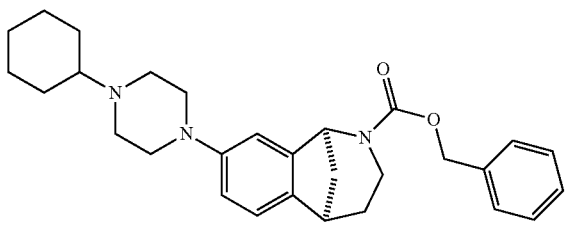

-continued

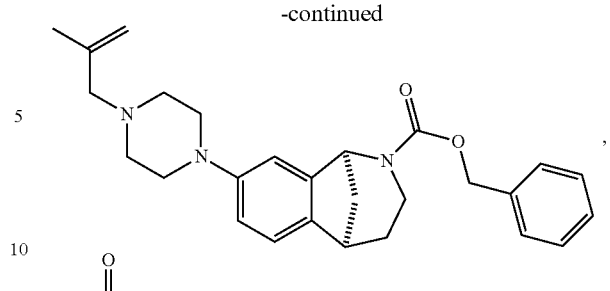

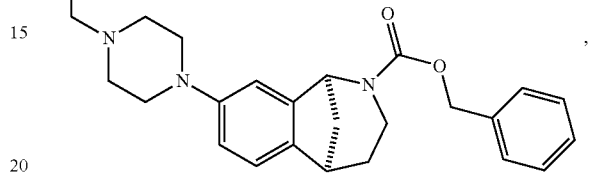

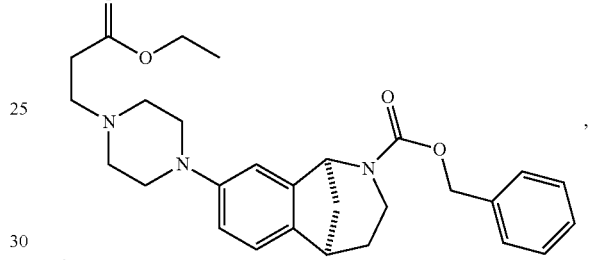

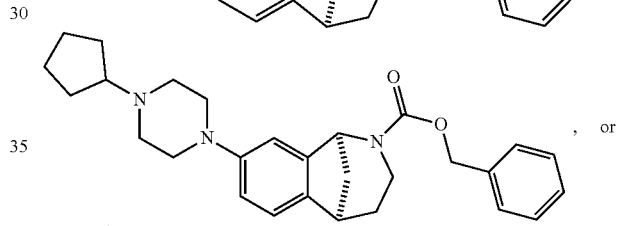, or

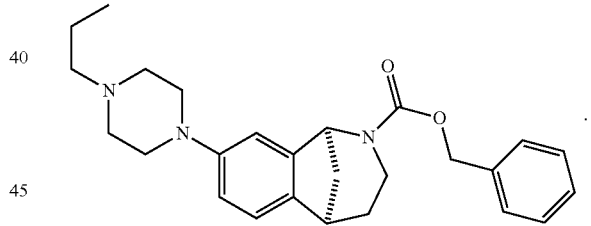

30. A pharmaceutical composition comprising a pharmaceutically acceptable excipient and a compound of one of embodiments 1 to 29, or a pharmaceutically acceptable salt thereof.

31. A method of treating cancer in a subject in need thereof, the method comprising administering an effective amount of a compound of one of embodiments 1 to 29.

32. A method of improving cognition in a subject, the method comprising administering an effective amount of a compound of one of embodiments 1 to 29.

33. A method to treating a neurodegenerative disease in a subject in need thereof, the method comprising administering an effective amount of a compound of one of embodiments 1 to 29.

34. The method of embodiment 33, wherein the neurodegenerative disease is Alzheimer's disease, Parkinson's disease, Huntington's disease, progressive supranuclear palsy, frontotemporal dementia, or amyotrophic lateral sclerosis.

35. A method of treating drug abuse in a subject in need thereof, the method comprising administering an effective amount of a compound of one of embodiments 1 to 29.

36. A method of embodiment 35, wherein the drug is ethanol, nicotine, cocaine, amphetamine, methamphetamine, an opiate, or an opioid.

37. A method of treating anxiety, depression, schizophrenia, or epilepsy in a subject in need thereof, the method comprising administering an effective amount of a compound of one of embodiments 1 to 29.

38. A method of treating migraine or neuropathic pain in a subject in need thereof, the method comprising administering an effective amount of a compound of one of embodiments 1 to 29.

39. A method of treating amnesia, traumatic brain injury, inflammatory pain, stroke, a cardiovascular disease, multiple sclerosis, or retinal neural degeneration in a subject in need thereof, the method comprising administering an effective amount of a compound of one of embodiments 1 to 29.

40. A method of treating traumatic brain injury in a subject in need thereof, the method comprising administering an effective amount of a compound of one of embodiments 1 to 29.

41. The method of embodiment 40, wherein the compound has the formula:

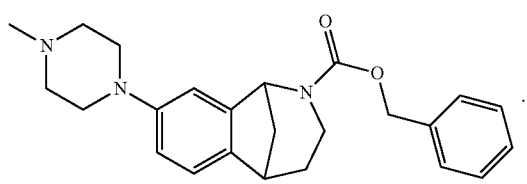 [SMILES: CN1CCN(c2ccc3c(c2)C2CC3CCN2C(=O)OCc2ccccc2)CC1]

42. The method of embodiment 40, wherein the compound has the formula:

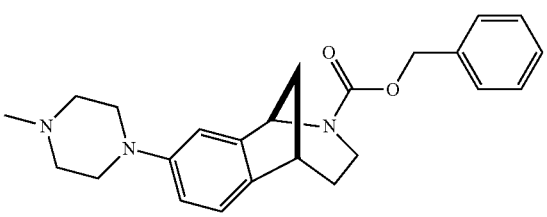

43. The method of embodiment 40, wherein the compound has the formula:

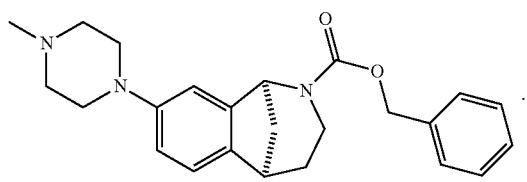

44. The method of embodiment 40, wherein the compound has the formula:

45. The method of embodiment 40, wherein the compound has the formula:

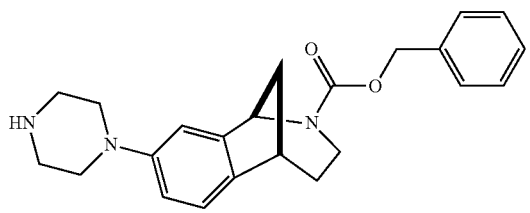

46. The method of embodiment 40, wherein the compound has the formula:

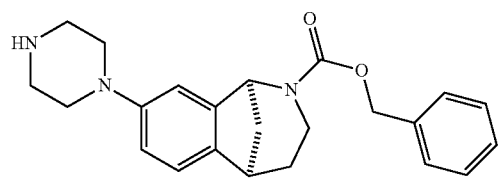

47. A method of modulating a sigma 2 receptor, the method comprising contacting a sigma 2 receptor with a compound of one of embodiments 1 to 29, thereby modulating said sigma 2 receptor.

48. A method of modulating progesterone receptor membrane component 1, the method comprising contacting a progesterone receptor membrane component 1 with a compound of one of embodiments 1 to 29, thereby modulating said progesterone receptor membrane component 1.

49. The method of one of embodiments 47 to 48, wherein the modulating is inhibiting.

50. The method of one of embodiments 47 to 48, wherein the modulating is antagonizing.

51. The method of one of embodiments 47 to 48, wherein the modulating is activating.

52. The method of one of embodiments 47 to 48, wherein the modulating is agonizing.

53. The method of one of embodiments 31 to 39 and 47 to 52, wherein the compound is

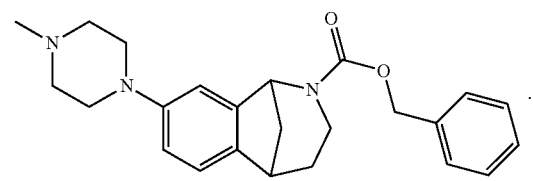 [SMILES: CN1CCN(c2ccc3c(c2)C2CC3CCN2C(=O)OCc2ccccc2)CC1]

54. The method of one of embodiments 31 to 39 and 47 to 52, wherein the compound is 55. The method of one of embodiments 31 to 39 and 47 to 52, wherein the compound is

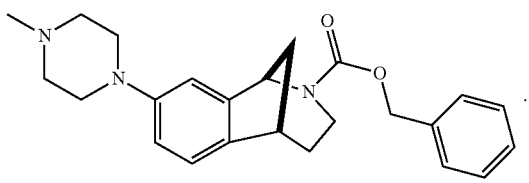

56. The method of one of embodiments 31 to 39 and 47 to 52, wherein the compound is

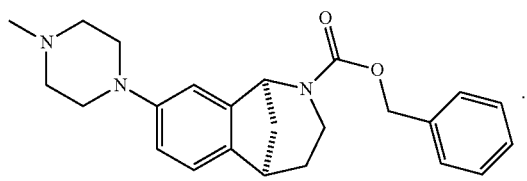

57. The method of one of embodiments 31 to 39 and 47 to 52, wherein the compound is

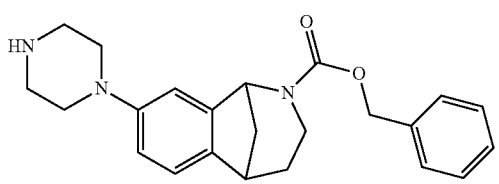

58. The method of one of embodiments 31 to 39 and 47 to 52, wherein the compound is

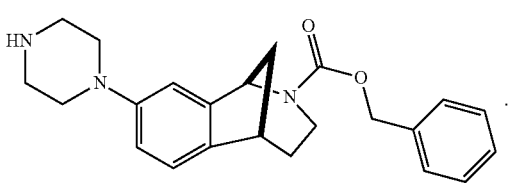

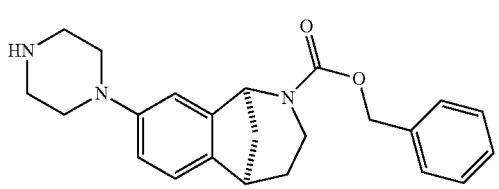

H. Examples

Example 1. Synthesis of Chloro-Scaffold Intermediate

Scheme 1. Synthesis of the key intermediate 12 occurs via a Mannich-type multicomponent assembly process (MCAP) followed by sequential ring closing metathesis, Heck cyclization, and olefin reduction as described

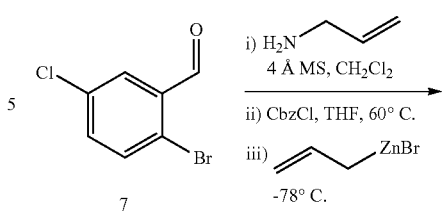

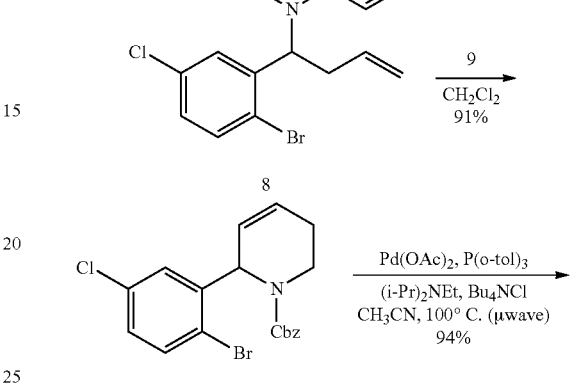

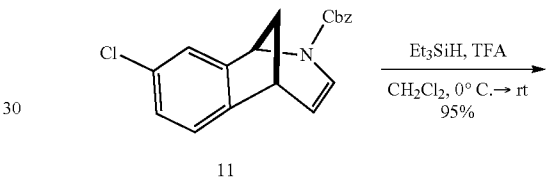

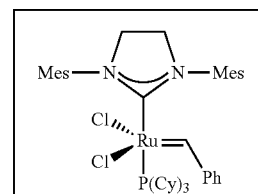

Scaffold 12 proved to be well-suited for generating a variety of analogs, including those represented by general structure 13. Cbz is a carboxybenzyl moiety. The chemical structure of 13 follows

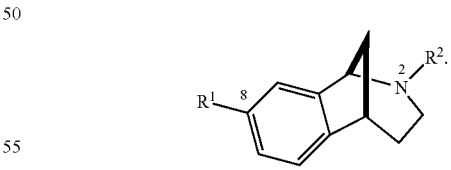

$R^1$ = piperazinyl; morpholinyl; aryl $R^2$ = acyl; sulfonyl; alkyl

The aryl chloride functional handle on 12 enabled derivatization via palladium catalyzed cross-coupling reactions to deliver analogs having a range of electrostatic properties and varying degrees of lipophilicity, such as the anilines 14-16 and the biaryls 21-23, depicted in Schemes 2 and 3.

Scheme 2 depicts cross-coupling reactions of aryl chloride, 12, to generate aniline analogs, using the following reagents and conditions: a) Pd(OAc)₂, JohnPhos®, NaOt- Bu, toluene, 100° C.; c) TMSI, CH$_2$Cl$_2$, 0° C.→rt, then HCl; and d) TMSI, CH$_2$Cl$_2$, 0° C.→rt, then NaHCO$_3$(aq).

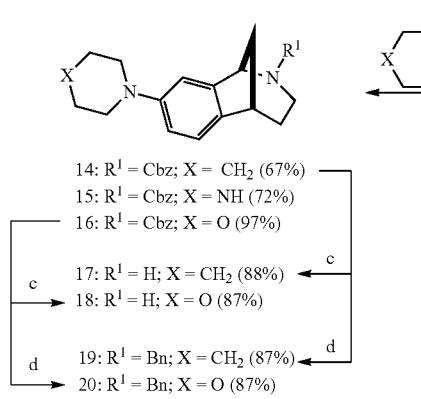

14: R$^1$ = Cbz; X = CH$_2$ (67%)
15: R$^1$ = Cbz; X = NH (72%)
16: R$^1$ = Cbz; X = O (97%)
17: R$^1$ = H; X = CH$_2$ (88%)
18: R$^1$ = H; X = O (87%)
19: R$^1$ = Bn; X = CH$_2$ (87%)
20: R$^1$ = Bn; X = O (87%)

Scheme 3 depicts cross-coupling reactions of aryl chloride, 12, to generate biaryl analogs, using the following reagents and conditions: b) Pd[P(t-Bu)$_3$]$_2$, Cs$_2$CO$_3$, 1,4-dioxane, 100° C.; c) TMSI, CH$_2$Cl$_2$, 0° C.→rt, then HCl; and d) TMSI, CH$_2$Cl$_2$, 0° C.→rt, then NaHCO$_3$(aq).

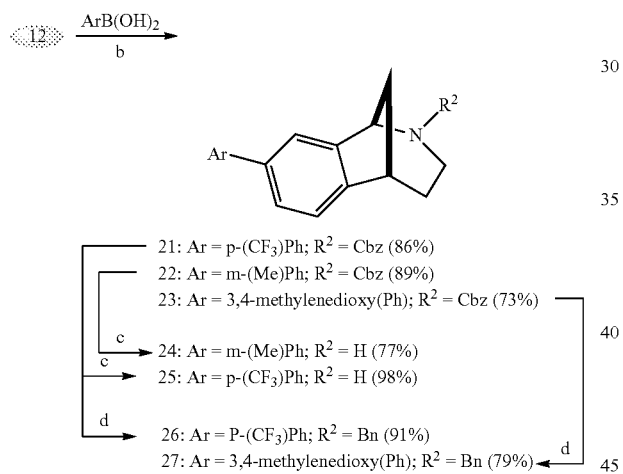

21: Ar = p-(CF$_3$)Ph; R$^2$ = Cbz (86%)
22: Ar = m-(Me)Ph; R$^2$ = Cbz (89%)
23: Ar = 3,4-methylenedioxy(Ph); R$^2$ = Cbz (73%)
24: Ar = m-(Me)Ph; R$^2$ = H (77%)
25: Ar = p-(CF$_3$)Ph; R$^2$ = H (98%)
26: Ar = P-(CF$_3$)Ph; R$^2$ = Bn (91%)
27: Ar = 3,4-methylenedioxy(Ph); R$^2$ = Bn (79%)

The cyclic secondary amines piperidine, piperazine, and morpholine were selected as the initial coupling partners in Buchwald-Hartwig reactions to provide analogs having amino groups at C(8) of the norbenzomorphan nucleus with varying degrees of basicity. Six-membered, cyclic amines were used in these studies to eliminate any conformational variables amongst the different aryl amino analogs, which vary primarily in the Lewis basic nature of the C(8) substituent. Boronic acid coupling partners for the Suzuki reactions were chosen to provide both electron rich and deficient biaryl products. The Cbz group on N(2) of 14,16 and 21-23 was then removed using iodotrimethylsilane (TMSI) followed by either acidic or basic to give the corresponding tertiary N-benzyl compounds 19-20 and 26-27 and the secondary amines 17, 18, 24 and 25.

To diversify the substituents on the two nitrogen atoms of 15, the secondary amino group on the piperazine ring of 15 was first N-alkylated using standard procedures to give tertiary amines 28-32.

The chemical structures of tertiary amines 28-32 follows

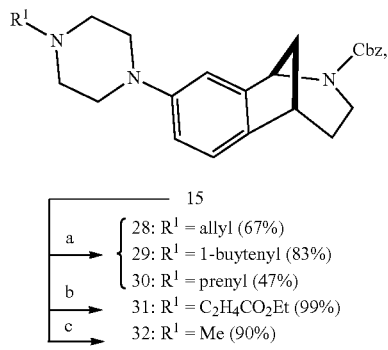

28: R$^1$ = allyl (67%)
29: R$^1$ = 1-buytenyl (83%)
30: R$^1$ = prenyl (47%)
31: R$^1$ = C$_2$H$_4$CO$_2$Et (99%)
32: R$^1$ = Me (90%)

where the reactions and conditions use a) alkyl brome, CH$_3$CN, K$_2$CO$_3$; b) ethyl acrylate, EtOH; c) aldehyde, Na(OAc)$_3$BH, CH$_3$COOH, CH$_2$Cl$_2$.

Substitution at the carbamoyl nitrogen of 32 was then varied by removing the Cbz group using TMSI followed by an acidic workup to give 33, and subsequent N-sulfonylation or N-acylation of 33 under standard conditions delivered 34-37, following

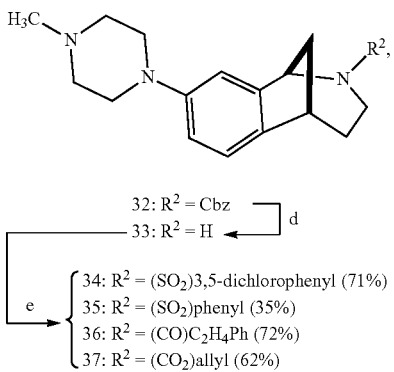

32: R$^2$ = Cbz
33: R$^2$ = H
34: R$^2$ = (SO$_2$)3,5-dichlorophenyl (71%)
35: R$^2$ = (SO$_2$)phenyl (35%)
36: R$^2$ = (CO)C$_2$H$_4$Ph (72%)
37: R$^2$ = (CO$_2$)allyl (62%)

where the reactions and conditions utilize d) TMSI, CH$_2$Cl$_2$, 0° C. rt, then NaHCO$_3$(aq) and e) acyl or sulfonyl chloride.

Reductive amination of 17 and 18 using several aryl aldehydes and sodium triacetoxyborohydride [Na(OAc)$_3$BH] provided 38-40, following

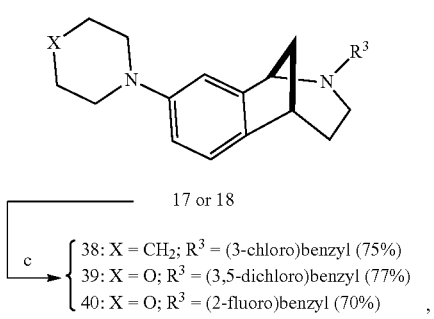

17 or 18

38: X = CH$_2$; R$^3$ = (3-chloro)benzyl (75%)
39: X = O; R$^3$ = (3,5-dichloro)benzyl (77%)
40: X = O; R$^3$ = (2-fluoro)benzyl (70%)

where the reactions and conditions use c) aldehyde, Na(OAc)$_3$BH, CH$_3$COOH, CH$_2$Cl$_2$.

Similarly, reductive aminations of 21 and 22 led to analogs 41-44,

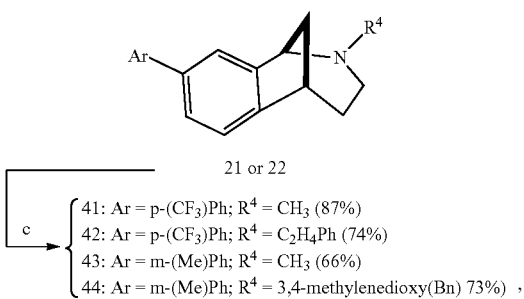

21 or 22 c ⇒
- 41: Ar = p-(CF₃)Ph; R⁴ = CH₃ (87%)
- 42: Ar = p-(CF₃)Ph; R⁴ = C₂H₄Ph (74%)
- 43: Ar = m-(Me)Ph; R⁴ = CH₃ (66%)
- 44: Ar = m-(Me)Ph; R⁴ = 3,4-methylenedioxy(Bn) 73%)

where the reactions and conditions use c) aldehyde, Na(OAc)$_3$BH, CH$_3$COOH, CH$_2$Cl$_2$.

Example 2. Pharmacology of Norbenzomorphans

An assortment of norbenzomorphans was screened against a comprehensive panel of CNS-based proteins at the National Institute of Mental Health Psychoactive Drug Screening Program (NIMH PDSP). A subset of compounds was identified that exhibited high affinity and subtype selectivity for σ2R versus σ1R. Receptor binding data collected for analogs listed in Table 1 show that σ2R affinity and subtype selectivity is maintained over a range of peripheral groups on the norbenzomorphan nucleus.

TABLE 1

Sigma receptor affinity of norbenzomorphan analogs.

| Compound | $R^1$ | $R^2$ | σ1 $K_i$ (nM)[a] pK$_i$ ± SEM[b] | σ2 $K_i$ (nM) pK$_i$ ± SEM | $K_i$(σ1)/ $K_i$(σ2) |
|---|---|---|---|---|---|
| 12 | Cl | —C(O)OCH$_2$Ph | *[c] | * | — |
| 16 | morpholine-N | —C(O)OCH$_2$Ph | * | * | — |
| 20 | morpholine-N | —CH$_2$Ph | 3,777 5.42 ± 0.09 | 1,034 5.99 ± 0.07 | 4 |
| 39 | morpholine-N | —CH$_2$(3,5-Cl$_2$Ph) | 2,975 5.53 ± 0.09 | 92 7 ± 0.1 | 32 |
| 40 | morpholine-N | —CH$_2$(2-FPh) | 4,544 5.34 ± 0.09 | 1,258 5.9 ± 0.1 | 4 |
| 19 | piperidine-N | —CH$_2$Ph | 2,429 5.61 ± 0.06 | 318 6.5 ± 0.1 | 8 |

TABLE 1-continued

Sigma receptor affinity of norbenzomorphan analogs.

| Compound | R¹ | R² | σ1 $K_i$ (nM)[a] p$K_i$ ± SEM[b] | σ2 $K_i$(nM) p$K_i$ ± SEM | $K_i$(σ1)/ $K_i$(σ2) |
|---|---|---|---|---|---|
| 38 | piperidin-1-yl | 3-chlorobenzyl | 3,519<br>5.5 ± 0.1 | 746<br>6.1 ± 0.1 | 5 |
| 27 | benzo[d][1,3]dioxol-5-yl | benzyl | 3,039<br>5.5 ± 0.1 | 723<br>6.14 ± 0.09 | 4 |
| 41 | 4-(trifluoromethyl)phenyl | CH₃ | 156<br>6.81 ± 0.09 | 43<br>7.36 ± 0.08 | 4 |
| 42 | 4-(trifluoromethyl)phenyl | 2-phenylethyl | 1,058<br>6.0 ± 0.1 | 166<br>6.8 ± 0.1 | 6 |
| 43 | 3-methylphenyl | CH₃ | 391<br>6.41 ± 0.08 | 133<br>6.88 ± 0.07 | 3 |
| 44 | 3-methylphenyl | benzo[d][1,3]dioxol-5-ylmethyl | 4,612<br>5.34 ± 0.08 | 828<br>6.08 ± 0.08 | 6 |
| 32 | 4-methylpiperazin-1-yl | benzyloxycarbonylmethyl | 497<br>6.31 ± 0.06 | 71<br>7.1 ± 0.1 | 7 |
| 33 | 4-methylpiperazin-1-yl | H | * | * | — |
| 34 | 4-methylpiperazin-1-yl | (3,5-dichlorophenyl)sulfonyl | 442<br>6.36 ± 0.06 | 27<br>7.58 ± 0.08 | 16 |

TABLE 1-continued

Sigma receptor affinity of norbenzomorphan analogs.

| Compound | R[1] | R[2] | σ1 $K_i$ (nM)[a] pK$_i$ ± SEM[b] | σ2 $K_i$(nM) pK$_i$ ± SEM | $K_i$(σ1)/ $K_i$(σ2) |
|---|---|---|---|---|---|
| 35 | 4-methylpiperazin-1-yl | phenylsulfonyl | * | 764 6.12 ± 0.07 | — |
| 36 | 4-methylpiperazin-1-yl | 3-phenylpropanoyl | 294 6.53 ± 0.08 | 357 6.45 ± 0.06 | 1 |
| 37 | 4-methylpiperazin-1-yl | allyloxycarbonyl | 2105 5.68 ± 0.07 | 442 6.37 ± 0.07 | 5 |
| 28 | 4-allylpiperazin-1-yl | benzyloxycarbonyl | 589 6.23 ± 0.06 | 34 7.47 ± 0.08 | 17 |
| 29 | 4-(but-3-en-1-yl)piperazin-1-yl | benzyloxycarbonyl | 172 6.76 ± 0.05 | 16 7.79 ± 0.05 | 11 |
| 30 | 4-(3-methylbut-2-en-1-yl)piperazin-1-yl | benzyloxycarbonyl | 62 7.21 ± 0.05 | 23 7.64 ± 0.07 | 3 |
| 31 | 4-(3-ethoxy-3-oxopropyl)piperazin-1-yl | benzyloxycarbonyl | 9294[d] 5.1 ± 0.1 | 16.2[e] 7.8 ± 0.16 | 574 |

[a]$K_i$ values obtained from non-linear regression of radioligand competition binding isotherms;
[b]SEM calculated for pK$_i$;
[c] Less than 50% inhibition of radioligand binding with 10 μM test ligand;
[d]average of two IC$_{50}$ determinations;
[e]average of three IC$_{50}$ determinations.

From the morpholine series comprising compounds 16, 20, 39, and 40, a second basic nitrogen atom in the molecule may be valuable in embodiments. This tentative assessment is based upon the observation that 16 did not bind, whereas the two N-benzyl derivatives 20 and 40 exhibited modest σ2R affinity (1,034 nM and 1,258 nM) and a 4-fold preference for σ2R relative to σ1R. The 3,5-dichlorobenzyl analog 39 benefits from a large increase in σ2R binding affinity (92 nM) coupled with a 32-fold increase in selectivity for σ2R over σ1R. The aryl piperidine derivative 19 displays moderate σ2R affinity (318 nM) and about 8-fold subtype selectivity favoring σ2R, and replacing the benzyl group of 19 with a 3-chlorobenzyl substituent (e.g., 38) affects a marginal decrease in both σ2R affinity and selectivity. For the series of biaryl compounds 27 and 41-44, sigma receptor affinity may be affected by the size of the alkyl group at N(2). For example, the N-methyl derivatives 41 and 43 exhibit enhanced binding affinity at both σ1R and σ2R relative to 42 and 44.

When the C(8) position of the norbenzomorphan is substituted with a piperazino moiety, σ2R binding affinity was typically high, and subtype selectivity could be tuned by altering either $R^2$ or the alkyl group on the aliphatic nitrogen atom of the piperazine ring. Changing the nature of the alkyl group led to only modest variations in σ2R affinities, whereas the effects on σ1R affinity were more pronounced. This is illustrated by comparing 31, which exhibits 574-fold selectivity for σ2R, with other members of this series. This represents one of the more selective σ2R ligands reported to date. Whereas replacing the Cbz group of 32 with a hydrocinnamoyl (e.g., 36) or an allyloxycarbonyl (e.g., 37) moiety led to a loss in σ2R binding affinity and selectivity, substituting a 3,5-dichlorobenzenesulfonamide group for Cbz afforded a 2- to 3-fold increase in σ2R binding affinity and selectivity. Notably, the corresponding nor-chloro analog 35 displayed much lower affinity for both σR subtypes, and the presence of a secondary amino group (e.g., 33) significantly reduced binding at σ2R and σ1R in embodiments.

The binding affinities for the compounds in Table 1 reveal that a number of substituents at $R^1$ and $R^2$ are tolerated and lead to ligands having modest to excellent preference for σ2R over σ1R, with a number of compounds exhibiting <50 nM affinity for σ2R. Notably, many compounds displayed significantly reduced affinity, relative to σ2R, at a broad range of other CNS proteins, including serotonin, adrenergic, dopamine, opioid, and neurotransmitter transporters. A few derivatives displayed strong affinity for several off-target sites, but these compounds are typically highly lipophilic (i.e., clogP>5), such as the dichlorophenylsulfonamide 34.

These data suggest that $R^1$ and $R^2$ on the norbenzomorphan scaffold can be tuned to enhance σ2R selectivity over both σ1R as well as an array of other CNS proteins.

Example 3. Discussion of Norbenzomorphans that Exhibit High Potency and Selectivity for σ2R Relative to σ1R A modular synthetic platform was exploited to rapidly access a variety of substituted norbenzomorphans that exhibit high potency and selectivity for σ2R relative to σ1R. Notably, it appears to be possible to modulate σR subtype selectivity by varying the nature of the groups at C(8) and N(2) of the norbenzomorphan scaffold. Compound 31 displayed a 574-fold preference for σ2R over σ1R, suggesting that exceptional σ2R subtype selectivity can be achieved. Many of these σ2R subtype selective ligands have molecular attributes likely to impart desirable absorption, distribution, metabolism, and excretion (ADME) properties. In embodiments, some compounds these may be promising leads for treating neurological disorders and cancers.

It is significant that the EU approved anxiolytic/antidepressant opipramol has appreciable affinity for σ2R and has been safely used for decades. Additionally, previous clinical trials with investigational σ2R ligands further suggest that pharmacological modulation of σ2R may be safe in man. The discovery of novel, highly selective σ2R ligands with drug like features, such as 31, will help pave the way to realizing the potential therapeutic value of pharmacological modulation of σ2R.

Example 4. Additional Compounds

Receptor binding data collected for analogs listed in Table 3 show that σ2R affinity and subtype selectivity is maintained additional peripheral groups on the norbenzomorphan nucleus.

TABLE 3

Sigma receptor affinity of additional norbenzomorphan analogs.

| Compound | $R^1$ | $R^2$ | σ1 $K_i$ (nM)$^a$ | σ2 $K_i$(nM) | $K_i$(σ1)/ $K_i$(σ2) |
|---|---|---|---|---|---|
| TH-2-42 | [piperazine-cyclopentyl] | [C(O)OCH2Ph] | 170 | 2.3 | 74 |
| JJS-4-198 | [piperazine-CH2-C(=CH2)CH3] | [C(O)OCH2Ph] | 430 | 17.5 | 25 |

TABLE 3-continued

Sigma receptor affinity of additional norbenzomorphan analogs.

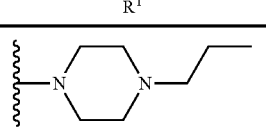

| Compound | R¹ | R² | σ1 $K_i$ (nM)$^a$ | σ2 $K_i$(nM) | $K_i$(σ1)/ $K_i$(σ2) |
|---|---|---|---|---|---|
| P1 | 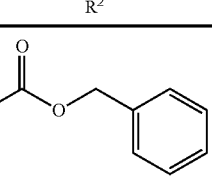 | 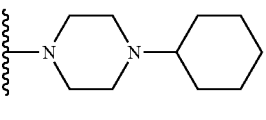 | 255 | 4.0 | 64 |
| P2 | 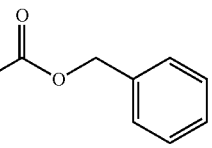 | 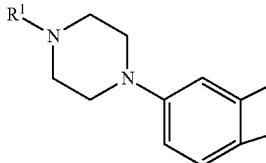 | 27 | 1.4 | 19 |

Example 5. Piperazine N-Derivatives

Analogs listed in Table 4 show additional substituents for piperazine N-derivatives attached to the norbenzomorphan nucleus.

TABLE 4

Additional norbenzomorphan piperazine N-derivatives for R¹.

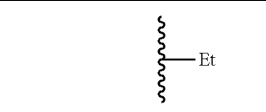

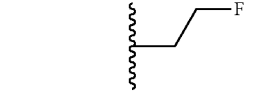

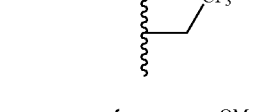

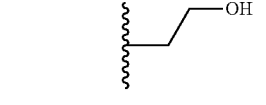

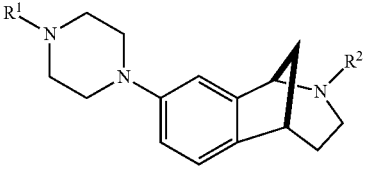

TABLE 4-continued

Additional norbenzomorphan piperazine N-derivatives for R¹.

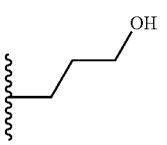 [SMILES: *CCCO]

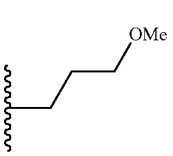 [SMILES: *CCCOC]

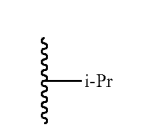 [SMILES: *C(C)C]

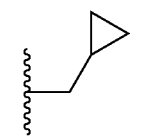 [SMILES: *CC1CC1]

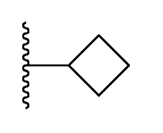 [SMILES: *C1CCC1]

TABLE 4-continued
Additional norbenzomorphan piperazine N-derivatives for R¹.
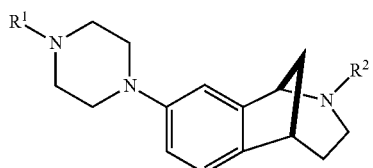
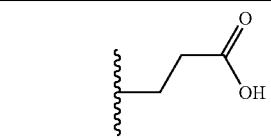
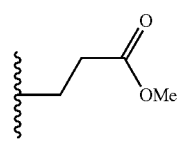 [SMILES: *CCC(=O)OC]
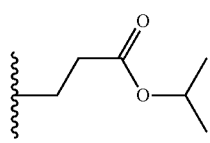 [SMILES: *CCC(=O)OC(C)C]
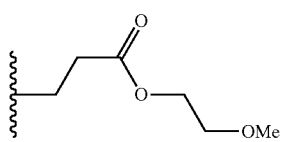 [SMILES: *CCC(=O)OCCOC]
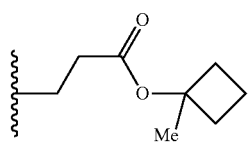 [SMILES: *CCC(=O)OC1(C)CCC1]
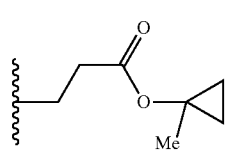 [SMILES: *CCC(=O)OC1(C)CC1]
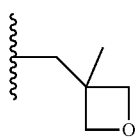 [SMILES: *CC1(C)COC1]
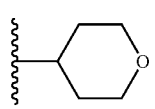
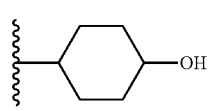
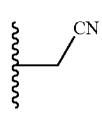 [SMILES: *CC#N]
TABLE 4-continued
Additional norbenzomorphan piperazine N-derivatives for R¹.
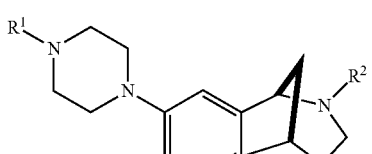
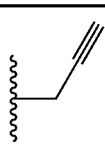
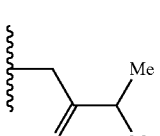
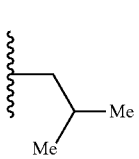
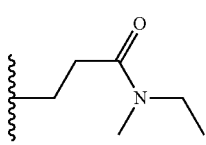 [SMILES: *CCC(=O)N(C)CC]
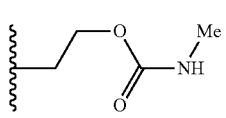 [SMILES: *CCOC(=O)NC]
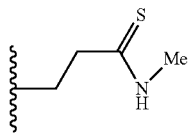 [SMILES: *CCC(=S)NC]
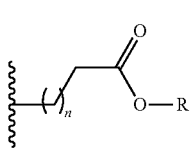
R²
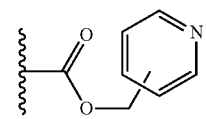

TABLE 4-continued
Additional norbenzomorphan piperazine N-derivatives for R[1].
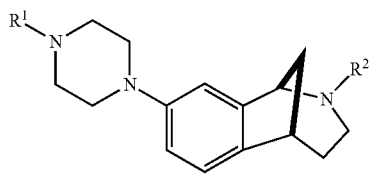
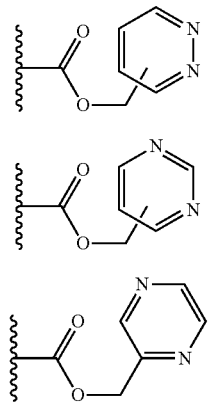
X = N, S, O
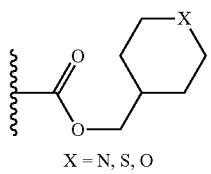
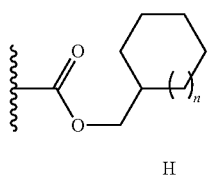
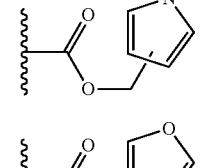
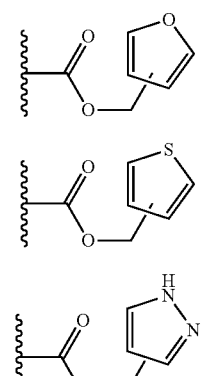
TABLE 4-continued
Additional norbenzomorphan piperazine N-derivatives for R[1].
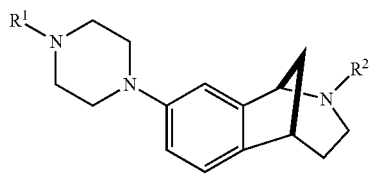
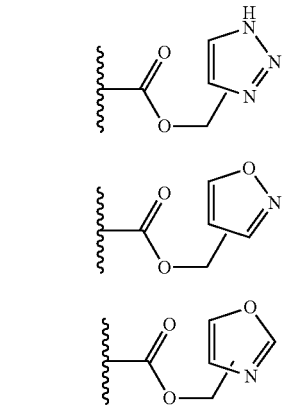
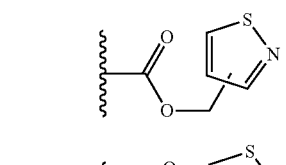
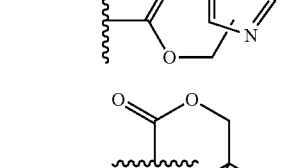
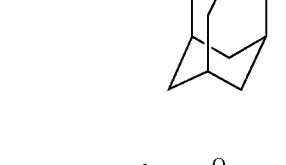
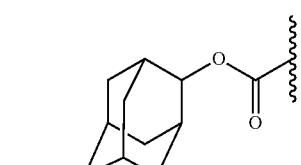
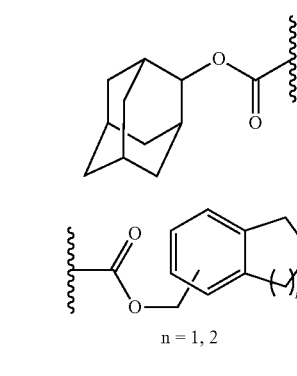
n = 1, 2
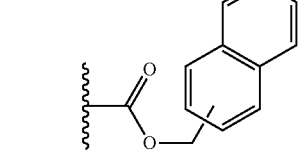

TABLE 4-continued

Additional norbenzomorphan piperazine N-derivatives for R¹.

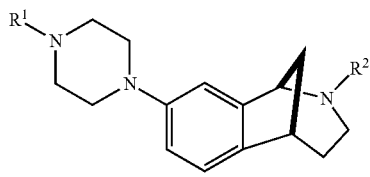

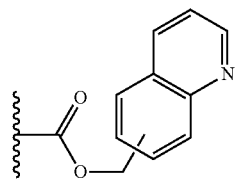

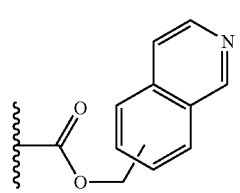

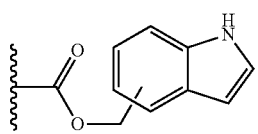

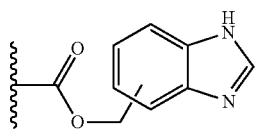

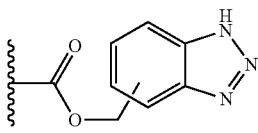

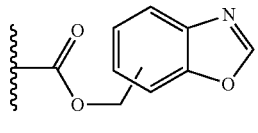

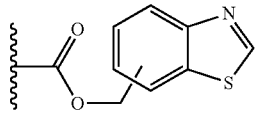

TABLE 5

Additional norbenzomorphan benzazepine N-derivatives for R², wherein X is any substituent (e.g., halogen).

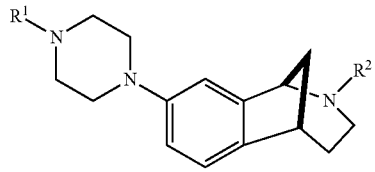

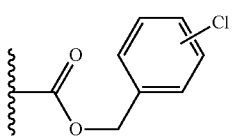

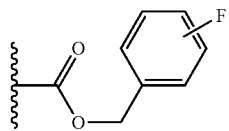

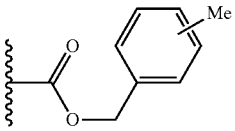

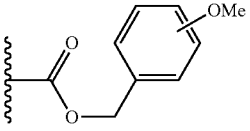

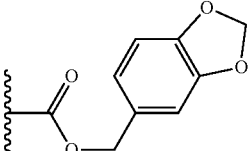

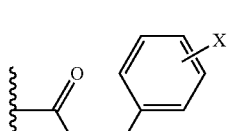

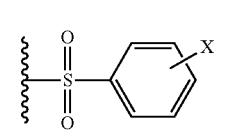

Example 6. Benzazepine N-Derivatives

Analogs listed in Table 5 show additional substituents for benzazepine N-derivatives attached to the norbenzomorphan nucleus.

Example 7. Specific Piperazine and Benzazepine N-Derivatives

Analogs listed in Table 6 show specific piperazine and benzazepine N-derivatives attached to the norbenzomorphan nucleus with sigma receptor affinity, where the $K_i$ values obtained from non-linear regression of radioligand competition binding isotherms.

TABLE 6

Sigma receptor affinity of specific norbenzomorphan analogs.

| Compound | σ1 K$_i$ (nM)$^a$ | σ2 K$_i$ (nM)$^a$ |
|---|---|---|
| (propyl-piperazinyl norbenzomorphan, Cbz) | 255 | 4.0 |
| (cyclopentyl-piperazinyl norbenzomorphan, Cbz) | 170 | 2.3 |
| (cyclohexyl-piperazinyl norbenzomorphan, Cbz) | 27 | 1.4 |
| (ethyl propanoate-piperazinyl norbenzomorphan, Cbz) | 9294 | 16.2 |
| (methallyl-piperazinyl norbenzomorphan, Cbz) | 413 | 17.5 |
| (propyl propanoate-piperazinyl norbenzomorphan, Cbz) | In progress | 58 |

Screening for Sig2R compounds. Sigma-2 receptors (Sig2R) are widely distributed proteins that are involved in cell proliferation and regulation of cytosolic calcium concentration. Recent evidence suggests that Sig2R may reside in the progesterone receptor membrane component 1 (PGRMC1), a gene with known orthologues in yeast, invertebrates, rodents, and humans. For clarity, the receptor is referred to as Sig2R/PGRMC1. Widely distributed in the central nervous system (CNS) and some periphery tissues, Sig2R/PGRMC1 are increasingly being implicated in cellular processes relevant to a variety of CNS disorders, including Alzheimer's disease. We were thus intrigued by the possibility that Sig2R/PGRMC1 binding ligands might be neuroprotective and useful as potential leads to treat neurodegenerative diseases. Accordingly, a collection of diverse small molecules, which was generated using a modular synthetic platform that enables facile access to a broad array of substituted heterocycles, was screened at the Psychoactive Drug Screening Program, University of North Carolina, Chapel Hill (see website pdsp.med.unc.edu/pdspw/binding.php). A number of norbenzomorphans were thus identified that bound with high affinity and selectivity to Sig2R/PGRMC1.

Sigma-2 receptor ligands and their binding assays. A collection of heterocyclic compounds were generated using a modular synthetic platform to afford a diverse array of substituted heterocycles that was screened against a panel of CNS targets. The compounds were dissolved in 100% DMSO prior to the receptor binding assays, which were performed by the Psychoactive Drug Screening Program (PDSP) at Chapel Hill, N.C. The assay protocol book can be accessed free of charge at: website pdsp.med.unc.edu/PDSP%20Protocols %20II %202013-03-28.pdf. Briefly, Sig2Rs were sourced from rat liver homogenates (PC12 cells). The Sig2R ligand binding affinity was determined through competition binding assays using the radioligand [$^3$H]-ditolylguanidine in the presence of (+)-pentazocine to block Sig1R binding sites. The radioactivity in the presence of the test compound is calculated with the following equation and expressed as a percent inhibition: % inhibition=(sample CPM non-specific CPM)/(Total CPM non-specific CPM)× 100 where CPM stands for counts per minute. To determine secondary binding data, CPM/well are pooled and fitted to a three parameter logistic function for competition binding in Prism v 5.0 to determine IC$_{50}$ values, which are converted to K$_i$ according to the Cheng-Prusoff equation.

Example 8. Specific Piperazine and Benzazepine N-Derivatives

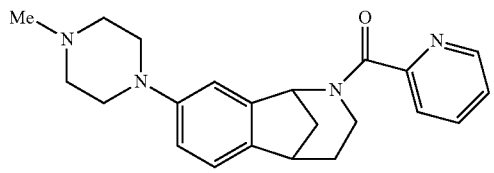 [SMILES: CN1CCN(c2ccc3c(c2)C2CC3CCN2C(=O)c2ccccn2)CC1]

(±)-(8-(4-Methylpiperazin-1-yl)-1,3,4,5-tetrahydro-2H-1,5-methanobenzo-[c]azepin-2-yl)(pyridin-2-yl)methanone (TH-1-127). Isobutyl chloroformate (16 mg, 0.015 mL, 0.117 mmol) and N-methylmorpholine (12 mg, 0.013 mL, 0.122 mmol) were added sequentially to a stirred solution of picolinic acid (19 mg, 0.117 mmol) in CH$_2$Cl$_2$ (1 mL) at −20° C. The solution was stirred for 1 h, whereupon a solution of (±)-8-(4-methylpiperazin-1-yl)-2,3,4,5-tetrahydro-1H-1,5-methanobenzo[c]azepine (15 mg, 0.058 mmol) in CH$_2$Cl$_2$ (1 mL) was added. The cooling bath was removed, and stirring was continued for 2 h. NH$_4$OH (1 mL) was added, and the layers were separated. The aqueous layer was extracted with CH$_2$Cl$_2$ (3×10 mL), and the combined organic extracts were washed with water (1×10 mL), dried (Na$_2$SO$_4$), and concentrated in vacuo.

The residue was purified via flash column chromatography (SiO$_2$), eluting with a MeOH/triethylamine/Et$_2$O (2:3:95) mixture, to afford 20 mg (83%) of (±)-TH-1-127 as a clear oil: $^1$H NMR (400 MHz, CDCl$_3$, as a mixture of rotamers) δ 8.69 (d, J=4.1 Hz, 0.45H), 8.54 (d=4.1 Hz, 0.55H), 7.84 (td, J=7.5, 1.4 Hz, 0.45H), 7.74 (td, J=7.5, 1.3 Hz, 0.55H), 7.66 (d, J=7.5 Hz, 0.45H), 7.54 (d, J=7.9 Hz, 0.55H), 7.40-7.33 (m, 0.45H), 7.32-7.26 (m, 0.55H), 7.16-7.10 (m, 1H), 7.06 (d, J=1.7 Hz, 0.55H), 6.87-6.79 (comp, 1.45H), 5.95 (d, J=3.8 Hz, 0.55H), 5.10 (d, J=3.8 Hz, 0.45H), 4.32 (dd, J=13.7, 6.2 Hz, 0.45H), 3.54 (dd, J=13.7, 5.8 Hz, 0.55H), 3.31-3.12 (comp, 5H), 2.74 (td, J=13.0, 4.8 Hz, 0.55H), 2.66-2.53 (comp, 4H), 2.46 (td, J=13.4, 5.2 Hz, 0.45H), 2.39-2.26 (comp, 4H), 2.18-1.89 (comp, 3H), 1.76-1.66 (m, 0.45H), 1.52-1.43 (m, 0.55H); $^{13}$C NMR (125 MHz, CDCl$_3$, as a mixture of rotamers) δ 167.3, 167.2, 155.1, 154.8, 151.2, 151.2, 148.8, 148.6, 141.8, 141.6, 138.2, 138.0, 137.2, 137.0, 124.4, 124.3, 123.8, 123.5, 123.3, 123.1, 116.6, 116.1, 113.0, 112.5, 61.0, 56.1, 55.3, 55.3, 49.8, 49.7, 46.2, 46.2, 44.4, 44.4, 42.2, 39.5, 39.3, 37.4, 31.5, 30.6; IR (neat) 2937, 2798, 1622, 1418, 1239 cm$^{-1}$; HRMS (ESI) m/z calcd for C$_{22}$H$_{26}$N$_4$O (M+H)$^+$, 363.2179; found 363.2179.

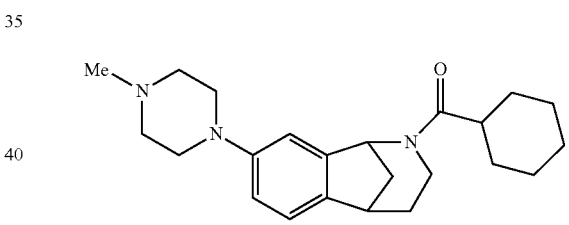

(±)-Cyclohexyl(8-(4-methylpiperazin-1-yl)-1,3,4,5-tetrahydro-2H-1,5-methanobenzo[c]azepin-2-yl)methanone (TH-1-106). Cyclohexanoyl chloride (22 mg, 20 μL, 0.222 mmol) was added to a stirred solution of (±)-8-(4-methylpiperazin-1-yl)-2,3,4,5-tetrahydro-1H-1,5-methanobenzo[c]azepine (20 mg, 0.08 mmol) and diisopropylethylamine (29 mg, 40 μL, 0.222 mmol) in CH$_2$Cl$_2$ (1 mL) at 0° C. NH$_4$OH (1 mL) was added, and the layers were separated. The aqueous layer was extracted with CH$_2$Cl$_2$ (3×10 mL), and the combined organic extracts were washed with water (1×10 mL), dried (Na$_2$SO$_4$), and concentrated in vacuo. Purification via FCC, eluting with triethylamine/Et$_2$O (2% v/v), afforded 23 mg (84%) of (±)-TH-1-106 as a colorless foam: $^1$H NMR (400 MHz, CDCl$_3$, as a mixture of rotamers) δ 7.10 (d, J=8.2 Hz, 1H), 6.93 (d, J=2.0 Hz, 0.66H), 6.85-6.78 (comp, 1.34H), 5.89 (d, J=4.1 Hz, 0.66H), 5.06 (d, J=3.7 Hz, 0.33H), 4.26 (dd, J=13.3, 6.3 Hz, 0.33H), 3.54 (dd, J=13.0, 6.1 Hz, 0.66H), 3.27-2.99 (comp, 5H), 2.71-2.54 (comp, 5H), 2.37 (s, 3H), 2.34-2.11 (comp, 2H), 1.97-1.87 (m, 1H), 1.87-1.11 (comp, 12H); HRMS (ESI) m/z calcd for C$_{23}$H$_{33}$N$_3$O (M+H)$^+$, 368.2696; found 368.2697.

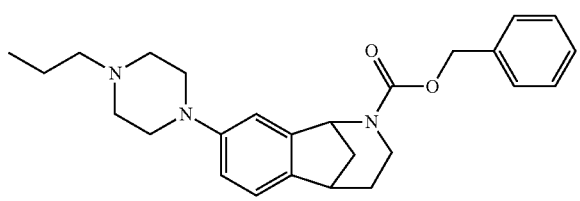 [SMILES: CCCN1CCN(c2ccc3c(c2)C2CC3CCN2C(=O)OCc2ccccc2)CC1]

(±)-Benzyl-8-(4-propylpiperazin-1-yl)-1,3,4,5-tetrahydro-2H-1,5-methanobenzo[c]azepine-2-carboxylate (TH-2-41; DKR-1516). Propionaldehyde (7 mg, 8.6 µL, 0.12 mmol) was added to a stirred mixture of sodium triacetoxyborohydride (8.5 mg, 0.12 mmol) and (±)-benzyl-8-(piperazin-1-yl)-1,3,4,5-tetrahydro-2H-1,5-methanobenzo-[c]azepine-2-carboxylate (15 mg, 0.04 mmol) in 1,2-DCE (1 mL) at room temperature. The mixture was stirred for 3 h and then 1 M NaOH (2 mL) was added, stirred briefly, and the mixture poured into brine (5 mL). The mixture was extracted with Et$_2$O (3×10 mL), and the combined organic extracts were dried (MgSO$_4$), and concentrated under reduced pressure. The residue was purified via preparative TLC to afford 9.2 mg (55%) of (±)-DKR-1516 as a clear oil: $^1$H NMR (400 MHz, CDCl$_3$, as a mixture of rotamers) δ 7.47-7.26 (comp, 5H), 7.10 (d, J=8.3 Hz, 1H), 6.98 (brs, 0.5H), 6.85-6.77 (comp, 1.5H), 5.45 (brs, 0.5H), 5.34 (brs, 0.5H), 5.27-5.03 (comp, 2H), 3.88-3.70 (m, 1H), 3.27-3.09 (comp, 5H), 2.67-2.56 (m, 4H), 2.52-2.34 (m, 1H), 2.37 (t, J=7.6 Hz, 2H), 2.24 (m, 1H), 2.02-1.87 (m, 1H), 1.84 (d, J=10.5 Hz, 1H), 1.62-1.47 (m, 1H), 1.56 (sex, 7.5 Hz, 2H), 0.93 (t, J=7.4 Hz, 3H); $^{13}$C NMR (100 MHz, CDCl$_3$, as a mixture of rotamers) δ 155.1, 154.8, 151.1, 142.1, 141.8, 137.5, 137.2, 136.9, 128.5, 127.9, 127.8, 123.1, 123.0, 116.0, 115.7, 112.4, 112.1, 66.9, 60.7, 58.0, 57.7, 53.3, 49.6, 43.8, 39.0, 38.7, 30.5, 20.0, 12.0; IR (neat): 2936, 1696, 1417, 1237 cm$^{-1}$; HRMS (ESI) m/z calcd for C$_{26}$H$_{33}$N$_3$O$_2$ (M+H)$^+$, 420.2646; found 420.2643.

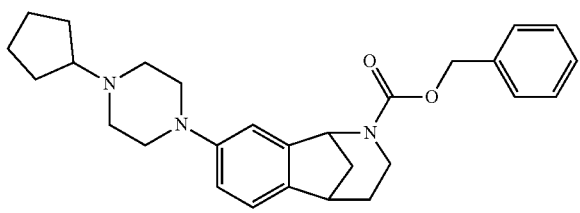 [SMILES: O=C(OCc1ccccc1)N1CCC2CC1c1cc(N3CCN(C4CCCC4)CC3)ccc12]

(±)-Benzyl-8-(4-cyclopentylpiperazin-1-yl)-1,3,4,5-tetrahydro-2H-1,5-methanobenzo[c]azepine-2-carboxylate (TH-4-65). Cyclopentanone (20 mg, 21 µL, 0.237 mmol) was added to a stirred mixture of sodium triacetoxyborohydride (34 mg, 0.159 mmol) and (±)-benzyl-8-(piperazin-1-yl)-1,3,4,5-tetrahydro-2H-1,5-methanobenzo-[c]azepine-2-carboxylate (30 mg, 0.079 mmol) in 1,2-DCE (1 mL) at room temperature. The mixture was stirred for 3 h, whereupon 1 M NaOH (2 mL) was added and the mixture poured into brine (5 mL). The mixture was extracted with Et$_2$O (3×10 mL), and the combined organic extracts were dried (MgSO$_4$) and concentrated under reduced pressure. The residue was purified via flash column chromatography (SiO$_2$), eluting with MeOH/CH$_2$Cl$_2$ (1% to 2% v/v), to afford 33 mg (94%) of (±)-TH-4-65 as a clear oil: $^1$H NMR (400 MHz, CDCl$_3$, as a mixture of rotamers) δ 7.44-7.26 (comp, 5H), 7.10 (d, J=8.2 Hz, 1H), 6.97 (brs, 0.55H), 6.82-6.77 (comp, 1.45H), 5.44 (d, J=2.7 Hz, 0.55H), 5.33 (d, J=2.7 Hz, 0.45H), 5.26-5.03 (comp, 2H), 3.86-3.70 (m, 1H), 3.24-3.12 (comp, 5H), 2.68 (t, J=4.8 Hz, 4H), 2.61-2.35 (comp, 2H), 2.25-2.10 (m, 1H), 2.01-1.40 (comp, 11H); $^{13}$C NMR (100 MHz, CDCl$_3$, as a mixture of rotamers) δ 155.2, 151.1, 142.2, 142.0, 137.7, 137.3, 137.0, 128.6, 128.0, 127.9, 123.2, 123.1, 116.1, 115.8, 112.6, 112.3, 67.7, 67.0, 58.1, 57.8, 52.5, 49.7, 43.9, 39.1, 38.8, 30.6, 30.5, 24.3; IR (neat): 2953, 1696, 1417, 1238 cm$^{-1}$; HRMS (ESI) m/z calcd for C$_{28}$H$_{35}$N$_3$O$_2$ (M+H)$^+$, 446.2802; found 446.2808.

Figure 2:
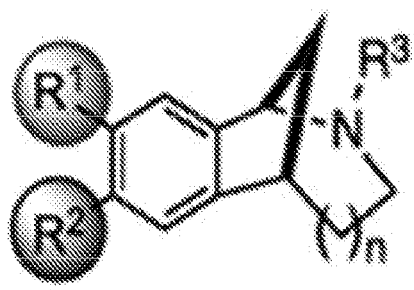
FIG. 2 Structure of sigma receptor binding ligands and compound SAS-101/SAS-0132/JJ-1-166.
Figure 2:
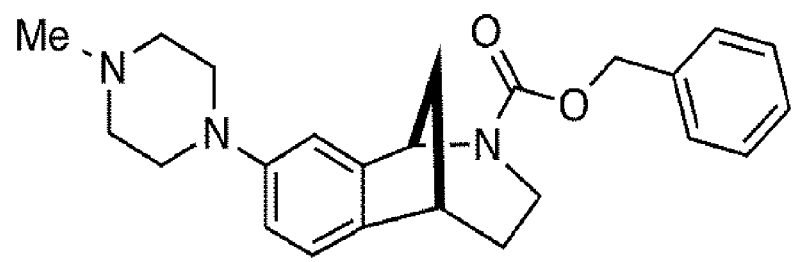
Figure 3:
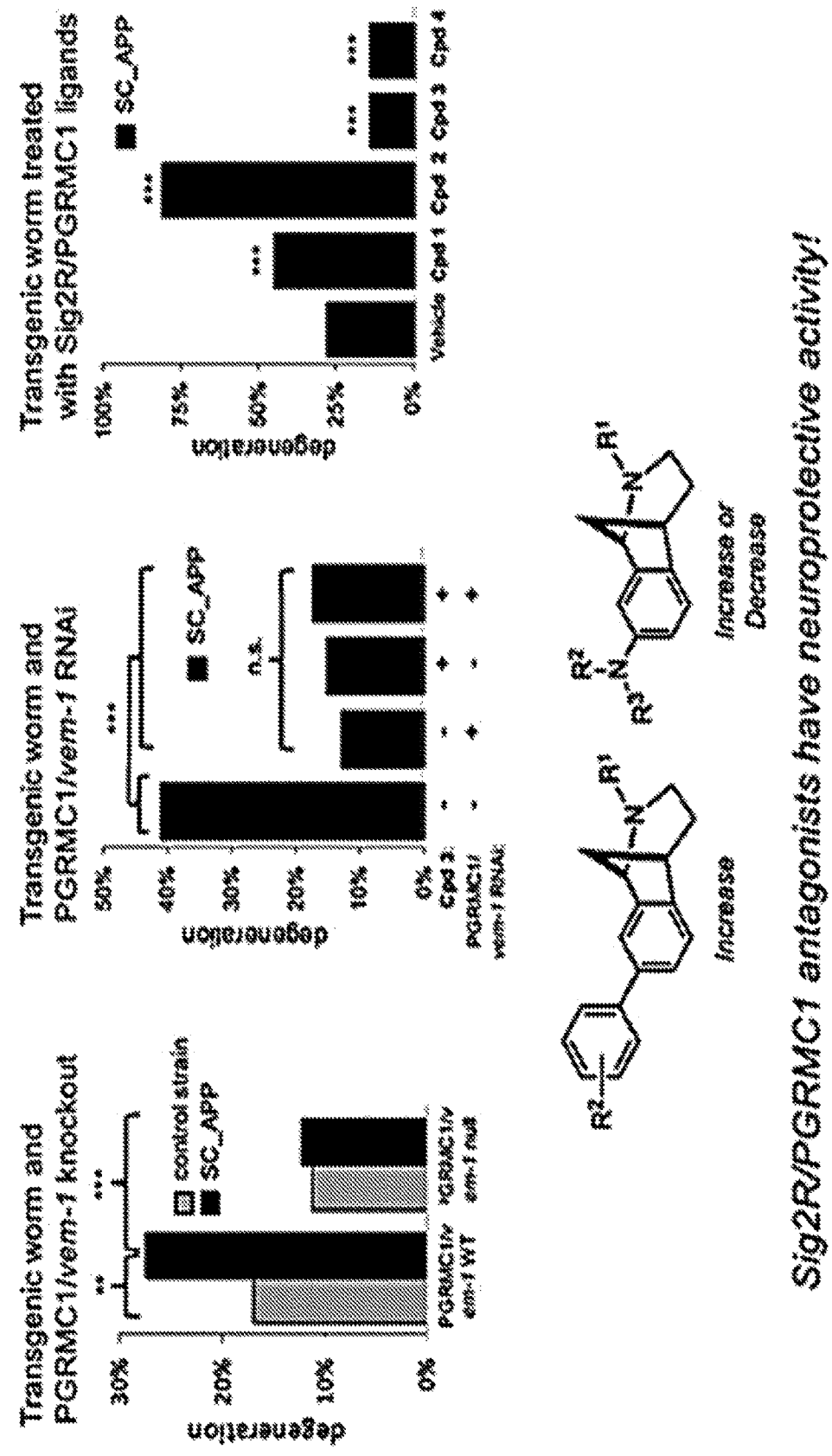
FIG. 3 Neurodegeneration assay including transgenic *C. elegans*; *C. elegans* SC_APP transgenic worm exhibits greater neurodegeneration than control (WT), *C. elegans* PGRMC1/vem-1 knockout (Null) exhibits reduced neurodegeneration relative to WT, RNAi experiments show ligands act via PGRMC1 mediated pathway; some Sig2R/PGRMC1 binding ligands increase neurodegeneration, but others are neuroprotective; it is significant that certain modulators of Sig2R/PGRMC1 have neuroprotective activity.

Example 9. Sigma Receptor Binding (±)-TH-1-127: sigma 1 receptor K$_i$<50 inhibition of radioligand binding at 10 uM; sigma 2 receptor K$_i$<50 inhibition of radioligand binding at 10 uM (±)-TH-1-106: sigma 1 receptor K$_i$ 1417 nM; sigma 2 receptor K, 144 nM (±)-DKR-1516: sigma 1 receptor K$_i$ 237.5 nM; sigma 2 receptor K, 4.0 nM DKR-1516 (S,R): sigma 1 receptor K$_i$ 251 nM; sigma 2 receptor K$_i$ 2.7 nM DKR-1516 (R,S): sigma 1 receptor K$_i$ 250 nM; sigma 2 receptor K$_i$ 20 nM (±)-TH-4-65: sigma 1 receptor K$_i$ 126.5 nM; sigma 2 receptor K, 2.3 nM TH-4-65 (S,R): sigma 1 receptor K$_i$ 61 nM; sigma 2 receptor K, 2.5 nM TH-4-65 (R,S): sigma 1 receptor K$_i$ 152 nM; sigma 2 receptor K, 4.2 nM (±)-SAS-0132 (formerly SAS-101, JJ-1-166): sigma 1 receptor K, 497 nM; sigma 2 receptor K$_i$ 71 nM Example 10. Compound Binding to Neuroreceptors Diverse classes of heterocyclic compounds, including as shown in FIG. 1, were screened in the NIHMH Psychoactive Drug Screening Program for binding and functional activity at cloned human or rodent receptors, GPCRs, channels, and transporters. Identification of a number that exhibited high potency and selectivity for a number of receptors and subtypes, including serotonin, dopamine, sigma, histamine, norepinephrine transporter, muscarinic, opioid, and benzodiazepine, was conducted. Further synthesis and screening of compounds having the general structure of FIG. 2 was subsequently done.

Example 11. Screening Compounds for CNS Activity Using *C. elegans*

Compounds were screened and/or assayed in WT *C. elegans* and/or mutant (SC_APP) *C. elegans*, including to evaluate extent of neurodegeneration/neuroprotection associated with compounds. Mutant SC_APP strain includes cholinergic neurons (VC4 and VC5) labeled with green fluorescent protein, copy of human amyloid precursor protein (APP) to form hAPP, and exhibits age-related, AD-like neurodegeneration (scission of cholinergic neurons).

Example 12. Sig2R/PGRMC1 Modulators for Improving Cognition

Assays were conducted with transgenic mice overexpressing human APP751 and contain London (V717I) and Swedish (K670M/N671L) mutations, which is an industry-accepted model that exhibits AD behavioral phenotypes observed in humans. Characterization of how administering Sig2R/PGRMC1 modulator to transgenic Thy-1 hAPPLond/

Figure 4:
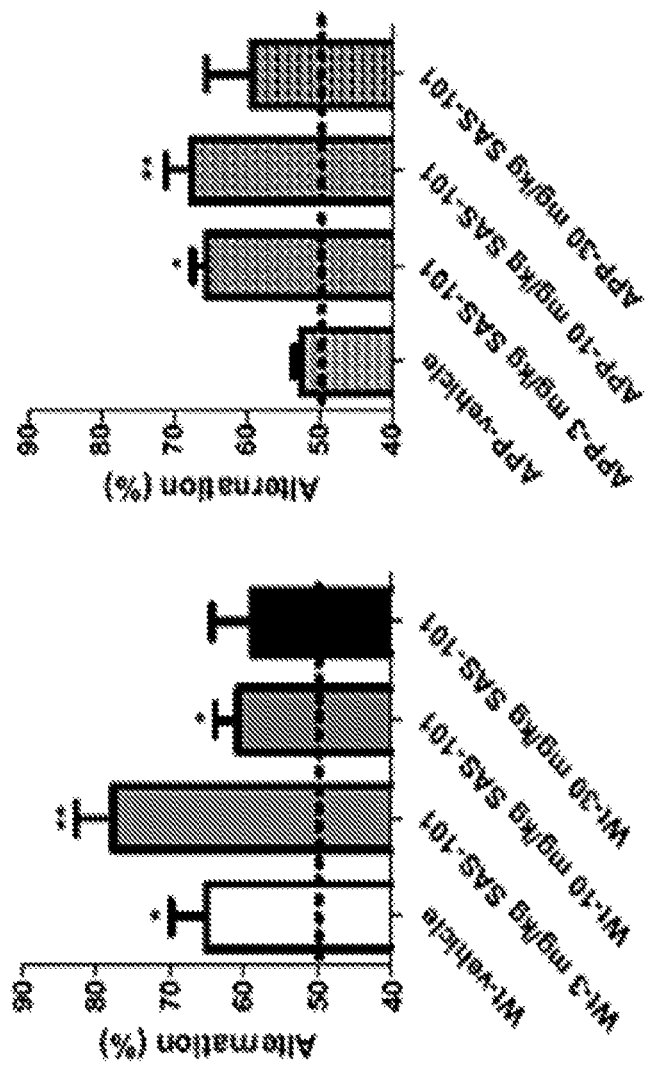
FIG. 4 Y-Maze Behavioral Test is a behavioral test measuring willingness of mice to explore new environments. Rodents typically prefer to investigate new arm of maze rather than returning to one previously visited; a modulator of Sig2R/PGRMC1 enhances reference and working memory in WT and transgenic APP mice.
Figure 4:
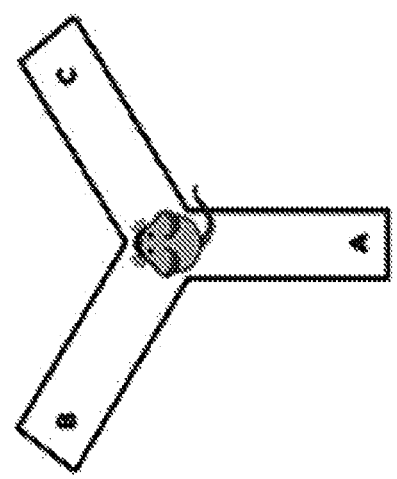
Figure 5:
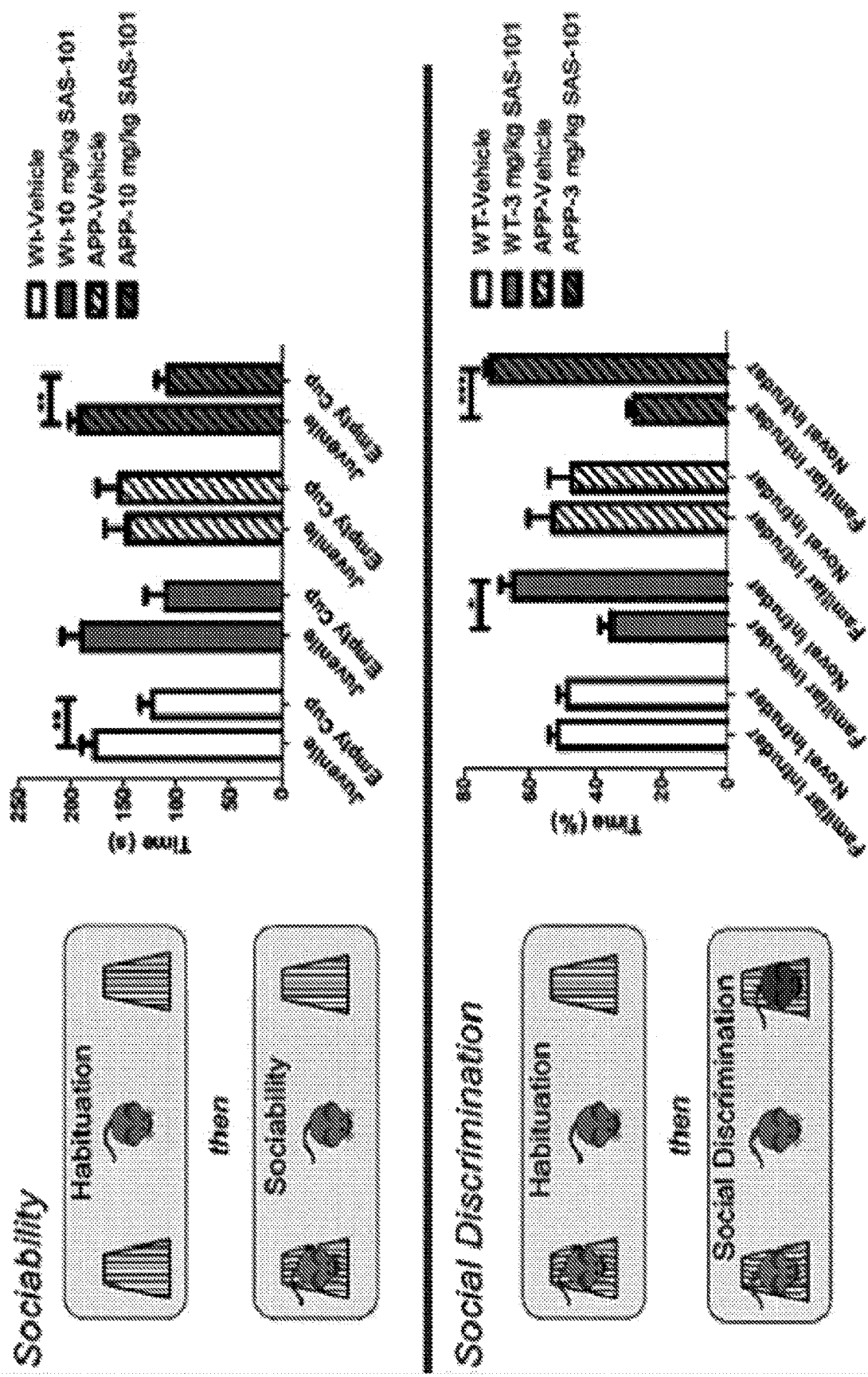
FIG. 5 Sociability and Social Discrimination Tests; Sig2R/PGRMC1 modulator rescues social deficits in WT and transgenic APP mice.
Figure 6:
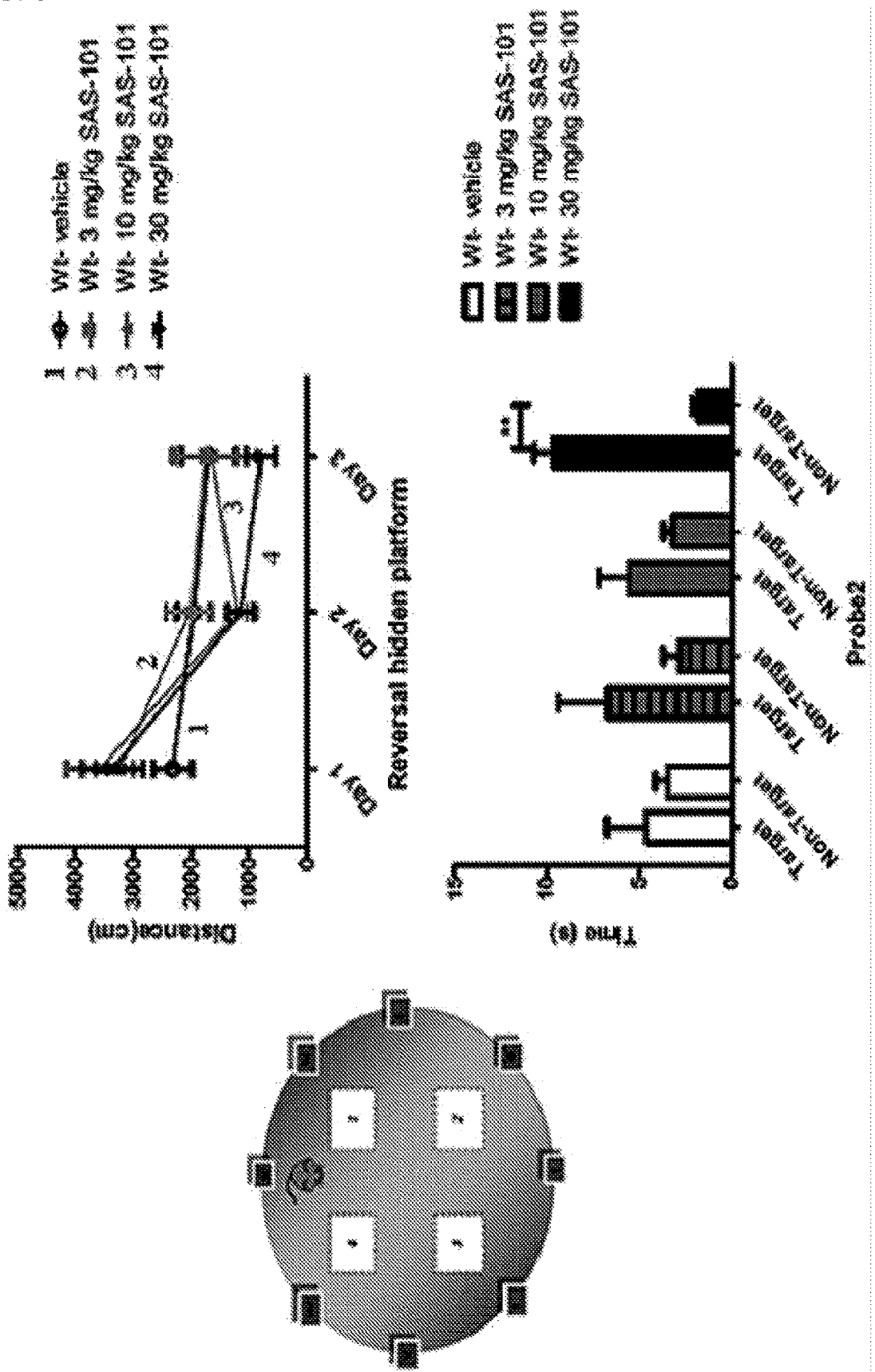
FIG. 6 Sig2R/PGRMC1 modulator enhances spatial and long term memory in WT mice; Morris Water Maze Test of WT mice is a test wherein mice dropped at different locations search for hidden platform (e.g. in quadrant 2); first assay: after training period platform is moved (e.g., quadrant 4), mice are dropped at different locations to see how far mice swim before finding platform; second assay: platform is removed, mice are dropped in maze at different locations and time spent swimming in quadrant where platform was initially is measured.
Figure 7:
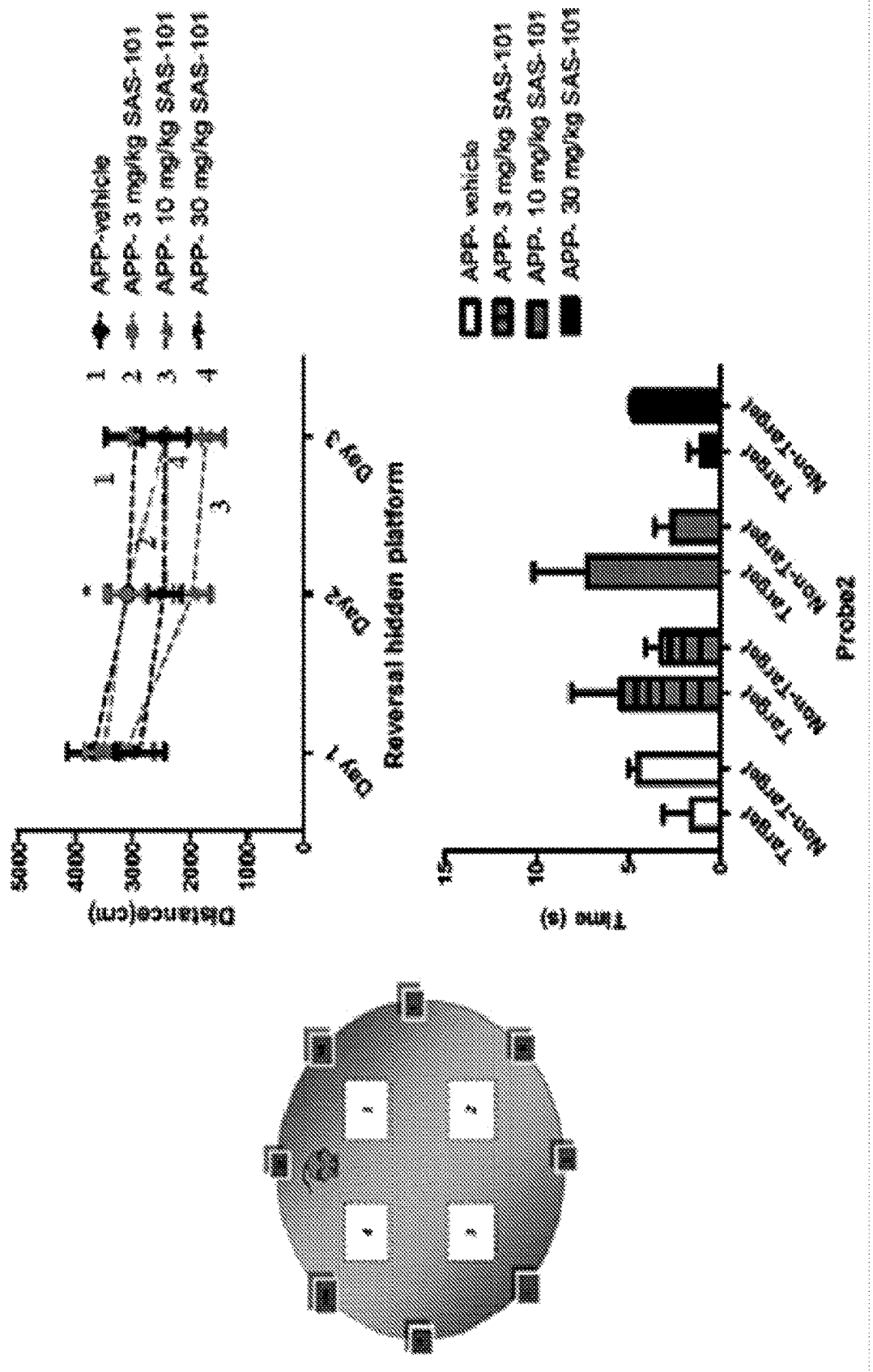
FIG. 7 Sig2R/PGRMC1 modulator enhances spatial and long term memory in WT and transgenic APP mice; Morris Water Maze Test for transgenic APP mice is a test wherein mice dropped at different locations search for hidden platform (e.g. in quadrant 2); first assay: after training period platform is moved (e.g., quadrant 4), mice are dropped at different locations to see how far mice swim before finding platform; second assay: platform is removed, mice are dropped in maze at different locations and time spent swimming in quadrant where platform was initially is measured.
Figure 8:
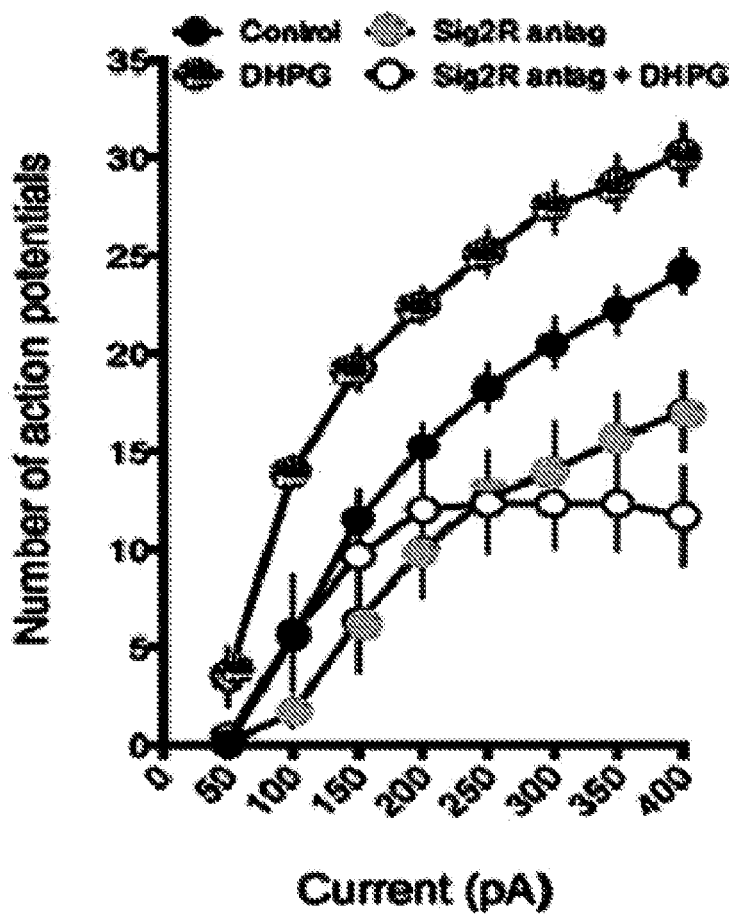
FIG. 8 Effect of Sig2R/PGRMC1 modulator on excitability; Acute hippocampal brain slices were made from 4 month-old wildtype C57BL/6 mice for whole-cell current clamp recordings from soma of CA1 pyramidal neurons. Action potential firing was elicited by using 500-msec long current injections of increasing amplitude (50-400 pA, 50 pA increments). Number of action potentials fired was plotted as a function of injected current amplitude. Control experiments were performed in normal extracellular saline, and the number of action potentials fired was measured before (baseline) and after activation of metabotropic glutamate receptors (100 μM DHPG for 5 min) (top two lines). In the Sig2R/PGRMC1 modulator experiments, 10 μM SAS-1, was present throughout the experiment and action potential firing was measured before and after DHPG application (bottom two lines); Sig2R/PGRMC1 antagonist reduces number of action potentials fired and prevents mGluR-mediated increase in excitability.
Figure 9:
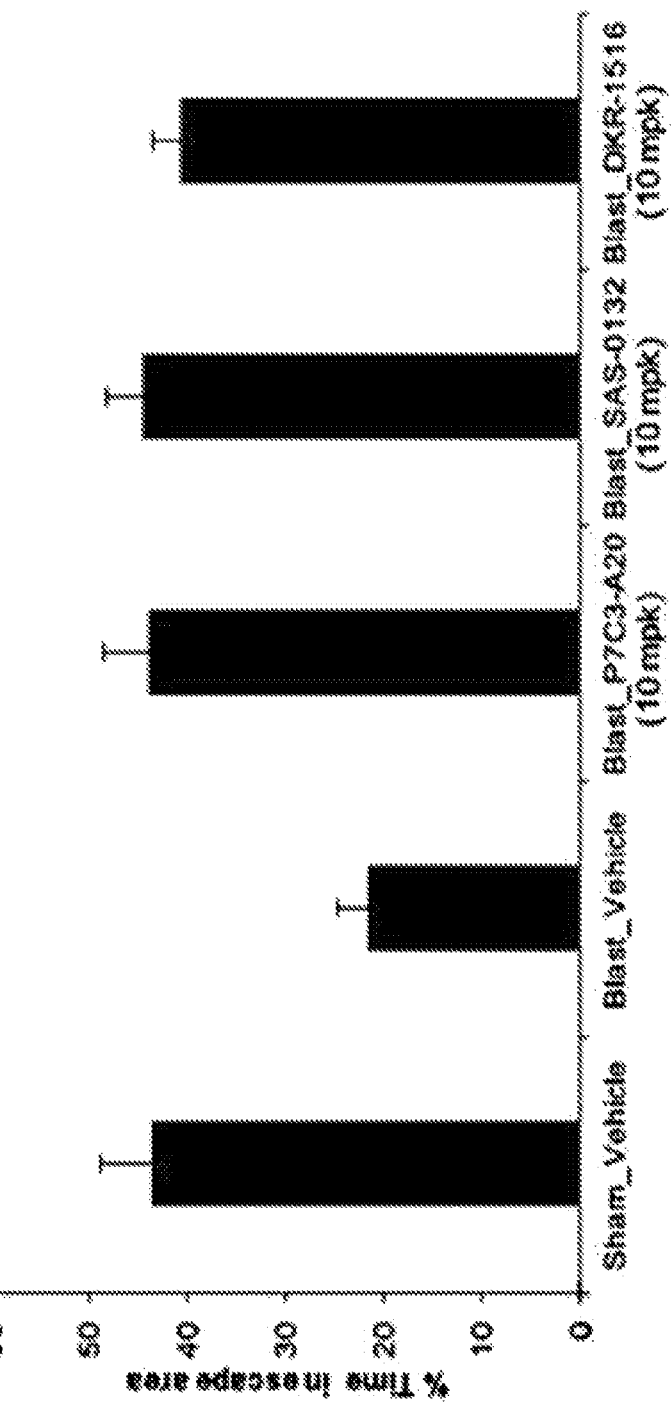
FIG. 9 Traumatic Brain Injury treatment; Barnes Maze (spatial and long term memory) after blast; Wild-type mice (C57BL/6) were subjected to either a Blast (brain injury) or Sham blast (no brain injury). The Blast animals that received seven days of daily treatment with either SAS-0132 (SAS-101) or DKR-1516, beginning the day after injury, performed significantly better in tests of spatial- and long term memory compared to animals that received no treatment (Veh).
Figure 10:
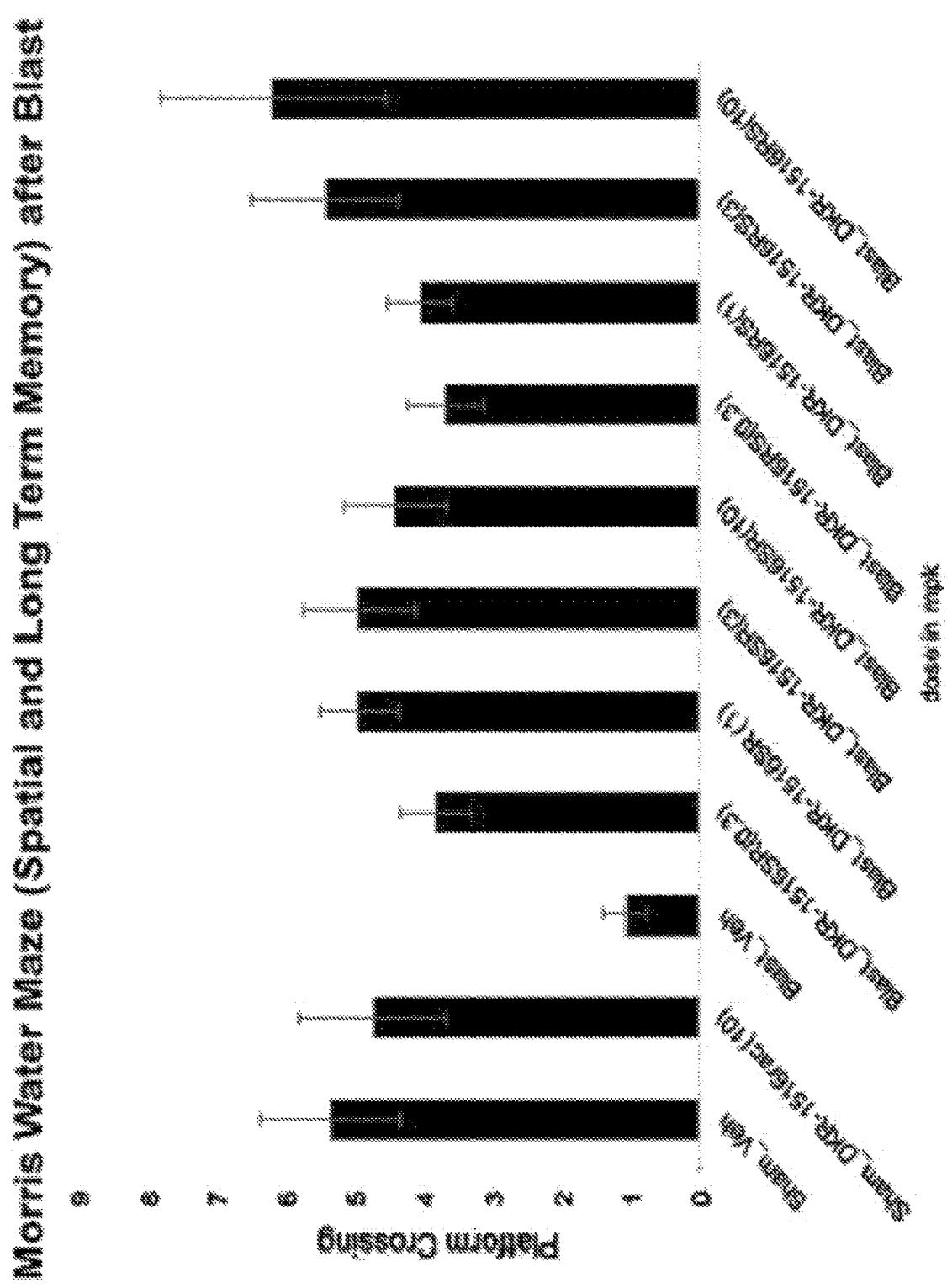
FIG. 10 Traumatic Brain Injury treatment; Morris Water Maze (spatial and long term memory) after blast; Wild-type mice (C57BL/6) were subjected to either a Blast (brain injury) or Sham blast (no brain injury). The Blast animals that received seven days of daily treatment with either DKR-1516 or either enantiomer of DKR-1516, beginning the day after injury, performed significantly better in tests of spatial- and long term memory compared to animals that received no treatment (Veh).
Figure 11:
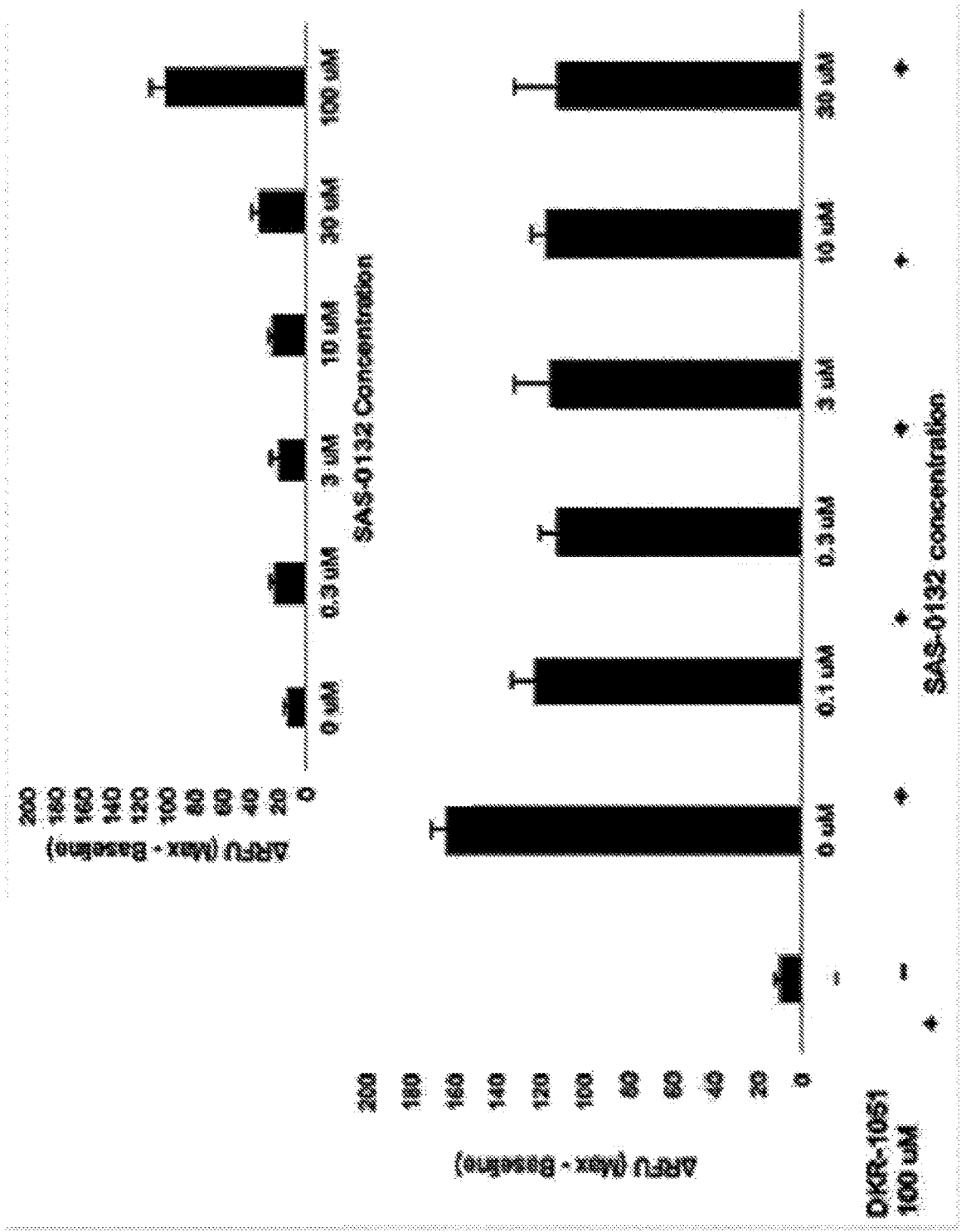
FIG. 11 Effects of Compounds on Calcium Ion Levels; In neuroblastoma cells, DKR-1051 induces concentration-dependent increases in intracellular Ca2+ concentration while SAS-0132 does not induce significant increases in intracellular Ca2+ at concentrations up to 30 µM. SAS-0132 produced concentration-dependent attenuation of DKR-1051-induced calcium response.
Figure 12:
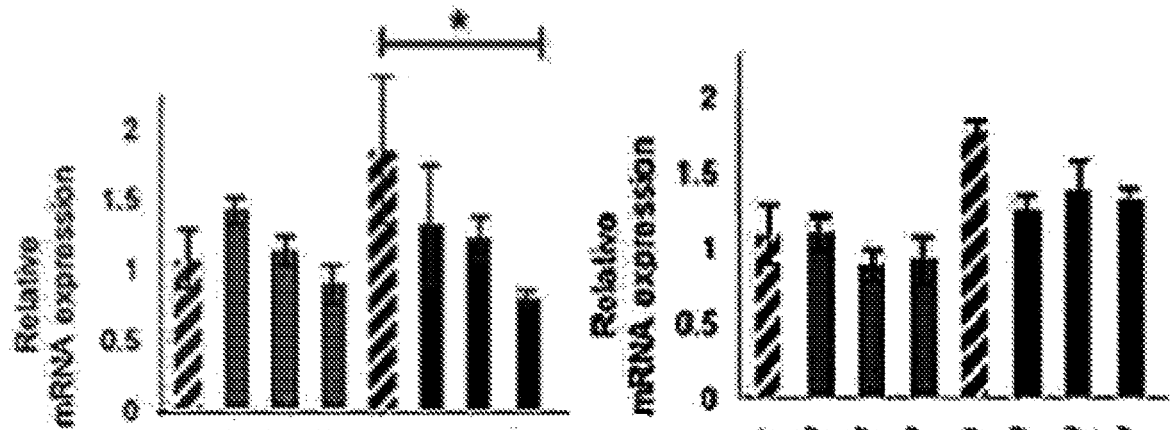
FIG. 12 Effects of SAS-0132 on levels of proinflammatory cytokines; Transgenic (Thy1-APPLond/Swe+) mice that received 60 days of treatment (30 mg/kg) with SAS-0132 showed a significant reduction in brain levels of IL-1β and reduction in brain levels of TNFα and CD14 was also observed (not statistically significant).
Figure 12:
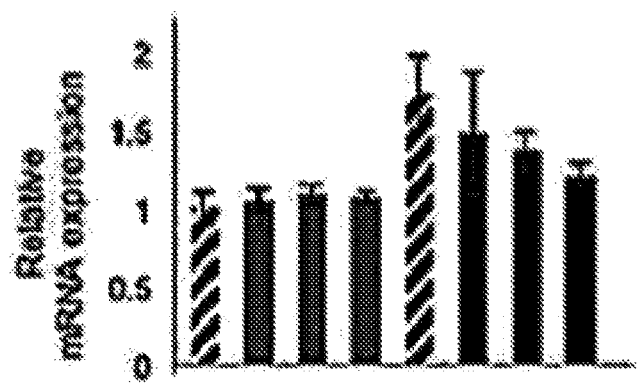
Figure 13:
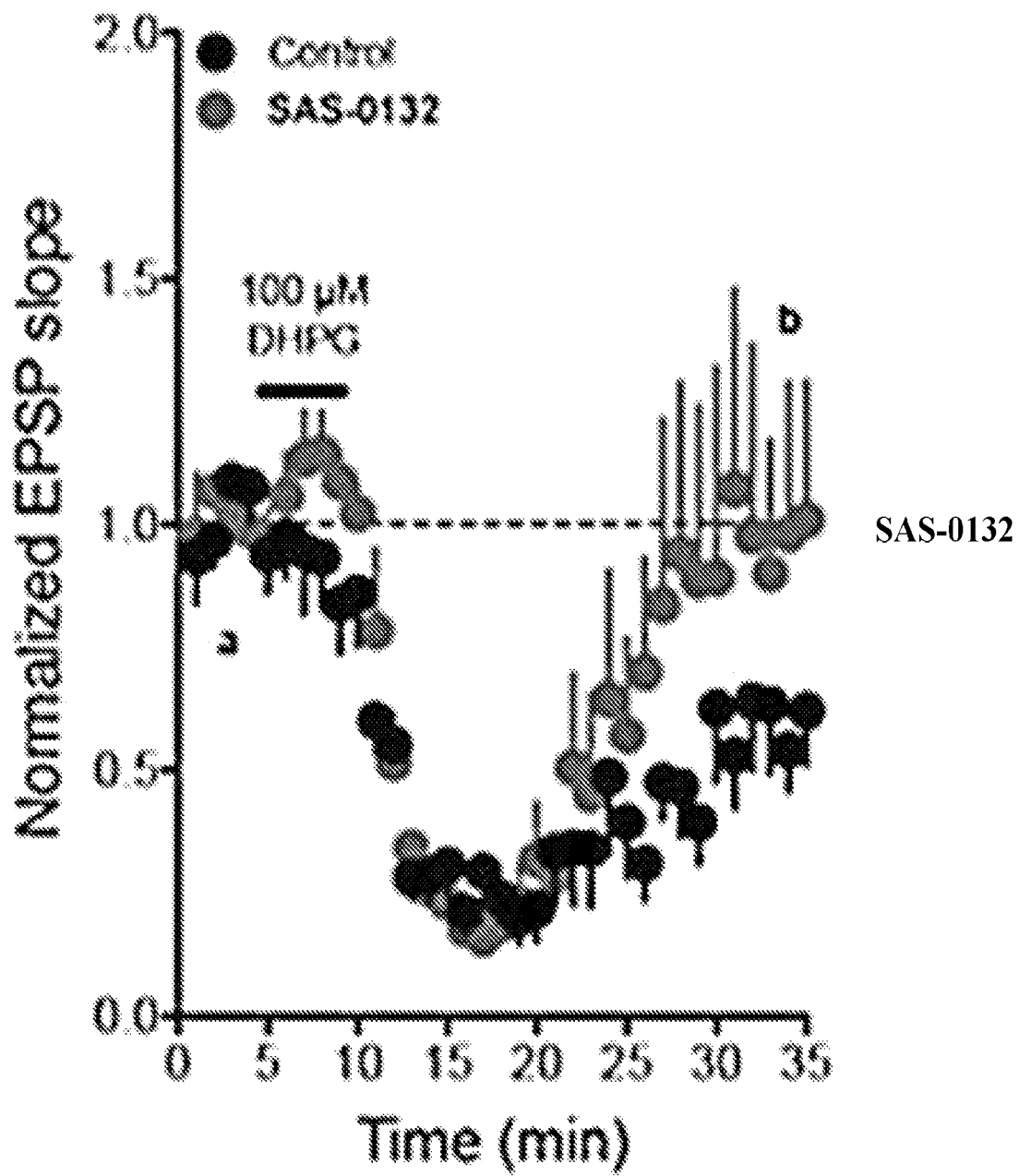
FIG. 13 Effect of SAS-0132 on Synaptic Long Term Depression (inhibition); effect of SAS-0132 on dihydroxyphenylglycine (DHPG) mediated increase in long term depression (LTD). Murine hippocampal neuron slices treated with DHPG showed increased LTD; when DHPG was administered with SAS-0132, the DHPG-mediated increase in LTD was blocked.
Figure 14A:
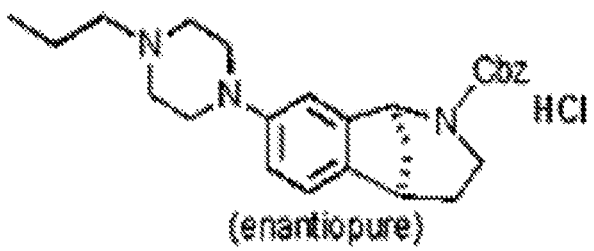
FIG. 14A-14B Effects of Compounds on Survival of Induced Motor Neurons Derived from Humans with Amyotrophic Lateral Sclerosis; Induced motor neurons (iMN) derived from humans with amyotrophic lateral sclerosis were treated with sigma 2 ligand (3 µm) or DMSO control; percent survival 0-100%, time 0-8 days. After 6 days of treatment, a number of ligands, including, but not limited to, SFM-1051 and TH-4-20, increased the percent survival of iMN relative to DMSO treatment.
Figure 14A:
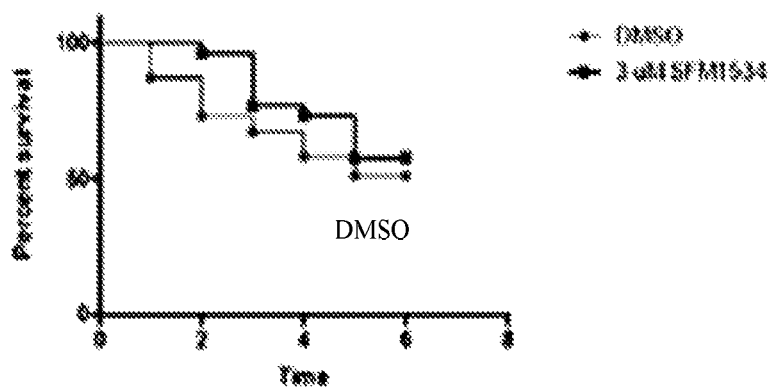
Figure 14A:
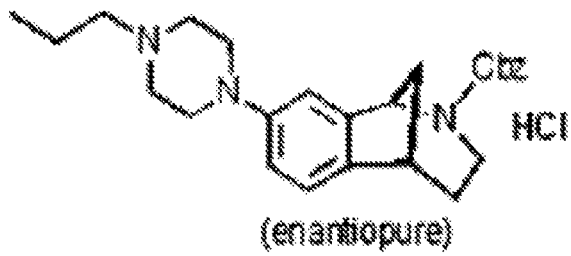
Figure 14A:
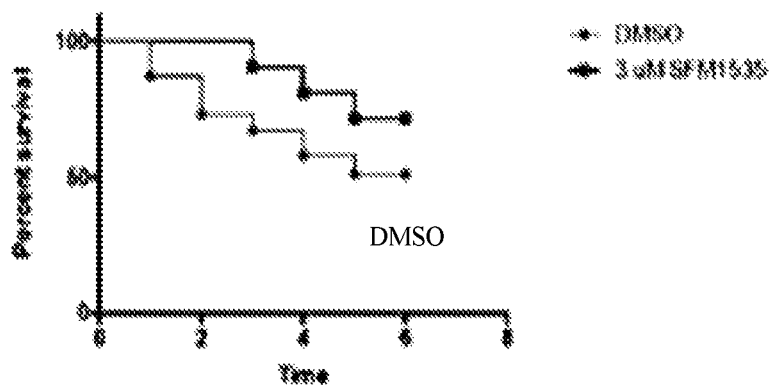
Figure 14B:
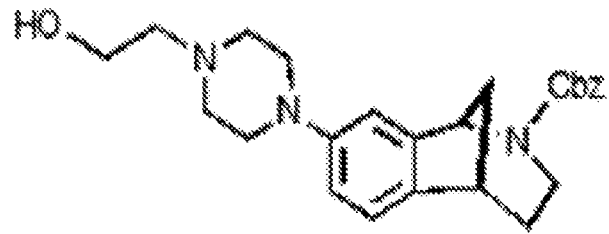
Figure 14B:
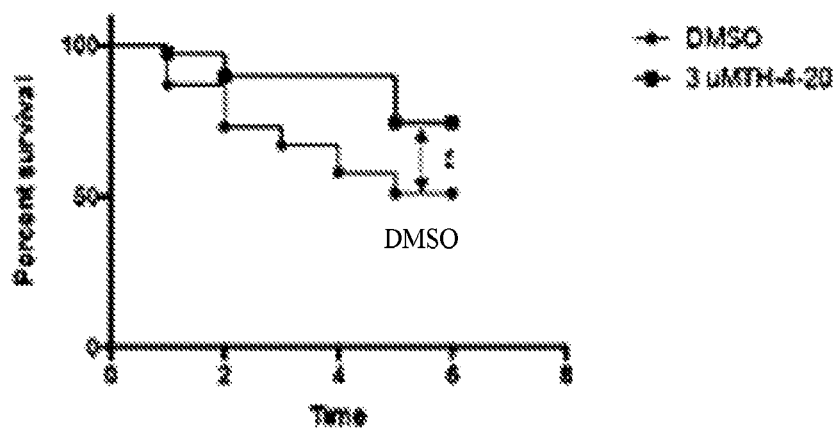
Figure 14B:
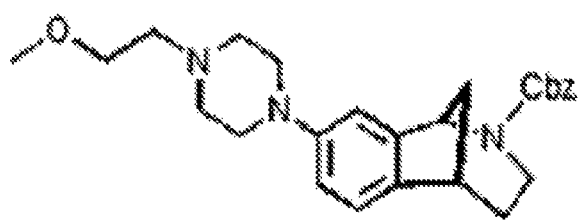
Figure 14B:
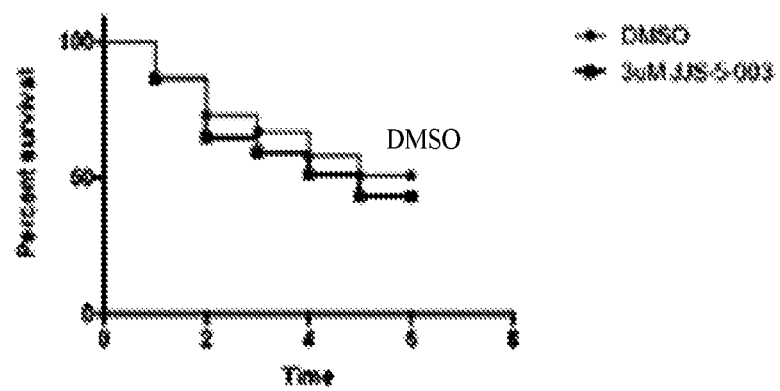
Figure 15:
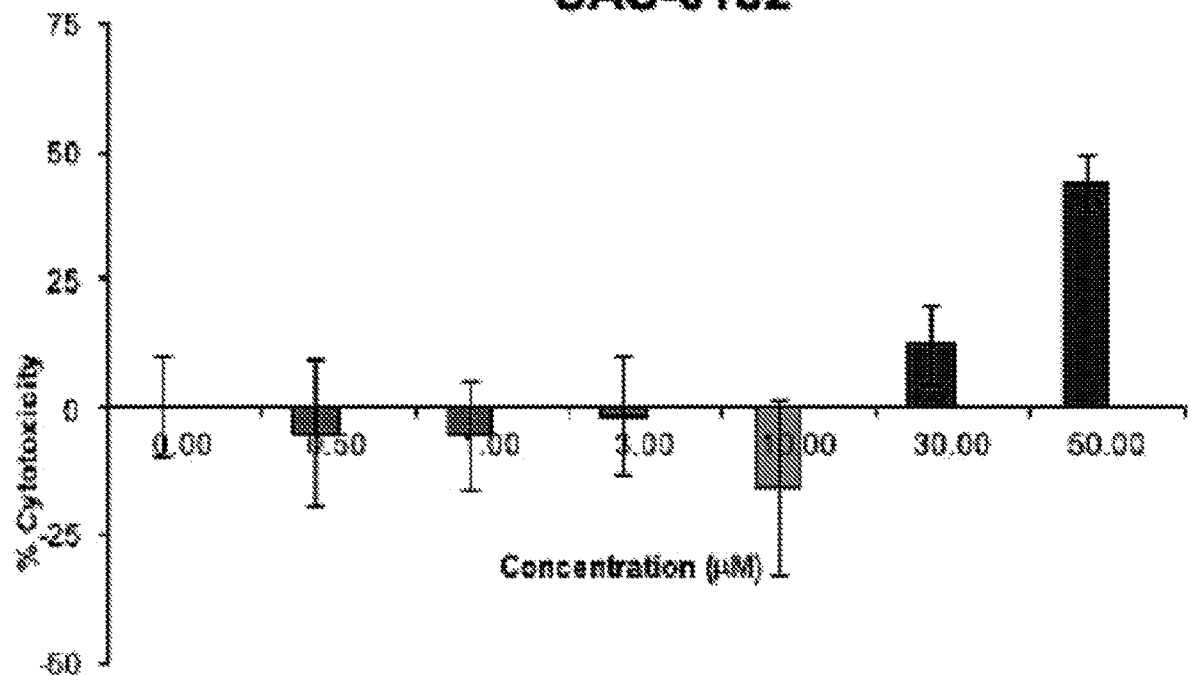
FIG. 15 MTT Assay in Neuroblastoma Cells; Sigma 2 receptor binding ligands were evaluated for effects in neuroblastoma cells. SAS-0132 was not toxic at low doses and began to demonstrate cytotoxicity around 30 microM.
Figure 15:
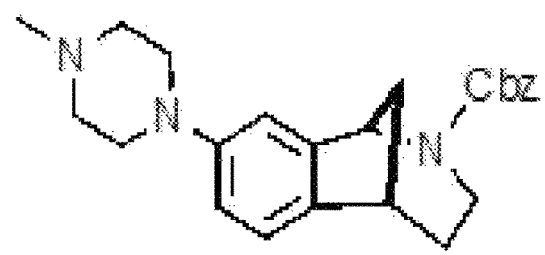
Figure 16:
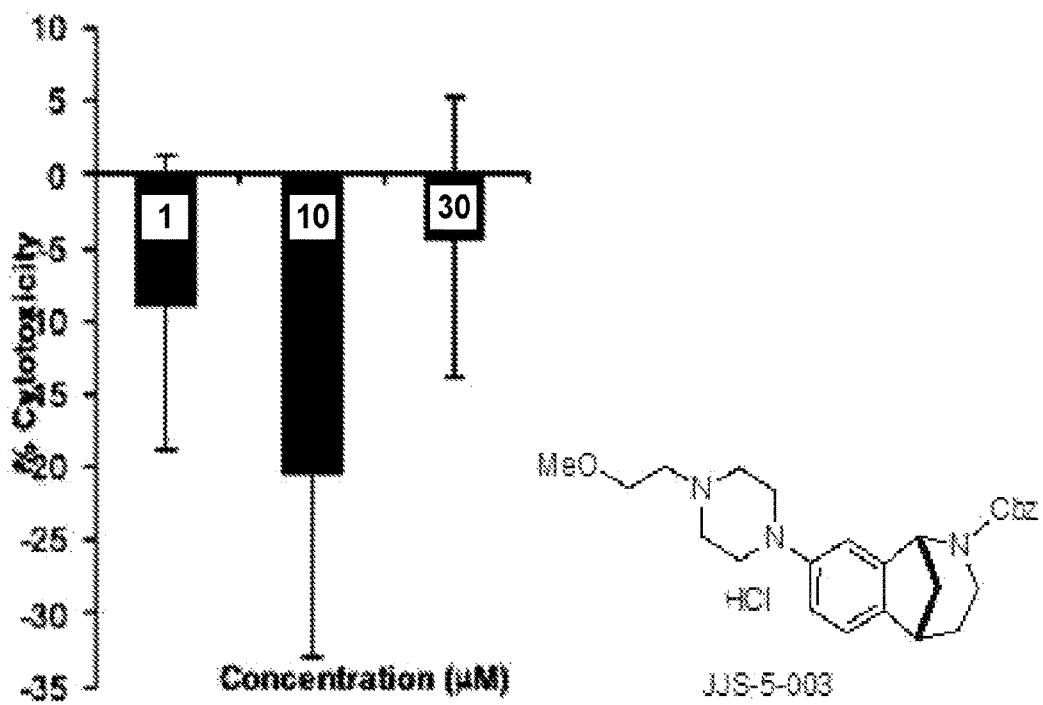
FIG. 16 MTT Assay in Neuroblastoma Cells; Sigma 2 receptor binding ligands were evaluated for effects in neuroblastoma cells. JJS-5-003 and TH-4-20 increased cellular metabolism of MTT and were generally non-toxic at concentrations up to 30 microM.
Figure 16:
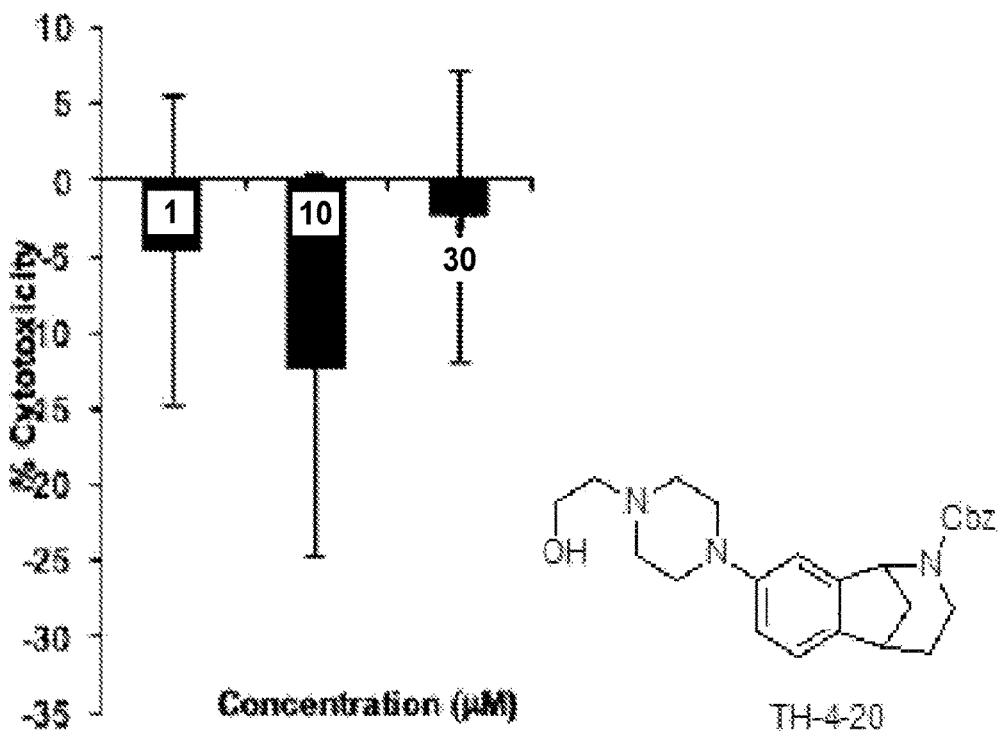

Swe+ (APP) mice affects cognition, using compound that is potent and selective for Sig2R/PGRMC1 (PGRMC1/Sig2R Ki=71 nM; Sig1R Ki=495 nM), nontoxic (MTD>100 mg/kg/d for 30 d), highly brain penetrant (ca 4 µM level in brain with single 10 mg/kg sc injection), bioavailable (45% SC; 7% PO) with plasma levels of 350 ng/mL (60 min) and 200 ng/mL (3 h), weak hERG binder (20 µM), and weak binder at opiod, serotonin, DAT, NET, SERT, and other CNS targets. Assays include Y-Maze behavioral test (FIG. 4) showing Sig2R/PGRMC1 modulator (e.g., antagonist, partial agonist, agonist) enhances reference and working memory in WT and transgenic APP mice, sociability and social discrimination tests (FIG. 5) showing Sig2R/PGRMC1 modulator (e.g., antagonist, partial agonist, agonist) rescues social deficits in WT and transgenic APP mice, and Morris water maze test (FIG. 6 and FIG. 7) showing Sig2R/PGRMC1 modulator (e.g., antagonist, partial agonist, agonist) enhances spatial and long term memory in WT and transgenic mice. Acute hippocampal brain slices were used to assay effects of Sig2R/PGRMC1 modulators (e.g., antagonists, partial agonists, agonists) on excitability (FIG. 8) showing that Sig2R/PGRMC1 modulator (e.g., antagonist, partial agonist, agonist) reduces number of action potentials fired and prevents mGluR-mediated increase in excitability.

Example 13. Charaterization of SAS-0132 Compound

Characterization of SAS-101 shows that Sig2R/PGRMC1 modulators (e.g., antagonists, partial agonists, agonists) are neuroprotective and potential therapeutics for Alzheimer's disease, Sig2R/PGRMC1 modulators (e.g., antagonists, partial agonists, agonists) tested rescues sociability, social discrimination, spatial, cued, working, and long-term memory deficits in WT and transgenic APP mice at doses as low as of 3 mg/kg (sc), and display no toxic effects after 10 mg/kg/d for 2 mo; more than 20 chemical blood plasma markers and histopathology of vital organs (heart, lung, spleen, kidneys, and liver); no adverse affects upon body weight or locomotor activity in mice.

Example 14. Receptor Binding Assays

Receptor binding assays were performed by the Psychoactive Drug Screening Program (PDSP) at Chapel Hill, N.C. The assay protocol book can be accessed free of charge at: website pdsp.med.unc.edu/PDSP %20Protocols %20II %202013-03-28.pdf, which is incorporated by reference in it's entirety for all purposes. Briefly, Sig1Rs and Sig2Rs were sourced from homogenates of Guinea pig brains and rat livers, respectively. Assessment of Sig1R binding affinity was determined via competition binding assays with the radioligand [3H]-(+)-pentazocine. Sig2R binding affinity was determined through competition binding assays using the radioligand [3H]-ditolylguanidine in the presence of (+)-pentazocine to block Sig1R binding sites. For primary binding results, non-specific binding in the presence of 10 mM is set as 100% inhibition; total binding in the absence of haloperidol is set to 0% inhibition. The radioactivity in the presence of the test compound is calculated with the following equation and expressed as a percent inhibition: % inhibition=(sample CPM non-specific CPM)/Total CPM−non-specific CPM)×100. The normalization process is carried out in Prism or Excel. To determine secondary binding results, CPM/well are pooled and fitted to a three parameter logistic function for competition binding in Prism v 5.0 to determine IC50 values, which are converted to Ki according to the Cheng-Prusoff equation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

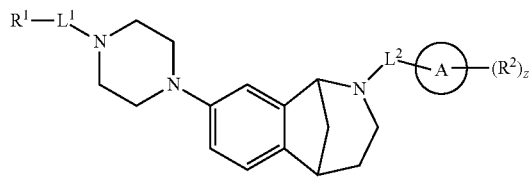 (I)

Ring A is aryl;

L¹ is a bond or unsubstituted alkylene;

L² is C(O)OCH₂—;

R¹ is —C(O)R⁹, —C(O)OR⁹, substituted alkyl, substituted or unsubstituted cycloalkyl, or substituted or unsubstituted heterocycloalkyl; and R² is independently a halogen, —CX₃², —OH, —NH₂, —OCX₃², —OCHX₂², substituted or unsubstituted alkyl, substituted or unsubstituted heteroalkyl; two R² substituents bonded to adjacent atoms may optionally be joined to form a substituted or unsubstituted heterocycloalkyl;

R⁹ is hydrogen, substituted or unsubstituted alkyl, substituted or unsubstituted cycloalkyl, or substituted or unsubstituted heterocycloalkyl;

z is 0, 1, or 2; and

X² is —Cl, —Br, —I, or —F;

wherein when a chemical group is used with the "substituted" modifier, one or more hydrogen atoms has been replaced, independently at each instance, by halogen, —CF₃, —CHF₂, —CH₂F, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, —OCH₂F, unsubstituted alkyl, unsubstituted heteroalkyl, unsubstituted cycloalkyl, unsubstituted heterocycloalkyl, unsubstituted aryl, unsubstituted heteroaryl; or alkyl, heteroalkyl, cycloalkyl, heterocycloalkyl, aryl, heteroaryl, optionally substituted with at least one substituent selected from oxo, halogen, —CF₃, —CHF₂, —CH₂F, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, or —OCH₂F; or a compound of the formula:

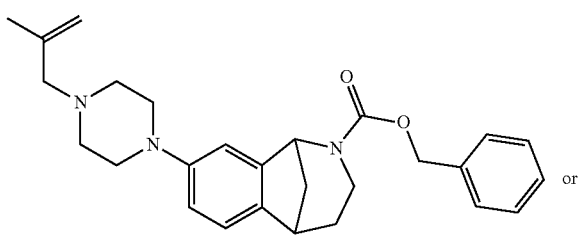 or

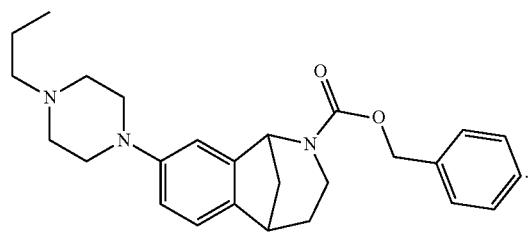

2. The compound of claim 1, wherein the compound has the formula:

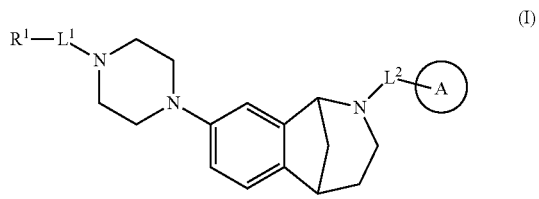 (I)

Ring A is phenyl;

L¹ is a bond or unsubstituted C₁-C₁₀ alkylene;

L² is C(O)OCH₂—;

R¹ is —C(O)OR⁹, or substituted or unsubstituted C₃-C₈ cycloalkyl; and

R⁹ is substituted or unsubstituted C₁-C₈ alkyl.

3. The compound of claim 1, wherein the compound has the formula:

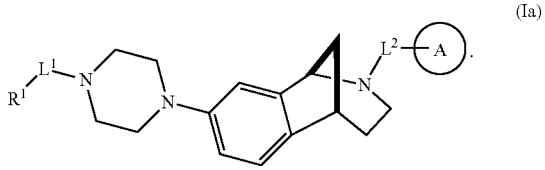 (Ia)

4. The compound of claim 1, wherein the compound has the formula:

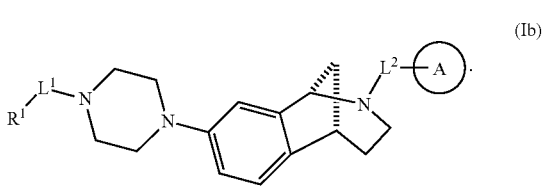 (Ib)

5. The compound of claim 1, wherein Ring A is phenyl.

6. The compound of claim 1, wherein L¹ is a bond.

7. The compound of claim 1, wherein L¹ is an unsubstituted C₁-C₃ alkylene; and R¹ is —C(O)OR⁹.

8. The compound of claim 1 selected from the group consisting of:

209
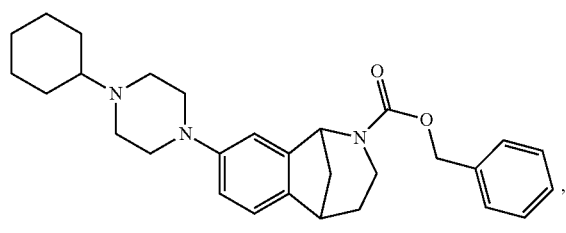
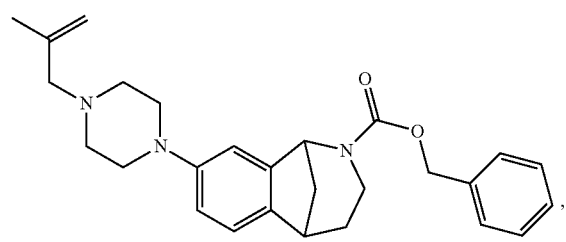
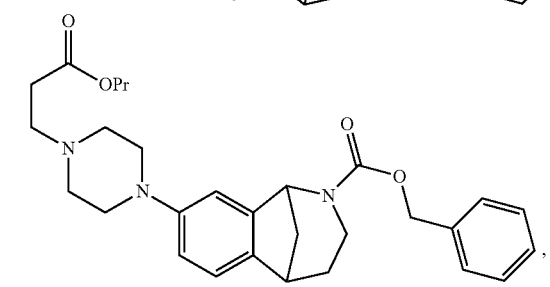
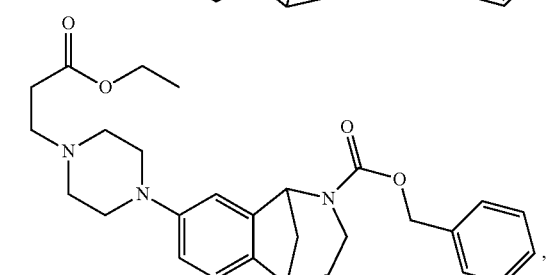
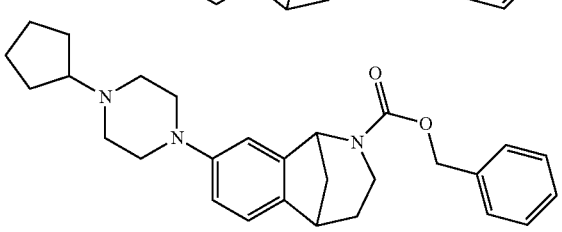
and
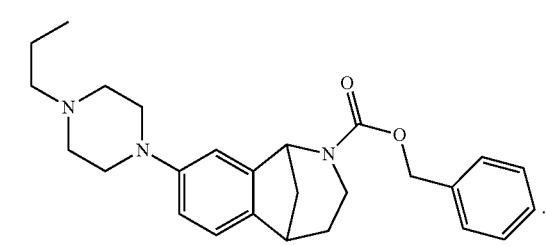
9. A pharmaceutical composition comprising a pharmaceutically acceptable excipient and a compound of claim 1, or a pharmaceutically acceptable salt thereof.
10. The compound of claim 8 selected from the group consisting of:
210
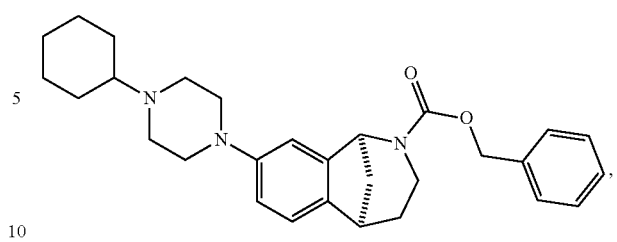
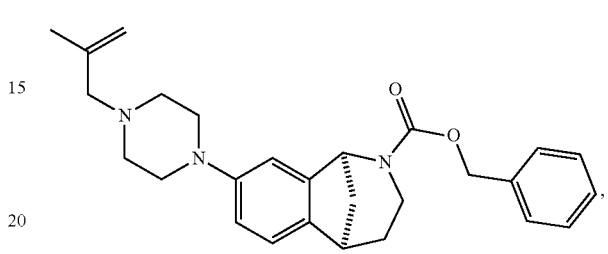
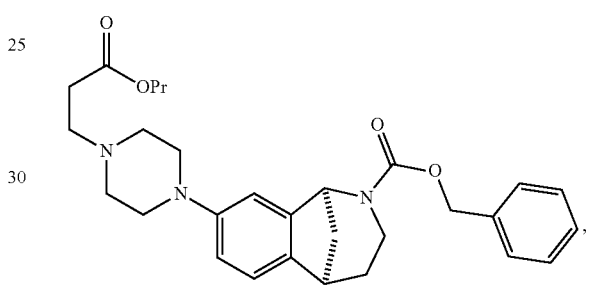
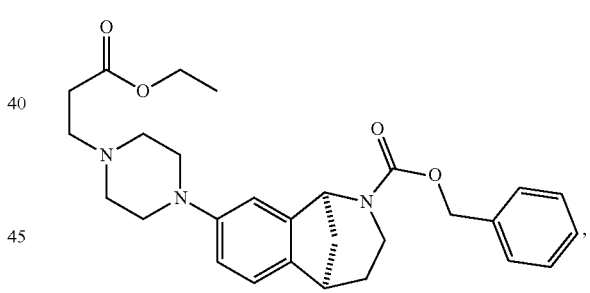
, and
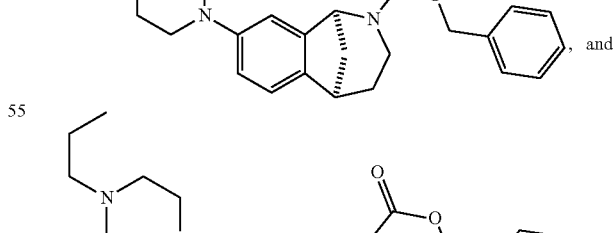
11. The compound of claim 8, selected from the group consisting of:

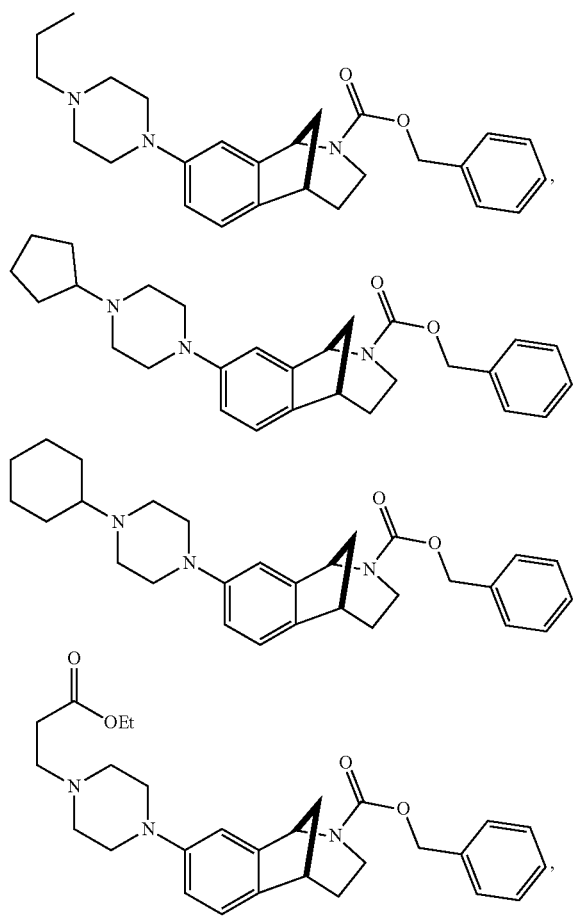

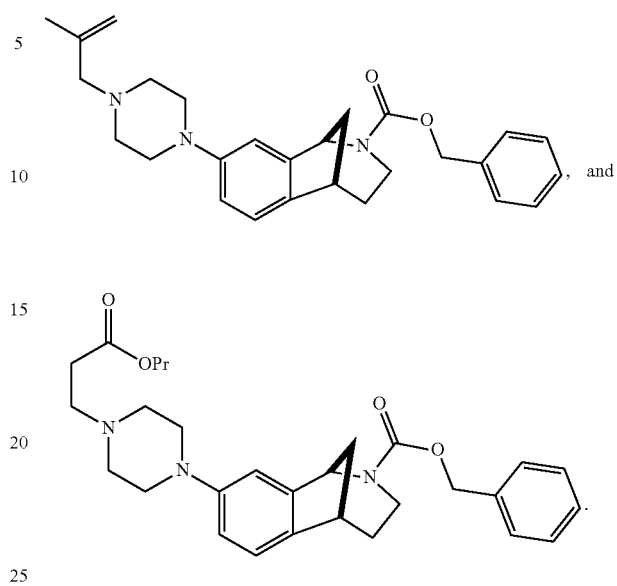

12. The compound of claim 1, wherein $R_1$ is substituted or unsubstituted $C_3$-$C_8$ cycloalkyl.

13. The compound of claim 1, wherein Ring A is a phenyl, $L^1$ is an unsubstituted $C_1$-$C_3$ alkylene, and $R^1$ is —C(O)OR$^9$, and $R^9$ is substituted or unsubstituted $C_1$-$C_8$ alkyl.

14. The compound of claim 1, wherein Ring A is a phenyl, $L^1$ is an unsubstituted $C_1$-$C_3$ alkylene, and $R^1$ is substituted or unsubstituted $C_3$-$C_8$ cycloalkyl.

* * * * *